US009193713B2

(12) United States Patent
Carroll et al.

(10) Patent No.: US 9,193,713 B2
(45) Date of Patent: *Nov. 24, 2015

(54) COMPOUNDS AS CANNABINOID RECEPTOR LIGANDS

(75) Inventors: William A. Carroll, Evanston, IL (US); Michael J. Dart, Highland Park, IL (US); Arturo Perez-Medrano, Grayslake, IL (US); Derek W. Nelson, Highland Park, IL (US); Tongmei Li, Lake Bluff, IL (US); Sridhar Peddi, Grayslake, IL (US); Jennifer Frost, Grayslake, IL (US); Teodozyj Kolasa, Lake Villa, IL (US); Bo Liu, Waukegan, IL (US); Steven P. Latshaw, Round Lake, IL (US); Xueqing Wang, Evanston, IL (US)

(73) Assignee: AbbVie Inc., North Chicago, IL (US)

( * ) Notice: Subject to any disclaimer, the term of this patent is extended or adjusted under 35 U.S.C. 154(b) by 779 days.

This patent is subject to a terminal disclaimer.

(21) Appl. No.: 12/246,808

(22) Filed: Oct. 7, 2008

(65) Prior Publication Data

US 2009/0105306 A1 Apr. 23, 2009

Related U.S. Application Data

(60) Provisional application No. 60/979,653, filed on Oct. 12, 2007.

(51) Int. Cl.
| C07D 405/06 | (2006.01) |
| C07D 405/14 | (2006.01) |
| C07D 413/06 | (2006.01) |
| C07D 413/14 | (2006.01) |
| C07D 417/06 | (2006.01) |
| C07D 417/14 | (2006.01) |

(52) U.S. Cl.
CPC ............ *C07D 405/06* (2013.01); *C07D 405/14* (2013.01); *C07D 413/06* (2013.01); *C07D 413/14* (2013.01); *C07D 417/06* (2013.01); *C07D 417/14* (2013.01)

(58) Field of Classification Search
CPC .. C07D 417/06; C07D 417/14; C07D 413/06; C07D 413/14; C07D 405/06; C07D 405/14
See application file for complete search history.

(56) References Cited

U.S. PATENT DOCUMENTS

| 3,843,683 | A | 10/1974 | Bell |
| 3,928,327 | A | 12/1975 | Takamizawa et al. |
| 4,885,295 | A | 12/1989 | Bell |
| 4,966,828 | A | 10/1990 | Doenges et al. |
| 4,973,587 | A | 11/1990 | Ward et al. |
| 4,978,664 | A | 12/1990 | Bell |
| 5,013,837 | A | 5/1991 | Ward et al. |
| 5,055,579 | A | 10/1991 | Pawlowski et al. |
| 5,250,498 | A | 10/1993 | Andree et al. |
| 5,468,722 | A | 11/1995 | Shibata et al. |
| 5,530,019 | A | 6/1996 | Okada et al. |
| 5,654,322 | A | 8/1997 | Hirata et al. |
| 6,323,214 | B1* | 11/2001 | Baraldi ......................... 514/301 |
| 6,358,992 | B1 | 3/2002 | Pamukcu et al. |
| 6,369,052 | B1* | 4/2002 | Kellar et al. ................... 514/221 |
| 6,559,186 | B1 | 5/2003 | Campbell |
| 7,214,716 | B2 | 5/2007 | Fride et al. |
| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 7,560,456 | B2 | 7/2009 | Araki et al. |
| 7,560,481 | B2 | 7/2009 | Frost et al. |
| 7,674,912 | B2 | 3/2010 | Sams et al. |
| 7,683,084 | B2 | 3/2010 | Faghih et al. |
| 7,741,365 | B2 | 6/2010 | Makriyannis et al. |
| 7,750,039 | B2 | 7/2010 | Frost et al. |

(Continued)

FOREIGN PATENT DOCUMENTS

| CA | 2587667 A1 | 5/2006 |
| DE | 1522361 A1 | 7/1969 |

(Continued)

OTHER PUBLICATIONS

Atwood et al. "CB2: Therapeutic target-in-waiting" Progress in Neuro-Psychopharmacology & Biological Psychiatry 2012, 38, 16-20.*
Campbell et al. British Journal of Pharmacology 2007, 152, 655-662.*
Mayo clinic, Alzheimer's disease, obtained from http://www.mayoclinic.com/health/alzheimers-disease/DS00161/DSECTION=prevention on Sep. 24, 2014.*
Mucke, L. Nature, 2009, 461, 895-897.*
Arevalo-Martin, A., et al., "Therapeutic Action of Cannabinoids in a Murine Model of Multiple Sclerosis," Journal of Neuroscience, 2003, 2511-2516, vol. 23, No. 7.
Benito, C. et al., "Cannabinoid CB2 Receptors and Fatty Acid Amide Hydrolase Are Selectively Overexpressed in Neuritic Plaque-Associated Glia in Alzheimer's Disease Brains," Journal of Neuroscience, 2003, 11136-11141, vol. 23—Issue 35.

(Continued)

*Primary Examiner* — Matthew Coughlin
(74) *Attorney, Agent, or Firm* — Lisa V. Mueller; Michael Best & Friedrich LLP

(57) ABSTRACT

The present invention relates compounds of formula (I)

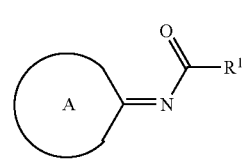

(I)

wherein A and $R^1$ are as defined in the specification, pharmaceutical compositions comprising such compounds, and methods of treating conditions and disorders using such compounds and pharmaceutical compositions.

24 Claims, No Drawings

(56) References Cited

U.S. PATENT DOCUMENTS

| | | | |
|---|---|---|---|
| 7,868,038 B2 | 1/2011 | Nelson et al. | |
| 7,872,006 B2 | 1/2011 | Moritani et al. | |
| 7,872,033 B2 | 1/2011 | Carroll et al. | |
| 7,875,639 B2 | 1/2011 | Florjancic et al. | |
| 7,875,640 B2 | 1/2011 | Kolasa et al. | |
| 7,923,465 B2 | 4/2011 | Muthuppalaniappan et al. | |
| 7,985,768 B2 | 7/2011 | Nelson et al. | |
| 8,044,071 B2 | 10/2011 | Carroll | |
| 8,058,293 B2 | 11/2011 | Kolasa et al. | |
| 8,158,663 B2 | 4/2012 | Carroll et al. | |
| 8,173,687 B2 | 5/2012 | Carroll et al. | |
| 8,236,822 B2 | 8/2012 | Wang et al. | |
| 8,288,428 B2 | 10/2012 | Wang et al. | |
| 8,338,467 B2 | 12/2012 | Kolasa et al. | |
| 8,481,574 B2 | 7/2013 | Meyer et al. | |
| 8,492,371 B2* | 7/2013 | Carroll et al. | 514/210.01 |
| 8,501,794 B2 | 8/2013 | Carroll et al. | |
| 8,586,596 B2 | 11/2013 | Dart et al. | |
| 2004/0023862 A1* | 2/2004 | Smart et al. | 514/12 |
| 2004/0029040 A1 | 2/2004 | Watanabe et al. | |
| 2004/0034090 A1 | 2/2004 | Barth et al. | |
| 2004/0077617 A1 | 4/2004 | Bennani et al. | |
| 2004/0166539 A1 | 8/2004 | Akhavan-Tafti et al. | |
| 2004/0259912 A1 | 12/2004 | Matsumoto et al. | |
| 2005/0176713 A1* | 8/2005 | Freyne et al. | 514/247 |
| 2006/0199817 A1 | 9/2006 | Tasker et al. | |
| 2007/0061360 A1 | 3/2007 | Holcombe et al. | |
| 2007/0155738 A1 | 7/2007 | Steeneck et al. | |
| 2008/0058335 A1 | 3/2008 | Florjancic et al. | |
| 2008/0058355 A1 | 3/2008 | Westheim et al. | |
| 2008/0139635 A1 | 6/2008 | Martin et al. | |
| 2008/0242654 A1 | 10/2008 | Kolasa et al. | |
| 2008/0287510 A1 | 11/2008 | Carroll et al. | |
| 2008/0312435 A1 | 12/2008 | Saito et al. | |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105305 A1 | 4/2009 | Butlin et al. | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |
| 2010/0041720 A1 | 2/2010 | Carroll et al. | |
| 2010/0063022 A1 | 3/2010 | Carroll et al. | |
| 2010/0069348 A1 | 3/2010 | Carroll et al. | |
| 2010/0069349 A1 | 3/2010 | Carroll et al. | |
| 2010/0093814 A1 | 4/2010 | Florjancic et al. | |
| 2010/0216760 A1 | 8/2010 | Frost et al. | |
| 2011/0065685 A1 | 3/2011 | Frost et al. | |
| 2011/0082116 A1 | 4/2011 | Carroll et al. | |
| 2011/0086832 A1 | 4/2011 | Kolasa et al. | |
| 2011/0086838 A1 | 4/2011 | Nelson et al. | |

FOREIGN PATENT DOCUMENTS

| | | |
|---|---|---|
| DE | 1772867 A1 | 6/1971 |
| DE | 2458933 A1 | 6/1975 |
| DE | 3533331 A1 | 3/1987 |
| EP | 412404 A2 | 2/1991 |
| EP | 568096 A1 | 11/1993 |
| EP | 0619316 A1 | 10/1994 |
| EP | 0639569 A1 | 2/1995 |
| EP | 1060734 A2 | 12/2000 |
| EP | 1219612 A1 | 7/2002 |
| EP | 1300401 A1 | 4/2003 |
| EP | 1640369 A1 | 3/2006 |
| EP | 1820504 A1 | 8/2007 |
| FR | 2254339 A1 | 7/1975 |
| FR | 2796643 A1 | 1/2001 |
| JP | 57171986 A | 10/1982 |
| JP | 6345736 A | 12/1994 |
| WO | 9507271 A1 | 3/1995 |
| WO | WO-9531448 A1 | 11/1995 |
| WO | WO-9601591 A1 | 1/1996 |
| WO | WO-9700860 A1 | 1/1997 |
| WO | 9710223 A1 | 3/1997 |
| WO | WO-0063207 A1 | 10/2000 |
| WO | WO-0116138 A1 | 3/2001 |
| WO | WO-0128557 A1 | 4/2001 |
| WO | 01/58869 A2 | 8/2001 |
| WO | WO-0155139 A1 | 8/2001 |
| WO | WO-0155140 A1 | 8/2001 |
| WO | WO-0183422 A1 | 11/2001 |
| WO | WO-0242269 A1 | 5/2002 |
| WO | WO-02060447 A1 | 8/2002 |
| WO | WO-02102232 A2 | 12/2002 |
| WO | WO-03049741 A1 | 6/2003 |
| WO | WO-03097605 A1 | 11/2003 |
| WO | WO-2004050086 A1 | 6/2004 |
| WO | WO-2004110453 A1 | 12/2004 |
| WO | WO-2005023818 A2 | 3/2005 |
| WO | WO-2005058887 A1 | 6/2005 |
| WO | WO-2005075464 A1 | 8/2005 |
| WO | 2005099353 A2 | 10/2005 |
| WO | WO-2005099353 A3 | 10/2005 |
| WO | WO-2005115972 A1 | 12/2005 |
| WO | WO-2005115986 A1 | 12/2005 |
| WO | 2006008754 A1 | 1/2006 |
| WO | WO-2006051704 A1 | 5/2006 |
| WO | WO-2006070106 A1 | 7/2006 |
| WO | WO-2006100208 A1 | 9/2006 |
| WO | WO-2007061360 A2 | 5/2007 |
| WO | WO 2007140385 A2 * | 12/2007 |
| WO | WO-2007140439 A2 | 12/2007 |
| WO | WO-2007140439 A3 | 1/2008 |
| WO | WO-2007140385 A3 | 2/2008 |
| WO | WO-2008063781 A2 | 5/2008 |
| WO | WO-2008079687 A1 | 7/2008 |
| WO | WO-2008121558 A1 | 10/2008 |
| WO | WO-2008130953 A2 | 10/2008 |
| WO | WO-2008144360 A1 | 11/2008 |
| WO | WO-2009009550 A1 | 1/2009 |
| WO | WO2009048936 A1 | 4/2009 |
| WO | WO-2009067613 A1 | 5/2009 |
| WO | WO-2009114566 A1 | 9/2009 |
| WO | WO2010019547 A1 | 2/2010 |
| WO | WO-2010033543 A2 | 3/2010 |
| WO | WO-2010054024 A2 | 5/2010 |
| WO | WO-2010071783 A1 | 6/2010 |
| WO | WO-2010111573 A1 | 9/2010 |
| WO | WO-2010111574 A1 | 9/2010 |

OTHER PUBLICATIONS

Berge, S.M. et al., "Journal of Pharmaceutical Sciences, Pharmaceutical Salts," J Pharmaceutical Sciences, 1977, 1-19, vol. 66.

Bouchard, J-F et al., "Contribution of endocannabinoids in the endothelial protection afforded by ischemic preconditioning in the isolated rat heart", Life Sciences, 2003, 1859-1870, vol. 72.

Boyle, W.J. et al., "Osteoclast differentiation and activation," (Binary/Image), 2003, 337-342, vol. 423.

Brennan, T.J. et al., "Characterization of a rat model of incisional pain," (Binary/Image), 1996, 493-501, vol. 64.

Buckley, N. E. et al., "Immunomodulation by cannabinoids is absent in mice deficient for the cannabinoid CB receptor," European Journal of Pharmacology, 2000, 141-149, vol. 396.

Carlisle, S.J. et al., "Differential expression of the CB2 cannabinoid receptor by rodent macrophages and macrophage-like cells in relation to cell activation," International Immunopharmacology, 2002, 69, vol. 2.

Carrier, E.J. et al., "Endocannabinoids in Neuroimmunology and Stress," Current Drug Targets—CNS & Neurological Disorders, 2005, 657-665, vol. 4.

Casanova, M.L. et al., "Inhibition of skin tumor growth and angiogenesis in vivo by activation of cannabinoid receptors," Journal of Clinical Investigation, 2003, 43-50, vol. 111.

Chaplan, S.R. et al., "Quantitative assessment of tactile allodynia in the rat paw," Journal of Neuroscience Methods, 1994, 55-63, vol. 53.

(56) References Cited

OTHER PUBLICATIONS

Cichewicz, D.L. et al., "Synergistic interactions between cannabinoid and opioid analgesics," Life Sciences, 2004, 1317-1324, vol. 74.
Clayton, N. et al., "CB1 and CB2 cannabinoid receptors are implicated in inflammatory pain," (Binary/Image), 2002, 253-260, vol. 96.
Cotarca et al., "Bis(trichloromethyl) carbonate in organic synthesis," Synthesis, pp. 553-576 (1996).
Dixon, W.J. "Efficient analysis of experimental observations," Annual Review of Pharmacology and Toxicology, 1980, 441-462, vol. 20.
Eckert H., Forster B., "Triphosgene, a Crystalline Phosgene Substitute", Angew Chem Int Ed Engl, 1987, 26/9, 894-895.
Filippo, C.D. et al., "Cannabinoid CB2 receptor activation reduces mouse myocardial ischemia-reperfusion injury: involvement of cytokine/chemokines and PMN," Journal of Leukocyte Biology, 2004, 453-459, vol. 75.
Galiégue, et al., "Expression of central and peripheral cannabinoid receptors in human immune tissues and leukocyte subpopulations," European Journal of Biochemistry, 1995, 54-61, vol. 232.
Grotenhermen, F. et al., "IACM 2nd Conference on Cannabinoids in Medicine," Expert Opinion in Pharmacotherapy, 2003, 2367-2371, vol. 4—Issue 12.
Hamuro Y, Marshall WJ, Scialdone MA, "Solid-Phase Synthesis of Acyclic and Cyclic Amino Acid Derived Urea Peptidomimetics Using Phoxime Resin", J Comb Chem, 1999, 1, 163-172.
Hanus, L. et al., "HU-308: a specific agonist for CB 2, a peripheral cannabinoid receptor," Proceedings of the National Academy of Science, 1999, 14228-14233, vol. 96.
Hohmann, A.G. et al., "Selective Activation of Cannabinoid CB2 Receptors Suppresses Hyperalgesia Evoked by Intradermal Capsaicin," Journal of Pharmacology and Experimental Therapeutics, 2004, 446-453, vol. 308.
Hutchins SM, Chapman KT, "A General Method for the Solid Phase Synthesis of Ureas", Tetrahedron Letters, 1994, 35/24, 4055-4058.
Hutchins SM, Chapman KT, "A Strategy for Urea Linked Diamine Libraries", Tetrahedron Letters, 1995, 36/15, 2583-2586.
Ibrahim, M.M. et al., "Activation of CB2 cannabinoid receptors by AM1241 inhibits experimental neuropathic pain: Pain inhibition by receptors not present in the CNS," Proceedings of the National Academy of Science, 2003, 10529-10533, vol. 100—Issue 18.
Ibrahim, M.M. et al., "CB2 cannabinoid receptor activation produces antinociception by stimulating peripheral release of endogenous opioids," Proceedings of the National Academy of Science, 2005, 3093-3098, vol. 102—Issue 8.
Ihenetu, K. et al., "Inhibition of interleukin-8 release in the human colonic epithelial cell line HT-29 by cannabinoids," European Journal of Pharmacology, 2003, 207-215, vol. 458.
International Search Report for application No. PCT/US08/079182, Mailed on Dec. 15, 2008, 1 page.
Izdebski J, Pawlak D, "A New Convenient Method for the Synthesis of Symmetrical and Unsymmetrical N,N'-Disubstituted Ureas", Synthesis, 1989, 423-425.
Joshi S.K. et al., "Comparison of Antinociceptive Actoins of Standard Analgesics in Attenuating Capsaicin and Nerve-Injury-Induced Mechanical Hypersensitivty," Neurosci, 587-596, vol. 143, 2006.
Julien, B, et al., "Antifibrogenic Role of the Cannabinoid Receptor CB2 in the Liver," Gastroenterology, 2005, 742-755, vol. 128.
Karsak, M, et al., "Cannabinoid receptor type 2 gene is associated with human osteoporosis," Human Molecular Genetics, 2005, 3389-3396, vol. 14—Issue 22.
Katritzky AR, Pleynet DPM, Yang B, "A General Synthesis of Unsymmetrical Tetrasubstituted Ureas", J Org Chem, 1997, 62, 4155-4158.
Knolker HJ, "A Novel Method for the Synthesis of Isocyanates Under Mild Conditions", Angew Chem Int Ed Engl, 1995, 34/22, 2497-2500.
Knolker HJ, "Synthesis of Symmetrical and Unsymmetrical Ureas by DMAP-Catalyzed Reaction of Alkyl- and Arylamines with Di-tert-butyldicarbonate", Synlett, 1996, 502-504.
Kruijtzer JAW, Lefeber DJ, Liskamp RMJ, "Approaches to the Synthesis of Ureapeptoid Peptidomimetics", Tetrahedron Letters, Pergamon, 1997, 38/30, 5335-5338.
Lamothe M, Perez M, Colovray-Gotteland V, Halazy S, "A Simple One-Pot Preparation of N,N'-unsymmetrical ureas from N-Boc Protected Primary Anilines and Amines", Synlett, 1996, 6, 507-508.
Lemoucheux L, Rouden J, Ibazizene M, "Debenzylation of Tertiary Amines Using Phosgene or Triphosgene: An Efficient and Rapid Procedure for the Preparation of Carbamoyl Chlorides and Unsymmetrical Ureas. Application in Carbon-11 Chemistry", J Org Chem, 2003, 68/19, 7289-7297.
Lepicier, P. et al., "Endocannabinoids protect the rat isolated heart against ischaemia," British Journal of Pharmacology, 2003, 805-815, vol. 139.
Leung M, Lai J, Lau K, Yu H, Hsiao H, "S,S-Dimethyl Dithiocarbonate: A Convenient Reagent for the Synthesis of Symmetrical and Unsymmetrical Ureas", J Org Chem, 1996, 61, 4175-4179.
Lotersztajn, S. et al., "Hepatic Fibrosis: Molecular Mechanisms and Drug Targets," Annual Review of Pharmacology and Toxicology, 2005, 605-628, vol. 45.
Majer P, Randad RS, "A Safe and Efficient Method for Preparation of N,"-Unsymmetrically Disubstituted Ureas Utilizing Triphosgene", J Org Chem, 1994, 59, 1937-1938.
Malan, T.P. et al., "CB2 cannabinoid receptor-mediated peripheral antinociception," (Binary/Image), 2001, 239-245, vol. 93.
Maresz, K, et al., "Modulation of the cannabinoid CB2 receptor in microglial cells in response to inflammatory stimuli," Journal of Neurochemistry, 2005, 437-445, vol. 95.
Mathison, R, et al., "Effects of cannabinoid receptor-2 activation on accelerated gastrointestinal transit in lipopolysaccharide-treated rats," British Journal of Pharmacology, 2004, 1247-1254, vol. 142.
McKallip, R.J. et al., "Targeting CB2 cannabinoid receptors as a novel therapy to treat malignant lymphoblastic disease," (Binary/Image), 2002, 627-634, vol. 15—Issue 2.
Nackley, A.G. et al., "Selective activation of cannabinoid CB2 receptors suppresses spinal fos protein expression and pain behavior in a rat model of inflammation," Neuroscience, 2003, 747-757, vol. 119.
Ni, X. et al., "Win 55212-2, a cannabinoid receptor agonist, attenuates leukocyte/endothelial interactions in an experimental autoimmune encephalomyelitis model," Multiple Sclerosis, 2004, 158-164, vol. 10.
Nieuwenhuijzen JW, Conti PGM, "Solid and Solution Phase Combinatorial Synthesis of Ureas", Tetrahedron Letters, Pergamon, 1998, 39, 7811-7814.
Patel, J.J. et al., "Inhibition of guinea-pig and human sensory nerve activity and the cough reflex in guinea-pigs by cannabinoid (CB2) receptor activation," British Journal of Pharmacology, 2003, 261-268, vol. 140.
Pertwee, R.G. "Cannabinoids and multiple sclerosis," Pharmacology & Therapeutics, 2002, 165-174, vol. 95.
Prescott et al., Methods in Cell Biology, 1976, vol. XIV, 33, Academic Press.
Quartilho, A. et al., "Inhibition of Inflammatory Hyperalgesia by Activation of Peripheral CB2 Cannabinoid Receptors," Anesthesiology, 2003, 955-960, vol. 99.
Ralston, S.H. "Regulation of bone mass, bone loss and osteoclast activity by cannabinoid receptors," Nature Medicine, 2005, 774-779, vol. 11.
Ramirez, B.G. et al., "Prevention of Alzheimer's Disease Pathology by Cannabinoids: Neuroprotection Mediated by Blockade of Microglial Activation," Journal of Neuroscience, 2005, 1904-1913, vol. 25—Issue 8.
Sanchez C. et al., "Inhibition of Glioma Growth in Vivo by Selective Activation of the CB2 Cannabinoid Receptor1," Cancer Research, 2001, 5784-5789, vol. 61.
Steffens S. et al., "Low dose oral cannabinoid therapy reduces progression of atherosclerosis in mice," (Binary/Image), 2005, 782-786, vol. 434.
Takeda K, Akagi Y, Saiki A, Tsukahara T, Ogura H, "Convenient Methods for Syntheses of Active Carbamates, Ureas and Nitrosoureas Using N,N-disuccinimido Carbonate (DSC)", Tetrahedron Letters, 1983, 24, 4569-4572.

(56) References Cited

OTHER PUBLICATIONS

Valenzano K.J. et al., "Pharmacological and pharmacokinetic characterization of the cannabinoid receptor 2 agonist, GW405833, utilizing rodent models of acute and chronic pain, anxiety, ataxia and catalepsy," Neuropharmacology, 2005, 658-672, vol. 48.
Walter L. et al., "Cannabinoids and neuroinflammation," Pharmacology, 2004, 775-785, vol. 141.
Warhurst A.C. et al., "Interferon ? induces differential upregulation of a and β chemokine secretion in colonic epithelial cell lines," (Binary/Image), 1998, 208-213, vol. 42.
Wright K. et al., "Differential Expression of Cannabinoid Receptors in the Human Colon: Cannabinoids Promote Epithelial Wound Healing," Gastroenterology, 2005, 437-453, vol. 129.
Yoshihara S. et al., "Cannabinoid Receptor Agonists Inhibit Sensory Nerve Activation in Guinea Pig Airways", American Journal of Respiratory and Critical Care Medicine, 2004, 941-946, vol. 170.
Yoshihara S. et al., "Endogenous Cannabinoid Receptor Agonists Inhibit Neurogenic Inflammations in Guinea Pig Airways" Allergy and Immunology, 2005, 80-87, vol. 138.
Yoshihara S. et al., "The Cannabinoid Receptor Agonist WIN 55212-2 Inhibits Neurogenic Inflammations in Airway Tissues," Journal of Pharmacological Sciences, 2005, 77-82, vol. 98—Issue 1.
Greene T., et al., "Protective Groups in Organic Synthesis," 1999, Third Edition, Table of Contents.
Miyaura N., et al., "Cross-Coupling Reactions. A Practical Guide," Springer, 2002, Table of Contents.
Negishi, "Handbook of Organopalladium Chemistry for Organic Synthesis," 2002, Table of Contents.
Scialdone MA et al., "Phosgenated p-Nitrophenyl (polystyrene) ketoxime or Phoxime Resin. A New Resin for the Solid-Phase Synthesis of Ureas via Thermolytic Cleavage of Oxime-Carbamates," J Org chem, 1998, vol. 63, pp. 4802-4807.
Beylot, M. et al., "In Vivo Studies of Intrahepatic Metabolic Pathways," Diabetes Metabolism, 1997, vol. 23 (3), pp. 251-257.
Blagojevic, N. et al., "Role of heavy water in Boron Neutron Capture Therapy," Topics in Dosimetry & Treatment Planning for Neutron Capture Therapy, 1994, pp. 125-134.
Blake, M. I. et al., "Studies With Deuterated Drugs," Journal of Pharmaceutical Sciences, 1975, vol. 64 (3), pp. 367-391.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Czajka, D. M. et al., "Effect of Deuterium Oxide on the Reproductive Potential of Mice," Annals of the New York Academy of Sciences, 1960, vol. 84, pp. 770-779.
Czajka, D. M. et al., "Physiological Effects of Deuterium on Dogs," American Journal of Physiology, 1961, vol. 201 (2), pp. 357-362.
Ebata T., et al., "Synthesis of Both Enantiomers of 4-Hexanolide and 4-Dodecanolide," Agriculture Biochemical, 1991, vol. 55 (6), pp. 1685-1686.
Foster, A. B. et al., "Deuterium Isotope Effects in the Metabolism of Drugs and Xenobiotics: Implications for Drug Design," Advances in Drug Research, 1985, vol. 14, pp. 2-36.
Greene T.W., et al., "Protection for the Amino group," Protective Groups in Organic Synthesis, 1999, Third Edition, pp. 494-653.
International Preliminary Report on Patentability and Written Opinion for Application No. PCT/US08/079182, mailed on Apr. 13, 2010, 5 pages.
International Preliminary Report on Patentability and Written Opinion for Application No. PCT/US2010/028790, mailed on Sep. 27, 2011, 5 pages.
International Search Report for Application No. PCT/US2010/028790, mailed Jul. 19, 2010, 3 pages.
Kato, S. et al., "Synthesis of Deuterated Mosapride Citrate," Journal of Labelled Compounds and Radiopharmaceuticals, 1995, vol. 36 (10), pp. 927-932.

Kushner, et al., "Pharmacological uses and perspectives of heavy water and deuterated compounds," Canadian Journal of Physiology and Pharmacology, 1999, vol. 77 (2), pp. 79-88.
Lizondo, J. et al., "Linezolid: Oxazolidinone antibacterial," Drugs of the Future, 1996, vol. 21 (11), pp. 1116-1123.
Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.
Morissette S.L., et al., "High-throughput Crystallization: Polymorphs, Salts, co-crystals and Solvates of Pharmaceutical Solids," Advanced Drug Delivery Reviews, 2004, vol. 56 (3), pp. 275-300.
Ohta H., et al., "N-Alkyidenearylcarboxamides as a new Potent and Selective CB2 Cannabinoid Receptor Agonist with an Analgesic Action," Bioorganic and Medicinal Chemistry Letters, 2007, vol. 17 (22), pp. 6299-6304.
Ozaki S., et al., "Recent Advances in Isocyanate Chemistry," Chemical Reviews, 1972, vol. 72 (5), pp. 457-496.
Schuart J., et al., "2-Aminooxazole and 2-iminooxazoline. 3. Chosen Examples of the Homologous Series of 3-substituted-2-imino-4-methyl-5-phenyloxazoline," Accession No. 403802, 1974.
Supplementary European Search Report for Application No. EP08837396, mailed on Jan. 16, 2012, 2 pages.
Thomson, J.F., "Physiological Effects of D2O in Mammals," Annals of the New York Academy of Sciences, 1960, vol. 84, pp. 736-744.
Vasileva V.F., et al., "Synthesis and Properties of 2-imino-3-benzyl-5-phenyl-1,3,4-oxadiazoline," Accession No. 121444, 1970.
Vippagunta S.R., et al., "Crystalline Solids," Advanced Drug Delivery Reviews, 2001, vol. 48 (1), pp. 3-26.
Abreo M.A., et al., "Novel 3-Pyridyl Ethers with Subnanomolar Affinity for Central Neuronal Nicotonic Acetylcholine Receptors," Journal of Medicinal Chemistry, 1996, vol. 39 (4), pp. 817-825.
Alfaro I., et al., "Dihydroaromatic Compounds in the Diels-Alder Reaction—III :In Situ Generation and Diels-Alder Reaction of Cyclohexa-1,3-Dienes," Tetrahedron, 1970, vol. 26, pp. 201-218.
Ambartsumova R.F., et al., "Effect of Various Factors on the Reaction of 2-Aminobenzothiazoles with Propylene Oxide," Chemistry of Heterocyclic Compounds, 2002, vol. 38 (8), pp. 994-999.
Andreani, et al., "Ring-opened, etc," Collection of Czechoslovak Chemical Communications, 1999, vol. 64, pp. 299-312.
Ansell M.F., et al., "The Synthesis of (+/-31 )-10a-Homo-11a-Carbathromboxane A1, a Stable Thromboxane A Analogue," Journal of Chemical Society Perkin Trans, 1984, pp. 1061-1068.
Araki, et al., (2003): STN International HCAPLUS database, (Columbus, OH). Accession No. 2003-931334.
Atwood B.K., et al., "CB : Therapeutic Target-in-Waiting," Progress in Neuro-Psychopharmacology & Biological Psychiatry, 2012, vol. 38 (1), pp. 16-20.
Bacon E.R., et al., "Synthesis of 7-Ethyl-4, 7-dihydro-4-oxo-2-(4-pyridinyl)thieno[2,3-b]pyridine-5-carboxylic Acid," Journal of Heterocyclic Chemistry, 1991, vol. 28, pp. 1953-1955.
Baker T.J., et al., "Regiospecific Vinyl Phosphate/β-Keto Phosphonate Rearrangements Initiated by Halogen-Metal Exchange," Journal of Organic Chemistry, 1998, vol. 63 (8), pp. 2613-2618.
Bartlett P.A., et al., "Chorismate Mutase Inhibitors: Synthesis and Evaluation of Some Potential Transition-State Analogues," Journal of Organic Chemistry , 1988, vol. 53, pp. 3195-3210.
Benito C., et al., "A Glial Endogenous Cannabinoid System is Upregulated in the Brains of Macaques with Simian Immunodeficiency Virus-Induced Encephalitis," Journal of Neuroscience, 2005, vol. 25 (10), pp. 2530-2536.
Bennett G.J., et al., "A Peripheral Mononeuropathy in Rat that Produces Disorders of Pain Sensation like those Seen in Man," Pain, 1988, vol. 33 (1), pp. 87-107.
Bermudez-Silva, et al., "Role of Cannabinoid CB2 Receptors in Glucose Homeostasis in Rats," European Journal of Pharmacology, 2007, vol. 565 (1-3), pp. 207-211.
Bozidar K., et al., "Transformations of 1,2,4-Thiadiazolo/2,3-X/ Azines," Heterocycles, 1987, vol. 26 (3), pp. 689-697.

(56) References Cited

OTHER PUBLICATIONS

Bruson H.A., et al., "Action of Sulfuric Acid upon Unsaturated Isothiocyanates: Mercaptothiazolines," Journal of American Chemical Society, 2011, vol. 59 (10), pp. 2011-2013.
Cai, et al., Ex Parte Appeal No. 2011005302, decided Jul. 12, 2011.
Campbell V.A., et al., "Alzheimer's Disease; Taking the Edge off with Cannabinoids?," British Journal of Pharmacology, 2007, vol. 152 (5), pp. 655-662.
Caplus Entry for International Application Publication No. WO2008130953, Accessed Aug. 14, 2012, with Structures Relevant to Claim 25 as Filed Aug. 11, 2011.
Caplus Entry for International Application Publication No. WO2008130953, Accessed Aug. 14, 2012, with Structures Relevant to Claim 35 as Filed Aug. 11, 2011.
"CAPLUS Record of U.S. Patent Application Publication No. 2008/0058335 by Westheim et al., 2007,".
"CAPLUS Record of U.S. Patent Application Publication No. 2008/0242654 by Kolasa et al., 2008,".
CAS Registry No. 1061668-81-2, which entered STN on Oct. 15, 2008.
Castejon P., et al., "A Convenient, Stereodivergent Approach to the Enantioselective Synthesis of N-Boc-Aminoalkyl Epoxides," Tetrahedron Letters, 1995, vol. 36 (17), pp. 3019-3022.
Chauhan M.S., "The Reaction of Some Heterocyclic Thiones with Ethyl Azidoformate," Canadian Journal of Chemistry, 1976, vol. 54 (24), pp. 3879-3883.
Chemical Abstracts Accession No. 1030770638, Jun. 26, 2008.
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Dart et al (2007): STN International HCAPLUS database, Columbus (OH), Accession No. 2007:1396538.
Database Registry [Online] Chemical Abstracts Service, Columbus, Ohio, US, Mar. 2, 2008, XP002687516, Database Accession No. 1006022-43-0.
Database Registry [Online] Chemical Abstracts Service, Columbus, Ohio, US, Mar. 2, 2008, XP002687517, Database Accession No. 1005993-02-1.
Database Registry [Online] Chemical Abstracts Service, Columbus, Ohio, US, Mar. 6, 2008, XP002687515, Database Accession No. 1006758-59-3.
Database Registry [Online] Chemical Abstracts Service, Columbus, Ohio, US, Mar. 7, 2008, XP002687514, Database Accession No. 1007004-94-5.
Database Registry [Online] Chemical Abstracts Service, Columbus, Ohio, US, Mar. 10, 2008, XP002687513, Database Accession No. 1007244-89-4.
Database Registry [Online] Chemical Abstracts Service, Columbus, Ohio, US, Feb. 29, 2008, XP002687518, Database Accession No. 1005931-81-6.
Dauben W.G., et al., "Organic Reactions at High Pressure Cycloadditions with Furans," Journal of the American Chemical Society, 1976, vol. 98 (7), pp. 1992-1993.
Dawood K.M., et al., "Synthesis, Anticonvulsant, and Anti-Inflammatory Evaluation of Some New Benzotriazole and Benzofuran-Based Heterocycles," Bioorganic & Medicinal Chemistry, 2006, vol. 14 (11), pp. 3672-3680.
Dellemijn P.L., et al., "Randomised Double-Blind Active-Placebo-Controlled Crossover Trial of Intravenous Fentanyl in Neuropathic Pain," Lancet, 1997, vol. 349 (9054), pp. 753-758.
DeWolfe R.H., "Reactions of Aromatic Amines with Aliphatic Ortho Esters. A Convenient Synthesis of Alkyl N-Arylimidic Esters," Journal of Organic Chemistry, 1962, vol. 27, pp. 490-493.
Dorsch J.B., et al., "The Preparation of Benzoylacetic Ester and Some of its Homologs," Journal of the American Chemical Society, 1932, vol. 54, pp. 2960-2964.
European Search Report for Application No. EP12187944, mailed on Nov. 20, 2012, 7 pages.

Ex Parte Quayle Action mailed Oct. 12, 2012 for U.S. Appl. No. 13/160,952, filed Jun. 15, 2011.
Fattori D., et al. "The Demjanov and Tiffeneau-Demjanov One-Carbon Ring Enlargements of 2-Aminomethyl-1-7-Oxabicyclo[2.2.1]Heptane derivatives. The Stereo- and Regioselective Additions of 8-Oxabicyclo[3.2.1]Oct-6-en-2-One to Soft Electrophiles," Tetrahedron, 1993, vol. 49 (8), pp. 1649-1664.
Final Office Action mailed Mar. 10, 2010 for U.S. Appl. No. 11/755,434, filed May 30, 2007.
Final Office Action mailed Sep. 14, 2011 for U.S. Appl. No. 12/274,105, filed Nov. 19, 2008.
Final Office Action mailed Feb. 15, 2011 for U.S. Appl. No. 12/120,969, filed May 15, 2008.
Final Office Action mailed Nov. 16, 2011 for U.S. Appl. No. 12/554,445, filed Sep. 4, 2009.
Final Office Action mailed Nov. 16, 2011 for U.S. Appl. No. 12/560,897, filed Sep. 16, 2009.
Final Office Action mailed Apr. 19, 2011 for U.S. Appl. No. 12/539,120, filed Aug. 11, 2009.
Final Office Action mailed Oct. 19, 2011 for U.S. Appl. No. 12/560,893, filed Sep. 16, 2009.
Final Office Action mailed Nov. 21, 2012 for U.S. Appl. No. 12/120,969, filed May 15, 2008.
Final Office Action mailed Apr. 23, 2013 for U.S. Appl. No. 12/967,275, filed Dec. 14, 2010.
Final Office Action mailed Mar. 24, 2011 for U.S. Appl. No. 11/755,434, filed May 30, 2007.
Final Office Action mailed Dec. 28, 2011 for U.S. Appl. No. 12/639,173, filed Dec. 16, 2009.
Florjancic A., et al (2009): Caplus Entry for WO2009067613, Accession No. 2009:649814.
Florjancic et al (2010): STN International HCAPLUS database, Columbus (OH), Accession No. 2010:478868.
Giron D., "Applications of Thermal Analysis and Coupled Techniques in Pharmaceutical Industry," Journal of Thermal Analysis and Calorimetry, 2002, vol. 68, pp. 335-357.
Giron D., "Investigations of Polymorphism and Pseudo-Polymorphism in Pharmaceuticals by Combined Thermoanalytical Techniques," The Journal of Thermal Analysis and Calorimetry, 2001, vol. 64, pp. 37-60.
Goerdeler J., et al., ""Uber Isothiazole, VIII. Synthese von Sulfonylamino-isothiazolen und Sulfonyliminoisothiazolinen aus Sulfonylsenfolen,"" Chemische Berichte, 1969, vol. 102 (7), pp. 2273-2284.
Golech S.A., et al., "Human Brain Endothelium: Coexpression and Function of Vannilloid and Endocannabinoid Receptors," Molecular Brain Research, 2004, vol. 132 (1), pp. 87-92.
Golub T.R., et al., "Molecular Classification of Cancer: Class Discovery and Class Prediction by Gene Expression Monitoring," Science, 1999, vol. 286 (5439), pp. 531-537.
Goodman A.J., et al., "CB2 Selective Sulfamoyl Benzamides; Optimization of the Amide Functionality," Bioorganic & Medicinal Chemistry Letters, 2009, vol. 19 (2), pp. 309-313.
Gouldson P., et al., "Mutational Analysis and Molecular Modelling of the Antagonist SR144528 Binding Site on the Human Cannabinoid CB2 Receptor," European Journal of Pharmacology, 2000, vol. 401 (1), pp. 17-25.
Hargreaves K., et al., "A New and Sensitive Method for Measuring Thermal Nociception in Cutaneous Hyperalgesia," Pain, 1988, . 32 (1), pp. 77-88.
Horig H., et al., "From Bench to Clinic and Back: Perspective on the 1st IQPC Translational Research conference," Journal of Translational Medicine, 2004, vol. 2 (44).
International Preliminary Report on Patentability and Written Opinion for Application No. PCT/US07/081263, mailed on Apr. 15, 2010, 8 pages.
International Preliminary Report on Patentability and Written Opinion for Application No. PCT/US08/069453, mailed on Jan. 12, 2010, 6 pages.
International Preliminary Report on Patentability and Written Opinion for Application No. PCT/US08/080253, mailed on Apr. 20, 2010, 6 pages.

(56) References Cited

OTHER PUBLICATIONS

International Preliminary Report on Patentability and Written Opinion for Application No. PCT/US2005/046480, mailed on Jun. 26, 2007, 8 pages.
International Preliminary Report on Patentability and Written Opinion for Application No. PCT/US2007/0087175, mailed on Jun. 23, 2009, 8 pages.
International Preliminary Report on Patentability and Written Opinion for Application No. PCT/US2007/069921, mailed on Dec. 3, 2008, 10 pages.
International Preliminary Report on Patentability and Written Opinion for Application No. PCT/US2007/070029, mailed on Dec. 3, 2008, 8 pages.
International Preliminary Report on Patentability and Written Opinion for Application No. PCT/US2007/077321, mailed on Mar. 3, 2009, 7 pages.
International Preliminary Report on Patentability and Written Opinion for Application No. PCT/US2008/057460, mailed on Sep. 29, 2009, 11 pages.
International Preliminary Report on Patentability and Written Opinion for Application No. PCT/US2008/060400, mailed on Oct. 20, 2009, 11 pages.
International Preliminary Report on Patentability and Written Opinion for Application No. PCT/US2008/063648, mailed on Nov. 24, 2009, 7 pages.
International Preliminary Report on Patentability and Written Opinion for Application No. PCT/US2008/084216, mailed on May 25, 2010, 5 pages.
International Preliminary Report on Patentability and Written Opinion for Application No. PCT/US2009/053369, mailed on Feb. 15, 2011, 6 pages.
International Preliminary Report on Patentability and Written Opinion for Application No. PCT/US2009/056179, mailed on Mar. 8, 2011, 9 pages.
International Preliminary Report on Patentability and Written Opinion for Application No. PCT/US2009/063318, mailed on May 10, 2011, 5 pages.
International Preliminary Report on Patentability and Written Opinion for Application No. PCT/US2009/068173, mailed on Jun. 21, 2011, 8 pages.
International Preliminary Report on Patentability for Application No. PCT/US2007/077320, mailed on Mar. 3, 2009, 1 page.
International Preliminary Report on Patentability for Application No. PCT/US2009/036715, mailed on Sep. 14, 2010, 1 page.
International Search Report and Written Opinion for Application No. PCT/US2007/077320, mailed on Feb. 7, 2008, 12 pages.
International Search Report and Written Opinion for Application No. PCT/US2009/036715, mailed on Jun. 10, 2009, 9 pages.
International Search Report for Application No. PCT/US07/069921, mailed on Nov. 27, 2007, 4 pages.
International Search Report for Application No. PCT/US07/070029, mailed on Nov. 30, 2007, 3 pages.
International Search Report for Application No. PCT/US07/081263, mailed on Nov. 27, 2008, 3 pages.
International Search Report for Application No. PCT/US08/057460, mailed on Aug. 20, 2008, 3 pages.
International Search Report for Application No. PCT/US08/060400, mailed on Oct. 17, 2008, 3 pages.
International Search Report for Application No. PCT/US08/063648, mailed on Aug. 13, 2008, 3 pages.
International Search Report for Application No. PCT/US08/069453, mailed on Sep. 25, 2008, 2 pages.
International Search Report for Application No. PCT/US08/080253, mailed on Mar. 3, 2009, 3 pages.
International Search Report for Application No. PCT/US2005/0046480, mailed on Apr. 18, 2006, 5 pages.
International Search Report for Application No. PCT/US2007/0077321, mailed on Feb. 1, 2008, 3 pages.
International Search Report for Application No. PCT/US2007/0087175, mailed on Apr. 8, 2008, 4 pages.
International Search Report for Application No. PCT/US2008/084216, mailed on Feb. 19, 2009, 1 page.
International Search Report for Application No. PCT/US2009/053369, mailed on Oct. 22, 2009, 3 pages.
International Search Report for Application No. PCT/US2009/056179, mailed on Jun. 9, 2010, 4 pages.
International Search Report for Application No. PCT/US2009/057088, mailed on Oct. 5, 2010, 4 pages.
International Search Report for Application No. PCT/US2009/063318, mailed on May 6, 2010, 3 pages.
International Search Report for Application No. PCT/US2009/068173, mailed on Feb. 5, 2010, 3 pages.
International Search Report for Application No. PCT/US2010/028794, mailed Jul. 20, 2010, 3 pages.
International Search Report for Application No. PCT/US2010/028796, mailed Jul. 16, 2010, 4 pages.
International Search Report for Application No. PCT/US2011/040501, mailed on Oct. 24, 2011, 2 pages.
Jain S., et al., "The Synthesis and Antimicrobial Screening of Some Novel Aza-Imidoxy Compounds as Potential Chemotherapeutic Agents," Phosphorus Sulfur and Silicon, 2006, vol. 181 (7), pp. 1665-1673.
Jasys V.J., et al., "Preparation of Fluoroadamantane Acids and Amines: Impact of Bridgehead Fluorine Substitution on the Solution- and Solid-State Properties of Functionalized Adamantanes," Journal of the American Chemical Society, 2000, vol. 122, pp. 466-473.
Jhaveri M.D., et al., "Cannabinoid CB2 Receptor-Mediated Anti-Nociception in Models of Acute and Chronic Pain," Molecular Neurobiology, 2007, vol. 36 (1), pp. 26-35.
Kherjee S., et al., "Species Comparison and Pharmacological Characterization of Rat and Human Cb2 Cannabinoid Receptors," European Journal of Pharmacology, 2004, vol. 505 (1-3), pp. 1-9.
Khusnutdinov R.I., et al., "Chlorination of Adamantane and its Derivatives by Carbon Tetrachloride in the Presence of Manganese-, Vanadium-, and molybdenum—Containing Catalysts," Neftekhimiya, 2004, vol. 44 (2), pp. 148-155.
Kim S.H., et al., "An Experimental Model for Peripheral Neuropathy Produced by Segmental Spinal Nerve Ligation in the Rat," Pain, 1992, vol. 50 (3), pp. 355-363.
Kolasa., "Thiazolylidene Derivatives as Cannabinoid Receptor Ligands and Their Preparation" Accession No. 2008:1184581, Mar. 22, 2011.
Koren B., et al., "Transformations of 1-(2-Chloropyridyl-3)-4-ethoxycarbonyl and 1-(2-Chloropyridyl-3)-4-ethoxycarbonylmethyl Thiosemicarbazides. Attempts to Prepare Pyrido [3,2-.e]-1,2,4-thiadiazine," Monatshefte Fur Chemie, 1988, vol. 119, pp. 333-339.
Kreutzberg G.W., et al., "Microglia: A Sensor for Pathological Events in the CNS," Trends in Neuroscience, 1996, vol. 19, pp. 312-318.
Kubinyi, "3D QSAR in Drug Design: Ligand Protein Interactions & Molecular Similarity, 800 pages," Springer, 1998, vol. 2-3, pp. 243-244.
Li, W., et al., "An Improved Synthesis of Pyran-3,5-Dione: Application to the Synthesis of Abt-598, A Potassium Channel Opener, Via Hantzsch Reaction," Journal of Organic Chemistry, 2006, vol. 71 (4), pp. 1725-1727.
Linn, et al., Journal of American Chemistry Society, 1963, 2032, vol. 85.
MacLennan S.J., et al., "Evidence for Inverse Agonism of SR141716A at Human Recombinant Cannabinoid CB1 and CB2 Receptors," British Journal of Pharmacology, 1998, vol. 124 (4), pp. 619-622.
Malan T.P., et al., "Inhibition of Pain Responses by Activation of CB(2) Cannabinoid Receptors," Chemistry and Physics of Lipids, 2002, vol. 121 (1-2), pp. 191-200.
Maligres, P.E., et al., "Stereocontrolled Preparation of a Nonpeptidal (−)-Spirobicyclic NK-1 Receptor Antagonist," Journal of Organic Chemistry, 2002, vol. 67 (4), pp. 1093-1101.
Mallat A., et al., "Cannabinoid Receptors as New Targets of Antifibrosing Strategies during Chronic Liver Diseases," Expert Opinion on Therapeutic Targets, 2007, vol. 11 (3), pp. 403-409.

(56) References Cited

OTHER PUBLICATIONS

Manaka A., et al., "2-Acylimino-3H-thiazoline Derivatives: A Novel Template for Platelet GPllb/llla Receptor Antagonists," Bioorganic & Medicinal Chemistry Letters, 2001, vol. 11, pp. 1031-1035.
Masciadri R., et al., "Regioselective Friedel_Crafts Alkylation of Anilines and Amino-Substituted Heteroarenes with Hexafluoroacetone Sesquihydrate," European Journal of Organic Chemistry, 2003, vol. 2003 (21), pp. 4286-4291.
Mayo clinic, Alzheimer's disease, [retrieved on Mar. 11, 2013]. Retrieved from the Internet:< URL:http://www.mayoclinic.com/health/alzheimers-disease/DS00161/DSECTION=prevention>.
Meyers A.I., et al., "Oxazolines. XX. Synthesis of Achiral and Chiral Thiiranes and Olefins by Reaction of Carbonyl Compounds with 2-(Alkylthio)-2-oxazolines ," Journal of Organic Chemistry, 1976, vol. 41 (10), pp. 1735-1742.
Molina-Holgado F., et al., "Endogenous Interleukin-1 Receptor Antagonist Mediates Anti-Inflammatory and Neuroprotective Actions of Cannabinoids in Neurons and Glia," Journal of Neuroscience, 2003, vol. 23 (16), pp. 6470-6474.
Morii T., et al., "A General Strategy to Determine a Target DNA Sequence of a Short Peptide: Application to a [D]-Peptide," Journal American Chemical Society, 2002, vol. 124 (2), pp. 180-181.
Mucke L., "Neuroscience: Alzheimer's Disease," Nature, 2009, vol. 461 (7266), pp. 895-897.
Non-Final Office Action mailed Jun. 1, 2011 for U.S. Appl. No. 12/554,445, filed Sep. 4, 2009.
Non-Final Office Action mailed Jun. 1, 2011 for U.S. Appl. No. 12/560,897, filed Sep. 16, 2009.
Non-Final Office Action mailed Jun. 2, 2009 for U.S. Appl. No. 11/755,434, filed May 30, 2007.
Non-Final Office Action mailed Sep. 7, 2010 for U.S. Appl. No. 12/120,969, filed May 15, 2008.
Non-Final Office Action mailed Mar. 9, 2012 for U.S. Appl. No. 12/732,428, filed Mar. 26, 2010.
Non-Final Office Action mailed Jan. 12, 2010 for U.S. Appl. No. 12/120,969, filed May 15, 2008.
Non-Final Office Action mailed May 17, 2011 for U.S. Appl. No. 12/560,893, filed Sep. 16, 2009.
Non-Final Office Action mailed Aug. 23, 2011 for U.S. Appl. No. 12/639,173, filed Dec. 16, 2009.
Non-Final Office Action mailed Jan. 27, 2011 for U.S. Appl. No. 12/274,105, filed Nov. 19, 2008.
Non-Final Office Action mailed Jun. 29, 2010 for U.S. Appl. No. 11/755,434, filed May 30, 2007.
Non-Final Office Action mailed Nov. 30, 2010 for U.S. Appl. No. 11/755,434, filed May 30, 2007.
Nunez E., et al., "Cannabinoid CB2 Receptors Are Expressed by Perivascular Microglial Cells in the Human Brain: An Immunohistochemical Study," Synapse, 2004, vol. 53, pp. 208-213.
Ohta H., et al., "Imine Derivatives as new Potent and Selective CB2 Cannabinoid Receptor agonist with an Analgesic Action," Bioorganic and Medicinal Chemistry, 2007, vol. 16 (3), pp. 1111-1124.
Opposition filed by "Asociacion de Industries Farmaceuticas Dominicanas Inc" for the Dominican Patent application Nr P2008-0060, received on Apr. 1, 2009, 8 pages.
Padgett L.W., et al., "Recent Developments in Cannabinoid Ligands," Life Sciences, 2005, vol. 77 (14), pp. 1767-1798.
Partch, R., et al., "2-Oxaadamantane-1-N,N,N-trimethylmethanaminium Iodide:1 Synthesis and Potential for Muscarinic Activity," Croatia Chemical Acta, 1985, vol. 58 (4), pp. 661-669.
Radulescu C., et al., "Actes Du Colloque Franco-Roumain De Chimie Appliquee, 3Rd, Bacau, Romania," 2004, pp. 117-120.
Radulescu C., et al., "The Comparative Study on the Synthesis Methods of a Heterocyclic System 2-Aminothiazolo[4,5-13] Pyricline," Revista de Chimie, 2004, vol. 56 (6), pp. 659-662.
Radulescu C., et al., "Synthesis and Characteristics of Compact Condensed Heterocyclic System 2-Aminothiazolo[4,5-c]Pyridine," Revista de Chimie, 2004, vol. 55 (11), pp. 889-893.

Ralston S.H., "Genetic Determinants of Susceptibility to Osteoporosis," Current Opinion in Pharmacology, 2003, vol. 3, pp. 286-290.
Rautio J., et al, "Prodrugs: Design and Clinical Applications," Nature Reviews Drug Discovery, 2008, vol. 7 (3), pp. 255-270.
Rezoni G.E., et al., "Synthesis of 7-Carboxytricyclo[33103,7]nonan-3-ol," Journal of Organic Chemistry, 1983, vol. 48, pp. 5231-5236.
Rodriquez-Spong B., et al., "General Principles of Pharmaceutical Solid Polymorphism: A Supramolecular Perspective," Advanced Drug Delivery Reviews, 2004, vol. 56 (3), pp. 241-274.
Ross W.J., et al., "Antianaphylactic agents. 1. 2-(Acylamino)oxazoles," Journal of Medicinal Chemistry, 1979, vol. 22(4), pp. 412-417.
Sabnis R.W., et al., "2-Aminothiophenes by the Gewald Reaction," Journal of Heterocyclic Chemistry, 1999, vol. 36, pp. 333-345.
Schafer S.,et al., "Failure is an Option: Learning from Unsuccessful Proof-of-concept Trials," Drug Discovery Today, 2008, vol. 13 (21-22), pp. 913-916.
Shultz D.A., et al., "Synthesis of Bis(semiquinone)s and their Electrochemical and Electron Paramagnetic Resonance Spectral Characterization," Journal of Organic Chemistry, 1998, vol. 63(25), pp. 9462-9469.
Smith D.A., "Do Prodrugs Deliver", Current Opinion in Drug Discovery and Development, 2007, vol. 10 (5), 550-559.
Souillac P., et al, "Characterization of Delivery Systems, Differential Scanning Calorimetry," Encyclopedia of Controlled Drug Delivery, 1999, pp. 217-218.
STN International HCAPLUS database Accession No. 2008:1184581, Columbus, Ohio, Lolasa et al, 2008.
Supplementary European Search Report for Application No. EP08852528, mailed on Nov. 8, 2010, 2 pages.
Testa B., "Prodrugs: Bridging Pharmacodynamic/Pharmacokinetic Gaps," Current Opinion in Chemical Biology, 2009, vol. 13 (3), pp. 338-344.
Viallet, et al., "2-Aminothiazoline, etc," 1980, CA 93:8074.
Wang B., et al., Drug Delivery: Principles and Applications, John Wiley & Sons, Inc., 2005, pp. 136-137.
Watkins L.R., et al., "Glial Activation: A Driving Force for Pathological Pain ," Trends in Neuroscience, 2001, vol. 24 (8), pp. 450-455.
Werbel L.M., et al., "1-Alkyl-3-(3 -alkyl-5-nitro-4-thiazolin-2-ylidene)ureas nd Related Compounds as Schistosomicides," Journal of Medicinal Chemistry, 1972, vol. 15 (9), pp. 955-963.
Wermuth, "The practice of Medicinal chemistry," 2003, Chapters 9-10, 2nd edition,768 pages.
Weyer V.R., et al., "Blutzuckersenkende Chinolin-8-Carboxamidoalkyl-Benzol Sulfonamid Derivate ," Arzneimittel-Forschung, 1974, vol. 24 (3), pp. 269-275.
Whiteside G.T., et al., "The Role of the Cannabinoid Cb2 Receptor in Pain Transmission and Therapeutic Potential of Small Molecule CB2 Receptor Agonists," Current medicinal chemistry, 2007, vol. 14 (8), pp. 917-936.
Widdowson D.A., et al., "Palladium Catalysed Suzuki Reactions of Fluoroarenes," Chemical Communication (Camb), 2003, vol. 5, pp. 578-579.
Williams K., et al., "Central Nervous System Perivascular Cells Are Immunoregulatory Cells that Connect the CNS tith the Peripheral mune System," Journal of Glia, 2001, vol. 36 (2), pp. 156-164.
Williams P.D., et al., "Renin Inhibitors Containing Conformationally Restricted P1-P1 Dipeptide Mimetics," Journal of Medicinal Chemistry, 1991, vol. 34 (3), pp. 887-900.
Wu K.M., et al., "Regulatory Perspectives of Type II Prodrug Development and Time-Dependent Toxicology Management: Nonclinical Pharm/Tox Analysis and the Role of Comparative Toxicology," Toxicology, 2007, vol. 236 (1-2), pp. 1-6.
Yao B.B., et al., "In Vitro Pharmacological Characterization of Am1241: A Protean Agonist at the Cannabinoid Cb2 Receptor," British Journal of Pharmacology, 2006, vol. 149 (2), pp. 145-154.
Zimmer A., et al., "Increased Mortality, Hypoactivity, and Hypoalgesia in Cannabinoid CB1 Receptor Knockout Mice," Proceedings of the National Academy of Science, 1999, vol. 96 (10), pp. 5780-5785.
Non-Final Rejection mailed Dec. 5, 2013 for U.S. Appl. No. 12/967,282, filed Dec. 14, 2010.

(56) References Cited

OTHER PUBLICATIONS

Office Action mailed Nov. 15, 2013 for European Application No. 05855099.7 filed Dec. 21, 2005.
Notice of Allowance mailed Jan. 17, 2014 for U.S. Appl. No. 12/120,969, filed May 15, 2008.
Notice of Allowance mailed Jun. 2, 2014 for U.S. Appl. No. 12/554,445, filed Sep. 4, 2009.
Notice of Allowance mailed Jun. 9, 2014 for U.S. Appl. No. 12/560,893, filed Sep. 16, 2009.
Notice of Allowance mailed Jun. 9, 2014 for U.S. Appl. No. 12/639,173, filed Dec. 16, 2009.
Notice of Allowance mailed Jun. 9, 2014 for U.S. Appl. No. 12/970,435, filed Dec. 16, 2010.
Notice of Allowance mailed May 14, 2014 for U.S. Appl. No. 12/274,105, filed Nov. 19, 2008.
Office Action mailed Jun. 30, 2014 for U.S. Appl. No. 12/970,480, filed Dec. 16, 2010.
Final Office Action mailed Mar. 14, 2014 for U.S. Appl. No. 12/970,480, filed Dec. 16, 2010.
Notice of Allowance mailed Apr. 14, 2014 for U.S. Appl. No. 12/967,282, filed Dec. 14, 2010.
Fernando-Ruiz et al., Mol. Cell Endocrinol., 286S: S91-96 (2008).
Shoemaker et al., J. Neurochem., 101: 87-98 (2007).
United States Patent Office Notice of Allowance for U.S. Appl. No. 12/970,480 dated Nov. 20, 2014 (7 pages).

\* cited by examiner

COMPOUNDS AS CANNABINOID RECEPTOR LIGANDS

This application claims priority to U.S. Ser. No. 60/979,653 filed Oct. 12, 2007 and is incorporated herein by reference.

TECHNICAL FIELD

The present invention relates to compounds that are $CB_2$ receptor ligands, compositions comprising such compounds, and methods of treating conditions and disorders using such compounds and compositions.

BACKGROUND (−)-$\Delta^9$-Tetrahydrocannabinol ($\Delta^9$-THC), the major psychoactive constituent of marijuana, exerts a broad range of biological effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in preclinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic).

Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

Accordingly, the need exists to further explore and develop $CB_2$ receptor ligands that exhibit immunomodulatory and anti-inflammatory properties. These $CB_2$ receptors ligands will offer a unique pharmacotherapy for the treatment of immune and inflammatory disorders.

SUMMARY

The present invention generally provides compounds that are $CB_2$ receptor ligands and pharmaceutical compositions and methods for the treatment of disorders using these compounds and pharmaceutical compositions.

In one embodiment, the present invention provides compounds of formula (I), or pharmaceutically acceptable salts, prodrugs, salts of prodrugs, or combinations thereof,

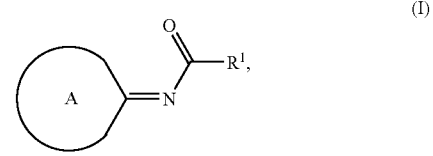

(I)

wherein $R^1$ is alkyl, haloalkyl, $G^1$, —$(CR^xR^y)_m$-$G^1$, or —$N(R^{1a})(R^z)$;

$R^z$ is alkyl, haloalkyl, $G^2$, —$(CR^xR^y)_m$-$G^2$, —$(CR^xR^y)_n$—$OR^{za}$, —$(CR^xR^y)_n$—$N(R^{za})(R^{zb})$, —$(CR^xR^y)_m$—$C(O)O(R^{za})$, —$(CR^xR^y)_m$—$C(O)R^{za}$, —$(CR^xR^y)_m$—$C(O)N(R^{za})(R^{zb})$, —$(CR^xR^y)_m$—$S(O)_2O(R^{za})$, —$(CR^xR^y)_m$—$S(O)_2R^{za}$, —$(CR^xR^y)_m$—$S(O)_2N(R^{za})(R^{zb})$, or —$(CR^xR^y)_m$—$CN$;

$G^1$ and $G^2$, at each occurrence, are each independently aryl, heteroaryl, heterocycle, cycloalkyl, or cycloalkenyl; wherein each ring is independently unsubstituted or substituted with 1, 2, 3, 4, 5, or 6 substituents independently selected from the group consisting of alkyl, alkenyl, alkynyl, —$NO_2$, —$CN$, halogen, oxo, —$OR^e$, —$O$—$(CR^jR^k)_n$—$N(R^w)_2$, —$OC(O)R^e$, —$SR^e$, —$SF_5$, —$S(O)R^f$, —$S(O)_2R^f$, —$S(O)_2N(R^e)(R^g)$, —$N(R^e)(R^g)$, —$N(R^g)C(O)R^e$, —$N(R^g)S(O)_2R^f$, —$N(R^g)C(O)N(R^e)(R^g)$, —$N(R^g)S(O)_2N(R^e)(R^g)$, —$C(O)R^e$, —$C(O)O(R^e)$, —$C(O)N(R^e)(R^g)$, alkoxyalkenyl, hydroxyalkenyl, haloalkyl, —$(CR^jR^k)_q$—$CN$, —$(CR^jR^k)_q$—$OR^e$, —$(CR^jR^k)_q$—$OC(O)R^e$, —$(CR^jR^k)_q$—$SR^e$, —$(CR^jR^k)_q$—$S(O)R^f$, —$(CR^jR^k)_q$—$S(O)_2R^f$, —$(CR^jR^k)_q$—$N(R^e)(R^g)$, —$(CR^jR^k)_q$—$N(R^g)C(O)R^e$, —$(CR^jR^k)_q$—$N(R^g)S(O)_2R^f$, —$(CR^jR^k)_q$—$N(R^g)C(O)N(R^e)(R^g)$, —$(CR^jR^k)_q$—$N(R^g)S (O)₂N(Rᵉ)(Rᵍ), —(CRʲRᵏ)_q—C(O)Rᵉ, —(CRʲRᵏ)_q—C(O)O (Rᵉ), —(CRʲRᵏ)_q—C(O)N(Rᵉ)(Rᵍ), —C(Rʷ)=N—ORʷ, and morpholinyl;

Ring A represents formula (a), (b), (c), or (d)

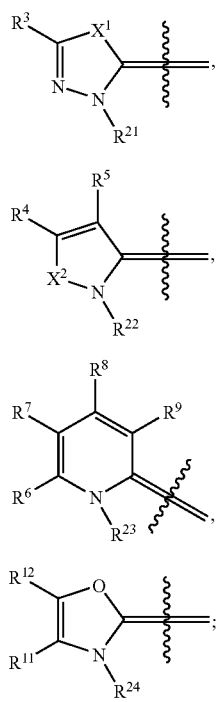

R²¹, R²², R²³, and R²⁴ are -alkylene-G³ wherein G³, at each occurrence, is independently a 4-, 5-, 6-, 7-, 8-, or 9-membered monocyclic heterocycle containing zero or one double bond, one or two oxygen, and zero or one nitrogen as ring atoms, and is optionally fused with a monocyclic ring selected from the group consisting of benzo, cycloalkyl, cycloalkenyl, heterocycle and heteroaryl; two non-adjacent atoms of each G³ are optionally linked by an alkenylene bridge of 2, 3, or 4 carbon atoms, or optionally linked by an alkylene bridge of 1, 2, 3, or 4 carbon atoms, and each G³ is independently unsubstituted or substituted with 1, 2, 3, 4, 5, or 6 substituents independently selected from the group consisting of oxo, alkyl, halogen, —OH, —O(alkyl), —O(haloalkyl), and haloalkyl;

Rʷ, at each occurrence, is independently hydrogen or alkyl;

R³, R⁶, R⁷, R⁸, R⁹, R¹¹, and R¹² are each independently hydrogen, alkyl, alkenyl, alkynyl, —NO₂, —CN, halogen, —ORᵃ, —N(Rᵃ)(Rᵇ), —C(O)Rᵃ, —C(O)O(Rᵃ), haloalkyl, —(CRᶜRᵈ)_p—ORᵃ, —(CRᶜRᵈ)_p—N(Rᵃ)(Rᵇ), —(CRᶜRᵈ)_p—C(O)Rᵃ, —(CRᶜRᵈ)_p—C(O)O(Rᵃ), cycloalkyl, cycloalkenyl, or heterocycle;

R⁴ and R⁵, are each independently hydrogen, alkyl, alkenyl, alkynyl, —NO₂, —CN, halogen, —ORᵃ, —N(Rᵃ)(Rᵇ), —C(O)Rᵃ, —C(O)O(Rᵃ), haloalkyl, —(CRᶜRᵈ)_p—ORᵃ, —(CRᶜRᵈ)_p—N(Rᵃ)(Rᵇ), —(CRᶜRᵈ)_p—C(O)Rᵃ, —(CRᶜRᵈ)_p—C(O)O(Rᵃ), cycloalkyl, cycloalkenyl, or heterocycle; or R⁴ and R⁵, together with the carbon atoms to which they are attached, form a monocyclic cycloalkyl ring which is optionally further substituted with 1, 2, 3, or 4 substituents selected from the group consisting of halogen, alkyl, haloalkyl, and oxo;

Rᵃ, Rᵇ, R¹ᵃ, Rᶻᵃ, and Rᶻᵇ, at each occurrence, are each independently hydrogen, alkyl, or haloalkyl;

Rˣ, at each occurrence, is independently hydrogen, halogen, alkyl, haloalkyl, or benzyl;

Rʸ, Rᶜ, and Rᵈ, at each occurrence, are each independently hydrogen, halogen, alkyl, or haloalkyl;

X¹ and X² are independently O, S, or N(R¹⁰) wherein R¹⁰ is alkyl, alkoxyalkyl, haloalkoxyalkyl, or haloalkyl;

the cycloalkyl, cycloalkenyl, and heterocycle, as represented by R³, R⁴, R⁵, R⁶, R⁷, R⁸, R⁹, R¹¹, and R¹² are each independently unsubstituted or substituted with 1, 2, 3, 4, 5, or 6 substituents independently selected from the group consisting of alkyl, alkenyl, alkynyl, —NO₂, —CN, halogen, oxo, —ORᵉ, —OC(O)Rᵉ, —SRᵉ, —S(O)Rᶠ, —S(O)₂Rᶠ, —S(O)₂N(Rᵉ)(Rᵍ), —N(Rᵉ)(Rᵍ), —N(Rᵍ)C(O)Rᵉ, —N(Rᵍ)S(O)₂Rᶠ, —N(Rᵍ)C(O)N(Rᵉ)(Rᵍ), —N(Rᵍ)S(O)₂N(Rᵉ)(Rᵍ), —C(O)Rᵉ, —C(O)O(Rᵉ), —C(O)N(Rᵉ)(Rᵍ), haloalkyl, —(CRʲRᵏ)_q—CN, —(CRʲRᵏ)_q—ORᵉ, —(CRʲRᵏ)_q—OC(O) Rᵉ, —(CRʲRᵏ)_q—SRᵉ, —(CRʲRᵏ)_q—S(O)Rᶠ, —(CRʲRᵏ)_q—S(O)₂Rᶠ, —(CRʲRᵏ)_q—N(Rᵉ)(Rᵍ), —(CRʲRᵏ)_q—N(Rᵍ)C(O) Rᵉ, —(CRʲRᵏ)_q—N(Rᵍ)S(O)₂Rᶠ, —(CRʲRᵏ)_q—N(Rᵍ)C(O)N (Rᵉ)(Rᵍ), —(CRʲRᵏ)_q—N(Rᵍ)S(O)₂N(Rᵉ)(Rᵍ), —(CRʲRᵏ)_q—C(O)Rᵉ, —(CRʲRᵏ)_q—C(O)O(Rᵉ) and —(CRʲRᵏ)_q—C(O)N(Rᵉ)(Rᵍ);

Rᵉ and Rᵍ, at each occurrence, are each independently hydrogen, alkyl, alkenyl, alknyl, alkoxyalkyl, cycloalkyl, cycloalkylalkyl, heterocycle, aryl, heteroaryl, haloalkoxyalkyl, or haloalkyl; wherein the aryl, the heteroaryl, the cycloalkyl, and the heterocycle moieties, by itself or as part of the substituents of Rᵉ and Rᵍ, are each independently unsubstituted or substituted with 1, 2, 3, 4, 5 or 6 substituents selected from the group consisting of alkyl, halogen, haloalkyl, hydroxy, oxo, and alkoxy;

Rᶠ, at each occurrence, is independently alkyl or haloalkyl;

Rʲ and Rᵏ, at each occurrence, are each independently hydrogen, halogen, alkyl, or haloalkyl;

m, p, and q, at Each Occurrence, are Each Independently 1, 2, 3, or 4; and n is 2, 3 or 4.

Another aspect of the invention relates to pharmaceutical compositions comprising therapeutically effective amount of compound(s) of the invention or pharmaceutically acceptable salts thereof, in combination with one or more pharmaceutically acceptable carrier. Such compositions can be administered in accordance with a method of the invention, typically as part of a therapeutic regimen for treatment or prevention of conditions and disorders related to cannabinoid (CB) receptor subtype, CB₂. More particularly, the method is useful for treating conditions related to neuropathic pain, nociceptive pain, inflammatory pain, inflammatory disorders, immune disorders, neurological disorders, cancers of the immune system, respiratory disorders, obesity, diabetes, cardiovascular disorders, or for providing neuroprotection.

Further, the present invention provides the use of compounds of the present invention or a pharmaceutically acceptable salt thereof, in the manufacture of a medicament for the treatment of the disease conditions described above, alone or in combination with one or more pharmaceutically acceptable carrier(s), particularly for the treatment of neuropathic pain, nociceptive pain, inflammatory pain, or combination thereof.

The compounds, compositions comprising the compounds, and methods for treating or preventing conditions and disorders by administering the compounds are further described herein.

These and other objects of the invention are described in the following paragraphs. These objects should not be deemed to narrow the scope of the invention.

DETAILED DESCRIPTION

Compounds of formula (I) are disclosed in this invention,

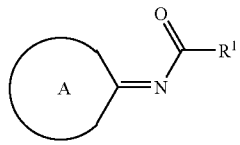

(I)

wherein $R^1$ and A are as defined above in the Summary of the Invention and below in the Detailed Description. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. DEFINITIONS

As used in the specification and the appended claims, unless specified to the contrary, the following terms have the meaning indicated:

The term "alkenyl" as used herein, means a straight or branched chain hydrocarbon containing from 2 to 10 carbons and containing at least one carbon-carbon double bond. Representative examples of alkenyl include, but are not limited to, ethenyl, 3-methylbut-2-enyl, prop-1-enyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of 2, 3, or 4 carbon atoms and contains at least one carbon-carbon double. Representative examples of alkenylene include, but are not limited to, —CH=CH— and —CH$_2$CH=CH—.

The term "alkoxy" as used herein, means an alkyl group, as defined herein, appended to the parent molecular moiety through an oxygen atom. Representative examples of alkoxy include, but are not limited to, methoxy, ethoxy, prop oxy, 2-prop oxy, butoxy, tert-butoxy, pentyloxy, and hexyloxy.

The term "alkoxyalkenyl" as used herein, means an alkoxy group, as defined herein, appended to the parent molecular moiety through an alkenyl group, as defined herein. Representative example of alkoxyalkenyl includes, but is not limited to, 3-methoxyprop-1-enyl.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 2-methoxyethyl, 3-methoxy-3-methylbutyl, 2-methoxypropyl, 3-methoxypropyl, 2-ethoxyethyl, 2-methoxyethyl, 3-ethoxypropyl, and methoxymethyl.

The term "alkyl" as used herein, means a saturated, straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 2-ethylhexyl, 3-methylhexyl, 2,2-dimethylpentyl, 2,3-dimethylpentyl, n-heptyl, n-octyl, n-nonyl, and n-decyl.

The term "alkylene" means a divalent group derived from a saturated, straight or branched chain hydrocarbon of from 1 to 10 carbon atoms. Representative examples of alkylene include, but are not limited to, —CH$_2$—, —CH(CH$_3$)—, —CH(C$_2$H$_5$), —CH(CH(CH$_3$)(C$_2$H$_5$))—, —C(H)(CH$_3$)CH$_2$CH$_2$—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 1,1-dimethylprop-2-ynyl, 1-propyl-pent-3-ynyl, 3-butynyl, 2-pentynyl, and 1-butynyl.

The term "aryl" as used herein, means phenyl, a bicyclic aryl or a tricyclic aryl. The bicyclic aryl is naphthyl, or a phenyl fused to a monocyclic cycloalkyl, or a phenyl fused to a monocyclic cycloalkenyl. Representative examples of the bicyclic aryl include, but are not limited to, dihydroindenyl, indenyl, naphthyl, dihydronaphthalenyl, and tetrahydronaphthalenyl (including 1,2,3,4-tetrahydronaphthalen-1-yl). The tricyclic aryl is exemplified by a bicyclic aryl fused to a monocyclic cycloalkyl, or a bicyclic aryl fused to a monocyclic cycloalkenyl, or a bicyclic aryl fused to a phenyl. Representative examples of tricyclic aryls include, but are not limited to, anthracene, phenanthrene, dihydroanthracenyl, fluorenyl, 1,2-dihydroacenaphthylenyl, and tetrahydrophenanthrenyl. The phenyl, bicyclic and tricyclic aryls are attached to the parent molecular moiety through any carbon atom contained within the phenyl, bicyclic and tricyclic aryls respectively.

The term "cycloalkenyl" as used herein, means a monocyclic or bicyclic ring system containing zero heteroatoms in the ring. The monocyclic cycloalkenyl has three-, four-, five-, six-, seven- or eight carbon atoms and zero heteroatoms. The three or four-membered ring systems have one double bond, the five- or six-membered ring systems have one or two double bonds, and the seven- or eight-membered ring systems have one, two or three double bonds. Representative examples of monocyclic cycloalkenyls include, but are not limited to, 2-cyclohexen-1-yl, 3-cyclohexen-1-yl, 2,4-cyclohexadien-1-yl and 3-cyclopenten-1-yl. Bicyclic cycloalkenyls are exemplified by a monocyclic cycloalkenyl fused to a monocyclic cycloalkyl, or a monocyclic cycloalkenyl fused to a monocyclic cycloalkenyl. Representative examples of bicyclic ring systems include, but are not limited to 3a,4,5,6,7,7a-hexahydro-1H-indenyl, 4,5,6,7-tetrahydro-3aH-indene, and octahydronaphthalenyl. The cycloalkenyl groups of the present invention are appended to the parent molecular moiety through any substitutable carbon atom within the groups, and may contain one or two alkylene bridges of 1, 2, 3, or 4 carbon atoms, wherein each bridge links two non-adjacent atoms within the groups.

The term "cycloalkyl" as used herein, means a monocyclic, or a bicyclic cycloalkyl, or a spirocyclic cycloalkyl. The monocyclic cycloalkyl is a carbocyclic ring system containing 3, 4, 5, 6, 7, or 8 carbon atoms and zero heteroatoms as ring atoms, and zero double bonds. Examples of monocyclic cycloalkyls include cyclopropyl, cyclobutyl, cyclopentyl, cyclohexyl, cycloheptyl, and cyclooctyl. Bicyclic cycloalkyl is exemplified by a monocyclic cycloalkyl fused to a monocyclic cycloalkyl. Representative examples of bicyclic cycloalkyls include, but are not limited to, bicyclo[4.1.0] heptane, bicyclo[6.1.0]nonane, octahydroindene, and decahydronaphthalene. The monocyclic and the bicyclic cycloalkyl groups of the present invention may contain one or two alkylene bridges of 1, 2, 3, or 4 carbon atoms, wherein each bridge links two non-adjacent atoms within the groups. Examples of such bridged cycloalkyls include, but are not limited to, 6,6-dimethylbicyclo[3.1.1]heptyl (including 6,6-dimethylbicyclo[3.1.1]hept-2-yl), bicyclo[2.2.1]heptyl, bicyclo[3.1.1]heptyl, bicyclo[2.2.2]octyl, bicyclo[3.3.1] nonyl, adamantyl (tricyclo[3.3.1.1$^{3,7}$]decane), and noradamantyl (octahydro-2,5-methanopentalene). Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The monocyclic, bicyclic, and spirocyclic cycloalkyl groups of the present invention can be appended to the parent molecular moiety through any substitutable carbon atom of the groups.

The term "cycloalkylalkyl" means a cycloalkyl group, as defined herein, appended to the parent moiety through an alkyl group, as defined herein.

The term "halo" or "halogen" as used herein, means —Cl, —Br, —I or —F.

The term "haloalkoxy" as used herein, means an alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "haloalkoxyalkyl" as used herein, means a haloalkoxy group, as defined herein, appended to the parent molecular moiety through an alkyl group, as defined herein.

The term "haloalkyl" as used herein, means an alkyl group, as defined herein, in which one, two, three, four, five, six, or seven hydrogen atoms are replaced by halogen. Representative examples of haloalkyl include, but are not limited to, chloromethyl, 2-fluoroethyl, 2-fluoropropyl, 2-fluoro-1-methylethyl, 2,2-difluoroethyl, trifluoromethyl, 2,2,2-trifluoroethyl, 2,2,2-trifluoro-1,1-dimethylethyl, difluoromethyl, 3-fluoro-3-methylbutyl, 3,3,3-trifluoropropyl, pentafluoroethyl, 2-chloro-3-fluoropentyl, and 2-iodoethyl.

The term "heteroaryl," as used herein, means a monocyclic heteroaryl or a bicyclic heteroaryl. The monocyclic heteroaryl is a 5- or 6-membered ring containing at least one heteroatom independently selected from the group consisting of O, N, and S. The 5-membered ring contains two double bonds and one, two, three, or four heteroatoms. The 6-membered ring contains three double bonds and one, two, three, or four heteroatoms. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is exemplified by a monocyclic heteroaryl fused to phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryls include, but are not limited to, benzofuranyl, benzoxadiazolyl, 1,3-benzothiazolyl, benzimidazolyl, benzodioxolyl, benzothienyl, chromenyl, cinnolinyl, furopyridine, indolyl, indazolyl, isoindolyl, isoquinolinyl, naphthyridinyl, oxazolopyridine, quinolinyl, and thienopyridinyl. The monocyclic and the bicyclic heteroaryl groups are connected to the parent molecular moiety through any substitutable carbon atom or any substitutable nitrogen atom contained within the groups. The nitrogen and sulfur heteroatoms of the heteroaryl rings may optionally be oxidized, and are contemplated within the scope of the invention.

The term "heterocycle" or "heterocyclic" as used herein, means a monocyclic, bicyclic, or a spirocyclic ring system containing at least one heteroatom. The monocyclic heterocycle is a 3-, 4- 5-, 6-, 7-, or 8-membered monocyclic ring containing at least one heteroatom independently selected from the group consisting of O, N, and S. The 3- or 4-membered ring contains 1 heteroatom selected from the group consisting of O, N and S, and optionally one double bond. The 5-membered ring contains zero or one double bond, and one, two or three heteroatoms in the ring selected from the group consisting of O, N and S. The 6-, 7-, or 8-membered ring contains zero, one, or two double bonds, and one, two, or three heteroatoms in the ring selected from the group consisting of O, N and S. Representative examples of monocyclic heterocycles include, but are not limited to, azetidinyl (including azetidin-3-yl), azepanyl, aziridinyl, diazepanyl, 1,3-dioxanyl, 1,4-dioxanyl, 1,3-dioxolanyl, 4,5-dihydroisoxazol-5-yl, 3,4-dihydropyran-6-yl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl (including 1,3-oxazolidin-4-yl), oxetanyl, piperazinyl, piperidinyl, pyranyl, pyrazolinyl, pyrazolidinyl, pyrrolinyl, pyrrolidinyl (including pyrrolidin-3-yl), tetrahydrofuranyl (including tetrahydrofuran-2-yl and tetrahydrofuran-3-yl), tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle of the present invention is exemplified by a monocyclic heterocycle fused to a phenyl group, or a monocyclic heterocycle fused to a monocyclic cycloalkyl group, or a monocyclic heterocycle fused to a monocyclic cycloalkenyl group, or a monocyclic heterocycle fused to a monocyclic heterocycle group. Representative examples of bicyclic heterocycle include, but are not limited to, 1,3-benzodioxol-4-yl, 1,3-benzodithiolyl, 2,3-dihydro-1,4-benzodioxinyl, 2,3-dihydrobenzofuranyl (including 2,3-dihydro-1-benzofuran-7-yl), 2,3-dihydro-1-benzothienyl, 2,3-dihydro-1H-indolyl, and 1,2,3,4-tetrahydroquinolinyl. Spirocyclic heterocycle means a monocyclic or bicyclic heterocycle ring wherein two substituents on the same carbon atom, together with said carbon atom, form a 4-, 5-, or 6-membered monocyclic cycloalkyl. One example of a spiroheterocycle is 5-oxaspiro [3,4]octane. The heterocycle groups are connected to the parent molecular moiety through any substitutable carbon atom or any substitutable nitrogen atom contained within the group. The monocyclic or bicyclic heterocycle groups of the present invention may contain an alkenylene bridge of 2, 3, or 4 carbon atoms, or one or two alkylene bridges of 1, 2, 3, or 4 carbon atoms, wherein each bridge links two non-adjacent carbon atoms within the groups. Examples of such bridged heterocycles include, but are not limited to, oxaadamantane (2-oxatricyclo[3.3.1.1$^{3,7}$]decane), octahydro-2,5-epoxypentalene, hexahydro-2H-2,5-methanocyclopenta[b]furan, hexahydro-1H-1,4-methanocyclopenta[c]furan, oxabicyclo [2.2.1]heptane and 2,4-dioxabicyclo[4.2.1]nonane. The nitrogen and sulfur heteroatoms in the heterocycle rings may optionally be oxidized and the nitrogen atoms may optionally be quarternized.

The term "hydroxyalkenyl" means an hydroxy group, as defined herein, appended to the parent molecular moiety through an alkenyl group, as defined herein. An example of hydroxyalkenyl includes, but is not limited to, 3-hydroxy-3-methylbut-1-enyl.

The term "hydroxyl" or "hydroxy" means an OH group.
The term "oxo" means =O.

b. Compounds

Compounds of the invention have the formula (I) as described above.

Particular values of variable groups in compounds of formula (I) are as follows. Such values may be used where appropriate with any of the other values, definitions, claims or embodiments defined hereinbefore or hereinafter.

In compounds of formula (I), $R^1$ is alkyl, haloalkyl, $G^1$, —$(CR^xR^y)_m$-$G^1$, or —$N(R^{1a})(R^z)$, wherein $G^1$, $R^x$, $R^y$, $R^{1a}$, $R^z$, and m are as disclosed in the Summary section.

In certain embodiments, $R^1$ is $G^1$ wherein $G^1$ is as disclosed in the Summary. For example, $G^1$ is phenyl or naphthyl, each of which is optionally substituted as described in the Summary. Preferably, $G^1$ is phenyl, substituted with 1, 2, or 3 substituents. Other embodiments of the invention relates to compounds of formula (I) wherein $R^1$ is $G^1$, and $G^1$ is cycloalkyl, optionally substituted as described in the Summary.

Yet other embodiments of the invention relate to compounds of formula (I) wherein $R^1$ is $G^1$, and $G^1$ is heterocycle, optionally substituted as described in the Summary. For example, $R^1$ is 2,3-dihydrobenzofuranyl (including 2,3-dihydro-1-benzofuran-7-yl).

Yet other embodiments of the invention relate to compounds of formula (I) wherein $R^1$ is $G^1$, and $G^1$ is heteroaryl, optionally substituted as described in the Summary. For example, $R^1$ is quinolinyl, optionally substituted with 1, 2, or 3 substituents wherein the optional substituents are as disclosed in the Summary.

Examples of the optional substituents of $G^1$ include, but are not limited to, alkenyl, alkyl, —CN, halogen, —$OR^e$, haloalkyl, —$SF_5$, —$SR^e$, —O—$(CR^jR^k)_n$—$N(R^w)_2$, alkoxyalkenyl, hydroxyalkenyl, —$(CR^jR^k)_q$—$OR^e$, and —$N(R^e)(R^g)$ wherein $R^e$, $R^j$, $R^k$, $R^w$, n, q, and $R^g$ are as disclosed in the Summary. For example, in certain embodiments, the optional substituents of $G^1$ are alkyl (e.g. methyl), alkenyl (e.g. prop-1-enyl), —CN, halogen (e.g. Cl, Br, F), —$OR^e$ (e.g, $R^e$ is hydrogen, alkyl such as methyl, ethyl, tert-butyl; alkoxyalkyl such as 3-methoxy3-methylbutyl, 2-methoxyethyl, 2-methoxypropyl, 3-ethoxypropyl, 3-methoxypropyl, 2-ethoxyethyl; alkenyl such as, but not limited to, 3-methylbut-2-enyl; haloalkyl such as 2,2,2-trifluoroethyl, 2-fluoroethyl, 2,2-difluoroethyl, 2-fluoropropyl, 2-fluoro-1-methylethyl, 3-fluoro-3-methylbutyl; cycloalkylalkyl such as cyclopropylmethyl, cyclobutylmethyl, cyclopentylethyl, wherein the cyclopropyl, cyclobutyl and the cyclopentyl moieties are each optionally substituted; optionally substituted heterocycle such as tetrahydrofuranyl, azetidinyl, pyrrolidinyl, each of which is optionally substituted); haloalkyl (e.g., trifluoromethyl), —$SF_5$, —$SR^e$ (e.g. $R^e$ is heteroaryl such as oxidopyridinyl), —O—$(CR^jR^k)$—$N(R^w)_2$ (e.g. $R^j$ and $R^k$ are hydrogen or alkyl such as, but not limited to, methyl, $R^w$ is hydrogen or alkyl such as methyl), alkoxyalkenyl (e.g. 3-methoxyprop-1-enyl), hydroxyalkenyl (e.g. 3-hydroxyl-3-methylbut-1-enyl), —$(CR^jR^k)_q$—$OR^e$ (e.g., $R^j$ and $R^k$ are hydrogen or alkyl such as, but not limited to, methyl, $R^e$ is hydrogen or alkyl such as, but not limited to, methyl), and —$N(R^e)(R^g)$ wherein $R^e$ is alkyl (e.g. methyl), haloalkyl (e.g., 2-fluoroethyl), or alkoxyalkyl (e.g. 2-methyoxyethyl), $R^g$, for example, is hydrogen or alkyl. Particular examples of the optional substituents of $G^1$ include, but are not limited to, methyl, chlorine, bromine, fluorine, —$O(CH_3)$, —$O(CF_3)$, —$CF_3$, and —$N(CH_3)_2$.

Other embodiment of the invention directs to compounds of formula (I) wherein $R^1$ is —$N(R^{1a})(R^z)$, and $R^{1a}$ and $R^z$ are as defined in the Summary. For example, $R^{1a}$ is hydrogen or alkyl. More particularly, $R^{1a}$ is hydrogen. Examples of $R^z$ include, but are not limited to, alkyl (e.g. $C_4$-$C_8$ alkyl such as, but not limited to, neopentyl, 2-ethylhexyl, tert-butyl, 1,2-dimethylpropyl, 1-ethylpropyl), $G^2$ such as optionally substituted cycloalkyl (e.g. cyclohexyl, cycloheptyl, each of which is optionally substituted), or optionally substituted aryl (e.g. optionally substituted 1,2,3,4-tetrahydronaphthalenyl); —$(CR^xR^y)_m$-$G^2$ ($G^2$, for example, is optionally substituted cycloalkyl such as, but not limited to, cyclohexyl, adamantyl or bicyclo[3.1.1]heptyl, each of which is optionally substituted, or optionally substituted aryl such as, but not limited to, optionally substituted phenyl; $R^x$ and $R^y$ are, for example, hydrogen or alkyl such as, but not limited to $C_1$-$C_4$ alkyl, and m is 1, 2, 3, or 4); —$(CR^xR^y)_m$—$C(O)N(R^{za})(R^{zb})$ (e.g. $R^{za}$ is hydrogen, $R^x$ is hydrogen, alkyl (e.g. $C_1$-$C_4$ alkyl such as, but not limited to, isopropyl, 1-methylpropyl, tert-butyl, isobutyl), or benzyl; $R^y$ is hydrogen, m is 1 or 2, $R^{zb}$ is hydrogen or alkyl (e.g. $C_1$-$C_4$ alkyl such as, but not limited to, methyl)); or —$(CR^xR^y)$, —$OR^{za}$ (e.g., $R^{za}$ is hydrogen, $R^x$ is hydrogen or alkyl (e.g. $C_1$-$C_4$ alkyl such as, but not limited to, isopropyl, 1-methylpropyl, tert-butyl, isobutyl); $R^y$ is hydrogen, and n is 2).

Ring A of formula (I) is described generally in the Summary.

In one embodiment, ring A is formula (a)

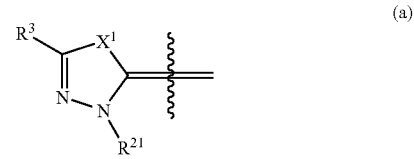

wherein $R^3$, $X^1$, and $R^{21}$ are as described in the Summary.

For example, compounds of the invention include, but are not limited to, those wherein $X^1$ is S.

For example, compounds of the invention include, but are not limited to, those wherein $R^3$ is alkyl (e.g. $C_1$-$C_4$ alkyl), alkenyl, alkynyl, haloalkyl, or optionally substituted cycloalkyl (e.g. $C_3$-$C_6$ cycloalkyl). Particular examples of $R^3$ include, but are not limited to, methyl, isopropyl, tert-butyl, 1,1-dimethylprop-2-ynyl, 2,2,2-trifluoro-1,1-dimethylethyl, cyclopropyl, and cyclobutyl, wherein the cyclopropyl and cyclobutyl are independently unsubstituted or substituted as described in the Summary. Examples of the optional substituents of cycloalkyl include, but are not limited to, alkyl (e.g. $C_1$-$C_4$ alkyl such as, but not limited to, methyl), haloalkyl (e.g. trifluoromethyl), and halogen (e.g. F).

In another embodiment, ring A is formula (b)

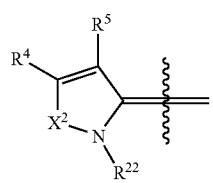

wherein $R^4$, $R^5$, $R^{22}$, and $X^2$ are as defined in the Summary.

For example, compounds of the invention include, but are not limited to, those wherein $R^4$ is alkyl. For example, $R^4$ is tert-butyl.

Certain compounds of the invention include, but are not limited to, those wherein $R^5$ is hydrogen, alkyl, or halogen. In certain embodiments, $R^5$ is hydrogen or halogen.

Certain embodiments of the invention include, but are not limited to, those wherein $R^4$ and $R^5$, together with the carbon atoms to which they are attached, form an optionally substituted monocyclic cycloalkyl ring (e.g an optionally substituted cyclopentyl).

In certain embodiments, $X^2$ is O.

In yet other embodiments, $X^2$ is $N(R^{10})$ wherein $R^{10}$ is as disclosed in the Summary. For example, $R^{10}$ is $C_1$-$C_4$ alkyl such as, but not limited to, methyl.

Yet another embodiment of the invention directs to compounds of formula (I) wherein ring A is formula (c)

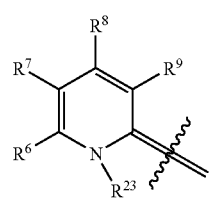

wherein $R^6$, $R^7$, $R^8$, $R^9$ and $R^{23}$ are as defined in the Summary.

$R^6$ and $R^9$ are, for example, hydrogen.

$R^7$ and $R^8$ are, for example, each independently hydrogen or $C_1$-$C_4$ alkyl such as, but not limited to, methyl, tert-butyl, and the like.

A further embodiment of the invention provides compounds of formula (I) wherein ring A is formula (d)

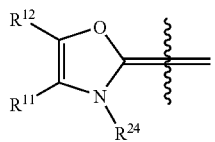

wherein $R^{11}$, $R^{12}$, and $R^{24}$ are as defined in the Summary.

For example, compounds of the invention include, but are not limited to, those wherein $R^{12}$ is alkyl (e.g. $C_1$-$C_4$ alkyl). For example, $R^{12}$ is tert-butyl.

Certain compounds of the invention include, but are not limited to, those wherein $R^{11}$ is hydrogen, alkyl, or halogen. In certain embodiments, $R^{11}$ is hydrogen.

$R^{21}$, $R^{22}$, $R^{23}$, a $R^{24}$ in formula (a), (b), (c), and (d) are as described generally in the Summary. For example, $R^{21}$, $R^{22}$, $R^{23}$, and $R^{24}$ are each independently -alkylene-$G^3$, and $G^3$, at each occurrence, is independently a 4-, 5-, or 6-membered monocyclic heterocycle containing zero or one double bond, one or two oxygen, and zero or one nitrogen as ring atoms, and each $G^3$ is optionally substituted as described in the Summary. For example, $G^3$ is a 4-, 5-, or 6-membered monocyclic heterocycle containing zero double bond, one or two oxygen, and zero or one nitrogen atom as ring atom, and $G^3$ is optionally substituted as described in the Summary. Examples of such monocyclic heterocycle rings include, but are not limited to, oxetanyl (including oxetan-2-yl), oxazolidinyl (including 1,3-oxazolidin-4-yl), tetrahydrofuranyl (including tetrahydrofuran-2-yl and tetrahydrofuran-3-yl), tetrahydropyranyl (including tetrahydropyran-2-yl, tetrahydropyran-3-yl and tetrahydropyran-4-yl), 1,3-dioxalanyl (including 1,3-dioxalan-2-yl and 1,4-dioxalan-2-yl), and 1,4-dioxanyl (including 1,4-dioxan-2-yl). Each of these exemplary rings is independently unsubstituted or substituted as described in the Summary. For example, each can be unsubstituted or substituted with 1 or 2 groups selected from alkyl such as, but not limited to, methyl, halogen (e.g. F), haloalkyl, oxo, —OH, —O(alkyl) (including, but not limited to —$OCH_3$), and —O(haloalkyl).

Other compounds of the invention include, but are not limited to, those wherein $R^{21}$, $R^{22}$, $R^{23}$ and $R^{24}$ are each independently -alkylene-$G^3$, and $G^3$ is tetrahydrofuranyl (including tetrahydrofuran-2-yl and tetrahydrofuran-3-yl), tetrahydropyranyl (including tetrahydropyran-2-yl, tetrahydropyran-3-yl and tetrahydropyran-4-yl), or oxazolidinyl (including 1,3-oxazolidin-4-yl), each of which is optionally substituted as described in the Summary and the preceding paragraph. Particularly, $R^{21}$, $R^{22}$, $R^{23}$, and $R^{24}$ are each tetrahydrofuranylmethyl, tetrahydropyranylmethyl, or oxazolidinylmethyl, wherein each of the tetrahydrofuranyl, tetrahydropyranyl, and oxazolidinyl moieties is independently unsubstituted or substituted as described in the Summary and in the preceding paragraph. More particularly, $R^{21}$, $R^{22}$ $R^{23}$ and $R^{24}$ are tetrahydrofuran-2-ylmethyl, tetrahydrofuran-3-ylmethyl, 1,3-oxazolidin-4-ylmethyl, or tetrahydropyran-2-ylmethyl wherein the tetrahydrofuran-2-yl, tetrahydrofuran-3-yl, 1,3-oxazolidin-4-yl, and the tetrahydropyran-2-yl moieties are each independently unsubstituted or substituted as described in the Summary and in the preceding paragraph.

It is appreciated that the present invention contemplates compounds of formula (I) with combinations of the above embodiments, including particular, more particular and preferred embodiments.

Accordingly, one aspect of the invention is directed to compounds of formula (I) wherein ring A is formula (a), or pharmaceutically acceptable salts, prodrugs, salts of prodrugs, or combinations thereof. Thus, it is understood that these compounds would have formula as represented by formula (Ia)

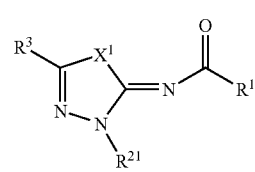

wherein $X^1$, $R^1$, $R^3$, and $R^{21}$ are as described in the Summary and the Detailed Description sections. In certain embodiments, $X^1$ is S.

Another aspect of the invention relates to compounds of formula (I) wherein ring A is formula (b), or pharmaceutically acceptable salts, prodrugs, salts of prodrugs, or combinations thereof. Such compounds are represented by formula (Ib)

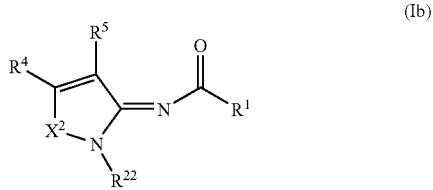

(Ib)

wherein $X^2$, $R^1$, $R^4$, $R^5$, and $R^{22}$ are as defined in the Summary and the Detailed Description sections. In certain embodiments, $X^2$ is O. In other embodiments, $X^2$ is $N(R^{10})$ wherein $R^{10}$ is alkyl (e.g. $C_1$-$C_4$ alkyl such as, but not limited to, methyl).

Yet another aspect of the invention relates to compounds of formula (I) wherein ring A is formula (c), or pharmaceutically acceptable salts, prodrugs, salts of prodrugs, or combinations thereof. Such compounds are represented by formula (Ic)

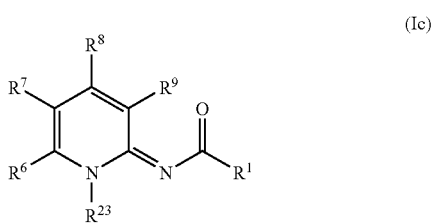

(Ic)

wherein $R^1$, $R^6$, $R^7$, $R^8$, $R^9$, and $R^{23}$ have values as disclosed in the Summary and the Detailed Description sections.

Yet another aspect of the invention contemplates compounds of formula (I) wherein ring A is formula (d), or pharmaceutically acceptable salts, prodrugs, salts of prodrugs, or combinations thereof. Such compounds are represented by formula (Id)

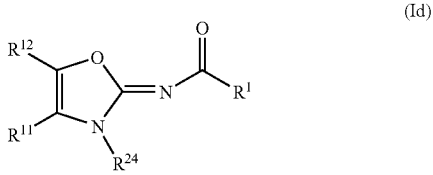

(Id)

wherein $R^1$, $R^{11}$, $R^{12}$, and $R^{24}$ are as described in the Summary and the Detailed Description sections.

For example, within each of the foregoing compounds, examples of a group include those having formula (I), (Ia), (Ib), (Ic), or (Id) wherein $R^{21}$, $R^{22}$, $R^{23}$, and $R^{24}$ are independently -alkylene-$G^3$, each $G^3$ is a 4-, 5-, or 6-membered monocyclic heterocycle containing zero or one double bond, one or two oxygen, and zero or one nitrogen as ring atoms, and each $G^3$ is optionally substituted as described in the Summary. For example, $G^3$ is a 4-, 5-, or 6-membered monocyclic heterocycle containing zero double bond, one or two oxygen, and zero or one nitrogen atom as ring atom, and $G^3$ is optionally substituted as described in the Summary. Examples of such monocyclic heterocycles include, but are not limited to, oxetanyl (including oxetan-2-yl), oxazolidinyl (including 1,3-oxazolidin-4-yl), tetrahydrofuranyl (including tetrahydrofuran-2-yl and tetrahydrofuran-3-yl), tetrahydropyranyl (including tetrahydropyran-2-yl, tetrahydropyran-3-yl, and tetrahydropyran-4-yl), 1,3-dioxalanyl (including 1,3-dioxalan-2-yl and 1,4-dioxalan-2-yl), and 1,4-dioxanyl (including 1,4-dioxan-2-yl). Each of these exemplary rings is independently unsubstituted or substituted as described in the Summary. For example, each can be independently unsubstituted or substituted with 1 or 2 alkyl groups such as, but not limited to, methyl, halogen (e.g. F), haloalkyl, oxo, —OH, —O(alkyl) (e.g. $OCH_3$), and —O(haloalkyl).

Examples of another group of compounds having formula (I), (Ia), (Ib), (Ic), or (Id) include, but are not limited to, those wherein $R^{21}$, $R^{22}$, $R^{23}$, and $R^{24}$ are each independently -alkylene-$G^3$, and each $G^3$ is tetrahydrofuranyl (including tetrahydrofuran-2-yl and tetrahydrofuran-3-yl), tetrahydropyranyl (including tetrahydropyran-2-yl, tetrahydropyran-3-yl, and tetrahydropyran-4-yl), or oxazolidinyl (including 1,3-oxazolidin-4-yl), each of which is optionally substituted as described in the Summary and the preceding paragraph.

Examples of yet another group of compounds having formula (I), (Ia), (Ib), (Ic), or (Id) include, but are not limited to, those wherein $R^{21}$, $R^{22}R^{23}$, and $R^{24}$ are -alkylene-$G^3$, and -alkylene-$G^3$ is independently tetrahydrofuranylmethyl, tetrahydropyranylmethyl, or oxazolidinylmethyl wherein each of the tetrahydrofuranyl, tetrahyropyranyl, and oxazolidinyl moieties is independently unsubstituted or substituted as described in the Summary and in the preceding paragraph.

Further examples of a group of compounds having formula (I), (Ia), (Ib), (Ic), or (Id) include, but are not limited to, those wherein $R^{21}$, $R^{22}$, $R^{23}$, and $R^{24}$ are each independently etrahydrofuran-2-ylmethyl, tetrahydrofuran-3-ylmethyl, 1,3-oxazolidin-4-ylmethyl, tetrahydropyran-2-ylmethyl, wherein the tetrahydrofuran-2-yl, tetrahydrofuran-3-yl, 1,3-oxazolidin-4-yl, and the tetrahydropyran-2-yl moieties are each independently unsubstituted or substituted as described in the Summary and in the preceding paragraph.

Within each group of compounds of formula (I), (Ia), (Ib), (Ic), or (Id) as described in the preceding paragraphs, $R^1$, $R^3$, $R^4$, $R^5$, $R^6$, $R^7$, $R^8$, $R^9$, $R^{11}$, $R^{12}$, $X^1$, and $X^2$ have values as disclosed in the Summary and the Detailed Description.

Thus, of each groups of compounds of formula (I), (Ia), (Ib), (Ic), or (Id) as described in the preceding paragraphs, examples of a subgroup include, but are not limited to, those wherein $R^1$ is $G^1$, and $G^1$ is as disclosed in the Summary.

Other examples of a subgroup include, but are not limited to, those wherein $G^1$ is phenyl or naphthyl, each of which is optionally substituted as described in the Summary and the Detailed Description sections. Preferably, $G^1$ is phenyl, substituted with 1, 2, or 3 substituents.

Yet other examples of a subgroup include those wherein $R^1$, for example, is cycloalkyl, optionally substituted as described in the Summary and the Detailed Description sections.

Still other examples of a subgroup include those wherein $R^1$ is $G^1$, and $G^1$ is heterocycle, optionally substituted as described in the Summary and in the Detailed Description. For example, $R^1$ is 2,3-dihydrobenzofuranyl (including 2,3-dihydro-1-benzofuran-7-yl).

Further examples of a subgroup include those wherein $R^1$ is heteroaryl, optionally substituted as described in the Summary and the Detailed Description. For example, $R^1$ is optionally substituted quinolinyl. The quinolinyl moiety is, for example, substituted with 1, 2, or 3 substituents wherein the optional substituents are as disclosed in the Summary and the Detailed Description sections.

Yet other examples of a subgroup include those wherein $R^1$ is —N($R^{1a}$)($R^z$) wherein $R^{1a}$ and $R^z$ are as defined in the Summary. For example, $R^{1a}$ is hydrogen or alkyl. More particularly, $R^{1a}$ is hydrogen. Examples of $R^z$ include, but are not limited to, alkyl (e.g. $C_4$-$C_8$ alkyl such as, but not limited to, neopentyl, 2-ethylhexyl, tert-butyl, 1,2-dimethylpropyl, 1-ethylpropyl), $G^2$ such as optionally substituted cycloalkyl (e.g. cyclohexyl, cycloheptyl, each of which is optionally substituted), or optionally substituted aryl (e.g. optionally substituted 1,2,3,4-tetrahydronaphthalenyl); —($CR^xR^y)_m$-$G^2$ ($G^2$, for example, is optionally substituted cycloalkyl such as, but not limited to, cyclohexyl, adamantyl or bicyclo[3.1.1] heptyl, each of which is optionally substituted, or optionally substituted aryl such as, but not limited to, optionally substituted phenyl; $R^x$ and $R^y$ are, for example, hydrogen or alkyl such as, but not limited to $C_1$-$C_4$ alkyl, and m is 1, 2, 3, or 4); —($CR^xR^y)_m$—C(O)N($R^{za}$)($R^{zb}$) (e.g. $R^{za}$ is hydrogen, $R^x$ is hydrogen, alkyl (e.g. $C_1$-$C_4$ alkyl such as, but not limited to, isopropyl, 1-methylpropyl, tert-butyl, isobutyl), or benzyl; $R^y$ is hydrogen, m is 1 or 2, $R^{zb}$ is hydrogen or alkyl (e.g. $C_1$-$C_4$ alkyl such as, but not limited to, methyl)); or —($CR^xR^y$)$_n$—$OR^{za}$ (e.g., $R^{za}$ is hydrogen, $R^x$ is hydrogen or alkyl (e.g. $C_1$-$C_4$ alkyl such as, but not limited to, isopropyl, 1-methylpropyl, tert-butyl, isobutyl); $R^y$ is hydrogen, and n is 2).

Of all examples of the groups and subgroups of compounds of formula (I), (Ia), (Ib), (Ic), or (Id) as discussed hereinabove, $R^3$, $R^4$, $R^5$, $R^6$, $R^7$, $R^8$, $R^9$, $R^{11}$, $R^{12}$, $X^1$, $X^2$, and the substituents of $G^1$ have values as defined in the Summary and the Detailed Description.

For example, for each of the foregoing groups and subgroups of compounds of formula (I) and (Ia), an example of $X^1$ is S. $R^3$ for compounds of formula (I) or (Ia) is, for example, alkyl (e.g. $C_1$-$C_4$ alkyl), alkenyl, alkynyl, haloalkyl, or optionally substituted cycloalkyl (e.g. $C_3$-$C_6$ cycloalkyl). Particular examples of $R^3$ include, but are not limited to, methyl, isopropyl, tert-butyl, 1,1-dimethylprop-2-ynyl, 2,2, 2-trifluoro-1,1-dimethylethyl, cyclopropyl, and cyclobutyl, wherein the cyclopropyl and cyclobutyl are independently unsubstituted or substituted as described in the Summary and in the Detailed Description sections. Examples of the optional substituents of cycloalkyl include, but are not limited to, alkyl (e.g. $C_1$-$C_4$ alkyl such as, but not limited to, methyl), haloalkyl (e.g. trifluoromethyl), and halogen (e.g. F).

For each of the foregoing groups and subgroups of compounds of formula (I) and (Ib), $R^4$, for example, is alkyl. Particularly, $R^4$ is tert-butyl. $R^5$, for example, is hydrogen, alkyl, or halogen. In certain embodiments, $R^1$ is hydrogen. In certain embodiments, $X^2$ is O. In another embodiment, $X^2$ is N($R^{10}$) wherein $R^{10}$ is as disclosed in the Summary. For example, $R^{10}$ is $C_1$-$C_4$ alkyl such as, but not limited to, methyl. Certain embodiments of the invention include the foregoing groups and subgroups of compounds of formula (I) or (Ib) described in the preceding paragraphs wherein $R^4$ and $R^5$, together with the carbon atoms to which they are attached, form an optionally substituted monocyclic cycloalkyl ring (e.g an optionally substituted cyclopentyl).

For each of the foregoing groups and subgroups of compounds of formula (I) and (Ic), $R^6$ and $R^9$ are, for example, hydrogen. $R^7$ and $R^8$ are, for example, each independently hydrogen or $C_1$-$C_4$ alkyl such as, but not limited to, methyl, tert-butyl, and the like.

For each of the foregoing groups and subgroups of compounds of formula (I) and (Id), $R^{12}$, for example, is alkyl (e.g. $C_1$-$C_4$ alkyl such as, but not limited to, tert-butyl and the like). $R^{11}$, for example, is hydrogen, alkyl, or halogen. In certain embodiments, $R^{11}$ is hydrogen.

Examples of the optional substituents of $G^1$ include, but are not limited to, alkenyl, alkyl, —CN, halogen, —$OR^e$, haloalkyl, —$SF_5$, —$SR^e$, —O—($CR^jR^k$)$_n$—N($R^w$)$_2$, alkoxyalkenyl, hydroxyalkenyl, —($CR^jR^k$)$_q$—$OR^e$, and —N($R^e$)($R^g$) wherein $R^e$, $R^j$, $R^k$, $R^w$, n, q, and $R^g$ are as disclosed in the Summary. For example, in certain embodiments, the optional substituents of $G^1$ are alkyl (e.g. methyl), alkenyl (e.g. prop-1-enyl), —CN, halogen (e.g. Cl, Br, F), —$OR^e$ (e.g, $R^e$ is hydrogen, alkyl such as methyl, ethyl, tert-butyl; alkoxyalkyl such as 3-methoxy3-methylbutyl, 2-methoxyethyl, 2-methoxypropyl, 3-ethoxypropyl, 3-methoxypropyl, 2-ethoxyethyl; alkenyl such as, but not limited to, 3-methylbut-2-enyl; haloalkyl such as 2,2,2-trifluoroethyl, 2-fluoroethyl, 2,2-difluoroethyl, 2-fluoropropyl, 2-fluoro-1-methylethyl, 3-fluoro-3-methylbutyl; cycloalkylalkyl such as cyclobutylmethyl, cyclopentylethyl, wherein the cyclobutyl and the cyclopentyl moieties are each optionally substituted; optionally substituted heterocycle such as tetrahydrofuranyl, azetidinyl, pyrrolidinyl, each of which is optionally substituted); haloalkyl (e.g., trifluoromethyl), —$SF_5$, —$SR^e$ (e.g. $R^e$ is heteroaryl such as oxidopyridinyl), —O—($CR^jR^k$)$_n$—N($R^w$)$_2$ (e.g. $R^j$ and $R^k$ are hydrogen or alkyl such as, but not limited to, methyl, $R^w$ is hydrogen or alkyl such as methyl), alkoxyalkenyl (e.g. 3-methoxyprop-1-enyl), hydroxyalkenyl (e.g. 3-hydroxyl-3-methylbut-1-enyl), —($CR^jR^k$)$_q$—$OR^e$ (e.g., $R^j$ and $R^k$ are hydrogen or alkyl such as, but not limited to, methyl, $R^e$ is hydrogen or alkyl such as, but not limited to, methyl), and —N($R^e$)($R^g$) wherein $R^e$ is alkyl (e.g. methyl), haloalkyl (e.g., 2-fluoroethyl), or alkoxyalkyl (e.g. 2-methyoxyethyl), $R^g$, for example, is hydrogen or alkyl. Particular examples of the optional substituents of $G^1$ include, but are not limited to, methyl, chlorine, bromine, fluorine, —O($CH_3$), —O($CF_3$), —$CF_3$, and —N($CH_3$)$_2$.

Exemplary compounds of the invention include, but are not limited to compounds of formula (I):

5-chloro-2-methoxy-N-[(2Z)-3-[(2R)-tetrahydrofuran-2-ylmethyl]-5-[1-(trifluoromethyl)cyclopropyl]-1,3,4-thiadiazol-2(3H)-ylidene]benzamide;

5-chloro-N-[(2Z)-5-cyclopropyl-3-(tetrahydrofuran-2-ylmethyl)-1,3,4-thiadiazol-2(3H)-ylidene]-2-methoxybenzamide;

N-[(2Z)-5-cyclopropyl-3-(tetrahydrofuran-2-ylmethyl)-1,3,4-thiadiazol-2(3H)-ylidene]-2-ethoxybenzamide;

N-[(2Z)-5-tert-butyl-3-[(2R)-tetrahydrofuran-2-ylmethyl]-1,3,4-thiadiazol-2(3H)-ylidene]-5-chloro-2-methoxybenzamide;

5-chloro-2-methoxy-N-[(2Z)-5-(1-methylcyclopropyl)-3-[(2R)-tetrahydrofuran-2-ylmethyl]-1,3,4-thiadiazol-2(3H)-ylidene]benzamide;

5-chloro-N-[(2Z)-5-(1,1-dimethylprop-2-ynyl)-3-[(2R)-tetrahydrofuran-2-ylmethyl]-1,3,4-thiadiazol-2(3H)-ylidene]-2-methoxybenzamide;

5-chloro-2-methoxy-N-[(2Z)-5-(2,2,3,3-tetrafluoro-1-methylcyclobutyl)-3-[(2R)-tetrahydrofuran-2-ylmethyl]-1,3,4-thiadiazol-2(3H)-ylidene]benzamide;

5-chloro-2-methoxy-N-[(2Z)-3-[(2R)-tetrahydrofuran-2-ylmethyl]-5-[1-(trifluoromethyl)cyclobutyl]-1,3,4-thiadiazol-2(3H)-ylidene]benzamide;

5-chloro-2-methoxy-N-[(2Z)-3-[(2R)-tetrahydrofuran-2-ylmethyl]-5-(2,2,2-trifluoro-1,1-dimethylethyl)-1,3,4-thiadiazol-2(3H)-ylidene]benzamide;

5-chloro-2-methoxy-N-[(2E)-5-methyl-1-(tetrahydrofuran-2-ylmethyl)pyridin-2(1H)-ylidene]benzamide;

N-[5-tert-butyl-2-[(2R)-tetrahydrofuran-2-ylmethyl]isoxazol-3(2H)-ylidene]-5-chloro-2-methoxybenzamide;

N-{5-tert-butyl-1-methyl-2-[(2S)-tetrahydrofuran-2-ylmethyl]-1,2-dihydro-3H-pyrazol-3-ylidene}-5-chloro-2-methoxybenzamide;

N-[5-tert-butyl-3-[(2R)-tetrahydrofuran-2-ylmethyl]-1,3-oxazol-2(3H)-ylidene]-5-chloro-2-methoxybenzamide;

N-{(3E)-5-tert-butyl-1-methyl-2-[(2R)-tetrahydrofuran-2-ylmethyl]-1,2-dihydro-3H-pyrazol-3-ylidene}-2-ethoxy-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-3-(pentafluoro-lambda-6-sulfanyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(cis-3-hydroxycyclobutyl)methoxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(3-oxocyclobutyl)methoxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(cis-3-methoxycyclobutyl)methoxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(3,3-difluorocyclobutyl)methoxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(3-methoxy-3-methylbutoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(2,2,2-trifluoroethoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(2-fluoroethoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(2-methoxyethoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-hydroxy-5-(trifluoromethyl)benzamide;

2-tert-butoxy-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[2-(dimethylamino)ethoxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(dimethylamino)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-{[(2S)-2-methoxypropyl]oxy}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(3-ethoxypropoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(3-methoxypropoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(2-ethoxyethoxy)-5-(trifluoromethyl)benzamide;

2-methoxy-N-[(3E)-1-methyl-2-[(2R)-tetrahydrofuran-2-ylmethyl]-1,4,5,6-tetrahydrocyclopenta[c]pyrazol-3(2H)-ylidene]-5-(trifluoromethyl)benzamide;

2-methoxy-N-{(3E)-1-methyl-5-(1-methylcyclopropyl)-2-[(2R)-tetrahydrofuran-2-ylmethyl]-1,2-dihydro-3H-pyrazol-3-ylidene}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(2-methoxyethyl)amino]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(2,2-difluoroethoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(3R)-tetrahydrofuran-3-yloxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(3S)-tetrahydrofuran-3-yloxy]-5-(trifluoromethyl)benzamide;

(E)-N-(5-tert-butyl-2-(((2R,3R)-3-fluorotetrahydrofuran-2-yl)methyl)-1-methyl-1H-pyrazol-3(2H)-ylidene)-2-methoxy-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(2-fluoroethyl)amino]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(2-fluoropropoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-{[(2R)-2-fluoropropyl]oxy}-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(2-fluoro-1-methylethoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-(3-fluoro-3-methylbutoxy)-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-[(1-hydroxycyclobutyl)methoxy]-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-5-chloro-2-methoxybenzamide;

N-{(3E)-5-tert-butyl-1-methyl-2-[(2R)-tetrahydrofuran-2-ylmethyl]-1,2-dihydro-3H-pyrazol-3-ylidene}-2-fluoro-3-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-methoxy-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-5-cyano-2-methoxybenzamide;

5-bromo-N-{(3E)-5-tert-butyl-1-methyl-2-[(2R)-tetrahydrofuran-2-ylmethyl]-1,2-dihydro-3H-pyrazol-3-ylidene}-2-methoxybenzamide;

N-{(3E)-5-tert-butyl-1-methyl-2-[(2R)-tetrahydrofuran-2-ylmethyl]-1,2-dihydro-3H-pyrazol-3-ylidene}-2-chloro-5-fluorobenzamide;

N-{(3E)-5-tert-butyl-1-methyl-2-[(2R)-tetrahydrofuran-2-ylmethyl]-1,2-dihydro-3H-pyrazol-3-ylidene}-2,3,5-trifluorobenzamide;

N-{(3E)-5-tert-butyl-1-methyl-2-[(2R)-tetrahydrofuran-2-ylmethyl]-1,2-dihydro-3H-pyrazol-3-ylidene}-3-chloro-2-fluoro-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-3-chloro-2-methoxy-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-2-chloro-5-(trifluoromethyl)benzamide;

N-{(3E)-5-tert-butyl-1-methyl-2-[(2R)-tetrahydrofuran-2-ylmethyl]-1,2-dihydro-3H-pyrazol-3-ylidene}-3,5-difluoro-2-methoxybenzamide;
N-{(3E)-5-tert-butyl-1-methyl-2-[(2R)-tetrahydrofuran-2-ylmethyl]-1,2-dihydro-3H-pyrazol-3-ylidene}-3-chloro-2-(2-methoxyethoxy)-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-3-chloro-2-(2-fluoroethoxy)-5-(trifluoromethyl)benzamide;
5-bromo-N-{(3E)-5-tert-butyl-1-methyl-2-[(2R)-tetrahydrofuran-2-ylmethyl]-1,2-dihydro-3H-pyrazol-3-ylidene}-2-(2-methoxyethoxy)benzamide;
5-bromo-N-{(3E)-5-tert-butyl-1-methyl-2-[(2R)-tetrahydrofuran-2-ylmethyl]-1,2-dihydro-3H-pyrazol-3-ylidene}-2-(2-fluoroethoxy)benzamide;
5-bromo-N-{(3E)-5-tert-butyl-1-methyl-2-[(2R)-tetrahydrofuran-2-ylmethyl]-1,2-dihydro-3H-pyrazol-3-ylidene}-2,3-dihydro-1-benzofuran-7-carboxamide;
N-[(2E)-4-tert-butyl-1-[(2R)-tetrahydrofuran-2-ylmethyl]pyridin-2(1H)-ylidene]-5-chloro-2-methoxybenzamide;
N-[(2E)-4-tert-butyl-1-[(2R)-tetrahydrofuran-2-ylmethyl]pyridin-2(1H)-ylidene]-2-methoxy-5-(trifluoromethyl)benzamide;
N-[(3E)-5-tert-butyl-1-methyl-2-(tetrahydro-2H-pyran-2-ylmethyl)-1,2-dihydro-3H-pyrazol-3-ylidene]-2-methoxy-5-(trifluoromethyl)benzamide;
N-((3E)-5-tert-butyl-1-methyl-2-{[(5R)-5-methyltetrahydrofuran-2-yl]methyl}-1,2-dihydro-3H-pyrazol-3-ylidene)-2-methoxy-5-(trifluoromethyl)benzamide;
N-((3E)-5-tert-butyl-1-methyl-2-{[(5S)-5-methyltetrahydrofuran-2-yl]methyl}-1,2-dihydro-3H-pyrazol-3-ylidene)-2-methoxy-5-(trifluoromethyl)benzamide;
N-[(2Z)-5-tert-butyl-3-[(2R)-tetrahydrofuran-2-ylmethyl]-1,3-oxazol-2(3H)-ylidene]-2-methoxy-5-(trifluoromethyl)benzamide;
N-[(2Z)-5-tert-butyl-3-[(2R)-tetrahydrofuran-2-ylmethyl]-1,3,4-thiadiazol-2(3H)-ylidene]-N'-(4-methylcyclohexyl)urea;
N-(1-adamantylmethyl)-N'-[(2Z)-5-tert-butyl-3-[(2R)-tetrahydrofuran-2-ylmethyl]-1,3,4-thiadiazol-2(3H)-ylidene]urea;
N-[(2Z)-5-tert-butyl-3-[(2R)-tetrahydrofuran-2-ylmethyl]-1,3,4-thiadiazol-2(3H)-ylidene]-N'-{[(1S,2R,5S)-6,6-dimethylbicyclo[3.1.1]hept-2-yl]methyl}urea;
N-[(2Z)-5-tert-butyl-3-[(2R)-tetrahydrofuran-2-ylmethyl]-1,3,4-thiadiazol-2(3H)-ylidene]-N'-[1-(hydroxymethyl)-3-methylbutyl]urea;
N-[(2Z)-5-tert-butyl-3-[(2R)-tetrahydrofuran-2-ylmethyl]-1,3,4-thiadiazol-2(3H)-ylidene]-N'-(1,2-dimethylpropyl)urea;
N-[(2Z)-5-tert-butyl-3-[(2R)-tetrahydrofuran-2-ylmethyl]-1,3,4-thiadiazol-2(3H)-ylidene]-N'-(1-ethylpropyl)urea;
N-[(2Z)-5-tert-butyl-3-[(2R)-tetrahydrofuran-2-ylmethyl]-1,3,4-thiadiazol-2(3H)-ylidene]-N'-1,2,3,4-tetrahydronaphthalen-1-ylurea;
N-[(2Z)-5-tert-butyl-3-[(2R)-tetrahydrofuran-2-ylmethyl]-1,3,4-thiadiazol-2(3H)-ylidene]-N'-[(1S)-1-cyclohexylethyl]urea;
N-(tert-butyl)-N'-[(2Z)-5-tert-butyl-3-[(2R)-tetrahydrofuran-2-ylmethyl]-1,3,4-thiadiazol-2(3H)-ylidene]urea;
N-[(2Z)-5-tert-butyl-3-[(2R)-tetrahydrofuran-2-ylmethyl]-1,3,4-thiadiazol-2(3H)-ylidene]-N'-[(1S)-1-(hydroxymethyl)-2,2-dimethylpropyl]urea;
N-[(2Z)-5-tert-butyl-3-[(2R)-tetrahydrofuran-2-ylmethyl]-1,3,4-thiadiazol-2(3H)-ylidene]-N'-cycloheptylurea;
N-[(2Z)-5-tert-butyl-3-[(2R)-tetrahydrofuran-2-ylmethyl]-1,3,4-thiadiazol-2(3H)-ylidene]-N'-(2-ethylhexyl)urea;
N-[(2Z)-5-tert-butyl-3-[(2R)-tetrahydrofuran-2-ylmethyl]-1,3,4-thiadiazol-2(3H)-ylidene]-N'-(1-methyl-3-phenylpropyl)urea;
N-({[(2Z)-5-tert-butyl-3-[(2R)-tetrahydrofuran-2-ylmethyl]-1,3,4-thiadiazol-2(3H)-ylidene]amino}carbonyl)-L-phenylalaninamide;
$N^2$-({[(2Z)-5-tert-butyl-3-[(2R)-tetrahydrofuran-2-ylmethyl]-1,3,4-thiadiazol-2(3H)-ylidene]amino}carbonyl)-L-isoleucinamide;
$N^2$-({[(2Z)-5-tert-butyl-3-[(2R)-tetrahydrofuran-2-ylmethyl]-1,3,4-thiadiazol-2(3H)-ylidene]amino}carbonyl)-$N^1$,3-dimethyl-L-valinamide;
N-[(2Z)-5-tert-butyl-3-[(2R)-tetrahydrofuran-2-ylmethyl]-1,3,4-thiadiazol-2(3H)-ylidene]-N'-neopentylurea;
N-[(2Z)-5-tert-butyl-3-[(2R)-tetrahydrofuran-2-ylmethyl]-1,3,4-thiadiazol-2(3H)-ylidene]-N'-[(1S)-1-(hydroxymethyl)-2-methylpropyl]urea;
N-[(3E)-5-tert-butyl-1-methyl-2-(tetrahydrofuran-3-ylmethyl)-1,2-dihydro-3H-pyrazol-3-ylidene]-2-methoxy-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-methyl-5-(trifluoromethyl)benzamide;
N-{(3E)-4-bromo-5-tert-butyl-1-methyl-2-[(2R)-tetrahydrofuran-2-ylmethyl]-1,2-dihydro-3H-pyrazol-3-ylidene}-2-methyl-5-(trifluoromethyl)benzamide;
2-bromo-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-[(1E)-3-methoxyprop-1-enyl]-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-(3-methoxypropyl)-5-(trifluoromethyl)benzamide;
N-[(2Z)-5-tert-butyl-3-{[(4S)-2-oxo-1,3-oxazolidin-4-yl]methyl}-1,3,4-thiadiazol-2(3H)-ylidene]-5-chloro-2-methoxybenzamide;
2-(2-amino-2-methylpropoxy)-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-[(3-methylbut-2-enyl)oxy]-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-[2-(1-hydroxycyclopentyl)ethoxy]-5-(trifluoromethyl)benzamide;
2-(azetidin-3-yloxy)-N-[(2Z)-5-tert-butyl-3-[(2R)-tetrahydrofuran-2-ylmethyl]-1,3-oxazol-2(3H)-ylidene]-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-3-fluoro-5-(trifluoromethyl)benzamide;
N-[(2Z)-5-tert-butyl-3-[(2R)-tetrahydrofuran-2-ylmethyl]-1,3,4-thiadiazol-2(3H)-ylidene]-2-{[(3S)-1-methylpyrrolidin-3-yl]oxy}-5-(trifluoromethyl)benzamide;
N-[(2Z)-5-tert-butyl-3-[(2R)-tetrahydrofuran-2-ylmethyl]-1,3-oxazol-2(3H)-ylidene]-2-{[(3S)-1-methylpyrrolidin-3-yl]oxy}-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-[(1E)-prop-1-enyl]-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-[(1E)-3-hydroxy-3-methylbut-1-enyl]-5-(trifluoromethyl)benzamide; and N-{(3E)-5-tert-butyl-1-methyl-2-[(2R)-tetrahydrofuran-2-ylmethyl]-1,2-dihydro-3H-pyrazol-3-ylidene}-2-(3-hydroxy-3-methylbutyl)-5-(trifluoromethyl)benzamide.

Examples of compounds of formula (Id) that are contemplated include, but are not limited to, N-{5-tert-butyl-1-methyl-2-[(2R)-tetrahydrofuran-2-ylmethyl]-1,2-dihydro-3H-pyrazol-3-ylidene}-2-chloro-3-(trifluoromethyl)benzamide;

N-{5-tert-butyl-1-methyl-2-[(2R)-tetrahydrofuran-2-ylmethyl]-1,2-dihydro-3H-pyrazol-3-ylidene}-5-fluoro-2-methoxybenzamide;

N-{5-tert-butyl-1-methyl-2-[(2R)-tetrahydrofuran-2-ylmethyl]-1,2-dihydro-3H-pyrazol-3-ylidene}-4-chloro-5-fluoro-2-methoxybenzamide;

N-{5-tert-butyl-1-methyl-2-[(2R)-tetrahydrofuran-2-ylmethyl]-1,2-dihydro-3H-pyrazol-3-ylidene}-5-iodo-2-methoxybenzamide;

N-{5-tert-butyl-1-methyl-2-[(2R)-tetrahydrofuran-2-ylmethyl]-1,2-dihydro-3H-pyrazol-3-ylidene}-6-chloroquinoline-8-carboxamide;

N-{5-tert-butyl-1-methyl-2-[(2R)-tetrahydrofuran-2-ylmethyl]-1,2-dihydro-3H-pyrazol-3-ylidene}-2-chloronicotinamide;

N-{5-tert-butyl-1-methyl-2-[(2R)-tetrahydrofuran-2-ylmethyl]-1,2-dihydro-3H-pyrazol-3-ylidene}-5-chloro-2-(2,2,2-trifluoroethoxy)benzamide;

N-{5-tert-butyl-1-methyl-2-[(2R)-tetrahydrofuran-2-ylmethyl]-1,2-dihydro-3H-pyrazol-3-ylidene}-5-chloro-2-(2-methoxyethoxy)benzamide;

N-{5-tert-butyl-1-methyl-2-[(2R)-tetrahydrofuran-2-ylmethyl]-1,2-dihydro-3H-pyrazol-3-ylidene}-1-benzofuran-5-carboxamide;

N-{5-tert-butyl-1-methyl-2-[(2R)-tetrahydrofuran-2-ylmethyl]-1,2-dihydro-3H-pyrazol-3-ylidene}-2,3-dichlorobenzamide;

N-{5-tert-butyl-1-methyl-2-[(2R)-tetrahydrofuran-2-ylmethyl]-1,2-dihydro-3H-pyrazol-3-ylidene}-2-chloro-3-(trifluoromethyl)benzamide;

N-{5-tert-butyl-1-methyl-2-[(2R)-tetrahydrofuran-2-ylmethyl]-1,2-dihydro-3H-pyrazol-3-ylidene}-3-chloro-2-methylbenzamide;

3-bromo-N-{5-tert-butyl-1-methyl-2-[(2R)-tetrahydrofuran-2-ylmethyl]-1,2-dihydro-3H-pyrazol-3-ylidene}-2-methylbenzamide;

2-bromo-N-{5-tert-butyl-1-methyl-2-[(2R)-tetrahydrofuran-2-ylmethyl]-1,2-dihydro-3H-pyrazol-3-ylidene}-3-methylbenzamide;

N-{5-tert-butyl-1-methyl-2-[(3-methyloxetan-3-yl)methyl]-1,2-dihydro-3H-pyrazol-3-ylidene}-2-fluoro-3-(trifluoromethyl)benzamide;

N-[5-tert-butyl-1-methyl-2-(oxetan-2-ylmethyl)-1,2-dihydro-3H-pyrazol-3-ylidene]-2-fluoro-3-(trifluoromethyl)benzamide;

N-[5-tert-butyl-1-methyl-2-(tetrahydrofuran-3-ylmethyl)-1,2-dihydro-3H-pyrazol-3-ylidene]-2-fluoro-3-(trifluoromethyl)benzamide;

N-[5-tert-butyl-2-(1,3-dioxolan-2-ylmethyl)-1-methyl-1,2-dihydro-3H-pyrazol-3-ylidene]-2-fluoro-3-(trifluoromethyl)benzamide;

N-{5-tert-butyl-1-methyl-2-[(3-methyl-4,5-dihydroisoxazol-5-yl)methyl]-1,2-dihydro-3H-pyrazol-3-ylidene}-2-fluoro-3-(trifluoromethyl)benzamide;

N-(5-tert-butyl-2-{[(4R)-2,2-dimethyl-1,3-dioxolan-4-yl]methyl}-1-methyl-1,2-dihydro-3H-pyrazol-3-ylidene)-2-fluoro-3-(trifluoromethyl)benzamide;

N-(5-tert-butyl-2-{[(4S)-2,2-dimethyl-1,3-dioxolan-4-yl]methyl}-1-methyl-1,2-dihydro-3H-pyrazol-3-ylidene)-2-fluoro-3-(trifluoromethyl)benzamide;

N-(5-tert-butyl-1-methyl-2-{[(2R)-5-oxotetrahydrofuran-2-yl]methyl}-1,2-dihydro-3H-pyrazol-3-ylidene)-2-fluoro-3-(trifluoromethyl)benzamide;

N-(5-tert-butyl-1-methyl-2-{[(2S)-5-oxotetrahydrofuran-2-yl]methyl}-1,2-dihydro-3H-pyrazol-3-ylidene)-2-fluoro-3-(trifluoromethyl)benzamide;

N-{5-tert-butyl-1-methyl-2-[(5-methyltetrahydrofuran-2-yl)methyl]-1,2-dihydro-3H-pyrazol-3-ylidene}-2-fluoro-3-(trifluoromethyl)benzamide;

N-[5-tert-butyl-1-methyl-2-(tetrahydro-2H-pyran-4-ylmethyl)-1,2-dihydro-3H-pyrazol-3-ylidene]-2-fluoro-3-(trifluoromethyl)benzamide;

N-[5-tert-butyl-1-methyl-2-(tetrahydro-2H-pyran-2-ylmethyl)-1,2-dihydro-3H-pyrazol-3-ylidene]-2-fluoro-3-(trifluoromethyl)benzamide;

N-[5-tert-butyl-1-methyl-2-(tetrahydro-2H-pyran-3-ylmethyl)-1,2-dihydro-3H-pyrazol-3-ylidene]-2-fluoro-3-(trifluoromethyl)benzamide; and N-[5-tert-butyl-2-(1,4-dioxan-2-ylmethyl)-1-methyl-1,2-dihydro-3H-pyrazol-3-ylidene]-2-fluoro-3-(trifluoromethyl)benzamide.

Compounds of the present invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

For example, compounds of formula (Ia), (Ib), (Ic), and (Id) wherein $R^{21}$, $R^{22}$, $R^{23}$, and $R^{24}$ are each tetrahydrofuran-2-ylmethyl, can have stereoisomers including, but not limited to, those shown below:

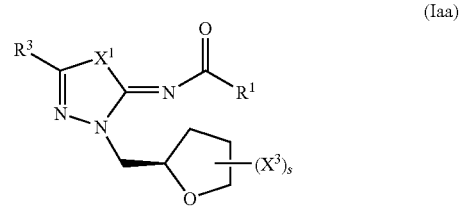

(Iaa)

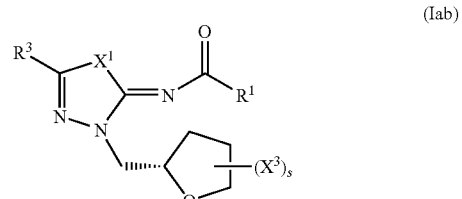

(Iab)

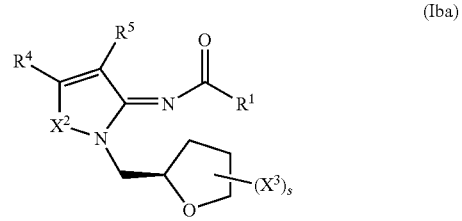

(Iba)

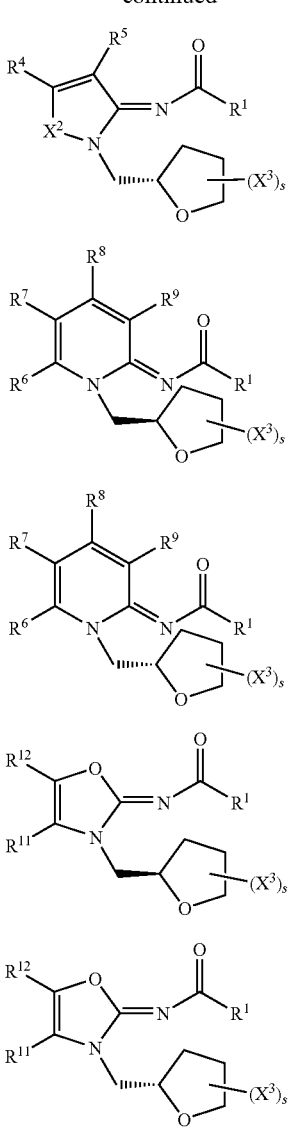

wherein s is 1, 2, 3, 4, 5, or 6, $X^3$ is oxo, alkyl, halogen, OH, O(alkyl), O(haloalkyl), or haloalkyl, and $R^1$, $R^3$, $R^4$, $R^5$, $R^6$, $R^7$, $R^8$, $R^9$, $R^{11}$, $R^{12}$, $X^1$, and $X^2$ are as disclosed in the Summary and the Detailed Description sections. It is understood that embodiments for $R^1$, $R^3$, $R^4$, $R^5$, $R^6$, $R^7$, $R^8$, $R^9$, $R^{11}$, $R^{12}$, $X^1$, and $X^2$, and combinations of embodiments, including particular, and more particular embodiments as described for formula (Ia), (Ib), (Ic), and (Id) are also contemplated for compounds of formula (Iaa), (Iab), (Iba), (Ibb), (Ica), (Icb), (Ida), and (Idb).

It will be appreciated two or more asymmetric centers may be present in the compounds of the invention, hence several diastereomers and enantiomers of the exemplified structures will often be possible, and that pure diastereomers and enantiomers represent preferred embodiments. It is intended that pure diasteromers, pure enantiomers, and mixtures thereof, are within the scope of the invention.

The present invention contemplates various stereoisomers (including enantiomers and diastereomers) and mixtures thereof. Individual stereoisomers of compounds of the present invention may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

c. Biological Data (i) In Vitro Methods—Human $CB_2$ and $CB_1$ Radioligand Binding Assays The $CB_1$ and $CB_2$ radioligand binding assays described herein are utilized to determine the selectivity of compounds of the present invention for binding to $CB_2$ relative to $CB_1$ receptors.

HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 μg/well for human $CB_2$) into wells of a deep well plate containing ([$^3$H] CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 μl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations of displacing ligands selected from the range of 0.01 nM to 10 μM. The addition of 10 μM unlabeled CP-55,940 (Tocris, Ellisville, Mo.) was used to assess nonspecific binding.

HEK293 cells stably expressing rat $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 20 μg/well for rat $CB_2$) into wells of a deep well plate containing [$^3$H]CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 45 min incubation at 30° C., binding reaction was terminated by the addition of 300 μl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations of displacing ligands selected from the range of 0.01 nM to 10 μM. The addition of 10 μM unlabeled CP-55,940 (Tocris, Ellisville, Mo.) was used to assess nonspecific binding.

Representative compounds of the present invention bound to $CB_2$ receptors with a $K_i$ of less than about 1,000 nM, preferably less than 400 nM, more preferably less than 200 nM and, most preferably lower than 100 nM.

HEK293 human $CB_1$ membranes were purchased from Perkin Elmer. Binding was initiated by the addition of membranes (8-12 μg per well) into wells (Scienceware 96-well DeepWell plate, VWR, West Chester, Pa.) containing [3H]CP-55,940 (120 Ci/mmol, Perkin Elmer, Boston, Mass.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 μL. After incubation (30° C. for 90 minutes), binding was terminated by the addition of 300 μL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP-55,940 and five concentrations (1 nM to 10 μM) of displacing ligands. The addition of 10 μM unlabeled CP-55,940 (Tocris, Ellisville, Mo.) was used to assess nonspecific binding. Representative compounds of the present invention bound to $CB_1$ receptors with $K_i$ of about 10 fold to about 1000 fold higher than that for $CB_2$ receptors. These results show that the compounds of the present invention preferably bind to $CB_2$ receptors, therefore are selective ligands for the $CB_2$ receptor.

(ii) In Vivo Data:

Animals

Adult male Sprague-Dawley rats (250-300 g body weight, Charles River Laboratories, Portage, Mich.) are used. Animal handling and experimental protocols are approved by the Institutional Animal Care and Use Committee (IACUC) at Abbott Laboratories. For all surgical procedures, animals are maintained under isoflurane anesthesia (4-5% to induce, 1-3% to maintain), and the incision sites are sterilized using a 10% povidone-iodine solution prior to and after surgeries.

Incisional Model of Postoperative Pain

A skin incision model of postoperative pain can be produced using the procedures described in Brennan et al., 1996, Pain, 64, 493. All rats are anesthetized with isoflurane delivered via a nose cone. Right hind paw incision is performed following sterilization procedures. The plantar aspect of the left hind paw is placed through a hole in a sterile plastic drape. A 1-cm longitudinal incision is made through the skin and fascia of the plantar aspect of the hind paw, starting 0.5 cm from the proximal edge of the heel and extending towards the toes, the plantar muscle is elevated and incised longitudinally leaving the muscle origin and insertion points intact. The skin is then closed with two mattress sutures (5-0 nylon). After surgery, animals are then allowed to recover for 2 hours, at which time tactile allodynia is assessed as described below. To evaluate the anti-nociceptive effects, animals are i.p. administered vehicle or test compound 90 minutes following skin incision and tactile allodynia is assessed 30 minutes after compound administration.

Tactile allodynia can be measured using calibrated von Frey filaments (Stoelting, Wood Dale, Ill.) as described in Chaplan, S. R., F. W. Bach, J. W. Pogrel, J. M. Chung and T. L. Yaksh, 1994, Quantitative Assessment of Tactile Allodynia in the Rat Paw, J. Neurosci. Methods, 53, 55. Rats are placed into inverted individual plastic cage (20×12.5×20 cm) on top of a suspended wire mesh grid, and are acclimated to the test chambers for 20 minutes. The von Frey filaments are applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses include an abrupt withdrawal of the hind paw from the stimulus, or flinching behavior immediately following removal of the stimulus. A 50% withdrawal threshold can be determined using an up-down procedure (Dixon, W. J., 1980, Efficient Analysis of Experimental Observations, Ann. Rev. Pharmacol. Toxicol., 20, 441).

Capsaicin-Induced Secondary Mechanical Hypersensitivity:

Rats were allowed to acclimate to the study room for 1 hour. They were then briefly restrained, and capsaicin was administered at 10 μg in 10 μL of vehicle (10% ethanol and 2-hydroxypropyl cyclodextrin) by intraplantar injection into the center of the right hind paw. Secondary mechanical hyperalgesia was measured at the heel away from the site of injection at 180 min following capsaicin (Joshi et al 2006, Neuroscience 143, 587-596). Compounds are injected (i.p.) 30 min before testing (150 min post-capsaicin).

Tactile allodynia was measured as described above.

Representative compounds of the present invention showed a statistically significant change in paw withdrawal latency versus a saline vehicle at less than about 300 micromoles/kg. In a more preferred embodiment, compounds of the present invention showed efficacy of less than about 50 micromoles/kg.

MIA-Induced Knee Joint Osteoarthritic Pain Model

Unilateral knee joint osteoarthritis was induced in the rats by a single intra-articular (i.a.) injection of sodium monoiodoacetate (MIA, 3 mg in 0.05 mL sterile isotonic saline) into the right knee joint cavity under light isoflurane anesthesia using a 26 G needle. The dose of the MIA (3 mg/i.a. injection) was selected based on results obtained from preliminary studies wherein an optimal pain behavior was observed at this dose. Pain behavioral assessment of hind limb grip force were conducted by recording the maximum compressive force exerted on the hind limb strain gauge setup, in a commercially available grip force measurement system (Columbus Instruments, Columbus, Ohio). The grip force data was converted to a maximum hindlimb cumulative compressive force (CFmax) (gram force)/kg body weight for each animal. The analgesic effects of test compounds were determined 20 days following the i.a. injection of MIA. The vehicle control group for each compound being tested was assigned 0% whereas the age matched naïve group was assigned as being 100% (normal). The % effects for each dose group was then expressed as % return to normalcy compared to the naïve group. Compounds were administered either orally (p.o.) or intraperitoneally (i.p.). The assessment of the analgesic effects of test compounds is typically made anytime between about 1 hour and about 5 hours following oral administration. The assessment of the analgesic effects of test compounds is typically made anytime between about 0.5 hour and about 2 hours following i.p. administration. Selection of the preferred time points for measuring the analgesic effects of test compounds was based upon consideration of the individual pharmacokinetic characteristics of test compounds in the rat. Time points that were known or expected to provide higher plasma concentrations of test compounds were preferred over those that were known or expected to provide lower concentrations. The assessment of the analgesic effects of test compounds can be made following a single dose or following repeated dosing of test compounds wherein the frequency of dosing is 1 to 2 times daily. The duration of such repeated daily dosing may last for any time greater than or equal to one day. A typical duration of repeated daily dosing is about 5 days to about 12 days.

Representative compounds of the present invention showed a statistically significant change in hind limb grip force strength versus a saline vehicle at less than about 300 micromoles/kg in the MIA model of osteoarthritic pain following a single dose. In a more preferred embodiment, compounds of the present invention showed a statistically significant change in hind limb grip force strength versus a saline vehicle at less than about 50 micromoles/kg in the MIA model of osteoarthritic pain following a single dose.

d. Methods of Using the Compounds

One embodiment of the present invention provides a method for treating pain (for example, neuropathic pain or nociceptive pain) in a mammal (including human) in need of such treatment. The method comprises administering to the mammal a therapeutically effective amount of any of the compounds as described herein, or a pharmaceutically acceptable salt thereof. The method further comprises administration of compounds of the invention as a single dose. The method also comprises repeated or chronic administration of compounds of the invention over a period of days, weeks, months, or longer. In certain embodiments, the method comprises administering to the mammal a therapeutically effective amount of any of the compounds as described herein, or a pharmaceutically acceptable salt thereof, in combination with one or more nonsteroidal anti-inflammatory drug (NSAID), or with other analgesic agent (e.g. acetaminophen), or a combination thereof.

Another embodiment of the present invention provides a method for treating a disorder selected from the group consisting of inflammatory disorders, immune disorders, neurological disorders, cancers of the immune system, respiratory disorders, and cardiovascular disorders in a mammal in need of such treatment. The method comprises administering to the mammal a therapeutically effective amount of a compound of formula (I) or a pharmaceutically acceptable salt thereof.

Yet another embodiment of the present invention relates to a method for providing neuroprotection in a mammal in need of such treatment. This method comprises administering to the mammal a therapeutically effective amount of any compounds described herein or a pharmaceutically acceptable salt thereof.

Another embodiment of the present invention provides a method of increasing the therapeutic effectiveness or potency of compounds of the invention by repeated or chronic administration over a period of days, weeks, or months.

In addition to the data contained herein, several lines of evidence support the assertion that $CB_2$ receptors play a role in analgesia. HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabiniod ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260).

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators may be useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system.—Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands may be clinically useful for the treatment of neuroinflammation.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (i, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators may provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators may possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators may represent a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu. Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators may represent a unique approach for the treatment of liver fibrosis.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators may have utility as antitussive agents for the treatment of pulmonary inflammation, chronic cough, and a variety of airway inflammatory diseases including but not limited to asthma, chronic obstructive pulmonary disease, and pulmonary fibrosis.

There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators may be useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor may be clinically useful for the treatment of atheroscelorsis.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators may have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators may have utility for the treatment or prophylaxis of cardiovascular disease and the development of myocardial infarction.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of compounds of the invention may be required to achieve the desired therapeutic response. "Repeated or chronic administration" refers to the administration of compounds of the invention daily (i.e., every day) or intermittently (i.e., not every day) over a period of days, weeks, months, or longer. In particular, the treatment of chronic painful conditions is anticipated to require such repeated or chronic administration of compounds of the invention. Compounds of the invention may become more effective upon repeated or chronic administration such that the therapeutically effective doses on repeated or chronic administration may be lower than the therapeutically effective dose from a single administration.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

Compounds of the invention may be administered alone, or in combination with one or more other compounds of the invention, or in combination (i.e. co-administered) with one or more additional pharmaceutical agents. For example, a compound the invention, or a pharmaceutically acceptable salt or solvate thereof, may be administered in combination with acetaminophen, or with one or more nonsteroidal anti-inflammatory drug (NSAID) such as, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments of the invention, the nonsteroidal anti-inflammatory drug (NSAID) is ibuprofen. Combination therapy includes administration of a single pharmaceutical dosage formulation containing one or more of the compounds of invention and one or more additional pharmaceutical agents, as well as administration of the compounds of the invention and each additional pharmaceutical agent, in its own separate pharmaceutical dosage formulation. For example, a compound of the invention and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, compounds of the invention and one or more additional pharmaceutical agents may be administered at essentially the same time (e.g., concurrently) or at separately staggered times (e.g., sequentially).

The total daily dose of the compounds of this invention administered to a human or other animal range from about 0.01 mg/kg body weight to about 100 mg/kg body weight. More preferable doses can be in the range of from about 0.03 mg/kg body weight to about 30 mg/kg body weight. If desired, the effective daily dose can be divided into multiple doses for purposes of administration. Consequently, single dose compositions may contain such amounts or submultiples thereof to make up the daily dose. It is understood that the effective daily dose may vary with the duration of the treatment.

e. Pharmaceutical Compositions

The present invention further provides pharmaceutical compositions that comprise compounds of the present invention or a pharmaceutically acceptable salt or solvate thereof. The pharmaceutical compositions comprise compounds of the present invention that may be formulated together with one or more non-toxic pharmaceutically acceptable carriers.

Another aspect of the present invention is a pharmaceutical composition comprising a compound of formula (I), or a pharmaceutically acceptable salt thereof, and one or more pharmaceutically acceptable carriers, alone or in combination with one or more nonsteroidal anti-inflammatory drug (SAID).

The pharmaceutical compositions of this invention can be administered to humans and other mammals orally, rectally, parenterally, intracistemally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. General Synthesis

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups $R^1$, $R^{21}$, $R^{22}$, $R^{24}$, $R^3$, $R^4$, $R^5$, $R^6$, $R^7$, $R^8$, $R^9$, $R^{10}R^{11}$, $R^{12}$, $R^{1a}$, $R^z$, Ring A, $X^1$, and $X^2$ have the meanings as set forth in the summary section unless otherwise noted, can be synthesized as shown in Schemes 1-11.

As used in the descriptions of the schemes and the examples, certain abbreviations are intended to have the following meanings: DMSO for dimethyl sulfonamide, EtOAc for ethyl acetate, $Et_3N$ for triethylamine, MeOH for methanol, OMs or mesylate for methanesulfonate, THF for tetrahydrofuran, and OTs or tosylate for p-toluenesulfonate.

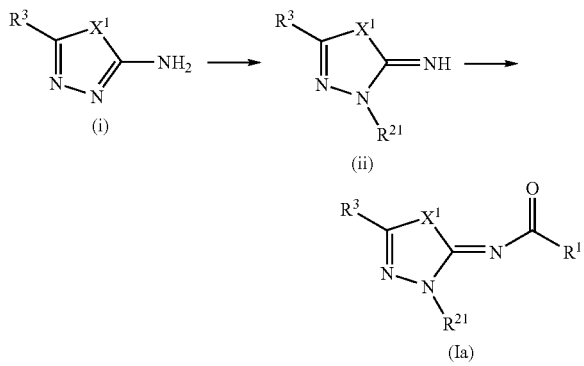

Scheme 1

Compounds of formula (Ia) may be prepared according to the 2-step method illustrated in Scheme 1. Amino compounds of formula (I) can be first reacted with compounds of formula $R^{21}$-$X^{101}$, wherein $X^{101}$ is Cl, Br, I, OTs, or OMs, to form the intermediate (ii). This reaction may be performed either neat or in a solvent such as, but not limited to, tetrahydrofuran, dimethylformamide, dimethylsulfoxide or dioxane, at about room temperature or up to 150° C., and optionally in the presence of a catalyst such as but not limited to tetrabutylammonium iodide or sodium iodide. In certain cases, it may be beneficial to conduct this reaction in the presence of a base such as, but not limited to, triethylamine, potassium carbonate, potassium tert-butoxide or sodium hydride. The intermediate (ii) can be converted to the product (iii) by reaction with an acid chloride ($R^1COCl$) or carboxylic acid ($R^1CO_2H$) under appropriate conditions. For example, intermediate (ii) can be reacted with $R^1COCl$ in a solvent such as, but not limited to, tetrahydrofuran, dimethylformamide or dichloromethane at a temperature from about 25° C. to about 50° C. in the presence of a base such as, but not limited to, triethylamine, diisopropylethylamine or potassium carbonate, and optionally in the presence of a catalyst such as 4-dimethylaminopyridine. Alternatively, intermediate (ii) can be reacted with $R^1CO_2H$ in a solvent such as, but not limited to, tetrahydrofuran or dimethylformamide in the presence of a coupling reagent such as 1,1'-carbonyldiimidazole (CDI), bis (2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), or O-benzotriazol-1-yl-N,N,N',N'-tetramethyluronium tetrafluoroborate (TBTU), in the presence or absence of a coupling auxiliary such as, but not limited to, 1-hydroxy-7-azabenzotriazole (HOAT) or 1-hydroxybenzotriazole hydrate (HOBT). The reaction is generally conducted in the presence or absence of a base such as, but not limited to, N-methyl morpholine, triethylamine, or diisopropylethylamine.

Alternatively, compounds of formula (Ia) can be prepared according to the general procedures as outlined in Scheme 2.

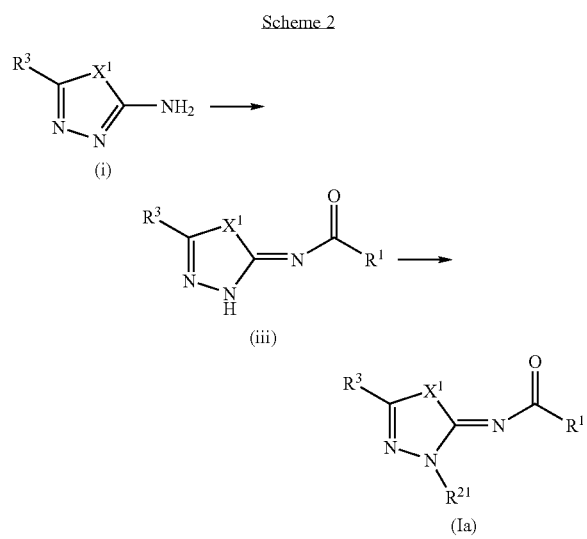

Compounds of formula (I) can be converted to intermediate (iii) by reaction with $R^1COCl$ or $R^1CO_2H$ using reaction conditions as described in Scheme 1. The intermediate (iii) can be converted to (Ia) by reaction with $R^{21}$-$X^{101}$, wherein $X^{101}$ is Cl, Br, I, OTs, or OMs, using reaction conditions as described in Scheme 1 for the transformation of (i) to (ii).

Similarly, compounds of general formula (I) wherein Ring A represents formula (b) or (c) can be prepared from the appropriate heteroarylamines using general procedures as illustrated in Scheme 1 or 2.

Heteroarylamines used to prepare compounds of the invention may be obtained from commercial sources or may be prepared using methods well-known to those skilled in the art. For example, heteroaryl amines of formula (I) wherein $X^1$ is sulfur can be prepared using general procedures as illustrated in Scheme 3.

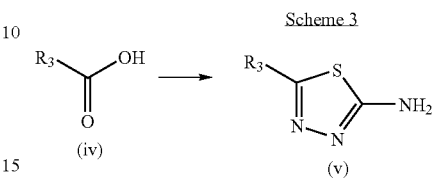

Carboxylic acids of formula (Iv) can be treated with thiosemicarbazide and phosphorus oxychloride at a temperature of about 90° C., in a solvent such as, but not limited to, dioxane to provide compounds of formula (v).

Compounds of general formula (I) wherein $R^1$ is —$N(R^{1a})$ ($R^z$) can be prepared, for example, as illustrated in Scheme 4.

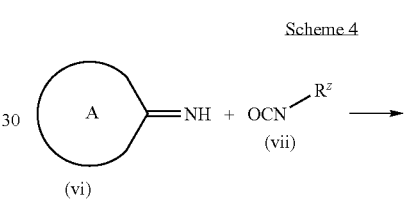

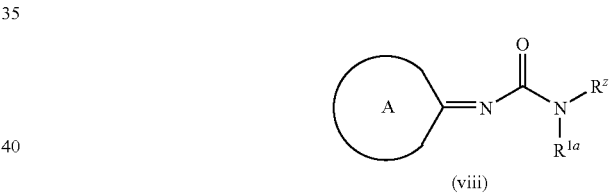

Reaction of compounds of formula (vi) with isocyanates of formula (vii) in a solvent such as, but not limited to, dichloromethane, toluene, dioxane, or dimethylformamide, at a temperature from about 25° C. to about 150° C. provides compounds of formula (viii) wherein $R^{1a}$ is hydrogen. Alternatively, treatment of compounds of formula (vii) with carbamylchlorides of formula $ClCONR^{1a}R^z$ in a solvent such as, but not limited to, dichloromethane, toluene, dioxane, or dimethylformamide, at a temperature from about 25° C. to about 150° C. provides compounds of formula (ix) wherein $R^{1a}$ is other than hydrogen.

Alternatively, compounds of formula (viii) can be prepared using general procedures as shown in Scheme 5.

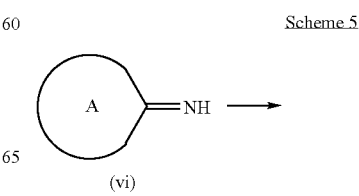

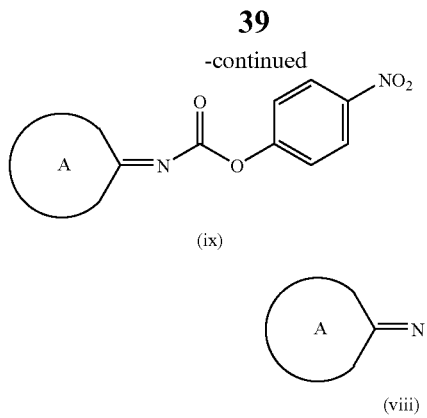

(ix)

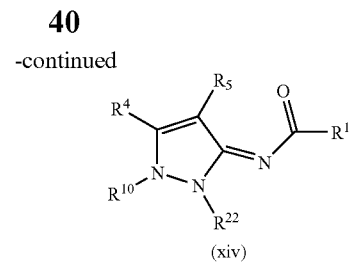

(xiv)

(viii)

Reaction of compounds of formula (vi) with 4-nitrophenylcarbonochloridate in a solvent such as, but not limited to, tetrahydrofuran in the presence of a base such as, but not limited to, diisopropylethylamine, at about room temperature provides the intermediate (ix). The intermediate (ix) may be converted to (viii) by reaction with amines of formula $HNR^{1a}R^z$ in a solvent such as, but not limited to, tetrahydrofuran or dimethylformamide, at temperatures from about 25° C. to about 150° C.

Many other methods for the preparation of ureas are known in the art and can be found, for example, in the following references: Chem. Rev., 1972, 72, 457-496; J. Org. Chem., 1994, 59, 1937-38; Synthesis, 1996, 553-76; Angew. Chem. Int. Ed. Engl., 1987, 26, 894-95; J. Org. Chem., 2003, 68, 7289-97; J. Org. Chem., 1997, 62, 4155-58; Tet. Lett., 1995, 36, 2583-86; Tet. Lett., 1994, 35, 4055-58; Tet. Lett., 1997, 38, 5335-38; Angew. Chem. Int. Ed. Engl., 1995, 34, 2497-2500; Synlett., 1996, 507-08; Synlett., 1996, 502-03; Tet. Lett., 1983, 24, 4569-72; Synthesis, 1989, 423-425; J. Org. Chem., 1996, 61, 4175-79; Tet. Lett., 1998, 39, 7811-14; J. Org. Chem., 1998, 63, 4802-07; and J. Comb. Chem., 1999, 1, 163-172.

Compounds of general formula (I) wherein $X^2$ is $N(R^{10})$ can be synthesized, for example, using the general procedures as outlined in Scheme 6.

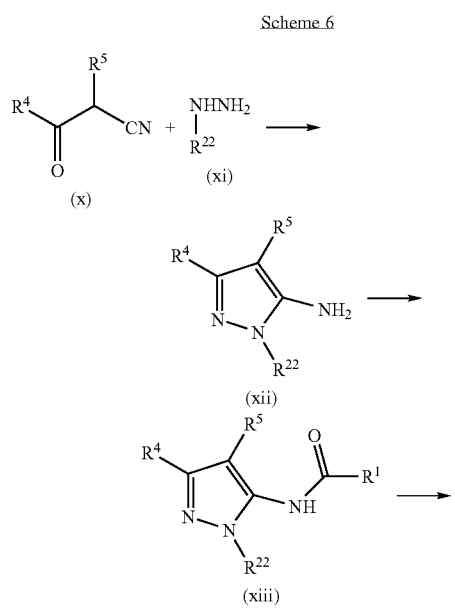

Hydrazines of formula (xi) can be reacted with ketonitriles (x) in a solvent such as, but not limited to, ethanol, at a temperature of between about 0° C. to about 80° C., to provide an intermediates of formula (xii). These intermediate aminopyrazoles (xii) can be treated with carboxylic acids of formula $R^1COOH$, acid chlorides of formula $R^1COCl$, or isocyanates of formula $R^1NCO$ according to the methods outlined in Schemes 1, 2, and 4 to provide pyrazoles (xiii). (xiii) can be converted (xiv) by reaction with an appropriate alkylating agent such as but not limited to a halide, mesylate, tosylate, sulfate or diphenylmethylsulfonium tetrafluoroborate either neat or in a solvent such as but not limited to tetrahydrofuran, toluene, acetonitrile or dioxane. This reaction may be conducted from about 0° C. to about 150° C. In certain cases the addition of a base may be beneficial. Examples of bases that may be used include triethylamine, diisopropylethylamine, potassium carbonate, sodium hydride, sodium hydroxide and lithium diisopropylamide.

Scheme 7 outlines general procedure for synthesizing compounds of general formula (Id).

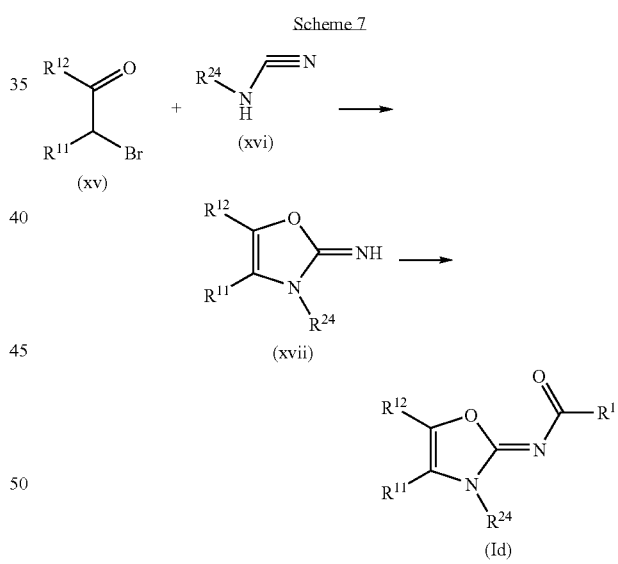

Compounds of formula (xv) when treated with compounds of formula (xvi) which are prepared according to procedures described herein, in the presence of potassium carbonate or sodium carbonate and in a solvent such as, but not limited to, methyl ethyl ketone, at a temperature from about 25° C. to about 100° C. provides intermediates of formula (xvii). Intermediates of formula (xvii) can be converted to compounds of formula (Id) by reaction with $R^1COCl$ or $R^1CO_2H$ using reaction conditions as described in Scheme 1.

Compounds of formula (xvi) can be obtained from reaction of amines of formula $R^{24}NH_2$ with cyanogen bromide in the presence of sodium carbonate or potassium carbonate in a solvent such as, but not limited to, ether, and at a temperature from about −25° C. to about 0° C. Compounds of formula (xiv) can also be prepared using the methods shown in Scheme 8.

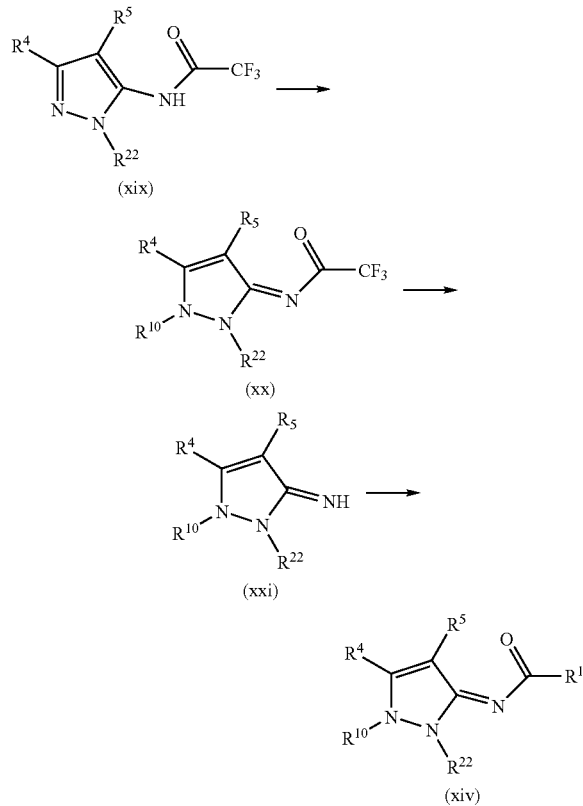

Compounds of formula (xix), prepared from (xii) by reaction with trifluoroacetic anhydride in solvents such as, but not limited to, methylene chloride and in the presence of a base such as, but not limited to, pyridine or triethylamine, can be converted to compounds of formula (xx) using the alkylation conditions of Scheme 6 for the conversion of (xiii) to (xiv). Compounds of formula (xx) can be converted to (xxi) by reaction with aqueous potassium or sodium hydroxide with methanol or ethanol as a co-solvent at temperatures from about room temperature to about 70° C. Compounds (xxi), in turn, can be treated with carboxylic acids of formula $R^1COOH$ or acid chlorides of formula $R^1COCl$ according to the methods outlined in Scheme 1 to give compounds of formula (xiv).

Compounds of formula (xii) can also be prepared using the methods shown in Scheme 9.

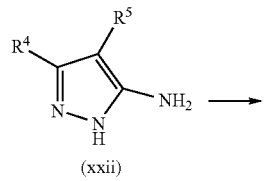

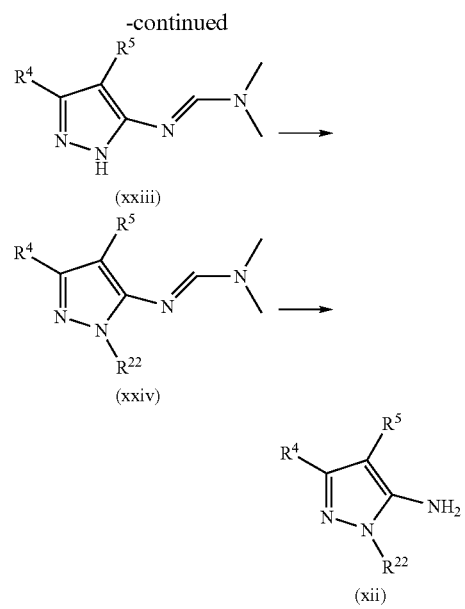

Aminopyrazoles (xxii) can be converted to the amidine intermediates (xxiii) by refluxing in dimethylformamide dimethylacetal or refluxing with a 2- to 3-fold excess of dimethylformamide dimethylacetal in dioxane or other aprotic solvent. Compounds (xxiii), in turn, can be alkylated with reagents $R^{22}$-$X^{202}$ under phase transfer conditions such as, but not limited to, conducting the reaction in a toluene/water mixture with a phase transfer reagent like tetrabutylammonium hydrogensulfate or tetrabutylammonium iodide at a temperature from 50-110° C., with potassium carbonate as base to provide the intermediates (xxiv). The intermediates (xxiv) can be converted to the intermediates (xii) by reaction with hydrazine hydrate in the presence of acetic acid in a solvent such as, but not limited to, dioxane at temperatures from about 50-100° C. The foregoing sequence to install the $R^{22}$ group can also be accomplished by using a triphenylmethyl (trityl) group on the exocyclic nitrogen of (xxii) instead of the amidine. Typical conditions for effecting the analogous alkylation in the presence of a trityl group include, but are not limited to, reaction with an alkylating agent $R^{22}$-$X^{202}$ in the presence of a base such as sodium hydride or potassium tert-butoxide in a solvent such as dimethylformamide or tetrahydrofuran. The trityl protecting group can be removed using methods well-known to those skilled in the art such as, for example, treatment of the compound with an acid such as, but not limited to, hydrochloric acid.

Certain compounds where $G^1$ is phenyl and said phenyl is substituted with the group —$OR^e$ can be prepared using the methods described in Scheme 10.

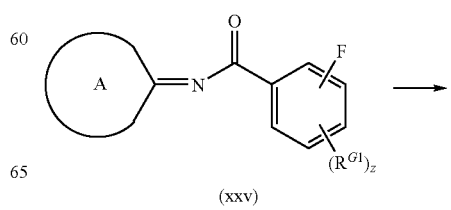

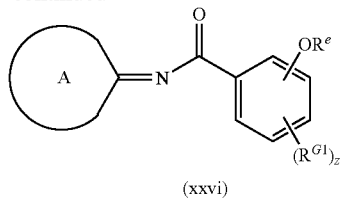

(xxvi)

Compounds of formula (xxvi), wherein the ring A is as defined in formula (I), $R^{G1}$ represents the optional substituents of $G^1$ as defined in formula (I), and z is 0, 1, 2, 3, or 4, can be prepared from compounds of formula (xxv) by reaction with an alcohol $HOR^e$ in the presence of a base such as, but not limited to, potassium tert-butoxide or sodium tert-butoxide in a solvent such as, but not limited to, tetrahydrofuran or dimethylformamide at temperatures between about 0° C. and 50° C. In certain instances, a protecting group may be attached to a functional group present in $R^e$. Such protecting groups can be removed using methods well-known to those skilled in the art. The group $R^e$ can also be further transformed to provide other compounds of the invention using standard chemical techniques well-known to those skilled in the art such as alkylation, acylation, reductive amination, sulfonylation, oxidation, reduction and the like.

Certain compounds wherein $G^1$ is phenyl and said phenyl is substituted with a group $R^{G2}$ wherein $R^{G2}$ is attached to said phenyl through a carbon atom of $R^{G2}$, can be prepared according to the carbon-carbon bond forming reactions described in Scheme 11.

Scheme 11

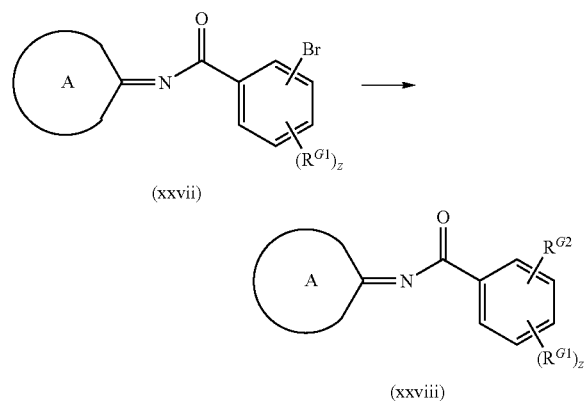

(xxvii)

(xxviii)

Compounds of formula (xxviii), wherein ring A is as described in formula (I), $R^{G1}$ is an optional substituent of $G^1$ as defined in formula (I), z is 0, 1, 2, 3, or 4, and $R^{G2}$ is selected from the group consisting of alkyl, alkenyl, alkynyl, alkoxyalkenyl, hydroxyalkenyl, haloalkyl, —$(CR^jR^k)_q$—CN, —$(CR^jR^k)_q$—$OR^e$, —$(CR^jR^k)_q$—$OC(O)R^e$, —$(CR^jR^k)_q$—$SR^e$, —$(CR^jR^k)_q$—$S(O)R^f$, —$(CR^jR^k)_q$—$S(O)_2R^f$, —$(CR^jR^k)_q$—$N(R^e)(R^g)$, —$(CR^jR^k)_q$—$N(R^g)C(O)R^e$, —$(CR^jR^k)_q$—$N(R^g)S(O)_2R^f$, —$(CR^jR^k)_q$—$N(R^g)C(O)N(R^e)(R^g)$, —$(CR^jR^k)_q$—$N(R^e)(R^g)S(O)_2N(R^e)(R^g)$, —$(CR^jR^k)_q$—$C(O)R^e$, —$(CR^jR^k)_q$—$C(O)OR^e$, —$(CR^jR^k)_q$—$C(O)N(R^e)(R^g)$, and —$C(R^w)$=N—$OR^w$, can be prepared from compounds of formula (xxvii). Reactions well-known in the chemical literature for effecting these transformations include the Suzuki, Heck, Stille, Sonogashira, and Negishi reactions. Typical reaction conditions for can be found in the following references: Negishi, E. A. Handbook of Organopalladium Chemistry for Organic Synthesis; Wiley-Interscience: New York, 2002; Miyaura, N. Cross-Coupling Reactions: A Practical Guide; Springer: New York, 2002. More specifically, where $R^{G2}$ is alkoxyalkenyl or alkenyl, compounds can be prepared using palladium tetrakistriphenyl phosphine as catalyst, cesium fluoride as base with the corresponding boronic acid or boronic ester under microwave conditions at temperatures from 100-140° C. In the conversion of (xxvii) to (xxviii), the —Br of (xxvii) may also be a triflate, —I, —Cl, a boronic acid (or derivative), stannyl or the like.

Compounds of formula (Ib) wherein $X^2$ is O and compounds of formula (Ic) may be prepared respectively from isoxazole-3-amines and pyridine-2-amines using synthetic methods that are analogous to those in Schemes 1, 2, 4, and 5. The starting isoxazole-3-amines and pyridine-2-amines are either commercially available or can be prepared by known synthetic methods described in the chemical literature.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

g. EXAMPLES

Example 1

5-chloro-2-methoxy-N-[(2Z)-3-[(2R)-tetrahydrofuran-2-ylmethyl]-5-[1-(trifluoromethyl)cyclopropyl]-1,3,4-thiadiazol-2(3H)-ylidene]benzamide

Example 1A

5-[1-(trifluoromethyl)cyclopropyl]-1,3,4-thiadiazol-2-amine

A mixture of 1-(trifluoromethyl)cyclopropanecarboxylic acid (1 g, 6.5 mmol) and thiosemicarbazide (0.6 g, 6.5 mmol) in dioxane (8 mL) was heated to 90° C. To the hot reaction mixture was added phosphorus oxychloride (0.6 mL, 6.5 mmol). The reaction mixture was stirred at 90° C. for 16 h. The reaction mixture was then cooled, diluted with ethyl acetate (10 mL) and quenched with saturated $NaHCO_3$ (10 mL). The aqueous layer was extracted with ethyl acetate (2×10 mL). The combined organic extracts were washed with water (15 mL), dried ($Na_2SO_4$), filtered and concentrated. The residue was triturated in hot hexanes to afford 0.5 g (37%) of the title compound. LC/MS ($ESI^+$) m/z 210 $(M+H)^+$.

Example 1B (2R)-tetrahydrofuran-2-ylmethyl 4-methylbenzenesulfonate

The title compound was prepared from commercially available (R)-(tetrahydrofuran-2-yl)methanol (Fluka) according to the procedure as described in Ebata, T.; Kawakami, H.; Koseki, K.; Matsushita, H. Agricultural and Biological Chemistry, 1991, 55(6), 1685-6. MS ($ESI^+$) m/z 257 $(M+H)^+$.

Example 1C

3-[(2R)-tetrahydrofuran-2-ylmethyl]-5-[1-(trifluoromethyl)cyclopropyl]-1,3,4-thiadiazol-2(3H)-imine A mixture of Example 1A (0.15 g, 0.7 mmol), Example 1B (0.20 g, 0.8 mmol) and tetrabutylammonium iodide (0.13 g, 0.36 mmol) in N,N-dimethylformamide (0.2 mL) was heated at 95° C. for 16 hr, cooled to room temperature and quenched with 1M $NaHCO_3$ (10 mL). The aqueous layer was extracted with dichloromethane (3×10 mL). The combined organic extracts were dried ($Na_2SO_4$), filtered and concentrated to afford 0.2 g (crude) of the title compound. LC/MS ($ESI^+$) m/z 294 $(M+H)^+$.

Example 1D 5-chloro-2-methoxy-N-[(2Z)-3-[(2R)-tetrahydrofuran-2-ylmethyl]-5-[1-(trifluoromethyl)cyclopropyl]-1,3,4-thiadiazol-2(3H)-ylidene]benzamide To a solution of Example 1C (crude, 0.2 g, 0.7 mmol) in tetrahydrofuran (10 mL) was added triethylamine (0.3 mL), 4-dimethylaminopyridine (2 mg) and the product from step A of Example 1° C. (0.15 g, 0.7 mmol). The reaction mixture was stirred at room temperature overnight, diluted with ethyl acetate (10 mL), washed with 1M $NaHCO_3$ (10 mL), and the layers were separated. The aqueous layer was extracted with ethyl acetate (2×10 mL). The combined organic extracts were dried ($Na_2SO_4$), filtered and concentrated. The residue was purified by column chromatography using an Analogix® Intelliflash280™ ($SiO_2$, 0-100% ethyl acetate in hexanes) to afford 16 mg (5%) of the title compound. $^1H$ NMR (300 MHz, DMSO-$d_6$) δ ppm 1.53-1.59 (m, 2H), 1.59-1.64 (m, 2H), 1.67-1.79 (m, 1H), 1.79-1.91 (m, 2H), 1.91-2.04 (m, 1H), 3.59-3.70 (m, 1H), 3.71-3.79 (m, 1H), 3.81 (s, 3H), 4.21-4.42 (m, 2H), 4.45-4.57 (m, 1H), 7.16 (d, J=8.7 Hz, 1H), 7.53 (dd, J=9.1, 2.8 Hz, 1H), 7.79 (d, J=2.8 Hz, 1H); MS ($ESI^+$) m/z 462 $(M+H)^+$.

Example 2

5-chloro-N-[(2Z)-5-cyclopropyl-3-(tetrahydrofuran-2-ylmethyl)-1,3,4-thiadiazol-2(3H)-ylidene]-2-methoxybenzamide

Example 2A 5-cyclopropyl-3-(tetrahydrofuran-2-ylmethyl)-1,3,4-thiadiazol-2(3H)-imine 5-cyclopropyl-1,3,4-thiadiazol-2-amine (ASD) and 2-(bromomethyl)tetrahydrofuran (Acros) were processed using the method described in Example 1C to afford the title compound.

Example 2B 5-chloro-N-[(2Z)-5-cyclopropyl-3-(tetrahydrofuran-2-ylmethyl)-1,3,4-thiadiazol-2(3H)-ylidene]-2-methoxybenzamide A mixture of the compound from Example 2A (70 mg, 0.31 mmol), 5-chloro-2-methoxybenzoic acid (64 mg, 0.34 mmol), O-(7-azabenzotriazol-1-yl)-N,N,N',N'-tetramethyluronium hexafluorophosphate (HATU) (185 mg, 0.46 mmol) and triethylamine (130 μL, 0.93 mmol) in N,N-dimethylformamide (5 mL) was stirred at room temperature for 12 hour. The mixture was diluted with water, and extracted with ethyl acetate (3×30 mL). The combined organic layers were dried over $MgSO_4$, filtered and concentrated under reduced pressure. The residue was purified by flash chromatography (silica gel, eluting with ethyl acetate/hexanes 2:3) to provide the title compound. $^1H$ NMR (300 MHz, DMSO-$d_6$) δ ppm 0.95-1.01 (m, 2H) 1.14-1.21 (m, 2H) 1.67-1.78 (m, 1H) 1.79-1.93 (m, 2H) 1.91-2.00 (m, 1H) 2.30-2.39 (m, 1H) 3.65 (dd, J=13.81, 7.06 Hz, 1H) 3.77 (dd, J=13.50, 6.75 Hz, 1H) 3.80 (s, 3H) 4.21 (dd, J=13.20, 4.60 Hz, 1H) 4.31-4.38 (m, 1H) 4.43 (dd, J=12.89, 7.36 Hz, 1H) 7.13 (d, J=8.90 Hz, 1H) 7.49 (dd, J=8.90, 2.76 Hz, 1H) 7.73 (d, J=2.76 Hz, 1H); MS ($ESI^+$) m/z 394 $(M+H)^+$.

Example 3

N-[(2Z)-5-cyclopropyl-3-(tetrahydrofuran-2-ylmethyl)-1,3,4-thiadiazol-2(3H)-ylidene]-2-ethoxybenzamide The product from Example 2A and 2-ethoxybenzoic acid (Aldrich) were processed using the method described in Example 2B to afford the title compound. $^1$H NMR (300 MHz, DMSO-$d_6$) δ ppm 0.95-1.02 (m, 2H) 1.13-1.19 (m, 2H) 1.32 (t, J=7.02 Hz, 3H) 1.65-1.73 (m, 1H) 1.79-1.90 (m, 2H) 1.92-2.00 (m, 1H) 2.30-2.37 (m, 1H) 3.64 (dd, J=13.73, 7.63 Hz, 1H) 3.77 (dd, J=14.34, 7.32 Hz, 1H) 4.07 (q, J=7.02 Hz, 2H) 4.21 (dd, J=13.12, 4.58 Hz, 1H) 4.32-4.39 (m, 1H) 4.44 (dd, J=13.43, 7.63 Hz, 1H) 6.98 (td, J=7.63, 0.92 Hz, 1H) 7.08 (d, J=7.93 Hz, 1H) 7.40-7.45 (m, 1H) 7.77 (dd, J=7.63, 1.83 Hz, 1H); MS (ESI$^+$) m/z 374 (M+H)$^+$.

Example 4

N-[(2Z)-5-tert-butyl-3-[(2R)-tetrahydrofuran-2-ylmethyl]-1,3,4-thiadiazol-2(3H)-ylidene]-5-chloro-2-methoxybenzamide

Example 4A

N-(5-tert-butyl-1,3,4-thiadiazol-2-yl)-5-chloro-2-methoxybenzamide

To a solution of 2-amino-5-tert-butyl-1,3,4-thiadiazole (Aldrich) (2.5 g, 16.3 mmol) in tetrahydrofuran (30 mL) were added 5-chloro-2-methoxybenzoic acid (Aldrich) (3.65 g, 19.6 mmol), triethylamine (5.5 mL, 39.5 mmol), and 1-propanephosphonic acid cyclic anhydride 50% solution in ethyl acetate (Aldrich) (11.6 mL, 19.6 mmol). The reaction mixture was stirred at about room temperature for 14 hours, cooled with external ice bath while quenching with saturated aqueous NaHCO$_3$ (20 mL). The aqueous layer was extracted with ethyl acetate (2×40 mL). The combined organic extracts were dried over anhydrous Na$_2$SO$_4$, filtered and concentrated under reduced pressure. The residue was purified by column chromatography using an Analogix® Intelliflash280™ (SiO$_2$, 0-100% ethyl acetate in hexanes) to afford 4.65 g of the title compound. $^1$H NMR (300 MHz, DMSO-$d_6$) δ ppm 1.43 (s, 9H), 3.88 (s, 3H), 7.22 (d, J=8.7 Hz, 1H), 7.55-7.64 (m, 2H), 12.41 (s, 1H); MS (ESI$^+$) m/z 326 (M+H)$^+$.

Example 4B

N-[(2Z)-5-tert-butyl-3-[(2R)-tetrahydrofuran-2-ylmethyl]-1,3,4-thiadiazol-2(3H)-ylidene]-5-chloro-2-methoxybenzamide To a solution of Example 4A (200 mg, 0.62 mmol) in N,N-dimethylformamide/tetrahydrofuran (1:4, 10 mL) were added a solution of potassium tert-butoxide (Aldrich, 103 mg, 0.92 mmol) and Example IB (189 mg, 0.74 mmol). The reaction mixture was stirred at 80° C. for 16 h, cooled to room temperature, quenched with saturated aqueous NaHCO$_3$ (10 mL). The aqueous layer was extracted with ethyl acetate (3×10 mL). The combined organic extracts were dried over anhydrous Na$_2$SO$_4$, filtered and concentrated under reduced pressure. The residue was purified by column chromatography using an Analogix® Intelliflash280™ (SiO$_2$, 0-1% methanol in dichloromethane) to afford the title compound. $^1$H NMR (300 MHz, DMSO-$d_6$) δ ppm 1.39 (s, 9H), 1.69-2.04 (m, 4H), 3.60-3.70 (m, 1H), 3.73-3.79 (m, 1H), 3.80 (s, 3H), 4.24 (dd, J=4.7, 15.0 Hz, 1H), 4.31-4.42 (m, 1H), 4.49 (dd, J=15.0, 7.5 Hz, 1H), 7.14 (d, J=8.8 Hz, 1H), 7.50 (dd, J=8.8, 2.7 Hz, 1H), 7.73 (d, J=3.1 Hz, 1H); MS (ESI$^+$) m/z 410 (M+H)$^+$.

Example 5

5-chloro-2-methoxy-N-[(2Z)-5-(1-methylcyclopropyl)-3-[(2R)-tetrahydrofuran-2-ylmethyl]-1,3,4-thiadiazol-2(3H)-ylidene]benzamide

Example 5A

5-(1-methylcyclopropyl)-1,3,4-thiadiazol-2-amine

Commercially available, 1-methyl-cyclopropane-1-carboxylic acid (Aldrich), thiosemicarbazide (Aldrich) and phosphorus oxychloride (Aldrich) were processed as described for Example 1A to obtain the title compound. $^1$H NMR (300 MHz, DMSO-$d_6$) δ ppm 0.84-0.93 (m, 2H), 0.93-1.03 (m, 2H), 1.41 (s, 3H), 6.94 (s, 2H); MS (ESI$^+$) m/z 156 (M+H)$^+$.

Example 5B

5-chloro-2-methoxy-N-[5-(1-methylcyclopropyl)-1,3,4-thiadiazol-2-yl]benzamide Example 5A and 5-chloro-2-methoxybenzoic acid (Aldrich) were processed as described for Example 4A to obtain the title compound. $^1$H NMR (300 MHz, DMSO-$d_6$) δ ppm 1.01-1.06 (m, 2H), 1.15-1.22 (m, 2H), 1.54 (s, 3H), 3.87 (s, 3H), 7.22 (d, J=8.8 Hz, 1H), 7.55-7.64 (m, 2H), 12.39 (s, 1H); MS (ESI$^+$) m/z 324 (M+H)$^+$.

Example 5C

5-chloro-2-methoxy-N-[(2Z)-5-(1-methylcyclopropyl)-3-[(2R)-tetrahydrofuran-2-ylmethyl]-1,3,4-thiadiazol-2(3H)-ylidene]benzamide Example 5B and Example 1B were processed as described for Example 4B to obtain the title compound. $^1$H NMR (300 MHz, DMSO-$d_6$) δ ppm 1.03-1.10 (m, 2H), 1.12-1.19 (m, 2H), 1.50 (s, 3H), 1.68-2.01 (m, 4H), 3.60-3.70 (m, 1H), 3.72-3.78 (m, 1H), 3.80 (s, 3H), 4.22 (dd, J=12.9, 4.4 Hz, 1H), 4.30-4.41 (m, 1H), 4.45 (dd, J=12.0, 7.5 Hz, 1H), 7.14 (d, J=8.8 Hz, 1H), 7.50 (dd, J=9.0, 2.9 Hz, 1H), 7.74 (d, J=3.1 Hz, 1H): MS (ESI$^+$) m/z 408 (M+H)$^+$.

Example 6

5-chloro-N-[(2Z)-5-(1,1-dimethylprop-2-ynyl)-3-[(2R)-tetrahydrofuran-2-ylmethyl]-1,3,4-thiadiazol-2(3H)-ylidene]-2-methoxybenzamide

Example 6A

5-(1,1-dimethylprop-2-ynyl)-1,3,4-thiadiazol-2-amine

Commercially available, 2,2-dimethylbut-3-ynoic acid (Betapharma), thiosemicarbazide (Aldrich) and phosphorus oxychloride (Aldrich) were processed as described for Example 1A to obtain the title compound. MS (ESI$^+$) m/z 168 (M+H)$^+$.

Example 6B

5-chloro-N-[5-(1,1-dimethylprop-2-ynyl)-1,3,4-thiadiazol-2-yl]-2-methoxybenzamide To a solution of Example 6A (0.46 g, 2.8 mmol) in tetrahydrofuran (10 mL) was added the product from step A of Example 11C (0.62 g, 3.0 mmol), triethylamine (1.1 mL, 8.2 mmol), and 4-dimethylaminopyridine (3 mg). The reaction mixture was stirred at 60° C. for 14 h, cooled, and quenched with saturated aqueous NaHCO$_3$ (20 mL). The aqueous layer was extracted with ethyl acetate (3×30 mL). The combined organic extracts were dried over anhydrous Na$_2$SO$_4$, filtered and concentrated under reduced pressure. The residue was purified by column chromatography using an Analogix® Intelliflash280™ (SiO$_2$, 0-100% ethyl acetate in hexanes) to afford 0.85 g (44%) of the title compound. MS (ESI$^+$) m/z 336 (M+H)$^+$.

Example 6C

5-chloro-N-[(2Z)-5-(1,1-dimethylprop-2-ynyl)-3-[(2R)-tetrahydrofuran-2-ylmethyl]-1,3,4-thiadiazol-2(3H)-ylidene]-2-methoxybenzamide To a solution of Example 6B (250 mg, 0.75 mmol) in N,N-dimethylformamide/tetrahydrofuran (1:4, 10 mL) was added a solution of potassium tert-butoxide (Aldrich, 125 mg, 1.1 mmol) and Example 1B (285 mg, 1.1 mmol). The reaction mixture was stirred at 80° C. for 16 h, cooled to room temperature, quenched with saturated aqueous NaHCO$_3$ (10 mL). The aqueous layer was extracted with ethyl acetate (3×10 mL). The combined organic extracts were dried over anhydrous Na$_2$SO$_4$, filtered and concentrated under reduced pressure. The residue was purified by column chromatography using an Analogix® Intelliflash280™ (SiO$_2$, 0-1% methanol in dichloromethane) to afford 90 mg (29%) of the title compound. $^1$H NMR (300 MHz, DMSO-d$_6$) δ ppm 1.65 (s, 6H), 1.69-1.81 (m, 1H), 1.80-1.92 (m, 2H), 1.92-2.05 (m, 1H), 3.57 (s, 1H), 3.59-3.72 (m, 1H), 3.72-3.79 (m, 1H), 3.81 (s, 3H), 4.21-4.31 (m, 1H), 4.31-4.43 (m, 1H), 4.44-4.58 (m, 1H), 7.15 (d, J=9.1 Hz, 1H), 7.52 (dd, J=8.9, 3.0 Hz, 1H), 7.77 (d, J=2.8 Hz, 1H); MS (ESI$^+$) m/z 420 (M+H)$^+$.

Example 7

5-chloro-2-methoxy-N-[(2Z)-5-(2,2,3,3-tetrafluoro-1-methylcyclobutyl)-3-[(2R)-tetrahydrofuran-2-ylmethyl]-1,3,4-thiadiazol-2(3H)-ylidene]benzamide

Example 7A

5-(2,2,3,3-tetrafluoro-1-methylcyclobutyl)-1,3,4-thiadiazol-2-amine

A mixture of 2,2,3,3-tetrafluoro-1-methylcyclobutanecarbonyl chloride (ABCR) (2 g, 9.78 mmol) and thiosemicarbazide (Aldrich) (0.891 g, 9.78 mmol) in 10 mL of dioxane was heated at 90° C. for 12 h. The solvent was evaporated under reduced pressure. The residue was dissolved in dichloromethane and washed with saturated NaHCO$_3$. The organic extract was dried over Na$_2$SO$_4$ and concentrated. The residue was purified by flash chromatography on SiO$_2$ (2% methanol in dichloromethane) to give the title compound. MS (ESI$^+$) m/z 242 (M+H)$^+$.

Example 7B

5-chloro-2-methoxy-N-[5-(2,2,3,3-tetrafluoro-1-methylcyclobutyl)-1,3,4-thiadiazol-2-yl]benzamide Example 7A and the product from step A of Example 11C were processed as described for Example 6B to obtain the title compound. LC/MS (ESI$^+$) m/z 410 (M+H)$^+$.

Example 7C

5-chloro-2-methoxy-N-[(2Z)-5-(2,2,3,3-tetrafluoro-1-methylcyclobutyl)-3-[(2R)-tetrahydrofuran-2-ylmethyl]-1,3,4-thiadiazol-2(3H)-ylidene]benzamide Example 7B and Example 1B were processed as described for Example 6C to obtain the title compound. $^1$H NMR (300 MHz, DMSO-d$_6$) δ ppm 1.71 (s, 3H), 1.73-1.99 (m, 4H), 2.91-3.15 (m, 1H), 3.38-3.59 (m, 1H), 3.61-3.71 (m, 1H), 3.71-3.80 (m, 1H), 3.82 (s, 3H), 4.26-4.45 (m, 2H), 4.48-4.64 (m, 1H), 7.17 (d, J=8.8 Hz, 1H), 7.53 (dd, J=9.0, 2.9 Hz, 1H), 7.80 (d, J=3.4 Hz, 1H); MS (ESI$^+$) m/z 494 (M+H)$^+$.

Example 8

5-chloro-2-methoxy-N-[(2Z)-3-[(2R)-tetrahydrofuran-2-ylmethyl]-5-[1-(trifluoromethyl)cyclobutyl]-1,3,4-thiadiazol-2(3H)-ylidene]benzamide

Example 8A

5-[1-(trifluoromethyl)cyclobutyl]-1,3,4-thiadiazol-2-amine

Commercially available, 1-(trifluoromethyl)cyclobutanecarboxylic acid (Oakwood), thiosemicarbazide (Aldrich) and phosphorus oxychloride (Aldrich) were processed as described for Example 1A to obtain the title compound. MS (ESI$^+$) m/z 224 (M+H)$^+$.

Example 8B

3-[(2R)-tetrahydrofuran-2-ylmethyl]-5-[1-(trifluoromethyl)cyclobutyl]-1,3,4-thiadiazol-2(3H)-imine Example 8A and Example 1B were processed as described for Example 1C to obtain the title compound. LC/MS (ESI$^+$) m/z 308 (M+H)$^+$.

Example 8C

5-chloro-2-methoxy-N-[(2Z)-3-[(2R)-tetrahydrofuran-2-ylmethyl]-5-[1-(trifluoromethyl)cyclobutyl]-1,3,4-thiadiazol-2(3H)-ylidene]benzamide Example 8B and the product from step A of Example 1C were processed as described for Example 1D to obtain the title compound. $^1$H NMR (300 MHz, DMSO-d$_6$) δ ppm 1.68-2.17 (m, 6H), 2.70 (t, J=8.1 Hz, 4H), 3.60-3.72 (m, 1H), 3.73-3.80 (m, J=6.6, 6.6 Hz, 1H), 3.81 (s, 3H), 4.27-4.48 (m, 2H), 4.51-4.62 (m, 1H), 7.17 (d, J=8.8 Hz, 1H), 7.53 (dd, J=9.0, 2.9 Hz, 1H), 7.79 (d, J=2.7 Hz, 1H); MS (ESI+) m/z 476 (M+H)+.

Example 9

5-chloro-2-methoxy-N-[(2Z)-3-[(2R)-tetrahydrofuran-2-ylmethyl]-5-(2,2,2-trifluoro-1,1-dimethylethyl)-1,3,4-thiadiazol-2(3H)-ylidene]benzamide

Example 9A 5-(2,2,2-trifluoro-1,1-dimethylethyl)-1,3,4-thiadiazol-2-amine

Commercially available, 3,3,3-trifluoro-2,2-dimethylpropanoic acid (Matrix), thiosemicarbazide (Aldrich) and phosphorus oxychloride (Aldrich) were processed as described for Example 1A to obtain the title compound. MS (ESI+) m/z 212 (M+H)+.

Example 9B 3-[(2R)-tetrahydrofuran-2-ylmethyl]-5-(2,2,2-trifluoro-1,1-dimethylethyl)-1,3,4-thiadiazol-2 (3H)-imine Example 9A and Example 1B were processed as described for Example 1C to obtain the title compound. LC/MS (ESI+) m/z 296 (M+H)+.

Example 9C 5-chloro-2-methoxy-N-[(2Z)-3-[(2R)-tetrahydrofuran-2-ylmethyl]-5-(2,2,2-trifluoro-1,1-dimethylethyl)-1,3,4-thiadiazol-2(3H)-ylidene]benzamide Example 9B and the product from step A of Example 11C were processed as described for Example 1D to obtain the title compound. $^1$H NMR (300 MHz, DMSO-d$_6$) δ ppm 1.64 (s, 6H), 1.69-2.03 (m, 4H), 3.60-3.71 (m, 1H), 3.71-3.79 (m, J=7.5, 7.5 Hz, 1H), 3.81 (s, 3H), 4.23-4.43 (m, 2H), 4.56 (d, 1H), 7.16 (d, J=8.8 Hz, 1H), 7.53 (dd, J=8.8, 2.7 Hz, 1H), 7.79 (d, J=2.7 Hz, 1H); MS (ESI+) m/z 464 (M+H)+.

Example 10

5-chloro-2-methoxy-N-[(2E)-5-methyl-1-(tetrahydrofuran-2-ylmethyl)pyridin-2(1H)-ylidene]benzamide

Example 10A 5-methyl-1-(tetrahydro furan-2-ylmethyl)pyridin-2 (1H)-imine

To a 25 mL, round-bottomed flask containing a magnetic stir bar were added solid 5-methylpyridin-2-amine (1.08 g, 10.0 mmol) and liquid (±)-2-(bromomethyl)tetrahydrofuran (Acros) (2.46 g, 15.0 mmol). A reflux condenser with N$_2$-inlet was attached and a heating mantle was applied. The mixture was heated to 60° C. and stirred overnight. The reaction mixture changed to a brown slurry while heating. After cooling to room temperature, ethyl acetate (20 mL) was added to precipitate the product. The tan solid was collected by vacuum filtration on a glass frit and dried under vacuum to give 2.68 g of the hydrobromide salt of the title compound. The crude product was used without further purification for the next step.

Example 10B 5-chloro-2-methoxy-N-[(2E)-5-methyl-1-(tetrahydrofuran-2-ylmethyl)pyridin-2(1H)-ylidene]benzamide The product of Example 10A (273 mg, 1.00 mmol), solid 5-chloro-2-methoxybenzoic acid (224 mg, 1.20 mmol), and solid 2-(1H-benzo[d][1,2,3]triazol-1-yl)-1,1,3,3-tetramethylisouronium tetrafluoroborate (TBTU) (385 mg, 1.20 mmol) were added to a 20-mL scintillation vial. Anhydrous acetonitrile (8 mL) was added via syringe. Neat triethylamine (486 mg, 669 mL, 4.80 mmol) was added via syringe and the mixture was stirred at room temperature for 24 h. The solvents/volatiles were removed by rotary evaporator. The crude product was dissolved in dichloromethane (10 mL) and washed with saturated NaHCO$_3$ solution (10 mL). The product was purified by flash chromatography (silica gel, 30% ethyl acetate in hexanes) to give 37.9 mg (10%) of the title compound as a white powder. $^1$H NMR (300 MHz, DMSO-d$_6$) δ 1.59-1.68 (m, 1H), 1.78-1.96 (m, 3H), 2.18 (s, 3H), 3.61-3.68 (m, 1H), 3.75 (s, 3H), 3.76-3.84 (m, 1H), 4.03 (dd, J=12.5, 8.1 Hz, 1H), 4.29-4.37 (m, 1H), 4.57 (dd, J=12.9, 3.4 Hz, 1H), 7.03 (d, J=8.8 Hz, 1H), 7.33 (dd, J=8.6, 2.9 Hz, 1H), 7.50 (d, J=2.7 Hz, 1H), 7.65 (dd, J=9.3, 2.2 Hz, 1H), 7.89 (br s, 1H), 8.20 (d, J=9.2 Hz, 1H). (MS (ESI+) m/z 362.1 (M+H)+. Anal. calcd for C$_{19}$H$_{21}$ClN$_2$O$_3$: C, 63.24; H, 5.87; N, 7.76. Found: C, 63.19; H, 5.83; N, 7.82.

Example 11

N-[5-tert-butyl-2-[(2R)-tetrahydrofuran-2-ylmethyl] isoxazol-3(2H)-ylidene]-5-chloro-2-methoxybenzamide

Example 11A (2R)-tetrahydrofuran-2-ylmethyl 4-methylbenzenesulfonate

To (R)-(tetrahydrofuran-2-yl)methanol (1.0 g, 9.8 mmol) in CH$_2$Cl$_2$ (3 mL) and pyridine (3 mL) at ambient temperature was added 4-methylbenzene-1-sulfonyl chloride (2.0 g, 10.3 mmol) portion-wise over 5 minutes. This mixture was stirred for 16 hours at ambient temperature then was quenched with 10 mL of 5% aqueous HCl and was extracted with 3×5 mL CH$_2$Cl$_2$. The combined organics were dried over anhydrous Na$_2$SO$_4$, filtered and concentrated under reduced pressure. The crude material was purified by column chromatography (SiO$_2$, 75% hexanes in ethyl acetate) to give the title compound (1.7 g, 6.8 mmol, 69% yield). MS (DCI/NH$_3$) m/z 257 (M+H)+ and 274 (M+NH$_4$)+.

Example 11B 5-tert-butyl-2-[(2R)-tetrahydrofuran-2-ylmethyl] isoxazol-3(2H)-imine A mixture of 5-tert-butylisoxazol-3-amine (1 g, 7.1 mmol) and the product from Example 11A (1.7 g, 6.8 mmol) in 1.5 mL N,N-dimethylformamide was warmed to 85° C. and was allowed to stir for 70 hours. The mixture was cooled to ambient temperature, concentrated under reduced pressure and purified by column chromatography (SiO$_2$, 50% hexanes in ethyl acetate then 10% CH$_3$OH in ethyl acetate) to provide the p-toluenesulfonate salt of the title compound (0.48 g, 1.2 mmol, 17% yield). MS (DCI/NH$_3$) m/z 225 (M+H)$^+$.

Example 11C

N-[5-tert-butyl-2-[(2R)-tetrahydrofuran-2-ylmethyl] isoxazol-3(2H)-ylidene]-5-chloro-2-methoxybenzamide Step A: 5-chloro-2-methoxybenzoyl chloride
A mixture of 5-chloro-2-methoxybenzoic acid (0.24 g, 1.3 mmol) and thionyl chloride (5 mL) was warmed to reflux and was allowed to stir for 2 hours. The mixture was cooled to ambient temperature, concentrated under reduced pressure and diluted with 10 mL toluene. The reaction mixture was again concentrated under reduced pressure and was again diluted with 10 mL toluene. This concentration and dilution was repeated and the crude product was used without further purification.
Step B
To a solution of the product of Example 11B (0.48 g, 1.2 mmol) in tetrahydrofuran (10 mL) was added triethylamine (0.68 mL, 4.8 mmol) followed by a solution of the product from Step A (1.3 mmol) in tetrahydrofuran (5 mL) via cannula. This mixture was warmed to 50° C. and was allowed to stir for 3 hours. The mixture was cooled to ambient temperature, was quenched with saturated, aqueous NH$_4$Cl (5 mL) and was diluted with ethyl acetate (5 mL). The layers were separated and the aqueous layer was extracted with ethyl acetate (3×5 mL). The combined organic extracts were dried over Na$_2$SO$_4$, filtered and concentrated under reduced pressure. The crude material was purified by column chromatography (SiO$_2$, 60% hexanes in ethyl acetate) to give the title compound (0.34 g, 0.87 mmol, 72% yield). $^1$H NMR (CDCl$_3$, 300 MHz) δ ppm 1.34 (s, 9H), 1.74-1.97 (m, 3H), 1.98-2.11 (m, 1H), 3.74-3.84 (m, 1H), 3.85-3.96 (m, 1H), 3.87 (s, 3H), 4.17-4.25 (m, 1H), 4.27-4.43 (m, 2H), 6.87 (d, J=8.7 Hz, 1H), 7.22 (s, 1H), 7.27-7.32 (m, 1H), 7.82 (d, J=2.8 Hz, 1H); MS (DCI/NH$_3$) m/z 393 (M+H)$^+$; Anal. (C$_{20}$H$_{25}$ClN$_2$O$_4$) Calc: C, 61.14; H, 6.41; N, 7.13. Found: C, 60.97; H, 6.57; N, 7.13.

Example 12

N-{5-tert-butyl-1-methyl-2-[(2S)-tetrahydrofuran-2-ylmethyl]-1,2-dihydro-3H-pyrazol-3-ylidene}-5-chloro-2-methoxybenzamide Example 12A (2S)-tetrahydrofuran-2-ylmethyl 4-methylbenzenesulfonate To (S)-(tetrahydrofuran-2-yl)methanol (2.0 g, 20 mmol) in CH$_2$Cl$_2$ (10 mL) at about 0° C. was added p-toluenesulfonyl chloride (4.2 g, 22.00 mmol), followed by drop-wise addition of triethylamine (5.6 mL, 40.0 mmol). The resulting solution was kept at 0° C. for 2 hours, and then at room temperature for another 2 hours. The reaction mixture was concentrated to dryness and diethylether (200 mL) and water (100 mL) were added. The organic layer was separated, dried over magnesium sulfate, filtered, and concentrated to yield the title compound (2.3 g, 13.00 mmol, 64%) as a colorless oil, which was used in the next step without purification.

Example 12B

[(2S)-tetrahydrofuran-2-ylmethyl]hydrazine

To the product from Example 12A (720 mg, 4.0 mmol) in ethanol (2 mL) was gradually added ice-cooled liquid hydrazine (2560 mg, 80 mmol). The temperature was allowed to rise to room temperature where it was kept for 2 hours before warming to 40° C. and kept at that temperature for 2 hours. The reaction solution was allowed to stand overnight at room temperature and concentrated. The residue was extracted with diethylether (3×60 mL). The combined ether layers were dried over MgSO$_4$, filtered, and concentrated to yield the title compound as a colorless oil (385 mg, 83%).

Example 12C 3-tert-butyl-1-[(2S)-tetrahydrofuran-2-ylmethyl]-1H-pyrazol-5-amine

To a stirred solution of the product from Example 12B (232 mg, 2.0 mmol) in ethanol (4 mL) was added 4,4-dimethyl-3-oxopentanenitrile (250 mg, 2.0 mmol). The mixture was refluxed for 2 hours. The ethanol was removed by evaporation under reduced pressure and the crude product was dissolved in CH$_2$Cl$_2$ (10 mL), which was used directly for the next step.

Example 12D

N-{3-tert-butyl-1-[(2S)-tetrahydrofuran-2-ylmethyl]-1H-pyrazol-5-yl}-5-chloro-2-methoxybenzamide To the mixture of the product from Example 12C (447 mg, 2.0 mmol) and the product from Step A of Example 11C (410 mg, 2.0 mmol) in CH$_2$Cl$_2$ (8 mL) at about 0° C. was added triethylamine (0.34 mL, 2.4 mmol) dropwise. After stirring for 1 hour at room temperature, water (10 mL) was added to quench the reaction, and CH$_2$Cl$_2$ (20 mL) was added. The organic layer was separated, washed with brine, dried over MgSO$_4$, filtered, and concentrated. The residue was purified by chromatography using an Analogix® IT280™ eluting with ethyl acetate/Hexanes in 0-50% gradient to yield the title compound (330 mg, 42%). $^1$H NMR (300 MHz, DMSO-d$_6$) δ ppm 10.26 (s, 1H), 7.81 (d, J=2.71 Hz, 1H), 7.62 (dd, J=8.98, 2.88 Hz, 1H), 7.28 (d, J=9.15 Hz, 1H), 6.31 (s, 1H), 4.05-4.23 (m, 3H), 3.97 (s, 3H), 3.54-3.72 (m, 2H), 1.83-2.01 (m, 1H), 1.62-1.82 (m, 2H), 1.43-1.60 (m, 1H), 1.24 (s, 9H). MS (ESI) m/z 392 (M+H)$^+$.

Example 12E

N-{5-tert-butyl-1-methyl-2-[(2S)-tetrahydrofuran-2-ylmethyl]-1,2-dihydro-3H-pyrazol-3-ylidene}-5-chloro-2-methoxybenzamide To the product from Example 12D (298 mg, 0.76 mmol) in toluene (6 mL) was added dimethylsulfate (0.145 mL, 1.52 mmol). The mixture was heated at 110° C. for 48 hours and concentrated under reduced pressure. The residue was dissolved in 1:1 dimethylsulfoxide/methanol and purified by reverse phase preparative HPLC on a Waters Nova-Pak® HR C18 6 um 60 Å Prep-Pak® cartridge column (40 mm×100 mm) using a gradient of 0% to 70% acetonitrile: 10 mM ammonium acetate over 8 min (10 min run time) at a flow rate of 70 mL/min to yield the title compound (150 mg, 48.6%). $^1$H NMR (300 MHz, DMSO-d$_6$) δ ppm 7.36 (d, J=2.74 Hz, 1H), 7.27 (dd, J=8.77, 2.82 Hz, 1H), 6.98 (d, J=8.69 Hz, 1H), 6.80 (s, 1H), 4.26-4.37 (m, 2H), 4.12-4.20 (m, 1H), 3.87 (s, 3H), 3.73-3.78 (m, 1H), 3.72 (s, 3H), 3.59-3.66 (m, 1H), 1.67-1.92 (m, 4H), 1.37 (m, 9H). MS (ESI) m/z 406 (M+H)$^+$.

Example 13

N-[5-tert-butyl-3-[(2R)-tetrahydrofuran-2-ylmethyl]-1,3-oxazol-2(3H)-ylidene]-5-chloro-2-methoxybenzamide

Example 13A (R)-tetrahydrofuran-2-ylmethyl-cyanamide

To a stirred mixture of cyanogen bromide (2.2 g, 20.8 mmol) and anhydrous $Na_2CO_3$ (4.2 g, 39.6 mmol) in dry ether (30 mL) at about −20 to about −10° C. was added (R)-(tetrahydro-furan-2-yl)-methylamine (Aldrich) (2.0 g, 9.8 mmol) over 10 minutes. Stirring was continued for an additional 1.5 hours at about −20 to about −10° C. Then the mixture was filtered and concentrated to provide 2.21 g of the title product. MS ($DCI/NH_3$) m/z 127 $(M+H)^+$.

Example 13B (R)-5-tert-butyl-3-((tetrahydrofuran-2-yl)methyl)oxazol-2(3H)-imine A mixture of Example 13A (2.35 g, 18.63 mmol), 1-bromo-3,3-dimethylbutan-2-one (Aldrich) (2.52 mL, 18.63 mmol) and potassium carbonate (2.57 g, 18.63 mmol) in 2-butanone (75 mL) was stirred at 80° C. overnight. The mixture was cooled, poured into water, and extracted with ethyl acetate (2×). The combined organic extracts were dried over $Na_2SO_4$, filtered, and concentrated under reduced pressure to afford the title compound. LC/MS ($ESI^+$) m/z 224 $(M+H)^+$.

Example 13C

N-[5-tert-butyl-3-[(2R)-tetrahydrofuran-2-ylmethyl]-1,3-oxazol-2(3H)-ylidene]-5-chloro-2-methoxybenzamide To a solution of Example 13B (1.24 g, 5.53 mmol) in tetrahydrofuran (10 mL) was added N-(3-dimethylaminopropyl)-N-ethylcarbodiimide hydrochloride (1.06 g, 5.53 mmol), 1-hydroxybenzotriazole (0.85 g, 5.55 mmol), triethylamine (0.45 mL, 3.2 mmol) and 5-chloro-2-methoxybenzoic acid (Aldrich) (1.03 g, 5.55 mmol). The mixture was stirred at 80° C. overnight, cooled to room temperature, diluted with ethyl acetate, washed with 1 M aqueous $NaHCO_3$, dried ($Na_2SO_4$), filtered and concentrated. The residue was purified by column chromatography using an Analogix® Intelliflash280™ ($SiO_2$, 0-50% ethyl acetate in hexanes) to provide the title product. MS ($ESI^+$) m/z 393 $(M+H)^+$; $^1H$ NMR (300 MHz, $CDCl_3$) δ ppm 1.20 (s, 9H), 1.59-1.71 (m, 1H), 1.83-1.97 (m, 2H), 2.02-2.14 (m, 1H), 3.66 (dd, J=14.2, 7.5 Hz, 1H), 3.75-3.82 (m, 1H), 3.82 (s, 3H), 3.82-3.92 (m, 1H), 4.07 (dd, J=14.2, 2.7 Hz, 1H), 4.13-4.24 (m, 1H), 6.52 (s, 1H), 6.83 (d, J=8.8 Hz, 1H), 7.27 (dd, J=9.0, 2.7 Hz, 1H), 7.74 (d, J=2.7 Hz, 1H).

Example 14

N-{(3E)-5-tert-butyl-1-methyl-2-[(2R)-tetrahydrofuran-2-ylmethyl]-1,2-dihydro-3H-pyrazol-3-ylidene}-2-ethoxy-5-(trifluoromethyl)benzamide

Example 14A (R)-N-(3-tert-butyl-1-((tetrahydrofuran-2-yl)methyl)-1H-pyrazol-5-yl)-2,2,2-trifluoroacetamide To a solution of the product of Example 45B (4.15 g, 18.6 mmol) and triethylamine (7.8 mL, 55.8 mmol) in $CH_2Cl_2$ (30 mL) at 0° C. was added 2,2,2-trifluoroacetic anhydride (2.6 mL, 18.6 mmol) dropwise via syringe pump over 20 min. The ice-bath was removed after the addition was complete and the mixture was stirred at ambient temperature for 1 h. The mixture was concentrated under reduced pressure and was purified by column chromatography ($SiO_2$, 40% hexanes/EtOAc) to provide the title compound (5.3 g, 16.6 mmol, 89% yield). MS ($DCI/NH_3$) m/z 320 $(M+H)^+$.

Example 14B

N-{(3E)-5-tert-butyl-1-methyl-2-[(2R)-tetrahydrofuran-2-ylmethyl]-1,2-dihydro-3H-pyrazol-3-ylidene}-2,2,2-trifluoroacetamide A mixture of the product of Example 14A (5.3 g, 16.6 mmol) and dimethyl sulfate (4.8 mL, 49.8 mmol) in toluene (7 mL) was warmed to 90° C. and was allowed to stir for 72 h then was cooled to ambient temperature and was concentrated under reduced pressure. The mixture was purified by column chromatography ($SiO_2$, 50% hexanes/EtOAc to 100% EtOAc to 9:1:0.1 EtOAc:MeOH:$Et_3N$) to give the title compound (2.8 g, 8.4 mmol, 51% yield). MS ($DCI/NH_3$) m/z 334 $(M+H)^+$.

Example 14C 5-tert-butyl-1-methyl-2-[(2R)-tetrahydrofuran-2-ylmethyl]-1,2-dihydro-3H-pyrazol-3-imine To a solution of the product of Example 14B (2.3 g, 6.8 mmol) in MeOH (12 mL) was added sodium hydroxide (1.4 g, 34.0 mmol) in water (2.5 mL). This mixture was warmed to 50° C. and was allowed to stir for 16 h then was cooled to ambient temperature. The mixture was concentrated under reduced pressure and then was diluted with 10 mL $CH_2Cl_2$ and 5 mL $H_2O$. The layers were separated and the aqueous layer was extracted with $CH_2Cl_2$ (3×5 mL). The combined organics were dried over anhydrous $Na_2SO_4$, filtered and concentrated under reduced pressure. The crude material was recrystallized from methanol and ethyl acetate to give the title compound (1.6 g, 6.7 mmol, 99% yield). MS ($DCI/NH_3$) m/z 238 $(M+H)^+$.

Example 14D

N-{(3E)-5-tert-butyl-1-methyl-2-[(2R)-tetrahydrofuran-2-ylmethyl]-1,2-dihydro-3H-pyrazol-3-ylidene}-2-ethoxy-5-(trifluoromethyl)benzamide A mixture of 2-ethoxy-5-(trifluoromethyl)benzoic acid (0.20 g, 0.84 mmol) and $SOCl_2$ (5 mL) was warmed to 90° C. for 2 h and then was cooled to ambient temperature and concentrated under reduced pressure. The crude material was diluted with 10 mL toluene and was concentrated again. This dilution/concentration was repeated two additional times to provide 2-ethoxy-5-(trifluoromethyl)benzoyl chloride, that was used directly below.

To a solution of the product of Example 14C (0.20 g, 0.84 mmol) in THF (10 mL) at ambient temperature was added $Et_3N$ (0.47 mL, 3.4 mmol) followed by 2-ethoxy-5-(trifluoromethyl)benzoyl chloride (0.84 mmol). This mixture was warmed to 50° C. and was allowed to stir for 2 h then was cooled to ambient temperature and was quenched with 5 mL saturated, aqueous $NaHCO_3$. EtOAc (10 mL) was added, the layers were separated and the aqueous layer was extracted with EtOAc (3×5 mL). The combined organics were dried over anhydrous $Na_2SO_4$, filtered, concentrated under reduced pressure and purified by column chromatography ($SiO_2$, 100% $CH_2Cl_2$ to 9:1:0.1 $CH_2Cl_2$:$CH_3OH$:$NH_4OH$) to give the title compound (0.11 g, 0.24 mmol, 29% yield). $^1H$ NMR (300 MHz, $CDCl_3$) δ ppm 1.41-1.44 (m, 3H), 1.42 (s, 9H), 1.69-1.90 (m, 3H), 1.94-2.08 (m, 1H), 3.66-3.80 (m, 2H), 3.86 (s, 3H), 4.11-4.26 (m, 3H), 4.28-4.38 (m, 1H), 4.45-4.55 (m, 1H), 6.95 (d, J=8.7 Hz, 1H), 7.06 (s, 1H), 7.48 (dd, J=8.7, 2.4 Hz, 1H), 7.98 (d, J=2.4 Hz, 1H); MS (DCI/$NH_3$) m/z 454 (M+H)$^+$; Anal. calculated for $C_{23}H_{30}F_3N_3O_3$; Calc: C, 60.91; H, 6.67; N, 9.27.; Found: C, 60.75; H, 6.75; N, 9.13.

Example 15

N-{(3E)-5-tert-butyl-1-methyl-2-[(2R)-tetrahydrofuran-2-ylmethyl]-1,2-dihydro-3H-pyrazol-3-ylidene}-3-(pentafluoro-lambda~6~-sulfanyl)benzamide A mixture of 3-(pentafluorothio)benzoic acid (Apollo Scientific, 0.42 g, 1.7 mmol) and $SOCl_2$ (1.2 mL, 16.9 mmol) was warmed to reflux and was allowed to stir for 2 h. The mixture was cooled to ambient temperature and concentrated under reduced pressure. The residue was dissolved in toluene (5 mL) and was concentrated under reduced pressure. This dilution with toluene and concentration was repeated two additional times to remove residual thionyl chloride and afford 3-(pentafluoro-$\lambda^6$-sulfanyl)benzoyl chloride, that was used directly below.

To a mixture of the product of Example 14C (0.20 g, 0.84 mmol) in THF (5 mL) was added $Et_3N$ (0.47 mL, 3.4 mmol) followed by 3-(pentafluoro-$\lambda^6$-sulfanyl)benzoyl chloride (1.7 mmol). This mixture was stirred at ambient temperature for 16 h then the mixture was quenched with saturated, aqueous $NaHCO_3$ (5 mL) and diluted with EtOAc (10 mL). The layers were separated and the aqueous layer was extracted with EtOAc (3×5 mL). The combined organics were dried over anhydrous $Na_2SO_4$, filtered, concentrated under reduced pressure and purified via column chromatography ($SiO_2$, 50% hex/EtOAc to 100% EtOAc to 15% MeOH in EtOAc) to provide the title compound (0.22 g, 0.47 mmol, 56% yield). $^1H$ NMR (300 MHz, $CDCl_3$) δ ppm 1.43 (s, 9H), 1.74-1.92 (m, 3H), 2.01-2.10 (m, 1H), 3.68-3.84 (m, 2H), 3.90 (s, 3H), 4.20-4.30 (m, 1H), 4.37 (dd, J=15.3, 5.8 Hz, 1H), 4.60 (dd, J=15.3, 3.1 Hz, 1H), 7.08 (s, 1H), 7.46 (t, J=8.0 Hz, 1H), 7.75 (ddd, J=8.2, 2.3, 1.0 Hz, 1H), 8.38 (d, J=7.8 Hz, 1H), 8.72 (dd, J=2.2, 1.5 Hz, 1H); MS (DCI/$NH_3$) m/z 468 (M+H)$^+$. Anal. calculated for $C_{20}H_{26}F_5N_3O_2S$; Calc: C, 51.38; H, 5.61; N, 8.99. Found: C, 51.35; H, 5.58; N, 8.82.

Example 16

N-{(3E)-5-tert-butyl-1-methyl-2-[(2R)-tetrahydrofuran-2-ylmethyl]-1,2-dihydro-3H-pyrazol-3-ylidene}-2-[(cis-3-hydroxycyclobutyl)methoxy]-5-(trifluoromethyl)benzamide

Example 16A

N-{3-tert-butyl-1-[(2R)-tetrahydrofuran-2-ylmethyl]-1H-pyrazol-5-yl}-2-fluoro-5-(trifluoromethyl)benzamide To a solution of the product of Example 45B (7.8 g, 35.0 mmol) and triethylamine (14.6 mL, 105 mmol) in THF (60 mL) at ambient temperature was added 2-fluoro-5-(trifluoromethyl)benzoyl chloride (5.3 mL, 35.0 mmol) dropwise over 10 min. The mixture was stirred at ambient temperature for 3 h. The mixture was quenched with saturated, aqueous $NaHCO_3$ (20 mL) and diluted with EtOAc (20 mL). The layers were separated and the aqueous layer was extracted with EtOAc (3×10 mL). The combined organics were dried over anhydrous $Na_2SO_4$, filtered and concentrated under reduced pressure. Purification by column chromatography ($SiO_2$, 40% hexanes/EtOAc) gave the title compound (11.0 g, 26.6 mmol, 76% yield). MS (DCI/$NH_3$) m/z 414 (M+H)$^+$.

Example 16B

N-{(3E)-5-tert-butyl-1-methyl-2-[(2R)-tetrahydrofuran-2-ylmethyl]-1,2-dihydro-3H-pyrazol-3-ylidene}-2-fluoro-5-(trifluoromethyl)benzamide A mixture of the product of Example 16A (14.2 g, 34.3 mmol) and dimethyl sulfate (9.9 mL, 103 mmol) in toluene (40 mL) was warmed to 90° C. and was allowed to stir for 18 h then was cooled to ambient temperature. The mixture was concentrated under reduced pressure and was purified by column chromatography ($SiO_2$, 50% hexanes/EtOAc to 100% EtOAc to 9:1:0.1 EtOAc:MeOH:$Et_3N$) to give the title compound (10.0 g, 23.4 mmol, 68% yield). MS (DCI/$NH_3$) m/z 428 (M+H)$^+$.

Example 16C (cis-3-(benzyloxymethyl)cyclobutoxy)(tert-butyl)dimethylsilane

To a solution of cis-3-(benzyloxymethyl)cyclobutanol (Albany Molecular, 1.0 g, 5.2 mmol) in $CH_2Cl_2$ (20 mL) was added imidazole (0.71 g, 10.4 mmol), DMAP (64 mg, 0.52 mmol) and tert-butyldimethylsilylchloride (TBSCl) (1.6 g, 10.4 mmol). This mixture was stirred at ambient temperature for 16 h, quenched with saturated, aqueous $NH_4Cl$ (5 mL) and diluted with EtOAc (10 mL). The layers were separated and the aqueous layer was extracted with EtOAc (3×5 mL). The combined organics were dried over anhydrous $Na_2SO_4$, filtered, concentrated under reduced pressure and purified via column chromatography ($SiO_2$, 50% hexanes/EtOAc) to give the title compound (1.15 g, 3.8 mmol, 72% yield). MS (DCI/$NH_3$) m/z 307 (M+H)$^+$.

Example 16D (cis-3-(tert-butyldimethylsilyloxy)cyclobutyl)methanol

A solution of the product of Example 16C (1.15 g, 3.8 mmol) in ethanol (20 mL) was degassed three times with a $N_2$ back-flush each time. Palladium on carbon (0.080 g, 0.75 mmol) was added and the mixture was degassed three times with an $N_2$ back-flush each time. The system was put under 1 atm of $H_2$ (balloon) and was allowed to stir at ambient temperature for 72 h at which time the mixture was degassed three times with a $N_2$ backflush each time. The mixture was filtered through Celite, concentrated under reduced pressure and purified via column chromatography ($SiO_2$, 50% hexanes/EtOAc) to give the title product (0.75 g, 3.5 mmol, 92% yield). MS (DCI/$NH_3$) m/z 217 (M+H)$^+$.

Example 16E

2-[(cis-3-{[tert-butyl(dimethyl)silyl]oxy}cyclobutyl)methoxy]-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide To a solution of the product of Example 16D (0.16 g, 0.75 mmol) in THF (5 mL) was added KOt-Bu (0.13 g, 1.1 mmol).

This mixture was stirred at ambient temperature for 20 min then the product of Example 16B (0.16 g, 0.37 mmol) in THF (5 mL) was added via cannula. The mixture was stirred at ambient temperature for 6 h. The mixture was quenched with saturated, aqueous NaHCO$_3$ (5 mL) and diluted with EtOAc (5 mL). The layers were separated and the aqueous layer was extracted with EtOAc (3×5 mL). The combined organics were dried over anhydrous Na$_2$SO$_4$, filtered, concentrated under reduced pressure and purified via column chromatography (SiO$_2$, 100% EtOAc to 10% MeOH in EtOAc) to provide the title compound (0.12 g, 0.19 mmol, 51% yield). MS (DCI/NH$_3$) m/z 624 (M+H)$^+$.

Example 16F

N-{(3E)-5-tert-butyl-1-methyl-2-[(2R)-tetrahydrofuran-2-ylmethyl]-1,2-dihydro-3H-pyrazol-3-ylidene}-2-[(cis-3-hydroxycyclobutyl)methoxy]-5-(trifluoromethyl)benzamide To a solution of the product of Example 16E (0.12 g, 0.19 mmol) in THF (5 mL) was added tetrabutylammonium fluoride (TBAF) (1M in THF, 0.39 mL, 0.39 mmol). This mixture was stirred at ambient temperature for 3 h then the mixture was concentrated under reduced pressure and purified via column chromatography (SiO$_2$, 50% hex/EtOAc to 100% EtOAc to 9:1:0.1 EtOAc, MeOH:Et$_3$N) to give the title compound (40 mg, 0.078 mmol, 41% yield). $^1$H NMR (300 MHz, CDCl$_3$) δ ppm 1.42 (s, 9H), 1.70-1.94 (m, 3H), 1.98-2.12 (m, 1H), 2.22-2.43 (m, 3H), 2.48-2.63 (m, 2H), 3.68-3.83 (m, 2H), 3.86 (s, 3H), 4.00 (d, J=2.0 Hz, 2H), 4.07-4.18 (m, 1H), 4.18-4.26 (m, 1H), 4.25-4.34 (m, 1H), 4.35-4.47 (m, 1H), 4.53 (dd, J=15.3, 3.1 Hz, 1H), 6.92 (d, J=8.8 Hz, 1H), 7.03 (s, 1H), 7.51 (dd, J=8.5, 1.7 Hz, 1H), 8.11 (d, J=2.0 Hz, 1H); MS (DCI/NH$_3$) m/z 510 (M+H)$^+$; Anal. calculated for C$_{26}$H$_{34}$F$_3$N$_3$O$_4$; Calc: C, 61.28; H, 6.73; N, 8.25. Found: C, 61.34; H, 6.80; N, 8.21.

Example 17

N-{(3E)-5-tert-butyl-1-methyl-2-[(2R)-tetrahydrofuran-2-ylmethyl]-1,2-dihydro-3H-pyrazol-3-ylidene}-2-[(3-oxocyclobutyl)methoxy]-5-(trifluoromethyl)benzamide To a solution of the product of Example 16F (0.38 g, 0.75 mmol) in CH$_2$Cl$_2$ (10 mL) at ambient temperature was added N-methylmorpholine N-oxide (0.44 g, 3.7 mmol) and a small amount of 4 Å powdered molecular sieves (~200 mg). The mixture was stirred for 10 min then was cooled to 0° C. Tetrapropylammonium perruthenate (TPAP, 0.039 g, 0.11 mmol) was added portion-wise and the mixture was stirred at 0° C. for 30 min then was allowed to warm to ambient temperature and was stirred for 2 h. The mixture was filtered through Celite and the filtrate was concentrated under reduced pressure. The crude material was purified via column chromatography (SiO$_2$, 50% hexanes/EtOAc to 100% EtOAc to 9:1:0.1 EtOAc/MeOH/Et$_3$N) to give the title compound (0.19 g, 0.37 mmol, 50% yield). $^1$H NMR (300 MHz, CDCl$_3$) δ ppm 1.43 (s, 9H), 1.66-1.90 (m, 3H), 1.94-2.06 (m, 1H), 2.82-2.99 (m, 1H), 3.10-3.17 (m, 4H), 3.65-3.79 (m, 2H), 3.86 (s, 3H), 4.13-4.20 (m, 1H), 4.24 (d, J=5.8 Hz, 2H), 4.26-4.33 (m, 1H), 4.47 (dd, J=15.3, 3.4 Hz, 1H), 6.96 (s, 1H), 6.98 (d, J=8.8 Hz, 1H), 7.49 (dd, J=8.8, 2.0 Hz, 1H), 7.93 (d, J=2.4 Hz, 1H); MS (DCI/NH$_3$) m/z 508 (M+H)$^+$. Anal. calculated for C$_{26}$H$_{32}$F$_3$N$_3$O$_4$.0.5H$_2$O; Calc: C, 60.45; H, 6.44; N, 8.13. Found: C, 60.22; H, 6.28; N, 8.06.

Example 18

N-{(3E)-5-tert-butyl-1-methyl-2-[(2R)-tetrahydrofuran-2-ylmethyl]-1,2-dihydro-3H-pyrazol-3-ylidene}-2-[(cis-3-methoxycyclobutyl)methoxy]-5-(trifluoromethyl)benzamide Example 18A (((cis-3-methoxycyclobutyl)methoxy)methyl)benzene To a solution of cis-3-(benzyloxymethyl)cyclobutanol (Albany Molecular, 0.76 g, 4.0 mmol) in THF (10 mL) at 0° C. was added sodium hydride (0.47 g, 11.9 mmol). The mixture was stirred at 0° C. for 15 min then iodomethane (0.37 mL, 5.9 mmol) was added. The mixture was stirred for 5 min then the ice-bath was removed and the mixture was stirred at ambient temperature for 16 h. The mixture was quenched with 5 mL saturated, aqueous NaHCO$_3$ and diluted with 5 mL EtOAc. The layers were separated and the aqueous layer was extracted with EtOAc (3×5 mL). The combined organics were dried over anhydrous Na$_2$SO$_4$, filtered, concentrated under reduced pressure and purified via column chromatography (SiO$_2$, 75% hexanes/EtOAc) to provide the title compound (0.69 g, 3.3 mmol, 85% yield). MS (DCI/NH$_3$) m/z 207 (M+H)$^+$.

Example 18B (cis-3-methoxycyclobutyl)methanol

A solution of the product of Example 18A (0.69 g, 3.3 mmol) in ethyl acetate (10 mL) was degassed three times with a N$_2$ back-flush each time. Palladium on carbon (0.071 g, 0.067 mmol) was added and the mixture was again degassed three times with a nitrogen back-flush each time. The reaction mixture was put under 1 atm of hydrogen (balloon) and was allowed to stir for 70 h. The mixture was degassed three times with a nitrogen back-flush each time then was filtered through Celite and the filtrate was concentrated under reduced pressure to give the title compound (0.38 g, 3.3 mmol, 98% yield). MS (DCI/NH$_3$) m/z 117 (M+H)$^+$.

Example 18C

N-{(3E)-5-tert-butyl-1-methyl-2-[(2R)-tetrahydrofuran-2-ylmethyl]-1,2-dihydro-3H-pyrazol-3-ylidene}-2-[(cis-3-methoxycyclobutyl)methoxy]-5-(trifluoromethyl)benzamide To a solution of the product of Example 18B (0.2 g, 1.7 mmol) in THF (10 mL) was added KOt-Bu (1 M in THF, 2.6 mL, 2.6 mmol). This mixture was stirred at ambient temperature for 20 min then the product of Example 16B (0.37 g, 0.86 mmol) in THF (5 mL) was added via cannula. The mixture was stirred at ambient temperature for 6 h then was quenched with saturated, aqueous NaHCO$_3$ (5 mL) and diluted with EtOAc (5 mL). The layers were separated and the aqueous layer was extracted with EtOAc (3×5 mL). The combined organics were dried over anhydrous Na$_2$SO$_4$, filtered, concentrated under reduced pressure and purified via column chromatography (SiO$_2$, 50% hexanes/EtOAc to 100% EtOAc to 9:1:0.1 EtOAc/MeOH/Et$_3$N) to provide the title compound (0.39 g, 0.75 mmol, 87% yield). $^1$H NMR (300 MHz, CDCl$_3$)

δ ppm 1.43 (s, 9H), 1.70-1.80 (m, 4H), 1.82-1.89 (m, 1H), 1.95-2.09 (m, 1H), 2.30-2.45 (m, 3H), 3.20 (s, 3H), 3.67-3.80 (m, 3H), 3.85 (s, 3H), 4.07 (d, J=6.1 Hz, 2H), 4.13-4.23 (m, 1H), 4.30 (dd, J=15.3, 5.8 Hz, 1H), 4.49 (dd, J=15.3, 3.1 Hz, 1H), 6.93 (d, J=8.8 Hz, 1H), 7.01 (s, 1H), 7.46 (dd, J=8.5, 2.0 Hz, 1H), 7.94 (d, J=2.4 Hz, 1H); MS (DCI/NH$_3$) m/z 524 (M+H)$^+$; Anal. calculated for $C_{27}H_{36}F_3N_3O_4 \cdot 0.2H_2O$; Calc: C, 61.51; H, 6.96; N, 7.97. Found: C, 61.33; H, 7.19; N, 8.10.

Example 19

N-{(3E)-5-tert-butyl-1-methyl-2-[(2R)-tetrahydrofuran-2-ylmethyl]-1,2-dihydro-3H-pyrazol-3-ylidene}-2-[(3,3-difluorocyclobutyl)methoxy]-5-(trifluoromethyl)benzamide Example 19A (3,3-difluorocyclobutyl)methanol To a solution of 3,3-difluorocyclobutanecarboxylic acid (Parkway Scientific, 1.0 g, 7.4 mmol) in THF (20 mL) at −10° C. was added N-methylmorpholine (0.81 mL, 7.4 mmol). The mixture was stirred for 1 min then ethyl chloroformate (0.70 mL, 7.4 mmol) was added dropwise. This mixture was stirred at −10° C. for 15 min then was filtered through Celite and the filtrate was added dropwise via syringe to a mixture of NaBH$_4$ (0.63 g, 16.5 mmol) in water (10 mL) at 5° C. The ice-bath was removed after the addition was complete and the mixture was stirred at ambient temperature for 2 h. The mixture was quenched with saturated, aqueous NH$_4$Cl (10 mL) and diluted with EtOAc (10 mL). The layers were separated and the aqueous layer was extracted with EtOAc (3×5 mL). The combined organics were dried over anhydrous Na$_2$SO$_4$, filtered and concentrated under reduced pressure to give the title compound (1.0 g, 8.2 mmol, 111% yield) which was used without further purification. $^1$H NMR (300 MHz, CDCl$_3$) δ ppm 1.81-1.89 (m, 1H), 2.26-2.43 (m, 2H), 2.57-2.70 (m, 2H), 3.70 (t, J=5.2 Hz, 2H), 3.72-3.77 (m, 1H).

Example 19B

N-{(3E)-5-tert-butyl-1-methyl-2-[(2R)-tetrahydrofuran-2-ylmethyl]-1,2-dihydro-3H-pyrazol-3-ylidene}-2-[(3,3-difluorocyclobutyl)methoxy]-5-(trifluoromethyl)benzamide To a solution of the product of Example 19A (0.21 g, 1.8 mmol) in THF (5 mL) was added KOt-Bu (0.33 g, 2.9 mmol). This mixture was stirred at ambient temperature for 20 min then the product of Example 16B (0.25 g, 0.59 mmol) in THF (5 mL) was added via cannula. The mixture was stirred at ambient temperature for 1 h then was quenched with saturated, aqueous NaHCO$_3$ (5 mL) and diluted with EtOAc (5 mL). The layers were separated and the aqueous layer was extracted with EtOAc (3×5 mL). The combined organics were dried over anhydrous Na$_2$SO$_4$, filtered, concentrated under reduced pressure and purified via column chromatography (SiO$_2$, 100% EtOAc to 10% MeOH in EtOAc) to provide the title compound (0.20 g, 0.34 mmol, 65% yield). $^1$H NMR (300 MHz, CDCl$_3$) δ ppm 1.43 (s, 9H), 1.69-1.80 (m, 2H), 1.81-1.91 (m, 1H), 1.95-2.03 (m, 1H), 2.49-2.72 (m, 5H), 3.69-3.80 (m, 3H), 3.86 (s, 3H), 4.08-4.14 (m, 2H), 4.14-4.20 (m, 1H), 4.29 (dd, J=15.3, 5.4 Hz, 1H), 4.48 (dd, J=15.3, 3.1 Hz, 1H), 6.94 (d, J=8.8 Hz, 1H), 6.98 (s, 1H), 7.48 (dd, J=8.8, 1.7 Hz, 1H), 7.91 (d, J=2.0 Hz, 1H); MS (DCI/NH$_3$) m/z 530 (M+H)$^+$; Anal. calculated for $C_{26}H_{32}F_5N_3O_3$; Calc: C, 58.97; H, 6.09; N, 7.94. Found: C, 58.78; H, 6.16; N, 7.86.

Example 20

N-{(3E)-5-tert-butyl-1-methyl-2-[(2R)-tetrahydrofuran-2-ylmethyl]-1,2-dihydro-3H-pyrazol-3-ylidene}-2-(3-methoxy-3-methylbutoxy)-5-(trifluoromethyl)benzamide Potassium t-butoxide (0.47 mL, 1M in THF) was added to 3-methoxy-3-methylbutan-1-ol (58 mg, 0.49 mmol) in 0.25 mL of THF and stirred for 10 minutes. Example 16B (0.1 g, 0.23 mmol) in 0.6 mL of THF was added and the mixture stirred for 3 hours. The mixture was diluted with dichloromethane, 15 µL of glacial acetic acid was added and the resulting mixture filtered, loaded onto silica and chromatographed (0 to 25% MeOH in EtOAc) to afford the title compound (0.05 g, 0.1 mmol, 41% yield). $^1$H NMR (300 MHz, CDCl$_3$) δ ppm 1.21 (s, 6H), 1.42 (s, 9H), 1.70-1.93 (m, 3H), 1.96-2.11 (m, 3H), 3.19 (s, 3H), 3.63-3.81 (m, 2H), 3.86 (s, 3H), 4.13-4.24 (m, 3H), 4.26-4.37 (m, 1H), 4.44-4.56 (m, 1H), 6.98 (d, J=8.8 Hz, 1H), 7.03 (s, 1H), 7.49 (dd, J=8.8, 1.7 Hz, 1H), 7.95 (d, J=2.4 Hz, 1H). MS (DCI/NH$_3$) m/z 526.3 (M+H)$^+$. Analytical calculated for $C_{27}H_{38}F_3N_3O_4$: C, 61.70; H, 7.29; N, 7.99. Found: C, 61.43; H, 7.38; N, 7.84.

Example 21

N-{(3E)-5-tert-butyl-1-methyl-2-[(2R)-tetrahydrofuran-2-ylmethyl]-1,2-dihydro-3H-pyrazol-3-ylidene}-2-(2,2,2-trifluoroethoxy)-5-(trifluoromethyl)benzamide Potassium t-butoxide (0.47 mL, 1M in THF) was added to 2,2,2-trifluoroethanol (35 µL, 0.49 mmol) in 0.25 mL THF and stirred for 10 minutes. Example 16B (0.1 g, 0.23 mmol) in 0.25 mL of THF was added and the resulting mixture stirred for 3 hours. The mixture was diluted with dichloromethane, 25 µL glacial acetic acid was added, the mixture filtered, loaded onto silica and chromatographed (0 to 25% MeOH in EtOAc) to afford the title compound (0.05 g, 0.1 mmol, 42% yield). $^1$H NMR (300 MHz, CDCl$_3$) δ ppm 1.44 (s, 9H), 1.61-1.81 (m, 2H), 1.81-1.94 (m, 1H), 1.96-2.10 (m, 1H), 3.63-3.84 (m, 2H), 3.90 (s, 3H), 4.12-4.24 (m, 1H), 4.26-4.39 (m, 1H), 4.46-4.57 (m, 2H), 4.53-4.63 (m, 1H), 7.01 (s, 1H), 7.08 (d, J=8.5 Hz, 1H), 7.49-7.56 (m, 1H), 8.11 (d, J=2.4 Hz, 1H). MS (DCI/NH$_3$) m/z 508.2 (M+H)$^+$. Analytical calculated for $C_{23}H_{27}F_6N_3O_3$: C, 54.44; H, 5.36; N, 8.28. Found: C, 54.05; H, 5.35; N, 7.86.

Example 22

N-{(3E)-5-tert-butyl-1-methyl-2-[(2R)-tetrahydrofuran-2-ylmethyl]-1,2-dihydro-3H-pyrazol-3-ylidene}-2-(2-fluoroethoxy)-5-(trifluoromethyl)benzamide To potassium t-butoxide (0.47 mL, 1M in THF) was added 2-fluoroethanol (30 µL, 0.49 mmol) and stirred for 10 minutes. Example 16B (0.1 g, 0.23 mmol) in 0.6 mL of THF was added and the mixture stirred at ambient temperature for 2 hours. The mixture was diluted with dichloromethane, 15 µL of glacial acetic acid was added, the solution filtered, loaded onto silica and chromatographed (0 to 20% MeOH in EtOAc (0.1% NH$_4$OH)) to afford the title compound (0.04 g, 0.09 mmol, 36% yield). $^1$H NMR (300 MHz, CDCl$_3$) δ ppm 1.43

(s, 9H), 1.68-1.79 (m, 2H), 1.79-1.93 (m, 1H), 1.94-2.09 (m, 1H), 3.66-3.82 (m, 2H), 3.88 (s, 3H), 4.14-4.25 (m, 1H), 4.26-4.37 (m, 2H), 4.37-4.43 (m, 1H), 4.47-4.58 (m, 1H), 4.64-4.73 (m, 1H), 4.78-4.90 (m, 1H), 7.00 (d, J=9.1 Hz, 1H), 7.02 (s, 1H), 7.50 (dd, J=8.5, 2.6 Hz, 1H), 8.01 (d, J=2.0 Hz, 1H). MS (DCI/NH$_3$) m/z 472.3 (M+H)$^+$. Analytical calculated for C$_{23}$H$_{29}$F$_4$N$_3$O$_3$: C, 58.59; H, 6.20; N, 8.91. Found: C, 58.48; H, 6.25; N, 8.79.

Example 23

N-{(3E)-5-tert-butyl-1-methyl-2-[(2R)-tetrahydrofuran-2-ylmethyl]-1,2-dihydro-3H-pyrazol-3-ylidene}-2-(2-methoxyethoxy)-5-(trifluoromethyl)benzamide Potassium t-butoxide (0.47 mL, 1M in THF) was added to 2-methoxyethanol (39 μL, 0.49 mmol) and stirred for 10 minutes. Example 16B (0.1 g, 0.23 mmol) in 0.6 mL of THF was added and the mixture stirred for 2 hours. The mixture was diluted with dichloromethane, 15 μL of glacial acetic acid was added and the resulting mixture filtered, loaded onto silica and chromatographed (0 to 20% MeOH in CH$_2$Cl$_2$ (0.1% NH$_4$OH)) to afford the title compound (0.04 g, 0.08 mmol, 35% yield). $^1$H NMR (300 MHz, CDCl$_3$) δ ppm 1.43 (s, 9H), 1.70-1.82 (m, 2H), 1.81-1.94 (m, 1H), 1.95-2.09 (m, 1H), 3.41 (s, 3H), 3.66-3.75 (m, 2H), 3.78 (t, J=5.4 Hz, 2H), 3.86 (s, 3H), 4.14-4.23 (m, 1H), 4.23-4.28 (m, 2H), 4.28-4.37 (m, 1H), 4.45-4.55 (m, 1H), 6.98-7.05 (m, 2H), 7.49 (dd, J=8.5, 1.7 Hz, 1H), 7.99 (d, J=2.4 Hz, 1H). MS (DCI/NH$_3$) m/z 484.3 (M+H)$^+$. Analytical calculated for C$_{24}$H$_{32}$F$_3$N$_3$O$_4$: C, 59.62; H, 6.67; N, 8.69. Found: C, 59.50; H, 6.73; N, 8.52.

Example 24

N-{(3E)-5-tert-butyl-1-methyl-2-[(2R)-tetrahydrofuran-2-ylmethyl]-1,2-dihydro-3H-pyrazol-3-ylidene}-2-hydroxy-5-(trifluoromethyl)benzamide The title compound was obtained as the unexpected product in the reaction of 3-(hydroxymethyl)cyclobutanone with Example 16B using the method of Example 23. The crude product was chromatographed (solvent A—hexane: EtOAc: triethylamine (5:15:1); solvent B—hexane:EtOAc:MeOH: triethylamine (4:12:4:1); solvent A:solvent B (100:0 gradient to 0:100) over 240 mL then isocratic with solvent B for 300 mL) to afford the title compound. (0.05 g, 0.12 mmol, 71% yield). $^1$H NMR (300 MHz, CDCl$_3$) δ ppm 1.45 (s, 9H), 1.60-1.74 (m, 1H), 1.78-2.01 (m, 2H), 2.14-2.30 (m, 1H), 3.69-3.84 (m, 2H), 3.96 (s, 3H), 4.09-4.32 (m, 2H), 4.44-4.57 (m, 1H), 6.92 (d, J=8.8 Hz, 1H), 7.11 (s, 1H), 7.50 (dd, J=8.3, 2.2 Hz, 1H), 8.40 (d, J=2.4 Hz, 1H). MS (DCI/NH$_3$) m/z 426.2 (M+H)$^+$.

Example 25

2-tert-butoxy-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide The title compound was obtained as the unexpected product in the reaction of (S)-5-(hydroxymethyl)pyrrolidin-2-one (0.02 g, 0.17 mmol) with Example 16B using the general method of Example 23. The reaction was diluted with dichloromethane, loaded onto silica gel and chromatographed. (solvent A—hexane: EtOAc:triethylamine (5:15:1); solvent B—hexane:EtOAc:MeOH:triethylamine (4:12:4:1); solvent A to solvent B over 240 mL then isocratic for 300 mL) to afford the title compound. (15 mg, 0.03 mmol, 38% yield). $^1$H NMR (500 MHz, PYRIDINE-D5) δ ppm 1.18 (s, 9H), 1.53 (s, 9H), 1.54-1.62 (m, 2H), 1.63-1.72 (m, 1H), 1.74-1.83 (m, 1H), 3.54-3.61 (m, 1H), 3.68-3.75 (m, 1H), 3.79 (s, 3H), 4.23 (ddd, J=13.5, 6.8, 3.2 Hz, 1H), 4.34 (dd, J=15.3, 6.4 Hz, 1H), 4.57 (dd, J=15.3, 3.1 Hz, 1H), 7.33 (d, J=8.5 Hz, 1H), 7.47 (s, 1H), 7.60 (dd, J=8.5, 2.4 Hz, 1H), 8.43 (d, J=2.4 Hz, 1H). MS (DCI/NH$_3$) m/z 482.3 (M+H)$^+$.

Example 26

N-{(3E)-5-tert-butyl-1-methyl-2-[(2R)-tetrahydrofuran-2-ylmethyl]-1,2-dihydro-3H-pyrazol-3-ylidene}-2-[2-(dimethylamino)ethoxy]-5-(trifluoromethyl)benzamide Potassium t-butoxide (1.2 mL, 1M in THF) was added to 2-(dimethylamino)ethanol (0.12 mL, 1.2 mmol) and the solution stirred for 10 minutes. Example 16B (0.25 g, 0.59 mmol) in 1 mL of THF was added and the mixture stirred at ambient temperature for 1 hour. Saturated NH$_4$Cl (0.5 mL) was added and the mixture diluted with EtOAc, washed with 2N NaOH, water, brine, dried with MgSO$_4$ and the solvent removed. The residue was chromatographed (solvent A—hexane: EtOAc: triethylamine (1:3:0.1) solvent B—hexane:EtOAc:MeOH: triethylamine (1:3:1:0.1); 100% solvent A to 100% solvent B over 240 mL then isocratic for 300 mL) to afford the title compound (0.13 g, 0.26 mmol, 45% yield). $^1$H NMR (300 MHz, CDCl) δ ppm 1.43 (s, 9H), 1.75-1.81 (m, 2H), 1.82-1.92 (m, 1H), 1.94-2.13 (m, 1H), 2.31 (s, 6H), 2.79 (t, J=6.6 Hz, 2H), 3.65-3.82 (m, 2H), 3.85 (s, 3H), 4.13-4.24 (m, 3H), 4.25-4.35 (m, 1H), 4.42-4.56 (m, 1H), 6.98 (d, J=8.5 Hz, 1H), 7.02 (s, 1H), 7.49 (ddd, J=8.6, 2.5, 0.7 Hz, 1H), 7.96 (d, J=2.4 Hz, 1H). MS (DCI/NH$_3$) m/z 497.3 (M+H)$^+$. Analytical calculated for C$_{25}$H$_{35}$F$_3$N$_4$O$_3$: C, 60.47; H, 7.10; N, 11.28. Found: C, 60.46; H, 7.17; N, 11.02.

Example 27

N-{(3E)-5-tert-butyl-1-methyl-2-[(2R)-tetrahydrofuran-2-ylmethyl]-1,2-dihydro-3H-pyrazol-3-ylidene}-2-(dimethylamino)-5-(trifluoromethyl)benzamide Sodium hydride (0.09 g, 2.3 mmol, 60% in mineral oil) was added to (R)-5-(hydroxymethyl)pyrrolidin-2-one (0.14 g, 1.2 mmol) in 0.75 mL of dimethylformamide and stirred at ambient temperature for 10 minutes. Example 16B (0.25 g, 0.59 mmol) in 0.3 mL of DMF was added and the mixture stirred at 50° C. for 4 hours. The mixture was diluted with EtOAc, washed with 2N NaOH, water, brine, dried with MgSO$_4$ and the solvent removed under reduced pressure. The residue was chromatographed (solvent A—hexane: EtOAc:triethylamine (1:3:0.1) solvent B—hexane:EtOAc:MeOH:triethylamine (1:3:1:0.1); 100% solvent A to 100% solvent B over 240 mL then isocratic for 300 mL) to afford the title compound as an unexpected by-product. (20 mg, 0.04 mmol, 8% yield) $^1$H NMR (300 MHz, CDCl$_3$) δ ppm 1.43 (s, 9H), 1.72-1.83 (m, 2H), 1.84-1.93 (m, 1H), 1.96-2.10 (m, 1H), 2.95 (s, 6H), 3.69-3.82 (m, 2H), 3.86 (s, 3H), 4.14-4.23 (m, 1H), 4.26-4.36 (m, 1H), 4.49-4.56 (m, 1H), 6.84 (d, J=8.3 Hz, 1H), 7.05 (s, 1H), 7.38 (dd, J=8.7, 2.4 Hz, 1H), 7.87 (d, J=2.4 Hz, 1H). MS (DCI/NH$_3$) m/z 453.3 (M+H)$^+$.

Example 28

N-{(3E)-5-tert-butyl-1-methyl-2-[(2R)-tetrahydrofuran-2-ylmethyl]-1,2-dihydro-3H-pyrazol-3-ylidene}-2-{[(2S)-2-methoxypropyl]oxy}-5-(trifluoromethyl)benzamide Potassium t-butoxide (1.2 mL, 1M in THF) was added to (S)-2-methoxypropan-1-ol (0.11 g, 1.2 mmol) in 0.5 mL of THF and stirred for 10 minutes. Example 16B (0.25 g, 0.6 mmol) in 1 mL of THF was added and the mixture stirred for 1 hour. The mixture was diluted with dichloromethane (10 mL), filtered, and chromatographed. (solvent A—hexane: EtOAc:triethylamine (1:3:0.1); solvent B—hexane:EtOAc: MeOH:triethylamine (1:3:1:0.1) 100% solvent A to 100% solvent B over 450 mL then isocratic for 300 mL) to afford the title compound. (0.16 g, 0.32 mmol, 55% yield). $^1$H NMR (500 MHz, PYRIDINE-D5) δ ppm 1.17 (s, 9H), 1.31 (d, J=6.4 Hz, 3H), 1.53-1.61 (m, 2H), 1.64-1.72 (m, 1H), 1.78 (ddd, J=19.4, 7.0, 6.9 Hz, 1H), 3.40 (s, 3H), 3.55-3.61 (m, 1H), 3.69-3.76 (m, 1H), 3.79 (s, 3H), 3.80-3.84 (m, 1H), 4.09 (dd, J=9.9, 5.0 Hz, 1H), 4.21-4.28 (m, 2H), 4.37 (dd, J=15.1, 6.6 Hz, 1H), 4.59 (dd, J=15.1, 3.2 Hz, 1H), 7.17 (d, J=8.5 Hz, 1H), 7.47 (s, 1H), 7.64 (dd, J=8.5, 2.1 Hz, 1H), 8.48 (d, J=2.4 Hz, 1H). MS (DCI/NH$_3$) m/z 498.3 (M+H)$^+$. Analytical calculated for $C_{25}H_{34}F_3N_3O_4$: C, 60.35; H, 6.89; N, 8.45. Found: C, 60.16; H, 7.04; N, 8.48.

Example 29

N-{(3E)-5-tert-butyl-1-methyl-2-[(2R)-tetrahydrofuran-2-ylmethyl]-1,2-dihydro-3H-pyrazol-3-ylidene}-2-(3-ethoxypropoxy)-5-(trifluoromethyl)benzamide Potassium t-butoxide (1.2 mL, 1M in THF) was added to 3-ethoxypropan-1-ol (0.13 g, 1.2 mmol) in 0.5 mL of THF and stirred for 10 minutes. Example 16B (0.25 g, 0.6 mmol) in 1 mL of THF was added and the mixture stirred for 1 hour. The mixture was diluted with dichloromethane (10 mL), filtered, and chromatographed (solvent A—hexane:EtOAc:triethylamine (1:3:0.1); solvent B—hexane:EtOAc:MeOH:triethylamine (1:3:1:0.1); 100% solvent A to 100% solvent B over 450 mL then isocratic for 300 mL) to afford the title compound (0.13 g, 0.25 mmol, 43% yield). $^1$H NMR (500 MHz, PYRIDINE-D5) δ ppm 1.10 (t, J=7.0 Hz, 3H), 1.17 (s, 9H), 1.53-1.62 (m, 2H), 1.65-1.72 (m, 1H), 1.75-1.82 (m, 1H), 2.09-2.15 (m, 2H), 3.36 (q, J=7.0 Hz, 2H), 3.55-3.60 (m, 1H), 3.65 (t, J=6.3 Hz, 2H), 3.69-3.75 (m, 1H), 3.78 (s, 3H), 4.21-4.28 (m, 3H), 4.37 (dd, J=15.0, 6.4 Hz, 1H), 4.59 (dd, J=15.1, 3.2 Hz, 1H), 7.14 (d, J=8.5 Hz, 1H), 7.48 (s, 1H), 7.62 (dd, J=8.5, 2.1 Hz, 1H), 8.46 (d, J=2.4 Hz, 1H). MS (DCI/NH$_3$) m/z 512.3 (M+H)$^+$. Analytical calculated for $C_{26}H_{36}F_3N_3O_4$: C, 61.04; H, 7.09; N, 8.21. Found: C, 60.97; H, 7.19; N, 8.31.

Example 30

N-{(3E)-5-tert-butyl-1-methyl-2-[(2R)-tetrahydrofuran-2-ylmethyl]-1,2-dihydro-3H-pyrazol-3-ylidene}-2-(3-methoxypropoxy)-5-(trifluoromethyl)benzamide Potassium t-butoxide (0.64 mL, 1M in THF) was added to 3-methoxypropan-1-ol (0.063 g, 0.7 mmol) in 0.25 mL of THF and stirred for 10 minutes. Example 16B (0.25 g, 0.59 mmol) in 1.0 mL of THF was added and the mixture stirred at ambient temperature for 3 hours. The mixture was diluted with dichloromethane (10 mL), filtered and chromatographed (solvent A—hexane:EtOAc:triethylamine (1:3:0.1); solvent B—hexane:EtOAc:MeOH:triethylamine (1:3:1:0.1); 100% solvent A to 100% solvent B over 450 mL then isocratic for 300 mL) to afford the title compound (0.12 g, 0.24 mmol, 41% yield). $^1$H NMR (500 MHz, PYRIDINE-D5) δ ppm 1.17 (s, 9H), 1.53-1.61 (m, 2H), 1.65-1.72 (m, 1H), 1.75-1.82 (m, 1H), 2.07-2.13 (m, 2H), 3.21 (s, 3H), 3.55-3.61 (m, 3H), 3.69-3.75 (m, 1H), 3.78 (s, 3H), 4.21-4.26 (m, 3H), 4.37 (dd, J=15.1, 6.6 Hz, 1H), 4.59 (dd, J=15.1, 3.2 Hz, 1H), 7.13 (d, J=8.5 Hz, 1H), 7.48 (s, 1H), 7.62 (dd, J=8.5, 2.4 Hz, 1H), 8.47 (d, J=2.1 Hz, 1H). MS (DCI/NH$_3$) m/z 498.3 (M+H)$^+$. Analytical calculated for $C_{26}H_{36}F_3N_3O_4$: C, 61.04; H, 7.09; N, 8.21. Found: C, 60.97; H, 7.19; N, 8.31.

Example 31

N-{(3E)-5-tert-butyl-1-methyl-2-[(2R)-tetrahydrofuran-2-ylmethyl]-1,2-dihydro-3H-pyrazol-3-ylidene}-2-(2-ethoxyethoxy)-5-(trifluoromethyl)benzamide Potassium t-butoxide (09.4 mL, 1M in THF) was added to 2-ethoxyethanol (0.09 g, 0.98 mmol) in 0.5 mL of THF and the mixture stirred for 10 minutes. Example 16B (0.2 g, 0.47 mmol) in 0.8 mL of THF was added and the mixture stirred at ambient temperature for 1 hour. The mixture was diluted with 10 mL of dichloromethane, 50 µL of glacial acetic acid was added, the resulting solution was filtered and chromatographed (solvent A—hexane: EtOAc:triethylamine (1:3:0.1); solvent B—hexane:EtOAc:MeOH:triethylamine (1:3:1:0.1); 100% solvent A to solvent A:solvent B (25:75) over 450 mL then isocratic for 180 mL) to afford the title compound (0.13 g, 0.26 mmol, 56% yield). $^1$H NMR (500 MHz, PYRIDINE-D5) δ ppm 1.09 (t, J=7.0 Hz, 3H), 1.18 (s, 9H), 1.52-1.62 (m, 2H), 1.64-1.73 (m, 1H), 1.74-1.84 (m, 1H), 3.48 (q, J=7.0 Hz, 2H), 3.54-3.62 (m, 1H), 3.69-3.75 (m, 1H), 3.79 (s, 3H), 3.80-3.85 (m, 2H), 4.19-4.28 (m, 1H), 4.32-4.41 (m, 3H), 4.59 (dd, J=15.1, 3.2 Hz, 1H), 7.19 (d, J=8.5 Hz, 1H), 7.46 (s, 1H), 7.61 (dd, J=8.5, 2.1 Hz, 1H), 8.47 (d, J=2.4 Hz, 1H). MS (DCI/NH$_3$) m/z 498.3 (M+H)$^+$. Analytical calculated for $C_{25}H_{34}F_3N_3O_4$: C, 60.35; H, 6.89; N, 8.45. Found: C, 60.07; H, 7.00; N, 8.39.

Example 32

2-methoxy-N-[(3E)-1-methyl-2-[(2R)-tetrahydrofuran-2-ylmethyl]-1,4,5,6-tetrahydrocyclopenta[c]pyrazol-3(2H)-ylidene]-5-(trifluoromethyl)benzamide Example 32A (S)-2-((tetrahydrofuran-2-yl)methyl)-2,4,5,6-tetrahydrocyclopenta[c]pyrazol-3-amine The title compound was prepared from Example 45A using the procedure as described in Example 45B substituting 2-oxocyclopentanecarbonitrile for 4,4-dimethyl-3-oxopentanenitrile. MS (DCI/NH$_4$$^+$) m/z 208 (M+H)$^+$.

Example 32B 2-methoxy-N-{2-[(2R)-tetrahydrofuran-2-ylmethyl]-2,4,5,6-tetrahydrocyclopentaclpyrazol-3-yl}-5-(trifluoromethyl)benzamide To a solution of the product of Example 32A (340 mg, 1.64 mmol) and pyridine (535 µL, 6.56 mmol) in CH$_2$Cl$_2$ (20 mL) was added 2-methoxy-5-(trifluoromethyl)benzoyl chloride (470 mg, 1.97 mmol) dropwise. The mixture was stirred at ambient temperature for 1 h. The mixture was concentrated under reduced pressure and was purified by column chromatography (SiO$_2$, 40% hexanes/EtOAc) to provide the title compound 550 mg (82%). MS (DCI/NH$_3$) m/z 410 (M+H)$^+$.

Example 32C 2-methoxy-N-[(3E)-1-methyl-2-[(2R)-tetrahydrofuran-2-ylmethyl]-1,4,5,6-tetrahydrocyclopenta[c]pyrazol-3(2H)-ylidene]-5-(trifluoromethyl)benzamide A mixture of the product of Example 32B (550 mg, 1.34 mmol) and dimethyl sulfate (512 μL, 5.37 mmol) in toluene (5 mL) was warmed to 90° C. and was allowed to stir for 12 h then was cooled to ambient temperature and was concentrated under reduced pressure. The mixture was purified by column chromatography (SiO$_2$, 50% hexanes/EtOAc to 100% EtOAc to 9:1:0.1 EtOAc:MeOH:Et$_3$N) to give the title compound 73 mg (13%). $^1$H NMR (400 MHz, CHLOROFORM-D) δ ppm 1.66-1.78 (m, 1H) 1.80-1.93 (m, 2H) 2.03 (m, 1H) 2.39-2.50 (m, 2H) 2.73 (t, J=7.36 Hz, 2H) 3.02 (t, J=7.36, 6.75 Hz, 2H) 3.65 (s, 3H) 3.68-3.76 (m, 1H) 3.77-3.85 (m, 1H) 3.89 (s, 3H) 4.09 (dd, J=14.73, 6.14 Hz, 1H) 4.13-4.19 (m, 1H) 4.45 (dd, J=15.04, 2.76 Hz, 1H) 6.94 (d, J=8.59 Hz, 1H) 7.50 (dd, J=10.13, 1.53 Hz, 1H) 7.96 (d, J=2.15 Hz, 1H); MS (DCI/NH$_3$) m/z 424 (M+H)$^+$.

Example 33

2-methoxy-N-{(3E)-1-methyl-5-(1-methylcyclopropyl)-2-[(2R)-tetrahydrofuran-2-ylmethyl]-1,2-dihydro-3H-pyrazol-3-ylidene}-5-(trifluoromethyl)benzamide

Example 33A 3-(1-methylcyclopropyl)-3-oxopropanenitrile

To a solution of diisopropylamine (7.43 mL, 52.6 mmol) in 60 mL of THF was added n-BuLi (2.5M) (21.03 mL, 52.6 mmol) at −78° C. The reaction was stirred at −78° C. for 30 min, then acetonitrile (2.76 mL, 52.6 mmol) was added at −78° C. and the reaction was stirred for 30 min, then methyl 1-methylcyclopropanecarboxylate (3 g, 52.6 mmol) was added at −78° C. The reaction was stirred at −78° C. for 1 h and then allowed to warm up at rt overnight. The solvent was evaporated and the solid dissolved in water. The aqueous layer was washed with ether and then acidified with 6N HCl to pH 2-3. The aqueous layer was extracted with ether. The organic layer was dried with MgSO$_4$ and concentrated to afford the title compound (2.89 g, 89%). MS (DCI/NH$_3$) m/z 124 (M+H)$^+$.

Example 33B (R)-3-(1-methylcyclopropyl)-1-((tetrahydrofuran-2-yl)methyl)-1H-pyrazol-5-amine The title compound was prepared from Example 45A using the procedure as described in Example 45B substituting Example 33A for 4,4-dimethyl-3-oxopentanenitrile. MS (DCI/NH$_3$) m/z 222 (M+H)$^+$.

Example 33C 2-methoxy-N-{3-(1-methylcyclopropyl)-1-[(2R)-tetrahydrofuran-2-ylmethyl]-1H-pyrazol-5-yl}-5-(trifluoromethyl)benzamide The title compound was prepared using the procedure as described in Example 32B substituting Example 33B for Example 32A. MS (DCI/NH$_3$) m/z 424 (M+H)$^+$.

Example 33D 2-methoxy-N-{(3E)-1-methyl-5-(1-methylcyclopropyl)-2-[(2R)-tetrahydrofuran-2-ylmethyl]-1,2-dihydro-3H-pyrazol-3-ylidene}-5-(trifluoromethyl)benzamide The title compound was prepared using the procedure as described in Example 32C substituting Example 33C for Example 32B. $^1$H NMR (400 MHz, CHLOROFORM-D) δ ppm 0.78-0.85 (m, 2H) 0.91-1.00 (m, 2H) 1.37 (s, 3H) 1.72-1.85 (m, 2H) 1.83-1.92 (m, 1H) 1.97-2.09 (m, 1H) 3.68-3.80 (m, 2H) 3.84 (s, 3H) 3.91 (s, 3H) 4.16-4.32 (m, 2H) 4.50 (d, J=12.58 Hz, 1H) 6.96 (d, J=8.90 Hz, 1H) 7.04 (s, 1H) 7.51 (dd, J=8.90, 1.84 Hz, 1H) 7.99 (d, J=2.15 Hz, 1H) MS (DCI/NH$_3$) m/z 438 (M+H)$^+$.

Example 34

N-{(3E)-5-tert-butyl-1-methyl-2-[(2R)-tetrahydrofuran-2-ylmethyl]-1,2-dihydro-3H-pyrazol-3-ylidene}-2-[(2-methoxyethyl)amino]-5-(trifluoromethyl)benzamide A mixture of the product from Example 16B (100 mg, 0.234 mmol), 2-methoxyethanamine (52.7 mg, 0.702 mmol) and triethylamine (71 mg, 0.702 mmol) in THF (1 mL) was heated at 120° C. with microwave irradiation (Discover, CEM) for 60 min. The reaction mixture was diluted with H$_2$O and extracted with EtOAc (2×). The organic layer was dried over MgSO$_4$, filtered and concentrated. The residue was purified by column chromatography using an Analogix® Intelliflash280™ (SiO$_2$, 50% hexanes/EtOAc to 100% EtOAc to 9:1:0.1 EtOAc:MeOH:Et$_3$N) to afford 79 mg (70%) of the title compound. $^1$H NMR (400 MHz, CHLOROFORM-D) δ ppm 1.42 (s, 9H) 1.72-1.82 (m, 2H) 1.81-1.90 (m, 1H) 1.98-2.11 (m, 1H) 3.39 (s, 3H) 3.45 (q, J=5.52 Hz, 2H) 3.63 (t, J=5.83 Hz, 2H) 3.68-3.82 (m, 2H) 3.86 (s, 3H) 4.18-4.26 (m, 1H) 4.33 (dd, J=15.65, 5.83 Hz, 1H) 4.55 (dd, J=15.65, 3.38 Hz, 1H) 6.67 (d, J=8.59 Hz, 1H) 7.41 (dd, J=8.59, 2.15 Hz, 1H) 8.60 (d, J=1.84 Hz, 1H) 9.54 (brs, 1H) MS (DCI/NH$_3$) m/z 483 (M+H)$^+$.

Example 35

N-{(3E)-5-tert-butyl-1-methyl-2-[(2R)-tetrahydrofuran-2-ylmethyl]-1,2-dihydro-3H-pyrazol-3-ylidene}-2-(2,2-difluoroethoxy)-5-(trifluoromethyl)benzamide A mixture of the product from Example 16B (100 mg, 0.234 mmol), 2,2-difluoroethanol (38.4 mg, 0.468 mmol) and sodium tert-butoxide (45 mg, 0.468 mmol) in THF (2 mL) was heated at 40° C. for 12 hrs. The reaction mixture was diluted with H$_2$O and extracted with EtOAc (2×). The organic layer was dried over MgSO$_4$, filtered and concentrated. The residue was purified by column chromatography using an Analogix® Intelliflash280™ (SiO$_2$, 50% hexanes/EtOAc to 100% EtOAc to 9:1:0.1 EtOAc:MeOH:Et$_3$N) to afford 89 mg (80%) of the title compound. $^1$H NMR (500 MHz, CHLOROFORM-D) δ ppm 1.44 (m, 9H) 1.67-1.80 (m, 2H) 1.81-1.91 (m, 1H) 1.97-2.05 (m, 1H) 3.68-3.80 (m, 2H) 3.88 (s, 3H) 4.15-4.21 (m, 1H) 4.32 (td, J=13.12, 4.27 Hz, 3H) 4.51 (dd, J=15.26, 3.05 Hz, 1H) 6.15 (tt, J=55.23, 4.27 Hz, 1H) 7.00 (d, J=9.76 Hz, 1H) 7.02 (s, 1H) 7.52 (dd, J=8.54, 1.83 Hz, 1H) 8.05 (d, J=2.14 Hz, 1H) MS (DCI/NH$_3$) m/z 490 (M+H)$^+$.

Example 36

N-{(3E)-5-tert-butyl-1-methyl-2-[(2R)-tetrahydrofuran-2-ylmethyl]-1,2-dihydro-3H-pyrazol-3-ylidene}-2-[(3R)-tetrahydrofuran-3-yloxy]-5-(trifluoromethyl)benzamide The title compound was prepared using the procedure as described in Example 35 substituting (R)-tetrahydrofuran-2-ol for 2,2-difluoroethanol. $^1$H NMR (400 MHz, CHLOROFORM-D) δ ppm 1.43 (s, 9H) 1.69-1.80 (m, 2H) 1.81-1.90 (m, 1H) 1.96-2.04 (m, 1H) 2.12-2.27 (m, 2H) 3.67-3.80 (m, 2H) 3.85 (s, 3H) 3.84-3.91 (m, 1H) 3.92-4.01 (m, 1H) 4.00-4.04 (m, 2H) 4.15-4.22 (m, 1H) 4.31 (dd, J=15.34, 5.52 Hz, 1H) 4.48 (dd, J=15.04, 3.07 Hz, 1H) 4.99-5.07 (m, 1H) 6.89 (d, J=8.59 Hz, 1H) 6.98 (s, 1H) 7.48 (dd, J=8.59, 2.46 Hz, 1H) 7.97 (d, J=2.46 Hz, 1H)MS (DCI/NH$_3$) m/z 496 (M+H)$^+$.

Example 37

N-{(3E)-5-tert-butyl-1-methyl-2-[(2R)-tetrahydrofuran-2-ylmethyl]-1,2-dihydro-3H-pyrazol-3-ylidene}-2-[(3S)-tetrahydrofuran-3-yloxy]-5-(trifluoromethyl)benzamide The title compound was prepared using the procedure as described in Example 35 substituting (S)-tetrahydrofuran-2-ol for 2,2-difluoroethanol. $^1$H NMR (400 MHz, CHLOROFORM-D) δ ppm 1.42 (s, 9H) 1.69-1.79 (m, 2H) 1.80-1.89 (m, 1H) 1.96-2.03 (m, 1H) 2.12-2.27 (m, 2H) 3.66-3.81 (m, 2H) 3.85 (s, 3H) 3.85-3.90 (m, 1H) 3.92-4.01 (m, 1H) 4.00-4.04 (m, 2H) 4.15-4.23 (m, 1H) 4.31 (dd, J=15.34, 5.52 Hz, 1H) 4.48 (dd, J=15.04, 3.07 Hz, 1H) 4.99-5.06 (m, 1H) 6.90 (d, J=8.59 Hz, 1H) 6.98 (s, 1H) 7.47 (dd, J=8.59, 2.46 Hz, 1H) 7.97 (d, J=2.46 Hz, 1H); MS (DCI/NH$_3$) m/z 496 (M+H)$^+$.

Example 38

(E)-N-(5-tert-butyl-2-(((2R,3R)-3-fluorotetrahydrofuran-2-yl)methyl)-1-methyl-1H-pyrazol-3(2H)-ylidene)-2-methoxy-5-(trifluoromethyl)benzamide

Example 38A (2R,3S)-pentane-1,2,3,5-tetraol

Water (50 mL) and R$^a$—Ni, water-wet (5.03 g, 38.6 mmol) were added to (3S,4R)-3,4,5-trihydroxypentanal (25.19 g, 188 mmol) in a 300 mL SS reactor. The mixture was stirred for 1.5 hr at 70° C. under 800 psi (literature 570 psi) of Hydrogen. The 270 psi pressure drop was consistent with full conversion, and the DCI-MS showed only ions for the expected product. The mixture was filtered through a nylon membrane, the reactor was rinsed with water, and the filtrate was concentrated and afforded 25.8 g of the title compound. $^1$H NMR (400 MHz, DMSO-D6) δ ppm 1.36-1.48 (m, 1H) 1.66-1.77 (m, 1H) 3.20-3.27 (m, 1H) 3.33 (dd, J=11.66, 6.14 Hz, 1H) 3.38-3.59 (m, 4H) 4.25-4.33 (m, 3H) 4.40 (d, J=5.22 Hz, 1H); MS (ESI) m/z 137 (M+H)$^+$.

Example 38B
(2R,3S)-2-(hydroxymethyl)tetrahydrofuran-3-ol

A mixture of the product from Example 38A (25.8 g, 190 mmol) and 4-methylbenzenesulfonic acid monohydrate (710 mg, 3.73 mmol) was refluxed and the water removed as an azeotropic mixture with toluene by using a Dean-Stark apparatus. After 4 hrs of reflux, the reaction mixture was cooled and treated with solid NaHCO$_3$ (3.9 mmol) to neutralize the acid catalyst followed by removing the solid material by filtration. The filtrate was distilled and the fraction at 95-98° C. under a pressure of 0.6 Torr was collected as a colorless oil (15.3 g, 68%). $^1$H NMR (400 MHz, DMSO-D6) δ ppm 1.63-1.74 (m, 1H) 1.84-1.98 (m, 1H) 3.28-3.35 (m, 1H) 3.52-3.59 (m, 1H) 3.69-3.82 (m, 2H) 4.00-4.08 (m, 1H) 4.57 (t, J=5.52 Hz, 1H) 4.82 (d, J=3.99 Hz, 1H).

Example 38C (2R,3S)-2-((bis(4-methoxyphenyl)(phenyl)methoxy)methyl)tetrahydrofuran-3-ol The product from 38B (1.6 g, 13.54 mmol) in pyridine (20 mL) was treated with 4,4'-(chloro(phenyl)methylene)bis(methoxybenzene) (5.05 g, 14.9 mmol) for 12 hrs at rt. The solvent was removed in vacuo. The residue was diluted with CH$_2$Cl$_2$, washed with saturated NaHCO$_3$ and brine. The organic was dried over MgSO$_4$, filtered and concentrated. The residue was purified by column chromatography using an Analogix® Intelliflash280™ (SiO$_2$, 0-100% ethyl acetate in hexanes) to afford 4.25 g (75%) of the title compound. $^1$H NMR (400 MHz, CHLOROFORM-D) δ ppm 1.73 (d, J=3.99 Hz, 1H) 1.84-1.94 (m, 1H) 2.09-2.22 (m, 1H) 3.08 (dd, J=9.51, 6.14 Hz, 1H) 3.25 (dd, J=9.51, 4.60 Hz, 1H) 3.78 (s, 6H) 3.84-3.90 (m, 1H) 3.97 (dd, J=8.29, 5.52 Hz, 2H) 4.26-4.32 (m, 1H) 6.78-6.86 (m, 4H) 7.17-7.24 (m, 1H) 7.27-7.36 (m, 6H) 7.39-7.46 (m, 2H).

Example 38D (2R,3R)-3-fluoro-2-(((3-methoxyphenyl)(4-methoxyphenyl)(phenyl)methoxy)methyl)tetrahydrofuran The product from Example 38C (1.1 g, 2.62 mmol) in CH$_2$Cl$_2$ (10 mL) was treated dropwise with diethylaminosulfur trifluoride (DAST) (508 mg, 3.14 mmol) at −78° C. The reaction was allowed to warm up to rt for 12 hrs. The reaction mixture was quenched with saturated aqueous NaHCO$_3$ and extracted with CH$_2$Cl$_2$. The organic extract was dried (Na$_2$SO$_4$), filtered and concentrated. The residue was purified by column chromatography using an Analogix® Intelliflash280™ (SiO$_2$, 0-100% ethyl acetate in hexanes) to afford the title compound. $^1$H NMR (400 MHz, CDCl$_3$) δ ppm 2.05-2.27 (m, 2H) 3.32 (dd, J=9.21, 6.14 Hz, 1H) 3.35-3.43 (m, 1H) 3.79 (s, 6H) 3.84-3.95 (m, 2H) 4.03 (dd, J=15.96, 8.59 Hz, 1H) 5.20 (d, J=55.54 Hz, 1H) 6.77-6.86 (m, 4H) 7.17-7.23 (m, 1H) 7.24-7.30 (m, 2H) 7.31-7.38 (m, 4H) 7.44-7.49 (m, 2H).

Example 38E ((2R,3R)-3-fluorotetrahydrofuran-2-yl)methanol

The product from Example 38D (600 mg, 1.42 mmol) in CH$_2$Cl$_2$ (10 mL) and MeOH (10 mL) was treated with 4-methylbenzenesulfonic acid monohydrate (135 mg, 0.71 mmol). The mixture was stirred at rt for 1 hr. The mixture was neutralized with excess Et$_3$N. The solvent was removed and the residue was purified by column chromatography using an Analogix® Intelliflash280™ (SiO$_2$, 0-50% MeOH in ethyl acetate) to afford 35 mg (21%) of the title compound. $^1$H NMR (400 MHz, CHLOROFORM-D) δ ppm 2.02-2.42 (m, 2H) 3.51-3.79 (m, 1H) 3.81-3.94 (m, 3H) 4.03-4.15 (m, 1H) 5.24 (d, J=59.84 Hz, 1H).

Example 38F (((2R,3R)-3-fluorotetrahydrofuran-2-yl)methyl)hydrazine

The title compound was prepared using the 2-step procedure as described in Example 45A substituting Example 38E for (R)-(tetrahydrofuran-2-yl)methanol. MS (DCI/NH$_3$) m/z 135 (M+H)$^+$.

Example 38G 3-tert-butyl-1-(((2R,3R)-3-fluorotetrahydrofuran-2-yl)methyl)-1H-pyrazol-5-amine The title compound was prepared using the procedure as described in Example 45B substituting Example 38F for Example 45A. MS (DCI/NH$_3$) m/z 241 (M+H)$^+$.

Example 38H

N-(3-tert-butyl-1-(((2R,3R)-3-fluorotetrahydrofuran-2-yl)methyl)-1H-pyrazol-5-yl)-2-fluoro-5-(trifluoromethyl)benzamide The title compound was prepared using the procedure as described in Example 32B substituting Example 38G for Example 32A and 2-fluoro-5-(trifluoromethyl)benzoyl chloride for 2-methoxy-5-(trifluoromethyl)benzoyl chloride. MS (DCI/NH$_3$) m/z 432 (M+H)$^+$.

Example 38I (E)-N-(5-tert-butyl-2-(((2R,3R)-3-fluorotetrahydrofuran-2-yl)methyl)-1-methyl-1H-pyrazol-3(2H)-ylidene)-2-fluoro-5-(trifluoromethyl)benzamide The title compound was prepared using the procedure as described in Example 32C substituting Example 38H for Example 32B. MS (DCI/NH$_3$) m/z 446 (M+H)$^+$.

Example 38J (E)-N-(5-tert-butyl-2-(((2R,3R)-3-fluorotetrahydrofuran-2-yl)methyl)-1-methyl-1H-pyrazol-3(2H)-ylidene)-2-methoxy-5-(trifluoromethyl)benzamide The title compound was prepared using the procedure as described in Example 35 substituting Example 38I for Example 16B and methanol for 2,2-difluoroethanol. $^1$H NMR (400 MHz, CHLOROFORM-D) δ ppm 1.41 (s, 9H) 2.14-2.25 (m, 1H) 2.24-2.35 (m, 1H) 3.77-3.85 (m, 1H) 3.86 (s, 3H) 3.92 (s, 3H) 4.05-4.28 (m, 3H) 4.96 (d, J=15.65 Hz, 1H) 5.22 (d, J=53.70 Hz, 1H) 6.97 (d, J=8.59 Hz, 1H) 7.06 (s, 1H) 7.52 (d, J=7.67 Hz, 1H) 8.06 (s, 1H); MS (DCI/NH$_3$) m/z 458 (M+H)$^+$.

Example 39

N-{(3E)-5-tert-butyl-1-methyl-2-[(2R)-tetrahydrofuran-2-ylmethyl]-1,2-dihydro-3H-pyrazol-3-ylidene}-2-[(2-fluoroethyl)amino]-5-(trifluoromethyl)benzamide The title compound was prepared using the procedure as described in Example 34 substituting 2-fluoroethanamine for 2-methoxyethanamine. $^1$H NMR (400 MHz, CHLOROFORM-D) δ ppm 1.42 (s, 9H) 1.68-1.91 (m, 3H) 1.98-2.11 (m, 1H) 3.57 (dd, J=24.86, 8.29 Hz, 2H) 3.66-3.84 (m, 2H) 3.87 (s, 3H) 4.16-4.27 (m, 1H) 4.32 (dd, J=21.17, 5.83 Hz, 1H) 4.50-4.58 (m, 1H) 4.58 (t, J=5.22 Hz, 1H) 4.70 (t, J=5.22 Hz, 1H) 6.66 (d, J=8.59 Hz, 1H) 6.94-7.01 (m, 1H) 7.41 (dd, J=8.59, 2.15 Hz, 1H) 8.62 (s, 1H) 9.71 (s, 1H); MS (DCI/NH$_3$) m/z 471 (M+H)$^+$.

Example 40

N-{(3E)-5-tert-butyl-1-methyl-2-[(2R)-tetrahydrofuran-2-ylmethyl]-1,2-dihydro-3H-pyrazol-3-ylidene}-2-(2-fluoropropoxy)-5-(trifluoromethyl)benzamide The title compound was prepared using the procedure as described in Example 35 substituting 2-fluoropropan-1-ol for 2,2-difluoroethanol. $^1$H NMR (500 MHz, CHLOROFORM-D) δ ppm 1.39-1.49 (m, 3H) 1.42-1.45 (m, 9H) 1.68-1.79 (m, 1H) 1.80-1.91 (m, 1H) 2.02-2.09 (m, 3H) 3.67-3.81 (m, 2H) 3.90 (s, 3H) 4.08-4.27 (m, 3H) 4.34 (ddd, J=6.10, 1.83 Hz, 1H) 4.58 (dd, J=15.56, 2.75 Hz, 1H) 5.07 (d, J=7.15 Hz 1H) 6.99 (s, 1H) 7.51 (dd, J=8.54, 2.14 Hz, 1H) 7.98 (s, 1H); MS (DCI/NH$_3$) m/z 486 (M+H)$^+$.

Example 41

N-{(3E)-5-tert-butyl-1-methyl-2-[(2R)-tetrahydrofuran-2-ylmethyl]-1,2-dihydro-3H-pyrazol-3-ylidene}-2-{[(2R)-2-fluoropropyl]oxy}-5-(trifluoromethyl)benzamide The title compound was prepared using the procedure as described in Example 35 substituting (R)-2-fluoropropan-1-ol for 2,2-difluoroethanol. $^1$H NMR (400 MHz, CHLOROFORM-D) δ ppm 1.48 (s, 9H) 1.37-1.49 (m, 3H) 1.66-1.78 (m, 2H) 1.79-1.90 (m, 1H) 2.03-2.07 (m, 1H) 3.64-3.80 (m, 2H) 3.88 (s, 3H) 4.06-4.27 (m, 3H) 4.33 (dd, J=17.80, 5.83 Hz, 1H) 4.57 (dd, J=15.34, 3.07 Hz, 1H) 4.94-5.15 (m, 1H) 6.98 (d, J=7.06 Hz, 1H) 7.00 (s, 1H) 7.50 (dd, J=7.67, 1.23 Hz, 1H) 7.99 (d, J=1.84 Hz, 1H); MS (DCI/NH$_3$) m/z 486 (M+H)$^+$.

Example 42

N-{(3E)-5-tert-butyl-1-methyl-2-[(2R)-tetrahydrofuran-2-ylmethyl]-1,2-dihydro-3H-pyrazol-3-ylidene}-2-(2-fluoro-1-methylethoxy)-5-(trifluoromethyl)benzamide The title compound was prepared using the procedure as described in Example 35 substituting 1-fluoropropan-2-ol for 2,2-difluoroethanol. $^1$H NMR (500 MHz, CHLOROFORM-D) δ ppm 1.39 (d, J=7.63 Hz, 3H) 1.44 (s, 9H) 1.64-1.81 (m, 2H) 1.81-1.91 (m, 1H) 2.00-2.10 (m, 1H) 3.66-3.80 (m, 2H) 3.92 (s, 3H) 4.14-4.22 (m, 1H) 4.30-4.40 (m, 3H) 4.44-4.68 (m, 3H) 4.67-4.78 (m, 1H) 6.99 (s, 1H) 7.04 (d, J=8.85 Hz, 1H) 7.52 (dd, J=8.54, 2.14 Hz, 1H) 7.96 (s, 1H); MS (DCI/NH$_3$) m/z 486 (M+H)$^+$.

Example 43

N-{(3E)-5-tert-butyl-1-methyl-2-[(2R)-tetrahydrofuran-2-ylmethyl]-1,2-dihydro-3H-pyrazol-3-ylidene}-2-(3-fluoro-3-methylbutoxy)-5-(trifluoromethyl)benzamide

Example 43A

N-{(3E)-5-tert-butyl-1-methyl-2-[(2R)-tetrahydrofuran-2-ylmethyl]-1,2-dihydro-3H-pyrazol-3-ylidene}-2-(3-hydroxy-3-methylbutoxy)-5-(trifluoromethyl)benzamide The title compound was prepared using the procedure as described in Example 35 substituting 3-methylbutane-1,3-diol for 2,2-difluoroethanol. MS (DCI/NH$_3$) m/z 512 (M+H)$^+$.

Example 43B

N-{(3E)-5-tert-butyl-1-methyl-2-[(2R)-tetrahydrofuran-2-ylmethyl]-1,2-dihydro-3H-pyrazol-3-ylidene}-2-(3-fluoro-3-methylbutoxy)-5-(trifluoromethyl)benzamide The product from Example 43A (215 mg, 0.42 mmol) in CH$_2$Cl$_2$ (10 mL) was treated dropwise with DAST (66 µL, 0.504 mmol) at −78° C. The reaction mixture was allowed to warm up to room temperature for 4 hrs. The mixture was quenched with saturated NaHCO$_3$ and extracted with EtOAc (2×). The organic layer was dried over MgSO$_4$, filtered and concentrated. The residue was purified by column chromatography using an Analogix® Intelliflash280™ (SiO$_2$, 50% hexanes/EtOAc to 100% EtOAc to 9:1:0.1 EtOAc:MeOH:Et$_3$N) to afford 48 mg (22%) of the title compound. $^1$H NMR (400 MHz, CHLOROFORM-D) δ ppm 1.45 (d, J=21.48 Hz, 6H) 1.50 (s, 9H) 1.82-1.99 (m, 3H) 2.19-2.37 (m, 3H) 3.67-3.83 (m, 2H) 4.14-4.23 (m, 1H) 4.24 (s, 3H) 4.48 (t, J=7.36 Hz, 2H) 4.80-4.97 (m, 1H) 5.48 (d, J=17.18 Hz, 1H) 6.97 (s, 1H) 7.13 (d, J=8.59 Hz, 1H) 7.74 (dd, J=7.98, 1.84 Hz, 1H) 8.08 (d, J=2.15 Hz, 1H); MS (DCI/NH$_3$) m/z 514 (M+H)$^+$.

Example 44

N-{(3E)-5-tert-butyl-1-methyl-2-[(2R)-tetrahydrofuran-2-ylmethyl]-1,2-dihydro-3H-pyrazol-3-ylidene}-2-[(1-hydroxycyclobutyl)methoxy]-5-(trifluoromethyl)benzamide

Example 44A 1-(hydroxymethyl)cyclobutanol

Methylenecyclobutane (2.5 g, 36.7 mmol) in acetone (150 mL) and water (25 mL) was treated with osmium(VIII) oxide (467 mg, 1.835 mmol). The mixture was stirred at rt for 20 min. To the above mixture was added, in portions, 4-methylmorpholine N-oxide (12.9 g, 110 mmol). The reaction was stirred at rt for 12 hrs. The mixture was quenched with saturated Na$_2$S$_2$O$_3$, dried over MgSO$_4$, filtered and concentrated. The residue was purified by distillation (65-68° C. under 0.6 Torr) to provide the title compound (760 mg, 20%). $^1$H NMR (400 MHz, DMSO-D6) δ ppm 1.30-1.48 (m, 1H) 1.55-1.66 (m, 1H) 1.76-1.89 (m, 2H) 1.91-2.04 (m, 2H) 4.41 (s, 1H) 4.70 (s, 1H).

Example 44B

N-{(3E)-5-tert-butyl-1-methyl-2-[(2R)-tetrahydrofuran-2-ylmethyl]-1,2-dihydro-3H-pyrazol-3-ylidene}-2-[(1-hydroxycyclobutyl)methoxy]-5-(trifluoromethyl)benzamide The title compound was prepared using the procedure as described in Example 35 substituting Example 44A for 2,2-difluoroethanol. $^1$H NMR (400 MHz, CHLOROFORM-D) δ ppm 1.42 (s, 9H) 1.50-1.64 (m, 2H) 1.65-1.91 (m, 4H) 1.97-2.06 (m, 1H) 2.05-2.21 (m, 3H) 3.66-3.81 (m, 2H) 3.87 (s, 3H) 4.13-4.20 (m, 1H) 4.24 (s, 2H) 4.28 (dd, J=15.34, 5.83 Hz, 1H) 4.53 (dd, J=15.34, 3.07 Hz, 1H) 7.00 (s, 1H) 7.09 (d, J=8.59 Hz, 1H) 7.52 (dd, J=8.29, 2.45 Hz, 1H) 8.13 (d, J=2.15 Hz, 1H); MS (DCI/NH$_3$) m/z 510 (M+H)$^+$.

Example 45

N-{(3E)-5-tert-butyl-1-methyl-2-[(2R)-tetrahydrofuran-2-ylmethyl]-1,2-dihydro-3H-pyrazol-3-ylidene}-5-chloro-2-methoxybenzamide

Example 45A (R)-((tetrahydrofuran-2-yl)methyl)hydrazine dihydrochloride

To (R)-(tetrahydrofuran-2-yl)methanol (4.0 g, 39.2 mmol), di-tert-butyl hydrazine-1,2-dicarboxylate (3.64 g, 15.67 mmol) and triphenylphosphine (15.41 g, 58.7 mmol) in THF (100 mL) was added (E)-di-tert-butyl diazene-1,2-dicarboxylate (13.5 g, 5.87 mmol). The mixture was stirred at ambient temperature for 3 h then diluted with water and extracted with EtOAc (100 mL×2). The organic extract was washed with brine and concentrated. Purification by flash chromatography (silica gel, 5-30% EtOAc/hexane) afforded 10.2 g (82%) of (R)-di-tert-butyl 1-((tetrahydrofuran-2-yl)-methyl)-hydrazine-1,2-dicarboxylate, which was dissolved in a solution of 4M HCl in dioxane (40 mL) and stirred at ambient temperature overnight. The solvent was removed under reduced pressure and ethyl acetate (20 mL) was added with stirring. The solid precipitate was filtered, washed with ether (10 mL) and dried under vacuum to yield 7.8 g (97%) of the title compound as a white solid. $^1$H NMR (300 MHz, DMSO-d$_6$) δ ppm 1.48-1.63 (m, 1H), 1.73-1.88 (m, 2H), 1.90-2.02 (m, 1H), 2.84-3.01 (m, 2H), 3.61-3.71 (m, 1H), 3.72-3.83 (m, 1H), 3.97-4.08 (m, 1H), 5.76 (br, 5H); MS (ESI) m/z 117 (M+H)$^+$.

Example 45B (R)-3-tert-butyl-1-((tetrahydrofuran-2-yl)methyl)-1H-pyrazol-5-amine hydrochloride A mixture of Example 45A (7.8 g, 41.3 mmol) and 4,4-dimethyl-3-oxopentanenitrile (5.68 g, 45.4 mmol) in ethanol (50 mL) was refluxed at 90° C. for 6 h, then the solvent was removed under reduced pressure and ethyl acetate (10 mL) was added with stirring. The white solid that precipitated was collected, washed with ether and dried to yield 10.4 g (97%) of the title compound. $^1$H NMR (300 MHz, DMSO-d$_6$) δ ppm 1.14 (s, 9H), 1.60-1.97 (m, 4H), 3.50-3.66 (m, 1H), 3.67-3.79 (m, 1H), 3.83 (d, J=5.16 Hz, 2H), 3.99-4.16 (m, 1H), 4.85 (s, 2H), 5.15 (s, 1H); MS (ESI) m/z 224 (M+H)$^+$, 222 (M−H)$^−$.

Example 45C

N-{3-tert-butyl-1-[(2R)-tetrahydrofuran-2-ylmethyl]-1H-pyrazol-5-yl}-5-chloro-2-methoxybenzamide To the mixture of Example 45B (1.25 g, 5.6 mmol) in CH$_2$Cl$_2$ (50 mL) cooled with an ice-bath was added triethylamine (2.3 mL, 16.8 mmol), and 5-chloro-2-methoxybenzoyl chloride (the product from Step A of Example 11C) (1.15 g, 5.6 mmol) dropwise. The mixture was stirred at ambient temperature for 2 h, then treated with water (50 mL) and CH$_2$Cl$_2$ (50 mL). The organic layer was washed with brine and concentrated. Purification by flash chromatography (silica gel, Et$_3$N/MeOH/EtOAc, (1:10:90) in hexane in 10-40% gradient) afforded 1.75 g (80%) of the title compound. $^1$H NMR (300 MHz, DMSO-d$_6$) δ ppm 1.24 (s, 9H), 1.46-1.59 (m, 1H), 1.61-1.82 (m, 2H), 1.84-1.97 (m, 1H), 3.54-3.76 (m, 2H), 3.97 (s, 3H), 4.01-4.23 (m, 3H), 6.31 (s, 1H), 7.28 (d, J=8.72 Hz, 1H), 7.62 (dd, J=8.73, 2.78 Hz, 1H), 7.81 (d, J=2.78 Hz, 1H), 10.25 (s, 1H)); MS (ESI) m/z 392 [M+H]$^+$, 390 [M–H].

Example 45D

N-{(3E)-5-tert-butyl-1-methyl-2-[(2R)-tetrahydrofuran-2-ylmethyl]-1,2-dihydro-3H-pyrazol-3-ylidene}-5-chloro-2-methoxybenzamide A mixture of Example 45C (392 mg, 1.0 mmol) and dimethyl sulfate (0.38 mL, 4.0 mmol) in toluene (2 mL) was heated in a microwave at 130° C. for 1 hour. The solvent was removed under reduced pressure and the residue was purified by flash chromatography (silica gel, MeOH/Et$_3$N (90:10) in EtOAc in 10-60% gradient) to yield 223 mg (55%) of the title compound. $^1$H NMR (300 MHz, DMSO-d$_6$) δ ppm 1.44 (s, 9H), 1.51-1.68 (m, 1H), 1.79-1.97 (m, 2H), 2.01-2.18 (m, 1H), 3.62-3.84 (m, 2H), 3.92 (s, 3H), 4.07-4.12 (s, 3H), 4.14-4.26 (m, 1H), 4.50-4.63 (m, 1H), 4.65-4.79 (m, 1H), 6.92-7.02 (m, 1H), 7.31 (d, J=8.82 Hz, 1H), 7.63-7.75 (m, 2H); MS (ESI) m/z 406 [M+H]$^+$, 404 [M–H].

Example 46

N-{(3E)-5-tert-butyl-1-methyl-2-[(2R)-tetrahydrofuran-2-ylmethyl]-1,2-dihydro-3H-pyrazol-3-ylidene}-2-fluoro-3-(trifluoromethyl)benzamide The title compound was prepared from Example 45B according to the procedures described in Example 45C and Example 45D, substituting 2-fluoro-3-(trifluoromethyl)benzoyl chloride for 2-methoxy-5-chlorobenzoyl chloride. $^1$H NMR (300 MHz, DMSO-d$_6$) δ ppm 1.44 (s, 9H) 1.51-1.67 (m, 1H), 1.75-1.95 (m, 2H), 2.01-2.14 (m, 1H), 3.71-3.87 (m, 2H), 4.12 (s, 3H), 4.13-4.27 (m, 1H), 4.56-4.76 (m, 2H), 6.98 (s, 1H), 7.63 (t, J=7.73 Hz, 1H), 8.01-8.11 (m, 2H); MS (ESI) m/z 428 [M+H]$^+$.

Example 47

N-{(3E)-5-tert-butyl-1-methyl-2-[(2R)-tetrahydrofuran-2-ylmethyl]-1,2-dihydro-3H-pyrazol-3-ylidene}-2-methoxy-5-(trifluoromethyl)benzamide The title compound was prepared from Example 45B according to the procedures described in Example 45C and Example 45D, substituting 2-methoxy-5-(trifluoromethyl)benzoyl chloride for 2-methoxy-5-chlorobenzoyl chloride. $^1$H NMR (300 MHz, DMSO-d$_6$) δ ppm 1.38 (s, 9H), 1.65-1.93 (m, 4H), 3.58-3.67 (m, 1H), 3.69-3.76 (m, 1H), 3.80 (s, 3H), 3.88 (s, 3H), 4.12-4.22 (m, 1H), 4.31 (dd, J=4.96, 2.58 Hz, 2H), 6.81 (s, 1H), 7.15 (d, J=8.72 Hz, 1H), 7.59 (dd, J=8.92, 2.18 Hz, 1H), 7.68 (d, J=2.38 Hz, 1H); MS (ESI) m/z 440 [M+H]$^+$, 438 [M–H].

Example 48

N-{(3E)-5-tert-butyl-1-methyl-2-[(2R)-tetrahydrofuran-2-ylmethyl]-1,2-dihydro-3H-pyrazol-3-ylidene}-5-cyano-2-methoxybenzamide The title compound was prepared from Example 45B according to the procedures described in Example 45C and Example 45D, substituting 2-methoxy-5-cyanobenzoyl chloride for 2-methoxy-5-chlorobenzoyl chloride. $^1$H NMR (300 MHz, DMSO-d$_6$) δ ppm 1.38 (s, 9H), 1.62-1.86 (m, 4H), 3.57-3.66 (m, 1H), 3.70-3.76 (m, 1H), 3.81 (s, 3H), 3.88 (s, 3H), 4.12-4.21 (m, 1H), 4.27-4.35 (m, 2H), 6.80 (s, 1H), 7.10-7.18 (m, 1H) 7.68-7.78 (m, 2H); MS (ESI) m/z 397 [M+H]$^+$, 395 [M–H].

Example 49

5-bromo-N-{(3E)-5-tert-butyl-1-methyl-2-[(2R)-tetrahydrofuran-2-ylmethyl]-1,2-dihydro-3H-pyrazol-3-ylidene}-2-methoxybenzamide The title compound was prepared from Example 45B according to the procedures described in Example 45C and Example 45D, substituting 2-methoxy-5-bromobenzoyl chloride for 2-methoxy-5-chlorobenzoyl chloride. $^1$H NMR (300 MHz, DMSO-d$_6$) δ ppm 1.37 (s, 9H), 1.63-1.94 (m, 4H), 3.58-3.67 (m, 1H), 3.71 (s, 3H), 3.71-3.79 (m, 1H), 3.87 (s, 3H), 4.11-4.21 (m, 1H), 4.31 (dd, J=5.09, 2.71 Hz, 2H), 6.79 (s, 1H), 6.93 (d, J=8.82 Hz, 1H), 7.38 (dd, J=8.82, 2.71 Hz, 1H), 7.47 (d, J=2.71 Hz, 1H); MS (ESI) m/z 452 [M+H].

Example 50

N-{(3E)-5-tert-butyl-1-methyl-2-[(2R)-tetrahydrofuran-2-ylmethyl]-1,2-dihydro-3H-pyrazol-3-ylidene}-2-chloro-5-fluorobenzamide The title compound was prepared from Example 45B according to the procedures described in Example 45C and Example 45D, substituting 2-chloro-5-fluorobenzoyl chloride for 2-methoxy-5-chlorobenzoyl chloride. $^1$H NMR (300 MHz, DMSO-d$_6$) δ ppm 1.38 (s, 9H), 1.63-1.94 (m, 4H), 3.57-3.67 (m, 1H), 3.69-3.78 (m, 1H), 3.90 (s, 3H), 4.12-4.20 (m, 1H), 4.27-4.44 (m, 2H), 6.81 (s, 1H), 7.10-7.19 (m, 1H), 7.30-7.43 (m, 2H); MS (ESI) m/z 394 [M+H]$^+$.

Example 51

N-{(3E)-5-tert-butyl-1-methyl-2-[(2R)-tetrahydrofuran-2-ylmethyl]-1,2-dihydro-3H-pyrazol-3-ylidene}-2,3,5-trifluorobenzamide The title compound was prepared from Example 45B according to the procedures described in Example 45C and Example 45D, substituting 2,3,5-trifluorobenzoyl chloride for 2-methoxy-5-chlorobenzoyl chloride. $^1$H NMR (300 MHz, DMSO-d$_6$) δ ppm 1.38 (s, 9H), 1.65-1.82 (m, 3H), 1.84-1.95 (m, 1H), 3.58-3.69 (m, 1H), 3.69-3.81 (m, 1H), 3.91 (s, 3H), 4.11-4.25 (m, 1H), 4.30-4.46 (m, 2H), 6.82 (s, 1H), 7.34-7.53 (m, 2H); MS (ESI) m/z 396 [M+H]$^+$, 394 [M−H].

Example 52

N-{(3E)-5-tert-butyl-1-methyl-2-[(2R)-tetrahydrofuran-2-ylmethyl]-1,2-dihydro-3H-pyrazol-3-ylidene}-3-chloro-2-fluoro-5-(trifluoromethyl)benzamide The title compound was prepared from Example 45B according to the procedures described in Example 45C and Example 45D, substituting 3-chloro-2-fluoro-5-(trifluoromethyl)benzoyl chloride for 2-methoxy-5-chlorobenzoyl chloride. $^1$H NMR (300 MHz, DMSO-d$_6$) δ ppm 1.39 (s, 9H), 1.64-1.95 (m, 4H), 3.57-3.68 (m, 1H), 3.70-3.81 (m, 1H), 3.93 (s, 3H), 4.14-4.25 (m, 1H), 4.39 (t, J=5.16 Hz, 2H), 6.83 (s, 1H), 8.01-8.14 (m, 2H); MS (ESI) m/z 462 [M+H]$^+$, 460 [M−H].

Example 53

N-{(3E)-5-tert-butyl-1-methyl-2-[(2R)-tetrahydrofuran-2-ylmethyl]-1,2-dihydro-3H-pyrazol-3-ylidene}-3-chloro-2-methoxy-5-(trifluoromethyl)benzamide To methanol (48.1 mg, 1.5 mmol) in THF (4 mL) was added sodium tert-butoxide (144 mg, 1.5 mmol). The reaction mixture was stirred at ambient temperature for 10 minutes, then Example 52 (231 mg, 0.500 mmol) was added. The mixture was stirred for 2 hours and monitored by LC/MS. Saturated aqueous NaHCO$_3$ (10 mL) and ethyl acetate (10 mL) were added and the layers were separated. The organic layer was washed with brine and concentrated. Purification by flash chromatography (Et$_3$N/MeOH/EtOAc (1:10:90) in hexane at 10-60% gradient) afforded the title compound as a white solid (194 mg, 82%). $^1$H NMR (300 MHz, DMSO-d$_6$) δ ppm 1.39 (s, 9H), 1.62-1.94 (m, 4H), 3.56-3.68 (m, 1H), 3.69-3.79 (m, 1H), 3.89 (s, 3H), 3.91 (s, 3H), 4.08-4.23 (m, 1H), 4.35 (dd, J=5.16, 3.17 Hz, 2H), 6.83 (s, 1H), 7.74-7.83 (m, 2H); MS (ESI) m/z 474 [M+H]$^+$.

Example 54

N-{(3E)-5-tert-butyl-1-methyl-2-[(2R)-tetrahydrofuran-2-ylmethyl]-1,2-dihydro-3H-pyrazol-3-ylidene}-2-chloro-5-(trifluoromethyl)benzamide The title compound was prepared from Example 45B according to the procedures described in Example 45C and Example 45D, substituting 2-chloro-5-(trifluoromethyl)benzoyl chloride for 2-methoxy-5-chlorobenzoyl chloride. $^1$H NMR (300 MHz, DMSO-d$_6$) δ ppm 1.39 (s, 9H), 1.63-1.95 (m, 4H), 3.58-3.67 (m, 1H), 3.70-3.80 (m, 1H), 3.91 (s, 3H), 4.13-4.23 (m, 1H), 4.27-4.42 (m, 2H), 6.83 (s, 1H), 7.58-7.70 (m, 2H), 7.89 (s, 1H); MS (ESI) m/z 444 [M+H]$^+$, 442 [M−H].

Example 55

N-{(3E)-5-tert-butyl-1-methyl-2-[(2R)-tetrahydrofuran-2-ylmethyl]-1,2-dihydro-3H-pyrazol-3-ylidene}-3,5-difluoro-2-methoxybenzamide The title compound was prepared from Example 51 and methanol according to the procedure described in Example 53. $^1$H NMR (300 MHz, DMSO-d$_6$) δ ppm 1.38 (s, 9H), 1.59-1.94 (m, 4H), 3.55-3.66 (m, 1H), 3.73 (t, J=7.14 Hz, 1H), 3.80 (s, 3H), 3.89 (s, 3H), 4.10-4.22 (m, 1H), 4.28-4.45 (m, 2H), 6.83 (s, 1H) 7.10 (dd, J=9.12, 1.98 Hz, 1H), 7.17-7.29 (m, 1H); MS (ESI) m/z 408 [M+H]$^+$, 406 [M−H].

Example 56

N-{(3E)-5-tert-butyl-1-methyl-2-[(2R)-tetrahydrofuran-2-ylmethyl]-1,2-dihydro-3H-pyrazol-3-ylidene}-3-chloro-2-(2-methoxyethoxy)-5-(trifluoromethyl)benzamide The title compound was prepared from Example 52 and 2-methoxyethanol according to the procedure described in Example 53. $^1$H NMR (300 MHz, DMSO-d$_6$) δ ppm 1.39 (s, 9H), 1.62-1.86 (m, 4H), 3.26 (s, 3H), 3.54-3.68 (m, 3H) 3.73 (t, J=7.14 Hz, 1H), 3.91 (s, 3H), 4.16 (d, J=5.55 Hz, 1H), 4.19-4.26 (m, 2H), 4.37-4.39 (m, 2H), 6.81 (s, 1H), 7.72-7.85 (m, 2H); MS (ESI) m/z 518 [M+H]$^+$, 516 [M−H].

Example 57

N-{(3E)-5-tert-butyl-1-methyl-2-[(2R)-tetrahydrofuran-2-ylmethyl]-1,2-dihydro-3H-pyrazol-3-ylidene}-3-chloro-2-(2-fluoroethoxy)-5-(trifluoromethyl)benzamide The title compound was prepared from Example 52 and 2-fluoroethanol according to the procedure described in Example 53. $^1$H NMR (300 MHz, DMSO-d$_6$) δ ppm 1.39 (s, 9H), 1.63-1.93 (m, 4H), 3.59-3.68 (m, 1H), 3.73 (t, J=7.14 Hz, 1H), 3.91 (s, 3H), 4.10-4.22 (m, 1H), 4.28-4.38 (m, 3H), 4.39-4.46 (m, 1H), 4.58-4.63 (m, 1H), 4.73-4.79 (m, 1H), 6.82 (s, 1H), 7.82 (s, 2H); MS (ESI) m/z 506 [M+H]$^+$, 504 [M−H].

Example 58

5-bromo-N-{(3E)-5-tert-butyl-1-methyl-2-[(2R)-tetrahydrofuran-2-ylmethyl]-1,2-dihydro-3H-pyrazol-3-ylidene}-2-(2-methoxyethoxy)benzamide Example 58A 5-bromo-N-{(3E)-5-tert-butyl-1-methyl-2-[(2R)-tetrahydrofuran-2-ylmethyl]-1,2-dihydro-3H-pyrazol-3-ylidene}-2-fluorobenzamide The title compound was prepared from Example 45B according to the procedure described in Example 45C and Example 45D, substituting 5-bromo-2-fluorobenzoyl chloride for 2-methoxy-5-chlorobenzoyl chloride. $^1$H NMR (300 MHz, DMSO-d$_6$) δ ppm 1.38 (s, 9H), 1.65-1.96 (m, 4H), 3.59-3.69 (m, 1H), 3.74 (t, J=7.14 Hz, 1H), 3.90 (s, 3H), 4.13-4.24 (m, 1H), 4.32-4.44 (m, 2H), 6.81 (s, 1H), 7.13 (dd, J=10.31, 8.72 Hz, 1H), 7.48-7.57 (m, 1H), 7.92 (dd, J=6.74, 2.78 Hz, 1H); MS (ESI) m/z 438 [M+H]$^+$.

Example 58B 5-bromo-N-{(3E)-5-tert-butyl-1-methyl-2-[(2R)-tetrahydrofuran-2-ylmethyl]-1,2-dihydro-3H-pyrazol-3-ylidene}-2-(2-methoxyethoxy)benzamide The title compound was prepared from Example 58A and 2-methoxyethanol according to the procedure described in Example 53. $^1$H NMR (300 MHz, DMSO-d$_6$) δ ppm 1.37 (s, 9H), 1.65-1.92 (m, 4H), 3.27 (s, 3H), 3.57-3.67 (m, 3H), 3.70-3.78 (m, 1H), 0.87 (s, 3H), 4.07 (dd, J=5.43, 4.07 Hz, 2H), 4.10-4.20 (m, 1H), 4.29-4.36 (m, 2H), 6.77 (s, 1H), 6.94 (d, J=8.82 Hz, 1H), 7.36 (dd, J=8.82, 2.71 Hz, 1H), 7.49 (d, J=2.37 Hz, 1H); MS (ESI) m/z 496 [M+H]$^+$, 494 [M−H].

Example 59

5-bromo-N-{(3E)-5-tert-butyl-1-methyl-2-[(2R)-tetrahydrofuran-2-ylmethyl]-1,2-dihydro-3H-pyrazol-3-ylidene}-2-(2-fluoroethoxy)benzamide The title compound was prepared from Example 58A and 2-fluoroethanol according to the procedure described in Example 53. $^1$H NMR (300 MHz, DMSO-d$_6$) δ ppm 1.38 (s, 9H), 1.60-1.96 (m, 4H), 3.54-3.66 (m, 1H), 3.69-3.80 (m, 1H), 3.87 (s, 3H), 4.11-4.18 (m, 2H), 4.23-4.36 (m, 3H), 4.56-4.62 (m, 1H), 4.72-4.78 (m, 1H), 6.79 (s, 1H), 6.96 (d, J=8.82 Hz, 1H), 7.38 (dd, J=8.48, 2.71 Hz, 1H), 7.53 (d, J=2.71 Hz, 1H); MS (ESI) m/z 484 [M+H]$^+$, 482 [M−H].

Example 60

5-bromo-N-{(3E)-5-tert-butyl-1-methyl-2-[(2R)-tetrahydrofuran-2-ylmethyl]-1,2-dihydro-3H-pyrazol-3-ylidene}-2,3-dihydro-1-benzofuran-7-carboxamide The title compound was prepared from Example 45B according to the procedure described in Example 45C and Example 45D, substituting 5-bromo-2,3-dihydrobenzofuran-7-carbonyl chloride for 2-methoxy-5-chlorobenzoyl chloride. $^1$H NMR (300 MHz, DMSO-d$_6$) δ ppm 1.37 (s, 9H), 1.73-1.97 (m, 4H), 3.12-3.28 (m, 2H), 3.59-3.69 (m, 1H), 3.72-3.81 (m, 1H), 3.87 (s, 3H), 4.22 (dd, J=5.35, 3.77 Hz, 1H), 4.27-4.37 (m, 1H), 4.39-4.47 (m, 1H), 4.52 (t, J=8.72 Hz, 2H), 6.77 (s, 1H), 7.34 (d, J=2.38 Hz, 1H), 7.76 (d, J=1.98 Hz, 1H); MS (ESI) m/z 464 [M+H].

Example 61

N-[(2E)-4-tert-butyl-1-[(2R)-tetrahydrofuran-2-ylmethyl]pyridin-2(1H)-ylidene]-5-chloro-2-methoxybenzamide Example 61A (R)-4-tert-butyl-1-((tetrahydrofuran-2-yl)methyl)pyridin-2(1H)-imine A mixture of 4-tert-butylpyridin-2-amine (1.0 g, 6.7 mmol, LeadGen Labs), Example 11A (2.0 g, 8.0 mmol), and tetrabutylammonium iodide (1.2 g, 3.3 mmol) in N,N-dimethylformamide (1.3 mL) was heated at 95° C. for 16 h. The reaction was incomplete as monitored by LC/MS. One more equivalent of both Example 11A and tetrabutylammonium iodide were added. After stirring at 95° C. for 16 h, the reaction mixture was cooled and quenched with saturated NaHCO$_3$ (10 mL). The aqueous layer was extracted with dichloromethane (3×30 mL). The combined organic extracts were dried over anhydrous Na$_2$SO$_4$, filtered and concentrated under reduced pressure to provide the title compound. MS (ESI$^+$) m/z 235 (M+H)$^+$.

Example 61B

N-[(2E)-4-tert-butyl-1-[(2R)-tetrahydrofuran-2-ylmethyl]pyridin-2(1H)-ylidene]-5-chloro-2-methoxybenzamide To a solution of the crude product of Example 61A (0.8 g, 1.7 mmol) in tetrahydrofuran (10 mL) were added 5-chloro-2-methoxybenzoyl chloride (0.4 g, 1.9 mmol) and triethylamine (0.7 mL, 5.1 mmol). After stirring at 60° C. for 14 h, the reaction mixture was cooled and quenched with saturated NaHCO$_3$ (10 mL). The aqueous layer was extracted with ethyl acetate (3×20 mL). The combined organic extracts were dried over anhydrous Na$_2$SO$_4$, filtered and concentrated under reduced pressure. The residue was purified by column chromatography using an Analogix® Intelliflash280™ (SiO$_2$, 0-5% methanol in dichloromethane) to provide 60 mg of the title compound. $^1$H NMR (300 MHz, DMSO-d$_6$) δ ppm 1.26 (s, 9H), 1.50-1.69 (m, 1H), 1.69-2.09 (m, 3H), 3.57-3.70 (m, 1H), 3.75 (s, 3H), 3.76-3.86 (m, 1H), 4.00 (dd, J=12.9, 8.5 Hz, 1H), 4.30 (dd, 1H), 4.57 (dd, J=12.7, 3.2 Hz, 1H), 6.87 (dd, J=7.0, 2.2 Hz, 1H), 7.03 (d, J=8.8 Hz, 1H), 7.34 (dd, J=8.8, 2.7 Hz, 1H), 7.53 (d, J=2.7 Hz, 1H), 7.95 (d, J=7.1 Hz, 1H), 8.28 (d, J=2.4 Hz, 1H) MS (ESI$^+$) m/z 403 (M+H)$^+$.

Example 62

N-[(2E)-4-tert-butyl-1-[(2R)-tetrahydrofuran-2-ylmethyl]pyridin-2(1H)-ylidene]-2-methoxy-5-(trifluoromethyl)benzamide Example 61A, 2-methoxy-5-(trifluoromethyl)benzoyl chloride (JRD Fluorochemicals) and triethylamine were processed as described for Example 61B to provide the title compound. $^1$H NMR (300 MHz, DMSO-d$_6$) δ ppm 1.27 (s, 9H), 1.52-1.69 (m, 1H), 1.71-2.01 (m, 3H), 3.55-3.70 (m, 1H), 3.72-3.82 (m, 1H), 3.84 (s, 3H), 3.93-4.12 (m, 1H), 4.24-4.43 (m, 1H), 4.60 (dd, J=12.7, 3.2 Hz, 1H), 6.89 (dd, J=7.0, 2.2 Hz, 1H), 7.21 (d, J=8.5 Hz, 1H), 7.67 (dd, J=8.6, 2.5 Hz, 1H), 7.88 (d, J=2.4 Hz, 1H), 7.97 (d, J=7.1 Hz, 1H), 8.34 (d, J=2.0 Hz, 1H); MS (ESI$^+$) m/z 437 (M+H)$^+$ Example 63

N-[(3E)-5-tert-butyl-1-methyl-2-(tetrahydro-2H-pyran-2-ylmethyl)-1,2-dihydro-3H-pyrazol-3-ylidene]-2-methoxy-5-(trifluoromethyl)benzamide Example 63A (E)-N'-(3-tert-butyl-1H-pyrazol-5-yl)-N,N-dimethylformimidamide A mixture of 3-tert-butyl-1H-pyrazol-5-amine (5 g, 36 mmol, Alfa-aesar) and N,N-dimethylformamide dimethylacetal (153 mL, 1078 mmol, Aldrich) was refluxed overnight. The reaction mixture was then cooled, concentrated under reduced pressure and the residue was purified by column chromatography using an Analogix® Intelliflash280™ (SiO$_2$, 0-5% methanol in dichloromethane) to provide 6.9 g (99%) of the title compound. MS (ESI$^+$) m/z 195 (M+H)$^+$.

Example 63B (E)-N'-(3-tert-butyl-1-((tetrahydro-2H-pyran-2-yl)methyl)-1H-pyrazol-5-yl)-N,N-dimethylformimidamide To a solution of Example 63A (1.0 g, 5.2 mmol) in N,N-dimethylformamide (10 mL) were added sodium hydride (0.52 g, 12.9 mmol, 60% in mineral oil, Aldrich), 2-(bromomethyl)tetrahydro-2H-pyran (0.8 mL, 6.2 mmol) and sodium iodide (0.23 g, 1.5 mmol). After stirring at 65° C. for 16 h, the reaction mixture was cooled and quenched with saturated NaHCO$_3$ (10 mL). The aqueous layer was extracted with ethyl acetate (3×20 mL). The combined organic extracts were dried over anhydrous Na$_2$SO$_4$, filtered and concentrated under reduced pressure. The residue was purified by column chromatography using an Analogix® Intelliflash280™ (SiO$_2$, 0-10% methanol in dichloromethane) to provide 0.82 g (55%) of the title compound. $^1$H NMR (501 MHz, chloroform-d) δ ppm 1.22-1.33 (m, 1H), 1.27 (s, 9H), 1.34-1.49 (m, 3H), 1.51-1.62 (m, 1H), 1.72-1.83 (m, 1H), 2.87 (s, 3H), 2.95 (s, 3H), 3.36-3.49 (m, 1H), 3.73-3.83 (m, 1H), 3.95 (dd, J=11.3, 3.0 Hz, 1H), 4.02 (dd, J=13.4, 7.7 Hz, 1H), 4.17 (dd, J=13.4, 5.8 Hz, 1H), 5.55 (s, 1H), 8.00 (s, 1H). MS (ESI$^+$) m/z 293 (M+H)$^+$.

Example 63C 3-tert-butyl-1-((tetrahydro-2H-pyran-2-yl)methyl)-1H-pyrazol-5-amine To a solution of Example 63B (0.9 g, 3.1 mmol) in dioxane (10 mL) were added hydrazine (0.12 mL, 3.7 mmol, Aldrich) and acetic acid (0.35 mL, 6.2 mmol). After stirring at 85° C. for 16 h, the reaction mixture was cooled and quenched with saturated NaHCO$_3$ (10 mL). The aqueous layer was extracted with ethyl acetate (3×20 mL). The combined organic extracts were dried over anhydrous Na$_2$SO$_4$, filtered and concentrated under reduced pressure to provide the title compound. MS (APCI$^+$) m/z 238 (M+H)$^+$.

Example 63D

N-(3-tert-butyl-1-((tetrahydro-2H-pyran-2-yl)methyl)-1H-pyrazol-5-yl)-2-methoxy-5-(trifluoromethyl)benzamide To a solution of Example 63C (0.73 g, 3.1 mmol) in tetrahydrofuran (20 mL) were added 2-methoxy-5-(trifluoromethyl)benzoic acid (0.68 g, 3.1 mmol, JRD Fluorochemicals), 1-hydroxybenzotriazole (0.47 g, 3.1 mmol, Aldrich), N-(3-dimethylaminopropyl)-N-ethylcarbodiimide hydrochloride (0.59 g, 3.1 mmol) and triethylamine (1.3 mL, 9.2 mmol). After stirring at 60° C. for 16 h, the reaction mixture was cooled and quenched with saturated NaHCO$_3$ (20 mL). The aqueous layer was extracted with ethyl acetate (3×20 mL). The combined organic extracts were dried over anhydrous Na$_2$SO$_4$, filtered and concentrated under reduced pressure. The residue was purified by column chromatography using an Analogix® Intelliflash280™ (SiO$_2$, 0-50% ethyl acetate in hexanes) to provide 0.2 g of the title compound. MS (ESI$^+$) m/z 440 (M+H)$^+$.

Example 63E

N-[(3E)-5-tert-butyl-1-methyl-2-(tetrahydro-2H-pyran-2-ylmethyl)-1,2-dihydro-3H-pyrazol-3-ylidene]-2-methoxy-5-(trifluoromethyl)benzamide To a solution Example 63D (0.2 g, 0.455 mmol) in toluene (2.0 mL) was added dimethyl sulfate (0.130 mL, 1.365 mmol). The reaction mixture was heated at 150° C. with microwave irradiation for 60 min. The reaction mixture was then purified by column chromatography using an Analogix® Intelliflash280 (SiO$_2$, 0-100% of 7N methanol/methylene chloride (1:10) in methylene chloride) to provide the title compound. $^1$H NMR (300 MHz, DMSO-d$_6$) δ ppm 1.21-1.32 (m, 2H), 1.37 (s, 9H), 1.39-1.48 (m, 2H), 1.49-1.57 (m, 1H), 1.73-1.85 (m, 1H), 3.60-3.70 (m, 1H), 3.81 (s, 3H), 3.86 (s, 3H), 3.87-3.90 (m, 1H), 4.16 (s, 1H), 4.17-4.23 (m, 1H), 4.24-4.34 (m, 1H), 6.78 (s, 1H), 7.15 (d, J=8.6 Hz, 1H), 7.60 (dd, J=8.6, 2.5 Hz, 1H), 7.75 (d, J=2.5 Hz, 1H); MS (ESI$^+$) m/z 454 (M+H)$^+$.

Example 64

N-((3E)-5-tert-butyl-1-methyl-2-{[(5R)-5-methyltetrahydrofuran-2-yl]methyl}-1,2-dihydro-3H-pyrazol-3-ylidene)-2-methoxy-5-(trifluoromethyl)benzamide Example 64A ((5R)-5-methyltetrahydrofuran-2-yl)methanol To a solution of (R)-hex-5-en-2-ol (5.0 g, 50.0 mmol, Aldrich) in chloroform (100 mL) were added methyltrioxorhenium(VII) (0.37 g, 1.5 mmol, Aldrich) and hydrogen peroxide (5.7 g, 50.0 mmol, 30% in water, Aldrich). After stirring at room temperature for 16 hr, the reaction mixture was quenched with potassium carbonate, and extracted with diethyl ether (2×50 mL). The combined organic extracts were dried over anhydrous MgSO$_4$, filtered and concentrated under reduced pressure to provide 7.7 g (75%) of the title compound MS (DCI$^+$) m/z 134 (M+NH$_4$)$^+$.

Example 64B ((5R)-5-methyltetrahydrofuran-2-yl)methyl 4-methylbenzenesulfonate

To a solution of Example 64A (4.0 g, 25.8 mmol) in dichloromethane (100 mL) were added triethylamine (10.8 mL, 77.0 mmol) and p-toluenesulfonyl chloride (4.9 g, 25.8 mmol). The reaction mixture was stirred at room temperature overnight and then washed with water (50 mL) and brine (50 mL). The organic layer was dried (Na$_2$SO$_4$), filtered and concentrated under reduced pressure. The residue was purified by column chromatography using an Analogix® Intelliflash280™ (SiO$_2$, 0-25% ethyl acetate in hexanes) to provide 3.5 g (50%) of the title compound. MS (DCI$^+$) m/z 288 (M+NH$_4$)$^+$.

Example 64C (E)-N'-(3-tert-butyl-1-(((5R)-5-methyltetrahydrofuran-2-yl)methyl)-1H-pyrazol-5-yl)-N,N-dimethylformimidamide To a solution of Example 63A (1.6 g, 8.2 mmol) in toluene (100 mL) were added potassium carbonate (2.3 g, 16.5 mmol), Example 64B (2.7 g, 9.9 mmol), tetrabutylammonium iodide (70 mg), tetraethylammonium iodide (70 mg) and tetrabutylammonium hydrogensulfate (70 mg). The reaction mixture was refluxed for 16 h, cooled, filtered and concentrated under reduced pressure. The residue was purified by column chromatography using an Analogix® Intelliflash280 T (SiO$_2$, 0-10% methanol in dichloromethane) to provide 0.6 g (25%) of the title compound. MS (ESI$^+$) m/z 293 (M+H)$^+$.

Example 64D 3-tert-butyl-1-(((5R)-5-methyltetrahydrofuran-2-yl)methyl)-1H-pyrazol-5-amine Example 64C, hydrazine and acetic acid were processed as described for Example 63C to provide the title compound. LCMS (APCI$^+$) m/z 237 (M+H)$^+$.

Example 64E

N-(3-tert-butyl-1-{[(5R)-5-methyltetrahydrofuran-2-yl]methyl}-1H-pyrazol-5-yl)-2-methoxy-5-(trifluoromethyl)benzamide Example 64D, 2-methoxy-5-(trifluoromethyl)benzoic acid, 1-hydroxybenzotriazole, N-(3-dimethylaminopropyl)-N-ethylcarbodimide hydrochloride and triethylamine were processed as described in Example 63D to provide the title compound. MS (ESI$^+$) m/z 440 (M+H)$^+$.

Example 64F

N-((3E)-5-tert-butyl-1-methyl-2-{[(5R)-5-methyltetrahydrofuran-2-yl]methyl}-1,2-dihydro-3H-pyrazol-3-ylidene)-2-methoxy-5-(trifluoromethyl)benzamide Example 64E and dimethyl sulfate were processed as described in Example 63E to provide the title compound as a mixture of diastereomers (the NMR spectrum has duplicate signals for a few protons). $^1$H NMR (300 MHz, DMSO-d$_6$) δ ppm 1.09 (d, J=5.9 Hz, 3H), 1.09 (d, J=5.9 Hz, 3 H), 1.19-1.27 (m, 1H), 1.29-1.37 (m, 2H), 1.38 (s, 18H), 1.67-1.81 (m, 1H), 1.82-1.97 (m, 4H), 3.80 (s, 6H), 3.88 (s, 3H), 3.90 (s, 3H), 3.94-4.04 (m, 2H), 4.10-4.19 (m, 1H), 4.25-4.38 (m, 5H), 6.81 (s, 1H), 6.82 (s, 1H), 7.14 (d, J=8.7 Hz, 2H), 7.59 (dd, J=8.7, 2.4 Hz, 2H), 7.67 (d, J=1.6 Hz, 2H); MS (ESI$^+$) m/z 454 (M+H)$^+$.

Example 65

N-((3E)-5-tert-butyl-1-methyl-2-{[(5S)-5-methyltetrahydrofuran-2-yl]methyl}-1,2-dihydro-3H-pyrazol-3-ylidene)-2-methoxy-5-(trifluoromethyl)benzamide

Example 65A ((5S)-5-methyltetrahydrofuran-2-yl)methanol

Commercially available (S)-hex-5-en-2-ol (Aldrich), methyltrioxorhenium(VII) (Aldrich) and hydrogen peroxide (Aldrich) were processed as described for Example 64A to provide the title compound MS (DCI$^+$) m/z 134 (M+NH$_4$)$^+$.

Example 65B ((5S)-5-methyltetrahydrofuran-2-yl)methyl 4-methylbenzenesulfonate Example 65A, triethylamine and p-toluenesulfonyl chloride were processed as described for Example 64B to provide the title compound. MS (DCI$^+$) m/z 288 (M+NH$_4$)$^+$.

Example 65C (E)-N'-(3-tert-butyl-1-(((5S)-5-methyltetrahydrofuran-2-yl)methyl)-1H-pyrazol-5-yl)-N,N-dimethylformimidamide Example 63A, Example 65B and potassium carbonate were processed as described for Example 64C to provide the title compound. MS (ESI$^+$) m/z 293 (M+H)$^+$.

Example 65D 3-tert-butyl-1-(((5S)-5-methyltetrahydrofuran-2-yl)methyl)-1H-pyrazol-5-amine Example 65C, hydrazine and acetic acid were processed as described for Example 63C to provide the title compound. LCMS (APCI$^+$) m/z 237 (M+H)$^+$.

Example 65E

N-(3-tert-butyl-1-{[(5S)-5-methyltetrahydrofuran-2-yl]methyl}-1H-pyrazol-5-yl)-2-methoxy-5-(trifluoromethyl)benzamide Example 65D, 2-methoxy-5-(trifluoromethyl)benzoic acid, 1-hydroxybenzotriazole, N-(3-dimethylaminopropyl)-N-ethylcarbodimide hydrochloride and triethylamine were processed as described for Example 63D to provide the title compound. MS (ESI$^+$) m/z 440 (M+H)$^+$.

Example 65F

N-((3E)-5-tert-butyl-1-methyl-2-{[(5S)-5-methyltetrahydrofuran-2-yl]methyl}-1,2-dihydro-3H-pyrazol-3-ylidene)-2-methoxy-5-(trifluoromethyl)benzamide Example 65E and dimethyl sulfate were processed as described for Example 63E to provide the title compound as a diasteriomeric mixture (the NMR spectrum has duplicated signals for few proton types). $^1$H NMR (300 MHz, DMSO-d$_6$) δ ppm $^1$H NMR (400 MHz, DMSO-D6) δ ppm 1.09 (d, J=6.1 Hz, 3H), 1.09 (d, J=5.8 Hz, 3H), 1.19-1.26 (m, 1H), 1.32-1.37 (m, 1H), 1.38 (s, 18H), 1.69-1.78 (m, 1H), 1.81-1.98 (m, 5H), 3.80 (s, 6H), 3.87 (s, 3H), 3.90 (s, 3H), 3.96-4.06 (m, 2H), 4.10-4.20 (m, 1H), 4.23-4.39 (m, 5H), 6.81 (s, 1H), 6.82 (s, 1H), 7.14 (d, J=8.6 Hz, 2H), 7.59 (dd, J=8.6, 2.1 Hz, 2H), 7.68 (d, J=2.1 Hz, 2H); MS (ESI$^+$) m/z 454 (M+H)$^+$.

Example 66

N-[(2Z)-5-tert-butyl-3-[(2R)-tetrahydrofuran-2-ylmethyl]-1,3-oxazol-2(3H)-ylidene]-2-methoxy-5-(trifluoromethyl)benzamide

Example 66A (R)-5-tert-butyl-3-((tetrahydrofuran-2-yl)methyl)oxazol-2(3H)-imine A mixture of Example 13A (500 mg, 3.96 mmol), 1-bromo-3,3-dimethylbutan-2-one (Aldrich) (535 μL, 3.96 mmol) and cesium carbonate (2.58 g, 7.93 mmol) in 1,2-dimethoxyethane (8 mL) was stirred at 60° C. for 4 h. The mixture was cooled, poured into water, and extracted with ethyl acetate (2×). The combined organic extracts were dried over MgSO$_4$, filtered, and concentrated under reduced pressure to afford the title compound. LC/MS (ESI$^+$) m/z 225 (M+H)$^+$.

Example 66B

N-[(2Z)-5-tert-butyl-3-[(2R)-tetrahydrofuran-2-ylmethyl]-1,3-oxazol-2(3H)-ylidene]-2-methoxy-5-(trifluoromethyl)benzamide To a solution of Example 66A (100 mg, 0.45 mmol) in tetrahydrofuran (4 mL) was added N-(3-dimethylaminopropyl)-N-ethylcarbodiimide hydrochloride (85.0 mg, 0.45 mmol), 1-hydroxybenzotriazole (68.3 mg, 0.45 mmol), triethylamine (93 µL, 0.67 mmol) and 2-methoxy-5-trifluoromethylbenzoic acid (Alfa) (98.0 mg, 0.45 mmol). The mixture was stirred at 60° C. overnight, cooled to room temperature, diluted with ethyl acetate, washed with 1 M aqueous NaHCO$_3$, dried (MgSO$_4$), filtered and concentrated. The residue was purified by column chromatography using an Analogix® Intelliflash280™ (SiO$_2$, 0-50% ethyl acetate in hexanes) to provide the title product. MS (ESI$^+$) m/z 428 (M+H)$^+$; $^1$H NMR (300 MHz, CDCl$_3$) δ ppm 1.15-1.19 (m, 1H), 1.20 (s, 9H), 1.61-1.72 (m, 1H), 1.83-1.96 (m, 2H), 2.02-2.15 (m, 1H), 3.68 (dd, J=14.3, 7.1 Hz, 1H), 3.75-3.87 (m, 2H), 3.89 (s, 3H), 4.02-4.12 (m, 1H), 4.14-4.25 (m, 1H), 6.53 (s, 1H), 6.97 (d, J=8.7 Hz, 1H), 7.58 (dd, J=8.7, 2.4 Hz, 1H), 8.06 (d, J=2.0 Hz, 1H).

Example 67

N-[(2Z)-5-tert-butyl-3-[(2R)-tetrahydrofuran-2-ylmethyl]-1,3,4-thiadiazol-2(3H)-ylidene]-N'-(4-methylcyclohexyl)urea

Example 67A

Tert-butyl 5-tert-butyl-1,3,4-thiadiazol-2-ylcarbamate

To mixture of 5-tert-butyl-1,3,4-thiadiazol-2-amine (Aldrich) (20.0 g, 127 mmol) and N1,N1,N1,N1-tetramethylethane-1,2-diamine (0.19 mL, 1.27 mmol) in dichloromethane was added di-tertbutyl dicarbonate (30.5 g, 140 mmol). The reaction was stirred at room temperature for 12 h. The mixture was washed with aq. sodium bicarbonate, dried over Na$_2$SO$_4$ and concentrated under reduced pressure. The residue was purified by column chromatography using an Analogix® Intelliflash280™ (SiO$_2$, 0-15% ethyl acetate in hexanes) to give the title product. MS (ESI$^+$) m/z 258 (M+H)$^+$.

Example 67B tert-butyl[(2Z)-5-tert-butyl-3-[(2R)-tetrahydrofuran-2-ylmethyl]-1,34-thiadiazol-2(3H)-ylidene]carbamate To a mixture of Example 67A (1.88 g, 7.31 mmol) and Example 11A (2.25 g, 8.77 mmol) in THF/DMF (4/1) was added potassium tert-butoxide (1.12 g, 9.50 mmol). The reaction was heated at 75° C. for 16 h. The mixture was cooled to room temperature and diluted with ether, washed with aq. NaHCO$_3$, dried over MgSO$_4$ and concentrated under reduced pressure. The residue was purified by column chromatography using an Analogix® Intelliflash280™ (SiO$_2$, 0-50% ethyl acetate in hexanes) to give the title compound. MS (ESI$^+$) m/z 342 (M+H)$^+$.

Example 67C (R)-5-tert-butyl-3-((tetrahydrofuran-2-yl)methyl)-1,3,4-thiadiazol-2(3H)-imine Example 67B (619 mg, 1.81 mmol) and trifluoroacetic acid (1.12 mL, 14.5 mmol) were stirred at 22° C. for 8 h. The trifluoroacetic acid was evaporated and the residue was dissolved in dichloromethane and washed with saturated aq. NaHCO$_3$. The organic extract was dried over Na$_2$SO$_4$ and concentrated to dryness to yield the title compound. MS (ESI$^+$) m/z 242 (M+H)$^+$.

Example 67D

N-[(2Z)-5-tert-butyl-3-[(2R)-tetrahydrofuran-2-ylmethyl]-1,3,4-thiadiazol-2(3H)-ylidene]-N'-(4-methylcyclohexyl)urea To a solution of Example 67C (33 mg, 0.14 mmol) in tetrahydrofuran (0.3 mL), was added triethylamine (28 mg, 0.27 mmol). After shaking a solution of p-nitrophenyl carbamoyl chloride (28 mg, 0.14 mmol) was added in tetrahydrofuran (0.3 mL). A precipitate was formed and after shaking for 30 minutes a solution of 4-methylcyclohexanamine (21 mg, 0.19 mmol) in tetrahydrofuran (0.6 mL) was added. The mixture was heated to 50° C. overnight. The mixture was cooled to ambient temperature, and filtered through Si-Carbonate cartridge, washed with methanol checked by LC/MS and concentrated to dryness. The residue was dissolved in 1:1 DMSO/Methanol and purified by preparative HPLC on a Phenomenex Luna C8(2) 5 µm 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-6.0 min linear gradient 10-100% A, 6.0-7.0 min 100% A, 7.0-8.0 min linear gradient 100-10% A) to afford the title compound. $^1$H NMR (500 MHz, DMSO/D$_2$O) δ ppm 0.83-0.93 (m, 3H), 0.93-1.01 (m, 1H), 1.15-1.25 (m, 1H), 1.26-1.35 (m, 10H), 1.41-1.99 (m, 10H), 3.59-3.67 (m, 2H), 3.75-3.80 (m, 1H), 3.96-4.08 (m, 1H), 4.19-4.32 (m, 2H); MS (ESI) m/z 381 (M+H)$^+$.

Example 68

N-(1-adamantylmethyl)-N'-[(2Z)-5-tert-butyl-3-[(2R)-tetrahydrofuran-2-ylmethyl]-1,3,4-thiadiazol-2(3H)-ylidene]urea Example 67C (33 mg, 0.14 mmol) and adamantanemethylamine (31 mg, 0.19 mmol) were processed and the product purified according to the methods of Example 67D to afford the title compound. $^1$H NMR (500 MHz, DMSO/D$_2$O) δ ppm 1.24-1.40 (m, 9H), 1.40-2.03 (m, 19H), 2.75-2.85 (m, 2H), 3.59-3.67 (m, 1H), 3.74-3.81 (m, 1H), 3.98-4.07 (m, 1H), 4.22-4.36 (m, 2H); MS (ESI) m/z 433 (M+H)$^+$.

Example 69

N-[(2Z)-5-tert-butyl-3-[(2R)-tetrahydrofuran-2-ylmethyl]-1,3,4-thiadiazol-2(3H)-ylidene]-N'-{[(1S,2R,5S)-6,6-dimethylbicyclo[3.1.1]hept-2-yl]methyl}urea Example 67C (33 mg, 0.14 mmol) and ((1S,2R,5S)-6,6-dimethylbicyclo[3.1.1]heptan-2-yl)methanamine (29 mg, 0.19 mmol) were processed and the product purified according to the methods of Example 67D to afford the title compound. $^1$H NMR (500 MHz, DMSO/D$_2$O) δ ppm 1.00-1.35 (m, 15H), 1.38-2.37 (m, 13H), 2.88-3.20 (m, 2H), 3.61-3.67 (m, 1H), 3.76-3.80 (m, 1H), 3.94-4.08 (m, 1H), 4.20-4.34 (m, 2H); MS (ESI) m/z 421 (M+H)$^+$.

Example 70

N-[(2Z)-5-tert-butyl-3-[(2R)-tetrahydrofuran-2-ylmethyl]-1,3,4-thiadiazol-2(3H)-ylidene]-N'-[1-(hydroxymethyl)-3-methylbutyl]urea Example 67C (33 mg, 0.14 mmol) and (S)-2-amino-4-methylpentan-1-ol (22 mg, 0.19 mmol) were processed and the product purified according to the methods of Example 67D to afford the title compound. $^1$H NMR (500 MHz, DMSO/D$_2$O) δ ppm 0.80-0.93 (m, 6H), 1.26-1.35 (m, 11H), 1.49-1.72 (m, 2H), 1.76-2.01 (m, 3H), 3.21-3.38 (m, 2H), 3.60-3.66 (m, 1H), 3.69-3.75 (m, 1H), 3.78-3.82 (m, 1H), 3.97-4.13 (m, 1H), 4.18-4.34 (m, 2H); MS (ESI) m/z 385 (M+H)$^+$.

Example 71

N-[(2Z)-5-tert-butyl-3-[(2R)-tetrahydrofuran-2-ylmethyl]-1,3,4-thiadiazol-2(3H)-ylidene]-N'-(1,2-dimethylpropyl)urea Example 67C (33 mg, 0.14 mmol) and 3-methylbutan-2-amine (16 mg, 0.19 mmol) were processed and the product purified according to the methods of Example 67D to afford the title compound. $^1$H NMR (500 MHz, DMSO/D$_2$O) δ ppm 0.79-0.88 (m, 6H), 0.98-1.06 (m, 3H), 1.27-1.36 (m, 9H), 1.60-1.76 (m, 2H), 1.76-2.02 (m, 3H), 3.47-3.55 (m, 1H), 3.59-3.67 (m, 1H), 3.77-3.80 (m, 1H), 3.95-4.05 (m, 1H), 4.19-4.32 (m, 2H); MS (ESI) m/z 355 (M+H)$^+$.

Example 72

N-[(2Z)-5-tert-butyl-3-[(2R)-tetrahydrofuran-2-ylmethyl]-1,3,4-thiadiazol-2(3H)-ylidene]-N'-(1-ethylpropyl)urea Example 67C (33 mg, 0.14 mmol) and pentan-3-amine (16 mg, 0.19 mmol) were processed and the product purified according to the methods of Example 67D to afford the title compound. $^1$H NMR (500 MHz, DMSO/D$_2$O) δ ppm 0.72-0.87 (m, 6H), 1.24-1.33 (m, 9H), 1.33-1.57 (m, 4H), 1.58-1.76 (m, 1H), 1.74-2.05 (m, 3H), 3.36-3.48 (m, 1H), 3.59-3.69 (m, 1H), 3.77-3.82 (m, 1H), 3.93-4.11 (m, 1H), 4.20-4.31 (m, 2H); MS (ESI) m/z 355 (M+H)$^+$.

Example 73

N-[(2Z)-5-tert-butyl-3-[(2R)-tetrahydrofuran-2-ylmethyl]-1,3,4-thiadiazol-2(3H)-ylidene]-N'-1,2,3,4-tetrahydronaphthalen-1-ylurea Example 67C (33 mg, 0.14 mmol) and 1,2,3,4-tetrahydronaphthalen-1-amine (28 mg, 0.19 mmol) were processed and the product purified according to the methods of Example 67D to afford the title compound. $^1$H NMR (500 MHz, DMSO/D$_2$O) δ ppm 1.27-1.40 (m, 9H), 1.58-2.06 (m, 8H), 2.63-2.83 (m, 2H), 3.57-3.69 (m, 1H), 3.74-3.78 (m, 1H), 3.96-4.09 (m, 1H), 4.17-4.39 (m, 2H), 4.81-4.97 (m, 1H), 7.00-7.24 (m, 4H); MS (ESI) m/z 415 (M+H)$^+$.

Example 74

N-[(2Z)-5-tert-butyl-3-[(2R)-tetrahydrofuran-2-ylmethyl]-1,3,4-thiadiazol-2(3H)-ylidene]-N'-[(1S)-1-cyclohexylethyl]urea Example 67C (33 mg, 0.14 mmol) and (S)-1-cyclohexylethanamine (24 mg, 0.19 mmol) were processed and the product purified according to the methods of Example 67D to afford the title compound. $^1$H NMR (500 MHz, DMSO/D$_2$O) δ ppm 0.85-0.97 (m, 2H), 0.99-1.04 (m, 3H), 1.05-1.25 (m, 3H), 1.27-1.34 (m, 9H), 1.55-1.74 (m, 6H), 1.77-2.00 (m, 3H), 3.46-3.55 (m, 1H), 3.60-3.67 (m, 1H), 3.74-3.81 (m, 2H), 3.97-4.06 (m, 1H), 4.18-4.33 (m, 2H); MS (ESI) m/z 395 (M+H)$^+$.

Example 75

N-(tert-butyl)-N'-[(2Z)-5-tert-butyl-3-[(2R)-tetrahydrofuran-2-ylmethyl]-1,3,4-thiadiazol-2(3H)-ylidene]urea Example 67C (33 mg, 0.14 mmol) and 2-methylpropan-2-amine (14 mg, 0.19 mmol) were processed and the product purified according to the methods of Example 67D to afford the title compound. $^1$H NMR (500 MHz, DMSO/D$_2$O) δ ppm 1.25-1.34 (m, 18H), 1.60-1.72 (m, 1H), 1.77-2.03 (m, 3H), 3.59-3.66 (m, 1H), 3.75-3.80 (m, 1H), 3.97-4.05 (m, 1H), 4.21-4.30 (m, 2H); MS (ESI) m/z 341 (M+H)$^+$.

Example 76

N-[(2Z)-5-tert-butyl-3-[(2R)-tetrahydrofuran-2-ylmethyl]-1,3,4-thiadiazol-2(3H)-ylidene]-N'-[(1S)-1-(hydroxymethyl)-2,2-dimethylpropyl]urea Example 67C (33 mg, 0.14 mmol) and (S)-2-amino-3,3-dimethylbutan-1-ol (22 mg, 0.19 mmol) were processed and the product purified according to the methods of Example 67D to afford the title compound. $^1$H NMR (500 MHz, DMSO/D$_2$O) δ ppm 0.85-0.93 (m, 9H), 1.28-1.35 (m, 9H), 1.63-1.75 (m, 1H), 1.79-2.05 (m, 3H), 3.34-3.40 (m, 1H), 3.50-3.55 (m, 1H), 3.57-3.69 (m, 2H), 3.77-3.80 (m, 1H), 3.99-4.09 (m, 1H), 4.24-4.33 (m, 2H); MS (ESI) m/z 385 (M+H)$^+$.

Example 77

N-[(2Z)-5-tert-butyl-3-[(2R)-tetrahydrofuran-2-ylmethyl]-1,3,4-thiadiazol-2(3H)-ylidene]-N'-cycloheptylurea Example 67C (33 mg, 0.14 mmol) and cycloheptanamine (21 mg, 0.19 mmol) were processed and the product purified according to the methods of Example 67D to afford the title compound. $^1$H NMR (500 MHz, DMSO/D$_2$O) δ ppm 1.27-1.33 (m, 9H), 1.33-2.02 (m, 16H), 3.58-3.69 (m, 2H), 3.75-3.80 (m, 1H), 3.95-4.06 (m, 1H), 4.20-4.31 (m, 2H); MS (ESI) m/z 381 (M+H)$^+$.

Example 78

N-[(2Z)-5-tert-butyl-3-[(2R)-tetrahydrofuran-2-ylmethyl]-1,3,4-thiadiazol-2(3H)-ylidene]-N'-(2-ethylhexyl)urea Example 67C (33 mg, 0.14 mmol) and 2-ethylhexan-1-amine (25 mg, 0.19 mmol) were processed and the product purified according to the methods of Example 67D to afford the title compound. $^1$H NMR (500 MHz, DMSO/D$_2$O) δ ppm 1.12-1.36 (m, 23H), 1.38-1.48 (m, 1H), 1.59-1.73 (m, 1H), 1.76-2.00 (m, 3H), 2.88-3.04 (m, 3H), 3.58-3.72 (m, 1H), 3.94-4.07 (m, 1H), 4.20-4.34 (m, 2H); MS (ESI) m/z 397 (M+H)$^+$.

Example 79

N-[(2Z)-5-tert-butyl-3-[(2R)-tetrahydrofuran-2-ylmethyl]-1,3,4-thiadiazol-2(3H)-ylidene]-N'-(1-methyl-3-phenylpropyl)urea Example 67C (33 mg, 0.14 mmol) and 4-phenylbutan-2-amine (28 mg, 0.19 mmol) were processed and the product purified according to the methods of Example 67D to afford the title compound. $^1$H NMR (500 MHz, DMSO/D$_2$O) δ ppm 1.07-1.12 (m, 3H), 1.29-1.35 (m, 9H), 1.58-2.14 (m, 6H), 2.56-2.67 (m, 2H), 3.56-3.72 (m, 2H), 3.77-3.82 (m, 1H), 3.94-4.07 (m, 1H), 4.20-4.34 (m, 2H), 7.09-7.33 (m, 5H); MS (ESI) m/z 417 (M+H)$^+$.

Example 80

N-({[(2Z)-5-tert-butyl-3-[(2R)-tetrahydrofuran-2-ylmethyl]-1,3,4-thiadiazol-2(3H)-ylidene]amino}carbonyl)-L-phenylalaninamide Example 67C (33 mg, 0.14 mmol) and (S)-2-amino-3-phenylpropanamide (31 mg, 0.19 mmol) were processed and the product purified according to the methods of Example 67D to afford the title compound. $^1$H NMR (500 MHz, DMSO/D$_2$O) δ ppm 1.26-1.41 (m, 9H), 1.60-1.73 (m, 1H), 1.79-2.03 (m, 3H), 2.77-2.89 (m, 1H), 2.99-3.06 (m, 1H), 3.59-3.66 (m, 1H), 3.71-3.76 (m, 1H), 3.95-4.04 (m, 1H), 4.21-4.29 (m, 2H), 4.31-4.38 (m, 1H), 7.19-7.30 (m, 5H); MS (ESI) m/z 432 (M+H)$^+$.

Example 81

N$^2$-({[(2Z)-5-tert-butyl-3-[(2R)-tetrahydrofuran-2-ylmethyl]-1,3,4-thiadiazol-2(3H)-ylidene]amino}carbonyl)-L-isoleucinamide Example 67C (33 mg, 0.14 mmol) and (2S,3S)-2-amino-3-methylpentanamide (32 mg, 0.19 mmol) were processed and the product purified according to the methods of Example 67D to afford the title compound. $^1$H NMR (500 MHz, DMSO/D$_2$O) δ ppm 0.77-0.91 (m, 6H), 1.05-1.17 (m, 1H), 1.28-1.34 (m, 9H), 1.40-1.47 (m, 1H), 1.59-2.05 (m, 5H), 3.57-3.70 (m, 1H), 3.76-3.81 (m, 1H), 3.95-4.10 (m, 2H), 4.22-4.37 (m, 2H); MS (ESI) m/z 398 (M+H)$^+$.

Example 82

N$^2$-({[(2Z)-5-tert-butyl-3-[(2R)-tetrahydrofuran-2-ylmethyl]-1,3,4-thiadiazol-2(3H)-ylidene]amino}carbonyl)-N$^1$,3-dimethyl-L-valinamide Example 67C (30 mg, 0.12 mmol) and (S)-2-amino-N,3,3-trimethylbutanamide (24 mg, 0.17 mmol) were processed and the product purified according to the methods of Example 67D to afford the title compound. $^1$H NMR (500 MHz, DMSO/D$_2$O) δ ppm 0.90-0.95 (m, 9H), 1.29-1.33 (m, 9H), 1.61-1.76 (m, 1H), 1.78-2.02 (m, 3H), 2.58-2.61 (m, 3H), 3.59-3.68 (m, 1H), 3.74-3.77 (m, 1H), 4.03-4.05 (m, 1H), 4.05-4.12 (m, 1H), 4.24-4.31 (m, 2H); MS (ESI) m/z 412 (M+H)$^+$.

Example 83

N-[(2Z)-5-tert-butyl-3-[(2R)-tetrahydrofuran-2-ylmethyl]-1,3,4-thiadiazol-2(3H)-ylidene]-N'-neopentylurea Example 67C (30 mg, 0.12 mmol) and 2,2-dimethylpropan-1-amine (15 mg, 0.17 mmol) were processed and the product purified according to the methods of Example 67D to afford the title compound. $^1$H NMR (500 MHz, DMSO/D$_2$O) δ ppm 0.75-0.93 (m, 9H), 1.28-1.33 (m, 9H), 1.61-1.75 (m, 1H), 1.74-2.06 (m, 3H), 2.84-3.00 (m, 2H), 3.59-3.68 (m, 1H), 3.76-3.82 (m, 1H), 3.97-4.09 (m, 1H), 4.22-4.31 (m, 2H); MS (ESI) m/z 355 (M+H)$^+$.

Example 84

N-[(2Z)-5-tert-butyl-3-[(2R)-tetrahydrofuran-2-ylmethyl]-1,3,4-thiadiazol-2(3H)-ylidene]-N'-[(1S)-1-(hydroxymethyl)-2-methylpropyl]urea Example 67C (33 mg, 0.14 mmol) and (S)-2-amino-3-methylbutan-1-ol (19 mg, 0.19 mmol) were processed and the product purified according to the methods of Example 67D to afford the title compound. $^1$H NMR (500 MHz, DMSO/D$_2$O) δ ppm 0.81-0.90 (m, 6H), 1.28-1.34 (m, 9H), 1.61-1.74 (m, 1H), 1.78-2.00 (m, 4H), 3.40-3.45 (m, 2H), 3.46-3.53 (m, 1H), 3.61-3.66 (m, 1H), 3.77-3.79 (m, 1H), 4.00-4.09 (m, 1H), 4.23-4.33 (m, 2H); MS (ESI) m/z 371 (M+H)$^+$.

Example 85

N-[(3E)-5-tert-butyl-1-methyl-2-(tetrahydrofuran-3-ylmethyl)-1,2-dihydro-3H-pyrazol-3-ylidene]-2-methoxy-5-(trifluoromethyl)benzamide

Example 85A 3-tert-butyl-N-trityl-1H-pyrazol-5-amine

In a 20 mL vial, to a solution of 3-tert-butyl-1H-pyrazol-5-amine (150 mg, 1.078 mmol) in dichloromethane (2 mL) and triethylamine (0.180 mL, 1.293 mmol) was added (chloromethanetriyl)tribenzene (300 mg, 1.078 mmol). The reaction was stirred at 20° C. for 10 hour before toluene (5 mL) and ethyl acetate (10 mL) were added. The solid was filtered and the filtrate was concentrated to provide the crude title compound (320 mg). $^1$H NMR (300 MHz, DMSO-D6) δ ppm 0.95-1.02 (m, 9H) 4.82 (s, 1H) 5.75 (s, 1H) 7.15-7.37 (m, 15H) 11.13 (s, 1H); MS (DCI/NH$_3$) m/z 382 (M+H)$^+$.

Example 85B (tetrahydrofuran-3-yl)methyl 4-methylbenzenesulfonate

To a solution of (tetrahydrofuran-3-yl)methanol (5.15 g, 50.4 mmol) in dichloromethane (200 mL) were added triethylamine (21.08 mL, 151 mmol) and p-toluenesulfonyl chloride (9.61 g, 50.4 mmol) and the mixture was stirred at room temperature overnight. The reaction mixture was washed with water (100 mL) and brine (100 mL). The organic layer was dried with sodium sulfate, filtered and concentrated. The crude product was purified by column chromatography using an Analogix® Intelliflash280™ (SiO$_2$, 0-40% ethyl acetate in hexane) to provide the title compound (12.5 g, 97%) as colorless viscous liquid. $^1$H NMR (300 MHz, DMSO-D6) δ ppm 1.40-1.51 (m, 1H) 1.83-1.95 (m, 1H) 2.43 (s, 3H) 3.28-3.31 (m, 1H) 3.31-3.37 (m, 1H) 3.51-3.67 (m, 3H) 3.90-4.00 (m, 2H) 7.48-7.51 (m, 2H) 7.78-7.82 (m, 2H); MS (DCI/NH$_3$) m/z 274 (M+NH$_4$)$^+$.

Example 85C (3-tert-butyl-1-((tetrahydrofuran-3-yl)methyl)-N-trityl-1H-pyrazol-5-amine In a 200 mL round-bottomed flask, to a solution of Example 85A (5 g, 13.11 mmol) in N,N-dimethyl formamide (25 mL) was added sodium iodide (0.786 g, 5.24 mmol), Example 85B (4.03 g, 15.73 mmol), followed by addition of sodium hydride (1.310 g, 32.8 mmol) and the mixture was stirred at 60° C. for 6 hour. LC-MS, m/z 466 (M+H)$^+$ indicated an almost complete reaction. Water (150 mL) was added and the mixture was extracted with ethyl acetate (3×40 mL). The organics were combined, dried and concentrated in vacuo. The residue was purified by column chromatography using an Analogix® Intelliflash280™ (SiO$_2$, 10-70% ethyl acetate in hexanes) to afford the title compound (5.9 g, 97%) which was carried on without further spectral characterization.

Example 85D 3-tert-butyl-1-((tetrahydrofuran-3-yl)methyl)-1H-pyrazol-5-amine

In a 200 mL round-bottomed flask, to a solution of Example 85C (6.24 g, 13.4 mmol) in ethyl acetate (20 mL) was added hydrogen chloride (4 N in dioxane, 20 mL) and stirred at 20° C. for 2 hour. The reaction was concentrated and triturated with ethyl acetate. The solid was collected and dried to provide the title compound as the hydrogen chloride salt (2.12 g, 61%). $^1$H NMR (500 MHz, DMSO-d$_6$) δ ppm 1.28 (s, 9H) 1.61-1.69 (m, 1H) 1.81-1.89 (m, 1H) 2.73-2.81 (m, 1H) 3.45 (dd, J=8.85, 5.80 Hz, 1H) 3.61-3.67 (m, 3H) 3.78-3.84 (m, 1H) 4.17-4.26 (m, 2H) 5.53 (s, 1H) 7.07 (s, 2H); MS (DCI/NH$_3$) m/z 224 (M+H)$^+$.

Example 85E

N-(3-tert-butyl-1-((tetrahydrofuran-3-yl)methyl)-1H-pyrazol-5-yl)-2-methoxy-5-(trifluoromethyl)benzamide In a 40 mL vial, Example 85D (757 mg, 2.91 mmol) in tetrahydrofuran (3.2 mL) and sodium hydroxide (256 mg, 6.4 mmol) in water (3.20 mL) were mixed and treated with 2-methoxy-5-(trifluoromethyl)benzoyl chloride (695 mg, 2.91 mmol) and the reaction was stirred at 25° C. for 12 hour. The reaction was concentrated, extracted with ethyl acetate (3×10 mL), the organic layers were combined, dried with sodium sulfate, concentrated and the residue was purified by column chromatography using an Analogix® Intelliflash280™ (SiO$_2$, 0-100% ethyl acetate in hexanes) to afford the title compound (450 mg, 36.3%). $^1$H NMR (300 MHz, DMSO-d$_6$) δ ppm 1.24 (s, 9H) 1.56-1.67 (m, 1H) 1.83-1.95 (m, 1H) 2.61-2.73 (m, 1H) 3.47-3.53 (m, 1H) 3.58-3.66 (m, 2H) 3.70-3.78 (m, 1H) 3.90-4.04 (m, 5H) 6.21 (s, 1H) 7.40 (d, J=8.73 Hz, 1H) 7.87-7.93 (m, 2H) 10.15 (s, 1H); MS (DCI/NH$_3$) m/z 440 (M+H)$^+$.

Example 85F

N-[(3E)-5-tert-butyl-1-methyl-2-(tetrahydrofuran-3-ylmethyl)-1,2-dihydro-3H-pyrazol-3-ylidene]-2-methoxy-5-(trifluoromethyl)benzamide In a microwave vial a solution of Example 85E (100 mg, 0.24 mmol) and dimethyl sulfate (104 mg, 0.823 mmol) in toluene (0.8 mL) was heated at 140° C. for 1 hour. The reaction was concentrated, dissolved in dichloromethane, and purified by column chromatography using an Analogix® Intelliflash280™ (SiO$_2$, 0-10% solvent A in dichloromethane; Solvent A: 10% 7M ammonia in MeOH) to collect fractions containing the desired molecule. The fractions were combined and purified further by preparative HPLC on a Waters Symmetry C8 column (25 mm×100 mm, 7 μm particle size) using a gradient of 10% to 100% acetonitrile: 10 mM ammonium acetate over 8 min (10 min run time) at a flow rate of 40 mL/min to provide the title compound (25 mg, 25%). $^1$H NMR (300 MHz, DMSO-d$_6$) δ ppm 1.38 (s, 9H) 1.67-1.76 (m, 1H) 1.79-1.88 (m, 1H) 2.63-2.73 (m, 1H) 3.51-3.66 (m, 3H) 3.73-3.79 (m, 1H) 3.80 (s, 3H) 3.86 (s, 3H) 4.16-4.24 (m, 1H) 4.27-4.35 (m, 1H) 6.82 (s, 1H) 7.15 (d, J=8.82 Hz, 1H) 7.60 (dd, J=8.65, 1.86 Hz, 1H) 7.68-7.69 (m, 1H); MS (DCI/NH$_3$) m/z 440 (M+H)$^+$.

Example 86

N-{(3E)-5-tert-butyl-1-methyl-2-[(2R)-tetrahydrofuran-2-ylmethyl]-1,2-dihydro-3H-pyrazol-3-ylidene}-2-methyl-5-(trifluoromethyl)benzamide To a solution of Example 14C (237 mg, 1 mmol) in tetrahydrofuran (1.5 mL) and sodium hydroxide (120 mg, 3.00 mmol) in water (1.5 mL) was added 2-methyl-5-(trifluoromethyl)benzoyl chloride (445 mg, 2.0 mmol) and stirred for 4 hour at ambient temperature. The mixture was extracted with ethyl acetate. The organic layers were combined, dried, concentrated, and the residue was purified by column chromatography using an Analogix® Intelliflash280™ (SiO$_2$, 0-10% solvent A in dichloromethane; Sovlent A: 10% 7M ammonia in methyl alcohol) to provide the title compound (205 mg, 0.484 mmol, 48.4% yield). $^1$H NMR (300 MHz, DMSO-d$_6$) δ ppm 1.39 (s, 9H) 1.67-1.83 (m, 3H) 1.86-1.94 (m, 1H) 2.59 (s, 3H) 3.60-3.68 (m, 1H) 3.72-3.80 (m, 1H) 3.89 (s, 3H) 4.13-4.22 (m, 1H) 4.29-4.44 (m, 2H) 6.86 (s, 1H) 7.37 (d, J=7.80 Hz, 1H) 7.53 (dd, J=7.97, 1.86 Hz, 1H) 8.05 (d, J=2.03 Hz, 1H); MS (DCI/NH$_3$) m/z 424 (M+H)$^+$. Anal. calcd C$_{22}$H$_{28}$F$_3$N$_3$O$_2$.0.4H$_2$O: C, 61.35; H, 6.74; N, 9.76. Found: 61.65; H, 6.89; N, 9.76.

Example 87

N-{(3E)-4-bromo-5-tert-butyl-1-methyl-2-[(2R)-tetrahydrofuran-2-ylmethyl]-1,2-dihydro-3H-pyrazol-3-ylidene}-2-methyl-5-(trifluoromethyl)benzamide In a 5 mL vial, a solution of Example 86 (34 mg, 0.080 mmol), N-bromosuccinimide (14.29 mg, 0.080 mmol) and -2,2'-azobisisobutyronitrile (0.659 mg, 4.01 μmol) in carbon tetrachloride (0.3 mL) was heated at 80° C. for 4 hour. The reaction mixture was concentrated and purified by preparative HPLC on a Waters Symmetry C8 column (25 mm×100 mm, 7 µm particle size) using a gradient of 10% to 100% acetonitrile: 10 mM ammonium acetate over 8 min (10 min run time) at a flow rate of 40 mL/min to provide the title compound (19 mg, 0.038 mmol, 47.1% yield). $^1$H NMR (300 MHz, DMSO-d$_6$) δ ppm 1.55 (s, 9H) 1.61-1.67 (m, 1H) 1.71-1.87 (m, 3H) 2.58 (s, 3H) 3.58-3.69 (m, 1H) 3.70-3.78 (m, 1H) 3.97 (s, 3H) 4.13 (t, J=6.27 Hz, 1H) 4.34 (d, J=5.43 Hz, 2H) 7.37 (d, J=7.80 Hz, 1H) 7.53 (dd, J=7.97, 1.86 Hz, 1H) 7.93 (d, J=1.70 Hz, 1H); MS (DCI/NH$_3$) m/z 502 (M+H)$^+$.

Example 88

2-bromo-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide The title compound was prepared and isolated as described in Example 86, substituting 2-bromo-5-trifluoromethyl benzoyl chloride for 2-methyl-5-trifluoromethyl benzoyl chloride in 62% yield. $^1$H NMR (300 MHz, DMSO-D6) δ ppm 1.39 (s, 9H) 1.65-1.81 (m, 3H) 1.84-1.92 (m, 1H) 3.59-3.67 (m, 1H) 3.71-3.78 (m, 1H) 3.91 (s, 3H) 4.13-4.21 (m, 1H) 4.27-4.43 (m, 2H) 6.82 (s, 1H) 7.55 (dd, J=8.33, 2.38 Hz, 1H) 7.78-7.84 (m, 2H); MS (DCI/NH$_3$) m/z 488 (M+H)$^+$. Anal. calcd C$_{21}$H$_{25}$BrF$_3$N$_3$O$_2$: C, 51.65; H, 5.16; N, 8.60. Found: C, 51.37; H, 5.30; N, 8.54

Example 89

N-{(3E)-5-tert-butyl-1-methyl-2-[(2R)-tetrahydrofuran-2-ylmethyl]-1,2-dihydro-3H-pyrazol-3-ylidene}-2-[(1E)-3-methoxyprop-1-enyl]-5-(trifluoromethyl)benzamide To a solution of Example 88 (146 mg, 0.299 mmol) and (E)-2-(3-methoxyprop-1-enyl)-4,4,5,5-tetramethyl-1,3,2-dioxaborolane (148 mg, 0.747 mmol) in dimethoxyethane (1 mL) and methyl alcohol (0.5 mL) was added palladium tetrakistriphenyl phosphine (86 mg, 0.075 mmol) and cesium fluoride (159 mg, 1.05 mmol). This mixture was microwaved at 100° C. for 10 min. To the reaction was added ethyl acetate and the mixture was filtered through celite and purified by column chromatography using an Analogix® Intelliflash280™ (SiO$_2$, 0-100% solvent A in hexanes, solvent A: 10% MeOH in ethyl acetate) to afford the title compound (74 mg, 52%). $^1$H NMR (300 MHz, CHLOROFORM-D) δ ppm 1.44 (s, 9H) 1.71-1.85 (m, 3H) 1.98-2.07 (m, 1H) 3.37 (s, 3H) 3.69-3.82 (m, 2H) 3.88 (s, 3H) 4.11-4.13 (m, 2H) 4.18-4.32 (m, 2H) 4.48-4.58 (m, 1H) 6.22 (dt, J=15.96, 6.30 Hz, 1H) 7.03 (s, 1H) 7.46-7.53 (m, 1H) 7.57-7.65 (m, 2H) 8.20 (s, 1H); MS (DCI/NH$_3$) m/z 480 (M+H)$^+$.

Example 90

N-{(3E)-5-tert-butyl-1-methyl-2-[(2R)-tetrahydrofuran-2-ylmethyl]-1,2-dihydro-3H-pyrazol-3-ylidene}-2-(3-methoxypropyl)-5-(trifluoromethyl)benzamide A mixture of Example 89 (245 mg, 0.51 mmol) and platinum(IV) oxide (40 mg) in ethyl acetate (1 mL) and methyl alcohol (0.5 mL) was hydrogenated under a balloon filled with hydrogen at ambient temperature for 5 hour. The reaction mixture was filtered through celite, concentrated and the residue was purified by column chromatography using an Analogix® Intelliflash280™ (SiO$_2$, 0-100% solvent A in hexanes, solvent A: 10% MeOH in ethyl acetate) to afford the title compound (178 mg, 72%). $^1$H NMR (300 MHz, CDCl$_3$) δ ppm 1.44 (s, 9H) 1.70-1.89 (m, 3H) 1.91-2.07 (m, 3H) 3.08-3.22 (m, 2H) 3.32 (s, 3H) 3.40 (t, J=6.61 Hz, 2H) 3.68-3.82 (m, 2H) 3.87 (s, 3H) 4.15-4.31 (m, 2H) 4.54 (dd, J=14.92, 2.71 Hz, 1H) 7.00 (s, 1H) 7.30 (s, 1H) 7.46 (d, J=7.46 Hz, 1H) 8.10 (s, 1H); MS (DCI/NH$_3$) m/z 482 (M+H)$^+$.

Example 91

N-[(2Z)-5-tert-butyl-3-{[(4S)-2-oxo-1,3-oxazolidin-4-yl]methyl}-1,3,4-thiadiazol-2(3H)-ylidene]-5-chloro-2-methoxybenzamide A mixture of Example 4A (195 mg, 0.6 mmol), (S)-(2-oxazolidin-4-yl)methyl 4-methylbenzenesulfonate (190 mg, 0.7 mmol), potassium carbonate (170 mg, 1.23 mmol), tetrabutylammonium iodide (10 mg, 0.03 mmol), tetrabutylammonium hydrogen sulfate (10 mg, 0.03 mmol) and tetraethylammonium iodide (10 mg, 0.04 mmol) in toluene (25 mL) was refluxed for 12 h. The mixture was washed with water, brine, dried with MgSO$_4$ and concentrated under reduced pressure. The residue was purified by silica gel chromatography eluting with CH$_2$Cl$_2$:EtOAc (4:1) to afford 115 mg of the title compound. $^1$H NMR (300 MHz, CDCl$_3$) δ ppm 1.42 (s, 9H), 3.94 (s, 3H), 4.34-4.42 (m, 3H), 4.53-4.76 (m, 2H), 6.08 (s, 1H), 6.95 (d, J=8.8 Hz, 1H), 7.39 (dd, J=8.8, 2.7 Hz, 1H), 7.86 (d, J=2.7 Hz, 1H). MS (DCI/NH$_3$) m/z 425 (M+H)$^+$.

Example 92

2-(2-amino-2-methylpropoxy)-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide Potassium t-butoxide (1.2 mL, 1M in THF) was added to 2-amino-2-methylpropan-1-ol (0.11 g, 1.2 mmol) in 0.5 mL of THF and stirred for 10 minutes. Example 16B (0.25 g, 0.59 mmol) in 1.0 mL of THF was added and the mixture stirred for 1 hour. EtOAc (15 mL) was added and the organic phase washed with saturated NaHCO$_3$, water, brine, dried with MgSO$_4$ and the solvent removed. The residue was chromatographed to afford the title compound. (solvent A—hexane: EtOAc:triethylamine 1:3:0.2; solvent B—hexane:EtOAc: MeOH:triethylamine 1:3:1:0.2; 100% solvent A to 100% solvent B in a gradient over 600 mL then isocratic for 180 mL). (0.2 g, 0.4 mmol, 69% yield). $^1$H NMR (500 MHz, PYRIDINE-d$_5$) δ ppm 1.15 (s, 9H), 1.32 (s, 6H), 1.54-1.61 (m, 2H), 1.63-1.70 (m, 1H), 1.76-1.82 (m, 1H), 3.53-3.61 (m, 1H), 3.69-3.75 (m, 1H), 3.79 (s, 3H), 3.94 (s, 2H), 4.23 (qd, J=6.7, 3.4 Hz, 1H), 4.37 (dd, J=15.1, 6.6 Hz, 1H), 4.61 (dd, J=15.3, 3.1 Hz, 1H), 7.12 (d, J=8.5 Hz, 1H), 7.45 (s, 1H), 7.66 (dd, J=8.5, 2.4 Hz, 1H), 8.55 (d, J=2.4 Hz, 1H). MS (ESI) m/z 497.2 (M+H)$^+$.

Example 93

N-{(3E)-5-tert-butyl-1-methyl-2-[(2R)-tetrahydrofuran-2-ylmethyl]-1,2-dihydro-3H-pyrazol-3-ylidene}-2-[(3-methylbut-2-enyl)oxy]-5-(trifluoromethyl)benzamide Potassium t-butoxide (1.2 mL, 1M in THF) was added to 3-methylbut-2-en-1-ol (0.11 g, 1.2 mmol) in 0.5 mL of THF and stirred for 10 minutes. Example 16B (0.25 g, 0.59 mmol) in 1.0 mL of THF was added and the mixture stirred for 1 hour. EtOAc (15 mL) was added and the organic phase washed with saturated NaHCO$_3$, water, brine, dried with MgSO$_4$ and the solvent removed. The residue was chromatographed to afford the title compound. (solvent A—hexane:EtOAc:triethylamine 1:3:0.2; solvent B—hexane:EtOAc:MeOH:triethylamine 1:3:1:0.2; solvent A to solvent B over 600 mL then isocratic for 180 mL). (0.16 g, 0.32 mmol, 55% yield). $^1$H NMR (300 MHz, DMSO-d$_6$) δ ppm 1.38 (s, 9H), 1.69-1.74 (m, 8H), 1.74-1.81 (m, 1H), 1.82-1.89 (m, 1H), 3.58-3.66 (m, 1H), 3.69-3.78 (m, 1H), 3.87 (s, 3H), 4.11-4.20 (m, 1H), 4.31 (dd, J=5.1, 2.0 Hz, 2H), 4.61 (d, J=6.4 Hz, 2H), 5.34-5.40 (m, 1H), 6.80 (s, 1H), 7.13 (d, J=8.5 Hz, 1H), 7.56 (dd, J=8.8, 2.0 Hz, 1H), 7.67 (d, J=2.4 Hz, 1H). MS (ESI) m/z 494.2 (M+H)$^+$. Analytical calculated for C$_{26}$H$_{34}$F$_3$N$_3$O$_3$: C, 63.27; H, 6.94; N, 8.51. Found: C, 63.22; H, 7.10; N, 8.47.

Example 94

N-{(3E)-5-tert-butyl-1-methyl-2-[(2R)-tetrahydrofuran-2-ylmethyl]-1,2-dihydro-3H-pyrazol-3-ylidene}-2-[2-(1-hydroxycyclopentyl)ethoxy]-5-(trifluoromethyl)benzamide Example 94A 1-(2-hydroxyethyl)cyclopentanol 1,4-dibromobutane (10 g, 46.3 mmol) in THF (100 mL) was treated with magnesium (2.81 g, 116 mmol) and I$_2$ (100 mg) as initiator. The mixture was stirred at rt for 3 h. To the mixture was added dropwise oxetan-2-one (3.34 g, 46.3 mmol) in THF (25 mL). The reaction was stirred at rt for 12 h, quenched with saturated NH$_4$Cl, and the mixture was extracted with isopropanol/CH$_2$Cl$_2$ (1:3) (2×100 mL). The organic layers were combined and dried over MgSO$_4$, filtered and concentrated. The residue was purified by distillation at 95-100° C.@0.6 Torr to provide the title compound (1.1 g, 18%). MS (DCI/NH$_3$) m/z 148 (M+NH$_4$)$^+$.

Example 94B

N-{(3E)-5-tert-butyl-1-methyl-2-[(2R)-tetrahydrofuran-2-ylmethyl]-1,2-dihydro-3H-pyrazol-3-ylidene}-2-[2-(1-hydroxycyclopentyl)ethoxy]-5-(trifluoromethyl)benzamide The title compound was prepared using the procedure as described in Example 35 substituting Example 94A for 2,2-difluoroethanol. $^1$H NMR (400 MHz, CDCl$_3$) δ ppm 1.42 (s, 9H) 1.50-1.61 (m, 5H) 1.64-1.75 (m, 1H) 1.76-1.90 (m, 6H) 2.13 (t, J=5.83 Hz, 2H) 3.67-3.81 (m, 2H) 3.91 (s, 3H) 4.12-4.21 (m, 1H) 4.32 (t, J=5.83 Hz, 2H) 4.37 (d, J=6.14 Hz, 1H) 4.65 (dd, J=15.65, 3.07 Hz, 1H) 6.97 (s, 1H) 7.01 (d, J=8.59 Hz, 1H) 7.56 (dd, J=8.59, 2.76 Hz, 1H) 8.19 (d, J=2.46 Hz, 1H); MS (DCI/NH$_3$) m/z 538 (M+H)$^+$.

Example 95

2-(azetidin-3-yloxy)-N-[(2Z)-5-tert-butyl-3-[(2R)-tetrahydrofuran-2-ylmethyl]-1,3-oxazol-2(3H)-ylidene]-5-(trifluoromethyl)benzamide Example 95A N-[(2Z)-5-tert-butyl-3-[(2R)-tetrahydrofuran-2-ylmethyl]-1,3-oxazol-2(3H)-ylidene]-2-fluoro-5-(trifluoromethyl)benzamide The title compound was prepared using the procedure as described in Example 13C substituting 2-fluoro-5-(trifluoromethyl)benzoic acid for 2-methoxy-5-(trifluoromethyl)benzoic acid. MS (DCI/NH$_3$) m/z 415 (M+H)$^+$.

Example 95B tert-butyl 3-[2-{[(2Z)-5-tert-butyl-3-[(2R)-tetrahydrofuran-2-ylmethyl]-1,3-oxazol-2(3H)-ylidene]carbamoyl}-4-(trifluoromethyl)phenoxy]azetidine-1-carboxylate To a solution of tert-butyl 3-hydroxyazetidine-1-carboxylate (167 mg, 0.965 mmol) in THF (2 mL) was added sodium tert-butoxide (93 mg, 0.965 mmol). The reaction was stirred at room temperature for 20 min. The reaction was cooled to 0° C. and a solution of Example 95A (200 mg, 0.483 mmol) in THF (1 mL) was added. The reaction was stirred at 0-5° C. for 2 h. The reaction mixture was diluted with H$_2$O and extracted with EtOAc (2×). The organic layer was combined and dried over MgSO$_4$, filtered and concentrated to afford the title compound 260 mg (93%). MS (DCI/NH$_3$) m/z 568 (M+H)$^+$.

Example 95C 2-(azetidin-3-yloxy)-N-[(2Z)-5-tert-butyl-3-[(2R)-tetrahydrofuran-2-ylmethyl]-1,3-oxazol-2(3H)-ylidene]-5-(trifluoromethyl)benzamide The product from Example 95B (260 mg, 0.458 mmol) in CH$_2$Cl$_2$ (6 mL) was treated with trifluoroacetic acid (1.5 mL). The mixture was stirred at room temperature for 30 min. The solvent was evaporated and the residue was dissolved in saturated NaHCO$_3$. The aqueous layer was extracted with EtOAc. The organic layer was dried with MgSO$_4$ and concentrated. The residue was purified by column chromatography (SiO$_2$, CH$_2$Cl$_2$ to 9:1:0.1 CH$_2$Cl$_2$:MeOH:Et$_3$N) to give the title compound (54 mg, 13%). $^1$H NMR (400 MHz, CDCl$_3$) δ ppm 1.22 (s, 9H) 1.59-1.70 (m, 1H) 1.85-1.96 (m, 3H) 2.06-2.14 (m, 1H) 3.70 (dd, J=14.12, 7.36 Hz, 1H) 3.76-3.84 (m, 1H) 3.93-4.03 (m, 2H) 4.06 (dd, J=14.12, 2.76 Hz, 1H) 4.11-4.22 (m, 3H) 5.05-5.17 (m, 1H) 6.57 (s, 1H) 6.71 (d, J=8.29 Hz, 1H) 7.55 (d, J=8.29 Hz, 1H) 8.06 (s, 1H) MS (DCI/NH$_3$) m/z 468 (M+H)$^+$.

Example 96

N-{(3E)-5-tert-butyl-1-methyl-2-[(2R)-tetrahydrofuran-2-ylmethyl]-1,2-dihydro-3H-pyrazol-3-ylidene}-3-fluoro-5-(trifluoromethyl)benzamide The title compound was prepared according to the procedure described in Example 45C and Example 45D, substituting 3-fluoro-5-trifluorobenzoyl chloride for 2-methoxy-5-chlorobenzoyl chloride. $^1$H NMR (300 MHz, DMSO-d$_6$) δ ppm 1.44 (s, 9H), 1.65-2.20 (m, 4H), 3.69-3.82 (m, 2H), 3.91 (s, 3H), 4.24 (dd, J=5.43, 3.05 Hz, 1H), 4.33-4.45 (m, 1H), 4.54-4.64 (m, 1H), 7.08 (s, 1H), 7.32 (d, J=8.48 Hz, 1H), 8.11 (d, J=10.17 Hz, 1H), 8.35 (s, 1H); MS (DCI) m/z 428 [M+H].

Example 97

N-[(2Z)-5-tert-butyl-3-[(2R)-tetrahydrofuran-2-ylmethyl]-1,3,4-thiadiazol-2(3H)-ylidene]-2-{[(3S)-1-methylpyrrolidin-3-yl]oxy}-5-(trifluoromethyl)benzamide Example 97A (S)-2-(1-methylpyrrolidin-3-yloxy)-5-(trifluoromethyl)benzonitrile To a solution of 2-fluoro-5-(trifluoromethyl)benzonitrile (8.0 g, 42.3 mmol, Aldrich) in tetrahydrofuran (50 mL) were added sodium hydride (1.9 g, 46.5 mmol, 60% in mineral oil) and (S)-1-methylpyrrolidin-3-ol (4.7 mL, 46.5 mmol, Aldrich). After stirring at room temperature for 3 h, the reaction mixture was quenched with saturated NaHCO$_3$ (30 mL). The aqueous layer was extracted with ethyl acetate (3×30 mL). The combined organic extracts were dried over anhydrous Na$_2$SO$_4$, filtered and concentrated under reduced pressure to afford 10.9 g of the title compound. MS (ESI$^+$) m/z 271 (M+H)$^+$.

Example 97B (S)-2-(1-methylpyrrolidin-3-yloxy)-5-(trifluoromethyl)benzoic acid

To a solution of Example 97A (10.9 g, 40.5 mmol) in ethanol (50 mL) and water (15 mL) at 40° C. was added sodium hydroxide (7.5 mL, 142 mmol, 50% aqueous solution), followed by hydrogen peroxide (7.0 mL, 122 mmol, 50% aqueous solution), which was added in 4 portions, each portion one hour apart. The reaction was stirred at 40° C. for 4 more hours. The reaction was monitored by LC/MS. After almost all the nitrile was converted to the amide, sodium hydroxide (6.4 mL, 122 mmol, 50% aqueous solution) was added followed by 10 mL of water. Then the reaction mixture was stirred at 80° C., cooled, concentrated and dissolved in 100 mL of water. The resultant solution was washed with diethyl ether (2×25 mL). The aqueous solution was neutralized to pH 7 with 6N HCl. and then concentrated to dryness. The precipitate was suspended in ethanol/dichloromethane (100 mL, 1:1), heated to 60° C. and filtered. This process was repeated 3 times. The combined filtrates were concentrated and azeotroped with toluene to obtain 8.5 g (80%) of the title compound. MS (ESI$^+$) m/z 290 (M+H)$^+$.

Example 97C

N-[(2Z)-5-tert-butyl-3-[(2R)-tetrahydrofuran-2-ylmethyl]-1,3,4-thiadiazol-2(3H)-ylidene]-2-{[(3S)-1-methylpyrrolidin-3-yl]oxy}-5-(trifluoromethyl)benzamide Example 67C, Example 97B, 1-hydroxybenzotriazole, N-(3-dimethylaminopropyl)-N-ethylcarbodiimide hydrochloride and triethylamine were processed as described for Example 63D to obtain the title compound. $^1$H NMR (300 MHz, DMSO-d$_6$) δ ppm 1.39 (s, 9H), 1.68-1.91 (m, 4H), 1.91-2.06 (m, 1H), 2.25 (s, 3H), 2.28-2.43 (m, 2H), 2.57-2.71 (m, 2H), 2.75-2.87 (m, 1H), 3.57-3.70 (m, 1H), 3.71-3.83 (m, 1H), 4.24 (dd, J=13.2, 4.7 Hz, 1H), 4.30-4.42 (m, 1H), 4.44-4.59 (m, 1H), 4.90-5.14 (m, 1H), 7.22 (d, J=8.5 Hz, 1H), 7.77 (dd, J=8.8, 2.7 Hz, 1H), 8.07 (d, J=2.7 Hz, 1H); MS (ESI$^+$) m/z 513 (M+H)$^+$.

Example 98

N-[(2Z)-5-tert-butyl-3-[(2R)-tetrahydrofuran-2-ylmethyl]-1,3-oxazol-2(3H)-ylidene]-2-{[(3S)-1-methylpyrrolidin-3-yl]oxy}-5-(trifluoromethyl)benzamide Example 66A, Example 97B, 1-hydroxybenzotriazole, N-(3-dimethylaminopropyl)-N-ethylcarbodiimide hydrochloride and triethylamine were processed as described for Example 63D to obtain the title compound. $^1$H NMR (400 MHz, DMSO-d$_6$) δ ppm 1.04-1.09 (m, 9H), 1.55-1.66 (m, 1H), 1.65-1.75 (m, 1H), 1.77-1.88 (m, 2H), 1.89-2.03 (m, 1H), 2.27 (s, 3H), 2.28-2.34 (m, 1H), 2.35-2.45 (m, 1H), 2.52-2.59 (m, 1H), 2.59-2.70 (m, 1H), 2.80 (dd, J=10.3, 6.0 Hz, 1H), 3.62-3.71 (m, 1H), 3.72-3.84 (m, 3H), 4.14-4.23 (m, 1H), 4.89-4.97 (m, 1H), 7.01 (s, 1H), 7.12 (d, J=8.6 Hz, 1H), 7.65 (dd, J=8.9, 2.5 Hz, 1H), 7.72 (d, J=2.5 Hz, 1H); MS (ESI$^+$) m/z 496 (M+H)$^+$.

Example 99

N-{(3E)-5-tert-butyl-1-methyl-2-[(2R)-tetrahydrofuran-2-ylmethyl]-1,2-dihydro-3H-pyrazol-3-ylidene}-2-[(1E)-prop-1-enyl]-5-(trifluoromethyl)benzamide The title compound was prepared and isolated as described in Example 89, substituting trans-1-propen-1-ylboronic acid for (E)-2-(3-methoxyprop-1-enyl)-4,4,5,5-tetramethyl-1,3,2-dioxaborolane in 62% yield. $^1$H NMR (300 MHz, CDCl$_3$) δ ppm 1.44 (s, 9H) 1.65-1.88 (m, 3H) 1.88-1.92 (m, 3H) 1.98-2.11 (m, 1H) 3.69-3.82 (m, 2H) 3.88 (s, 3H) 4.18-4.33 (m, 2H) 4.48-4.58 (m, 1H) 6.14-6.26 (m, 1H) 7.05 (s, 1H) 7.92-7.33 (m, 1H) 7.44-7.50 (m, 1H) 7.55-7.58 (m, 1H) 8.12 (s, 1H); MS (DCI/NH$_3$) m/z 450 (M+H)$^+$.

Example 100

N-{(3E)-5-tert-butyl-1-methyl-2-[(2R)-tetrahydrofuran-2-ylmethyl]-1,2-dihydro-3H-pyrazol-3-ylidene}-2-[(1E)-3-hydroxy-3-methylbut-1-enyl]-5-(trifluoromethyl)benzamide Example 100A (E)-trimethyl(2-methyl-4-(4,4,5,5-tetramethyl-1,32-dioxaborolan-2-yl)but-3-en-2-yloxy)silane To a solution of trimethyl(2-methylbut-3-yn-2-yloxy)silane (1.5 g, 9.60 mmol) in tetrahydrofuran (15 mL) was added 4,4,5,5-tetramethyl-1,3,2-dioxaborolane (2.79 mL, 19.19 mmol), followed by addition of 9-BBN (9-borabicyclo[3.3.1]nonane) dimer (0.117 g, 0.480 mmol). This mixture was heated at 60° C. for 24 hour. The reaction was cooled and quenched carefully with saturated ammonium chloride solution. The reaction mixture was extracted with ethyl acetate (2×15 mL). The organics were combined, dried, concentrated and the residue was purified by column chromatography using an Analogix® Intelliflash280™ (SiO$_2$, 0-60% ethyl acetate in hexanes) to afford the title compound (600 mg, 22% yield). $^1$H NMR (300 MHz, DMSO-D6) δ ppm 0.06-0.08 (m, 9H) 1.19 (s, 12H) 1.25 (s, 6H) 5.41 (d, J=17.85 Hz, 1H) 6.53 (d, J=17.85 Hz, 1H); MS (DCI/NH$_3$) m/z 285 (M+H)$^+$.

Example 100B

N-{(3E)-5-tert-butyl-1-methyl-2-[(2R)-tetrahydrofuran-2-ylmethyl]-1,2-dihydro-3H-pyrazol-3-ylidene}-2-[(1E)-3-hydroxy-3-methylbut-1-enyl]-5-(trifluoromethyl)benzamide The title compound was prepared and isolated as described in Example 89, substituting Example 100A for (E)-2-(3-methoxyprop-1-enyl)-4,4,5,5-tetramethyl-1,3,2-dioxaborolane in 79% yield. $^1$H NMR (300 MHz, CDCl$_3$) δ ppm 1.42 (s, 6H) 1.43 (s, 9H) 1.73-1.88 (m, 3H) 1.98-2.10 (m, 1H) 3.68-3.80 (m, 2H) 3.87 (s, 3H) 4.17-4.28 (m, 2H) 4.49-4.56 (m, 1H) 6.29 (d, J=16.28 Hz, 1H) 6.99 (s, 1H) 7.47-7.60 (m, 3H) 8.17 (d, J=2.03 Hz, 1H); MS (DCI/NH$_3$) m/z 494 (M+H)$^+$.

Example 101

N-{(3E)-5-tert-butyl-1-methyl-2-[(2R)-tetrahydrofuran-2-ylmethyl]-1,2-dihydro-3H-pyrazol-3-ylidene}-2-(3-hydroxy-3-methylbutyl)-5-(trifluoromethyl)benzamide The title compound was prepared and isolated as described in Example 90, substituting Example 100B for Example 89 in 68% yield. $^1$H NMR (300 MHz, CHLOROFORM-D) δ ppm 1.22 (s, 6H) 1.42 (s, 9H) 1.70-1.83 (m, 2H) 1.83-1.95 (m, 3H) 2.00-2.11 (m, 1H) 3.12-3.18 (m, 2H) 3.69-3.82 (m, 2H) 3.89 (s, 3H) 4.18-4.24 (ddd, J=9.52, 6.54, 2.97 Hz, 1H) 4.25-4.35 (m, 1H) 4.56 (dd, J=15.07, 2.78 Hz, 1H) 7.02 (s, 1H) 7.29 (d, J=8.33 Hz, 1H) 7.47 (dd, J=7.93, 1.59 Hz, 1H) 8.19 (d, J=1.59 Hz, 1H); MS (DCI/NH$_3$) m/z 496 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound according to formula (I),

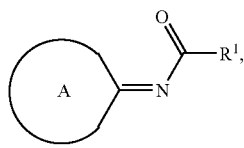

(I)

or a pharmaceutically acceptable salt, thereof, wherein
$R^1$ is alkyl, haloalkyl, $G^1$, —$(CR^xR^y)_m$-$G^1$, or —$N(R^{1a})(R^z)$;
$R^2$ is alkyl, haloalkyl, $G^2$, —$(CR^xR^y)_m$-$G^2$, —$(CR^xR^y)_m$—$OR^{za}$, —$(CR^xR^y)_m$—$N(R^{za})(R^{zb})$—$(CR^xR^y)_m$—$C(O)O(R^{za})$, $(CR^xR^y)_m$—$C(O)R^{za}$, —$(CR^xR^y)_m$—$C(O)N(R^{za})(R^{zb})$, —$(CR^xR^y)_m$—$S(O)_2O(R^{za})$, —$(CR^xR^y)_m$—$S(O)_2R^{za}$, —$(CR^xR^y)_m$—$S(O)_2N(R^{za})(R^{zb})$, or —$(CR^xR^y)_m$—CN;
$G^1$ and $G^2$, at each occurrence, are each independently aryl, heteroaryl, heterocycle, cycloalkyl, or cycloalkenyl; wherein each ring is independently unsubstituted or substituted with 1, 2, 3, 4, 5, or 6 substituents independently selected from the group consisting of alkyl, alkenyl, alkynyl, —$NO_2$, —CN, halogen, oxo, —$OR^e$, —O—$(CR^jR^k)_n$—$N(R^w)_2$, —$OC(O)R^e$, —$SR^e$, —$S(O)R^f$, —$S(O)_2R^f$, —$S(O)_2N(R^e)(R^g)$, —$N(R^e)(R^g)$, —$N(R^g)C(O)R^e$, —$N(R^g)S(O)_2R^f$, —$N(R^g)C(O)N(R^e)(R^g)$, —$N(R^g)S(O)_2N(R^e)(R^g)$, —$C(O)R^e$, —$C(O)O(R^e)$, —$C(O)N(R^e)(R^g)$, haloalkyl, —$(CR^jR^k)_q$—CN, —$(CR^jR^k)_q$—$OR^e$, —$(CR^jR^k)_q$—$OC(O)R^e$, —$(CR^jR^k)_q$—$SR^e$, —$(CR^jR^k)_q$—$S(O)R^f$, —$(CR^jR^k)_q$—$S(O)_2R^f$, —$(CR^jR^k)_q$—$N(R^e)(R^g)$, —$(CR^jR^k)_q$—$N(R^g)C(O)R^e$, —$(CR^jR^k)_q$—$N(R^g)S(O)_2R^f$, —$(CR^jR^k)_q$—$N(R^g)C(O)N(R^e)(R^g)$, —$(CR^jR^k)_q$—$N(R^g)S(O)_2N(R^e)(R^g)$, —$(CR^jR^k)_q$—$C(O)R^e$, —$(CR^jR^k)_q$—$C(O)O(R^e)$, —$(CR^jR^k)_q$—$C(O)N(R^e)(R^g)$, —$C(R^w)$=N—$OR^w$, and morpholinyl;

Ring A represents formula (a), (b), (c), or (d)

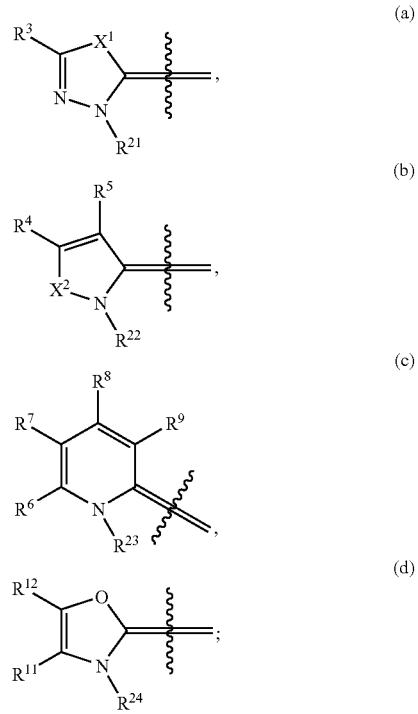

$R^{21}$, $R^{22}$, $R^{23}$, and $R^{24}$ are -alkylene-$G^3$ wherein $G^3$, at each occurrence, is independently a 4-, 5-, 6-, 7-, 8-, or 9-membered monocyclic heterocycle containing zero or one double bond, one or two oxygen, and zero or one nitrogen as ring atoms, and is optionally fused with a monocyclic ring selected from the group consisting of benzo, cycloalkyl, cycloalkenyl, heterocycle and heteroaryl; two non-adjacent atoms of each $G^3$ are optionally linked by an alkenylene bridge of 2, 3, or 4 carbon atoms, or optionally linked by an alkylene bridge of 1, 2, 3, or 4 carbon atoms, and each $G^3$ is independently unsubstituted or substituted with 1, 2, 3, 4, 5, or 6 substituents independently selected from the group consisting of oxo, alkyl, halogen, —OH, —O(alkyl), —O(haloalkyl), and haloalkyl;

$R^w$, at each occurrence, is independently hydrogen or alkyl;

$R^3$, $R^6$, $R^7$, $R^8$, $R^9$, $R^{11}$, and $R^{12}$ are each independently hydrogen, alkyl, alkenyl, alkynyl, —$NO_2$, —CN, halogen, —$OR^a$, —$N(R^a)(R^b)$, —$C(O)R^a$, —$C(O)O(R^a)$, haloalkyl, —$(CR^cR^d)_p$—$OR^a$, —$(CR^cR^d)_p$—$N(R^a)(R^b)$, —$(CR^cR^d)_p$—$C(O)R^a$, —$(CR^cR^d)_p$—$C(O)O(R^a)$, cycloalkyl, cycloalkenyl, or heterocycle;

$R^4$ and $R^5$, are each independently hydrogen, alkyl, alkenyl, alkynyl, —$NO_2$, —CN, halogen, —$OR^a$, —$N(R^a)(R^b)$, —$C(O)R^a$, —$C(O)O(R^a)$, haloalkyl, —$(CR^cR^d)_p$—$OR^a$, —$(CR^cR^d)_p$—$N(R^a)(R^b)$, —$(CR^cR^d)_p$—$C(O)R^a$, —$(CR^cR^d)_p$—$C(O)O(R^a)$, cycloalkyl, cycloalkenyl, or heterocycle;

$R^a$, $R^b$, $R^{1a}$, $R^{za}$, and $R^{zb}$, at each occurrence, are each independently hydrogen, alkyl, or haloalkyl;

$R^x$, at each occurrence, is independently hydrogen, halogen, alkyl, or haloalkyl;

$R^y$, $R^c$, and $R^d$, at each occurrence, are each independently hydrogen, halogen, alkyl, or haloalkyl;

$X^1$ and $X^2$ are independently O, S, or $N(R^{10})$ wherein $R^{10}$ is alkyl, alkoxyalkyl, haloalkoxyalkyl, or haloalkyl;

the cycloalkyl, cycloalkenyl, and heterocycle, as represented by $R^3$, $R^4$, $R^5$, $R^6$, $R^8$, and $R^9$ are each independently unsubstituted or substituted with 1, 2, 3, 4, 5, or 6 substituents independently selected from the group consisting of alkyl, alkenyl, alkynyl, $-NO_2$, $-CN$, halogen, oxo, $-OR^e$, $-OC(O)R^e$, $-SR^e$, $-S(O)R^f$, $-S(O)_2R^f$, $-S(O)_2N(R^e)(R^g)$, $-N(R^e)(R^g)$, $-N(R^g)C(O)R^e$, $-N(R^g)S(O)_2R^f$, $-N(R^g)C(O)N(R^e)(R^g)$, $-N(R^g)S(O)_2N(R^e)(R^g)$, $-C(O)R^e$, $-C(O)R^e$, $-C(O)O(R^e)$, $-C(O)N(R^e)(R^g)$, haloalkyl, $-(CR^jR^k)_q-CN$, $-(CR^jR^k)_q-OR^e$, $-(CR^jR^k)_q-OC(O)R^e$, $-(CR^jR^k)_q-SR^e$, $-(CR^jR^k)_q-S(O)R^f$, $-(CR^jR^k)_q-S(O)_2R^f$, $-(CR^jR^k)_q-N(R^e)(R^g)$, $-(CR^jR^k)_q-N(R^e)C(O)R^e$, $-(CR^jR^k)_q-N(R^g)S(O)_2R^f$, $-(CR^jR^k)_q-N(R^g)C(O)N(R^e)(R^g)$, $-(CR^jR^k)_q-N(R^g)S(O)_2N(R^e)(R^g)$, $-(CR^jR^k)_q-C(O)R^e$, $-(CR^jR^k)_q-C(O)O(R^e)$ and $-(CR^jR^k)_q-C(O)N(R^e)(R^g)$;

$R^e$ and $R^g$, at each occurrence, are each independently hydrogen, alkyl, alkoxyalkyl, cycloalkyl, cycloalkylalkyl, heterocycle, haloalkoxyalkyl, or haloalkyl; wherein the cycloalkyl, and the heterocycle moieties, by itself or as part of the substituents of $R^e$ and $R^g$, are each independently unsubstituted or substituted with 1, 2, 3, 4, 5 or 6 substituents selected from the group consisting of alkyl, halogen, and haloalkyl;

$R^f$, at each occurrence, is independently alkyl or haloalkyl;

$R^j$ and $R^k$, at each occurrence, are each independently hydrogen, halogen, alkyl, or haloalkyl;

m, p, and q, at each occurrence, are each independently 1, 2, 3, or 4; and n is 2, 3or 4.

2. The compound of claim 1 having formula (I), or a pharmaceutically acceptable salt thereof, wherein $R^{21}$, $R^{22}$, $R^{23}$, and $R^{24}$ are -alkylene-$G^3$, $G^3$, at each occurrence, is independently a 4-, 5-, or 6-membered monocyclic heterocycle containing zero or one double bond, one or two oxygen, and zero or one nitrogen as ring atoms, and each $G^3$ is independently unsubstituted or substituted with 1, 2, 3, 4, 5, or 6 substituents independently selected from the group consisting of oxo, alkyl, halogen, —OH, —O(alkyl), —O(haloalkyl), and haloalkyl.

3. The compound of claim 2 having formula (I), or a pharmaceutically acceptable salt thereof, wherein $G^3$, at each occurrence, is independently oxetanyl, oxazolidinyl, tetrahydrofuranyl, tetrahydropyranyl, 1,3-dioxalanyl, or 1,4-dioxanyl, each of which is independently unsubstituted or substituted.

4. The compound of claim 2 having formula (I), or a pharmaceutically acceptable salt thereof wherein $R^{21}$, $R^{22}$, $R^{23}$, and $R^{24}$ are each independently tetrahydrofuranylmethyl, tetrahydropyranylmethyl, or oxazolidinylmethyl, and the tetrahydrofuranyl, oxazolidinyl, and the tetrahydropyranyl moieties are each independently unsubstituted or substituted.

5. The compound of claim 2 having formula (I), or a pharmaceutically acceptable salt thereof, wherein ring A is formula (a).

6. The compound of claim 5 having formula (I), or a pharmaceutically acceptable salt thereof, wherein $X^1$ is S.

7. The compound of claim 6 having formula (I), or a pharmaceutically acceptable salt thereof, wherein $R^1$ is phenyl or naphthyl, each of which is optionally substituted.

8. The compound of claim 6 having formula (I), or a pharmaceutically acceptable salt thereof, wherein $R^1$ is —$N(R^{1a})(R^z)$.

9. The compound of claim 2 having formula (I), or a pharmaceutically acceptable salt thereof, wherein ring A is formula (b).

10. The compound of claim 9 having formula (I), or a pharmaceutically acceptable salt thereof, wherein $X^2$ is O.

11. The compound of claim 9 having formula (I), or a pharmaceutically acceptable salt thereof, wherein $X^2$ is $N(R^{10})$ and $R^{10}$ is alkyl.

12. The compound of claim 9 having formula (I), or a pharmaceutically acceptable salt thereof, wherein $R^1$ is phenyl or naphthyl, each of which is optionally substituted.

13. The compound of claim 2 having formula (I), or a pharmaceutically acceptable salt thereof, wherein ring A is formula (c).

14. The compound of claim 13 having formula (I), or a pharmaceutically acceptable salt thereof, wherein $R^1$ is phenyl or naphthyl, each of which is optionally substituted.

15. The compound of claim 2 having formula (I), or a pharmaceutically acceptable salt thereof, wherein ring A is formula (d).

16. The compound according to claim 1 or a pharmaceutically acceptable salt thereof, selected from the group consisting of 5-chloro-2-methoxy-N-[(2Z)-3-[(2R)-tetrahydrofuran-2-ylmethyl]-5-[1-(trifluoromethyl)cyclopropyl]-1,3,4-thiadiazol-2(3H)-ylidene]benzamide;

5-chloro-N-[(2Z)-5-cyclopropyl-3-(tetrahydrofuran-2-ylmethyl)-1,3,4-thiadiazol-2(3H)-ylidene]-2-methoxybenzamide;

N-[(2Z)-5-cyclopropyl-3-(tetrahydrofuran-2-ylmethyl)-1,3,4-thiadiazol-2(3H)-ylidene]-2-ethoxybenzamide;

N-[(2Z)-5-tert-butyl-3-[(2R)-tetrahydrofuran-2-ylmethyl]-1,3,4-thiadiazol-2(3H)-ylidene]-5-chloro-2-methoxybenzamide;

5-chloro-2-methoxy-N-[(2Z)-5-(1-methylcyclopropyl)-3-[(2R)-tetrahydrofuran-2-ylmethyl]-1,3,4-thiadiazol-2(3H)-ylidene]benzamide;

5-chloro-N-[(2Z)-5-(1,1-dimethylprop-2-ynyl)-3-[(2R)-tetrahydrofuran-2-ylmethyl]-1,3,4-thiadiazol-2(3H)-ylidene]-2-methoxybenzamide;

5-chloro-2-methoxy-N-[(2Z)-5-(2,2,3,3-tetrafluoro-1-methylcyclobutyl)-3-[(2R)-tetrahydrofuran-2-ylmethyl]-1,3,4-thiadiazol-2(3H)-ylidene]benzamide;

5-chloro-2-methoxy-N-[(2Z)-3-[(2R)-tetrahydrofuran-2-ylmethyl]-5-[1-(trifluoromethyl)cyclobutyl]-1,3,4-thiadiazol-2(3H)-ylidene]benzamide;

5-chloro-2-methoxy-N-[(2Z)-3-[(2R)-tetrahydrofuran-2-ylmethyl]-5-(2,2,2-trifluoro-1,1-dimethylethyl)-1,3,4-thiadiazol-2(3H)-ylidene]benzamide;

5-chloro-2-methoxy-N-[(2E)-5-methyl-1-(tetrahydrofuran-2-ylmethyl)pyridin-2(1H)-ylidene]benzamide;

N-[5-tert-butyl-2-[(2R)-tetrahydrofuran-2-ylmethyl]isoxazol-3(2H)-ylidene]-5-chloro-2-methoxybenzamide;

N-{5-tert-butyl-1-methyl-2-[(2S)-tetrahydrofuran-2-ylmethyl]-1,2-dihydro-3H-pyrazol-3-ylidene}-5-chloro-2-methoxybenzamide; and N-[5-tert-butyl-3-[(2R)-tetrahydrofuran-2-ylmethyl]-1,3-oxazol-2(3H)-ylidene]-5-chloro-2-methoxybenzamide.

17. A pharmaceutical composition comprising a therapeutically effective amount of a compound of formula (I) according to claim 1, or a pharmaceutically acceptable salt thereof, in combination with one or more pharmaceutically acceptable carrier.

18. A method for treating pain in a mammal in need of such treatment comprising administering to the mammal a therapeutically effective amount of a compound of formula (I) according to claim 1, or a pharmaceutically acceptable salt thereof.

19. A method for treating an inflammatory disorder in a mammal in need of such treatment comprising administering to the mammal a therapeutically effective amount of a compound of formula (I) according to claim 1, or a pharmaceutically acceptable salt thereof.

20. The compound according to claim 1 or a pharmaceutically acceptable salt thereof, selected from the group consisting of

- N-{(3E)-5-tert-butyl-1-methyl-2-[(2R)-tetrahydrofuran-2-ylmethyl]-1,2-dihydro-3H-pyrazol-3-ylidene}-2-ethoxy-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-[(3,3-difluorocyclobutyl)methoxy]-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-(3-methoxy-3-methylbutoxy)-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-(2,2,2-trifluoroethoxy)-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-(2-fluoroethoxy)-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-(2-methoxyethoxy)-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-hydroxy-5-(trifluoromethyl)benzamide;
- 2-tert-butoxy-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-[2-(dimethylamino)ethoxy]-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-(dimethylamino)-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-{[(2S)-2-methoxypropyl]oxy}-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-(3-ethoxypropoxy)-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-(3-methoxypropoxy)-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-(2-ethoxyethoxy)-5-(trifluoromethyl)benzamide;
- 2-methoxy-N-{(3E)-1-methyl-5-(1-methylcyclopropyl)-2-[(2R)-tetrahydrofuran-2-ylmethyl]-1,2-dihydro-3H-pyrazol-3-ylidene}-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-[(2-methoxyethyl)amino]-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-(2,2-difluoroethoxy)-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-[(3R)-tetrahydrofuran-3-yloxy]-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-[(3S)-tetrahydrofuran-3-yloxy]-5-(trifluoromethyl)benzamide;
- (E)-N-(5-tert-butyl-2-(((2R,3R)-3-fluorotetrahydrofuran-2-yl)methyl)-1-methyl-1H-pyrazol-3(2H)-ylidene)-2-methoxy-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-[(2-fluoroethyl)amino]-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-(2-fluoropropoxy)-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-{[(2R)-2-fluoropropyl]oxy}-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-(2-fluoro-1-methylethoxy)-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-(3-fluoro-3-methylbutoxy)-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-fluoro-3-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-methoxy-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-5-cyano-2-methoxybenzamide;
- N-{(3E)-5-tert-butyl-1-methyl-2-[(2R)-tetrahydrofuran-2-ylmethyl]-1,2-dihydro-3H-pyrazol-3-ylidene}-2-chloro-5-fluorobenzamide;
- N-{(3E)-5-tert-butyl-1-methyl-2-[(2R)-tetrahydrofuran-2-ylmethyl]-1,2-dihydro-3H-pyrazol-3-ylidene}-2,3,5-trifluorobenzamide;
- N-{(3E)-5-tert-butyl-1-methyl-2-[(2R)-tetrahydrofuran-2-ylmethyl]-1,2-dihydro-3H-pyrazol-3-ylidene}-3-chloro-2-fluoro-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-3-chloro-2-methoxy-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-2-chloro-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-3,5-difluoro-2-methoxybenzamide;
- N-{(3E)-5-tert-butyl-1-methyl-2-[(2R)-tetrahydrofuran-2-ylmethyl]-1,2-dihydro-3H-pyrazol-3-ylidene}-3-chloro-2-(2-methoxyethoxy)-5-(trifluoromethyl)benzamide;
- N-{(3E)-5-tert-butyl-1-methyl-2-[(2R)-tetrahydrofuran-2-ylmethyl]-1,2-dihydro-3H-pyrazol-3-ylidene}-3-chloro-2-(2-fluoroethoxy)-5-(trifluoromethyl)benzamide;
- 5-bromo-N-{(3E)-5-tert-butyl-1-methyl-2-[(2R)-tetrahydrofuran-2-ylmethyl]-1,2-dihydro-3H-pyrazol-3-ylidene}-2-(2-methoxyethoxy)benzamide;

5-bromo-N-{(3E)-5-tert-butyl-1-methyl-2-[(2R)-tetrahydrofuran-2-ylmethyl]-1,2-dihydro-3H-pyrazol-3-ylidene}-2-(2-fluoroethoxy)benzamide;
5-bromo-N-{(3E)-5-tert-butyl-1-methyl-2-[(2R)-tetrahydrofuran-2-ylmethyl]-1,2-dihydro-3H-pyrazol-3-ylidene}-2,3-dihydro-1-benzofuran-7-carboxamide;
N-[(2E)-4-tert-butyl-1-[(2R)-tetrahydrofuran-2-ylmethyl]pyridin-2(1H)-ylidene]-5-chloro-2-methoxybenzamide;
N-[(2E)-4-tert-butyl-1-[(2R)-tetrahydrofuran-2-ylmethyl]pyridin-2(1H)-ylidene]-2-methoxy-5-(trifluoromethyl)benzamide;
N-[(3E)-5-tert-butyl-1-methyl-2-(tetrahydro-2H-pyran-2-ylmethyl)-1,2-dihydro-3H-pyrazol-3-ylidene]-2-methoxy-5-(trifluoromethyl)benzamide;
N-((3E)-5-tert-butyl-1-methyl-2-{[(5R)-5-methyltetrahydrofuran-2-yl]methyl}-1,2-dihydro-3H-pyrazol-3-ylidene)-2-methoxy-5-(trifluoromethyl)benzamide;
N-((3E)-5-tert-butyl-1-methyl-2-{[(5S)-5-methyltetrahydrofuran-2-yl]methyl}-1,2-dihydro-3H-pyrazol-3-ylidene)-2-methoxy-5-(trifluoromethyl)benzamide;
N-[(2Z)-5-tert-butyl-3-[(2R)-tetrahydrofuran-2-ylmethyl]-1,3-oxazol-2(3H)-ylidene]-2-methoxy-5-(trifluoromethyl)benzamide;
N-[(2Z)-5-tert-butyl-3-[(2R)-tetrahydrofuran-2-ylmethyl]-1,3,4-thiadiazol-2(3H)-ylidene]-N'-(4-methylcyclohexyl)urea;
N-(1-adamantylmethyl)-N'-[(2Z)-5-tert-butyl-3-[(2R)-tetrahydrofuran-2-ylmethyl]-1,3,4-thiadiazol-2(3H)-ylidene]urea;
N-[(2Z)-5-tert-butyl-3-[(2R)-tetrahydrofuran-2-ylmethyl]-1,3,4-thiadiazol-2(3H)-ylidene]-N'-{[(1S,2R,5S)-6,6-dimethylbicyclo[3.1.1]hept-2-yl]methyl}urea;
N-[(2Z)-5-tert-butyl-3-[(2R)-tetrahydrofuran-2-ylmethyl]-1,3,4-thiadiazol-2(3H)-ylidene]-N'-[1-(hydroxymethyl)-3-methylbutyl]urea;
N-[(2Z)-5-tert-butyl-3-[(2R)-tetrahydrofuran-2-ylmethyl]-1,3,4-thiadiazol-2(3H)-ylidene]-N'-(1,2-dimethylpropyl)urea;
N-[(2Z)-5-tert-butyl-3-[(2R)-tetrahydrofuran-2-ylmethyl]-1,3,4-thiadiazol-2(3H)-ylidene]-N'-(1-ethylpropyl)urea;
N-[(2Z)-5-tert-butyl-3-[(2R)-tetrahydrofuran-2-ylmethyl]-1,3,4-thiadiazol-2(3H)-ylidene]-N'-1,2,3,4-tetrahydronaphthalen-1-ylurea;
N-[(2Z)-5-tert-butyl-3-[(2R)-tetrahydrofuran-2-ylmethyl]-1,3,4-thiadiazol-2(3H)-ylidene]-N'-[(1S)-1-cyclohexylethyl]urea;
N-(tert-butyl)-N'-[(2Z)-5-tert-butyl-3-[(2R)-tetrahydrofuran-2-ylmethyl]-1,3,4-thiadiazol-2(3H)-ylidene]urea;
N-[(2Z)-5-tert-butyl-3-[(2R)-tetrahydrofuran-2-ylmethyl]-1,3,4-thiadiazol-2(3H)-ylidene]-N'-[(1S)-1-(hydroxymethyl)-2,2-dimethylpropyl]urea;
N-[(2Z)-5-tert-butyl-3-[(2R)-tetrahydrofuran-2-ylmethyl]-1,3,4-thiadiazol-2(3H)-ylidene]-N'-cycloheptylurea;
N-[(2Z)-5-tert-butyl-3-[(2R)-tetrahydrofuran-2-ylmethyl]-1,3,4-thiadiazol-2(3H)-ylidene]-N'-(2-ethylhexyl) urea;
N-[(2Z)-5-tert-butyl-3-[(2R)-tetrahydrofuran-2-ylmethyl]-1,3,4-thiadiazol-2(3H)-ylidene]-N'-(1-methyl-3-phenylpropyl)urea;
$N^2$-({[(2Z)-5-tert-butyl-3-[(2R)-tetrahydrofuran-2-ylmethyl]-1,3,4-thiadiazol-2(3H)-ylidene]amino}carbonyl)-L-isoleucinamide;
$N^2$-({[(2Z)-5-tert-butyl-3-[(2R)-tetrahydrofuran-2-ylmethyl]-1,3,4-thiadiazol-2(3H)-ylidene]amino}carbonyl)-N',3-dimethyl-L-valinamide;
N-[(2Z)-5-tert-butyl-3-[(2R)-tetrahydrofuran-2-ylmethyl]-1,3,4-thiadiazol-2(3H)-ylidene]-N'-neopentylurea;
N-[(2Z)-5-tert-butyl-3-[(2R)-tetrahydrofuran-2-ylmethyl]-1,3,4-thiadiazol-2(3H)-ylidene]-N'-[(1S)-1-(hydroxymethyl)-2-methylpropyl]urea;
N-[(3E)-5-tert-butyl-1-methyl-2-(tetrahydrofuran-3-ylmethyl)-1,2-dihydro-3H-pyrazol-3-ylidene]-2-methoxy-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-methyl-5-(trifluoromethyl)benzamide;
N-{(3E)-4-bromo-5-tert-butyl-1-methyl-2-[(2R)-tetrahydrofuran-2-ylmethyl]-1,2-dihydro-3H-pyrazol-3-ylidene}-2-methyl-5-(trifluoromethyl)benzamide;
2-bromo-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-(3-methoxypropyl)-5-(trifluoromethyl)benzamide;
N-[(2Z)-5-tert-butyl-3-{[(4S)-2-oxo-1,3-oxazolidin-4-yl]methyl}-1,3,4-thiadiazol-2(3H)-ylidene]-5-chloro-2-methoxybenzamide;
2-(2-amino-2-methylpropoxy)-N-{(3E)-5-tert-butyl-1-methyl-2-[(2R)-tetrahydrofuran-2-ylmethyl]-1,2-dihydro-3H-pyrazol-3-ylidene}-5-(trifluoromethyl)benzamide;
2-(azetidin-3-yloxy)-N-[(2Z)-5-tert-butyl-3-[(2R)-tetrahydrofuran-2-ylmethyl]-1,3-oxazol-2(3H)-ylidene]-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-3-fluoro-5-(trifluoromethyl)benzamide;
N-[(2Z)-5-tert-butyl-3-[(2R)-tetrahydrofuran-2-ylmethyl]-1,3,4-thiadiazol-2(3H)-ylidene]-2-{[(3S)-1-methylpyrrolidin-3-yl]oxy}-5-(trifluoromethyl)benzamide;
N-[(2Z)-5-tert-butyl-3-[(2R)-tetrahydrofuran-2-ylmethyl]-1,3-oxazol-2(3H)-ylidene]-2-{[(3S)-1-methylpyrrolidin-3-yl]oxy}-5-(trifluoromethyl)benzamide;
N-{(3E)-5-tert-butyl-1-methyl-2-[(2R)-tetrahydrofuran-2-ylmethyl]-1,2-dihydro-3H-pyrazol-3-ylidene}-2-[(1E)-prop-1-enyl]-5-(trifluoromethyl)benzamide; and
N-{(3E)-5-tert-butyl-1-methyl-2-[(2R)-tetrahydrofuran-2-ylmethyl]-1,2-dihydro-3H-pyrazol-3-ylidene}-2-(3-hydroxy-3-methylbutyl)-5-(trifluoromethyl)benzamide.

21. A method for treating an immune disorder in a mammal in need of such treatment comprising administering to the mammal a therapeutically effective amount of a compound of formula (I) according to claim 1, or a pharmaceutically acceptable salt thereof, wherein the immune disorder is selected from the group consisting of multiple sclerosis, rheumatoid arthritis, systemic lupus, myasthenia gravis, type 1 diabetes, irritable bowel syndrome, psoriasis, psoriatic arthritis, hepatitis, tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

22. A method for treating Alzheimer's disease in a mammal in need of such treatment comprising administering to the mammal a therapeutically effective amount of a compound of formula (I) according to claim 1, or a pharmaceutically acceptable salt thereof.

23. A method for treating a respiratory disorder in a mammal in need of such treatment comprising administering to the mammal a therapeutically effective amount of a compound of formula (I) according to claim 1, or a pharmaceutically acceptable salt thereof, wherein the respiratory disorder is selected from the group consisting of pulmonary inflammation, chronic cough, asthma, chronic obstructive pulmonary disease, and pulmonary fibrosis.

24. A method for treating a cardiovascular disorder in a mammal in need of such treatment comprising administering to the mammal a therapeutically effective amount of a compound of formula (I) according to claim 1, or a pharmaceutically acceptable salt thereof, wherein the cardiovascular disorder is selected from the group consisting of atherosclerosis, ischemia, reperfusion, and myocardial infarction.

\* \* \* \* \*